(12) United States Patent
Robichaud et al.

(10) Patent No.: US 6,552,017 B1
(45) Date of Patent: Apr. 22, 2003

(54) SUBSTITUTED HETEROCYCLE FUSED GAMMA-CARBOLINES

(75) Inventors: Albert J. Robichaud, Landenberg, PA (US); Taekyu Lee, Wilmington, DE (US); Wei Deng, Wilmington, DE (US); Ian S. Mitchell, Philadelphia, PA (US); Michael Guang Yang, Wilmington, DE (US); Simon Haydar, Niskayuna, NY (US); Wenting Chen, Exton, PA (US); Christopher D. Mc Clung, Wilmington, DE (US); Emilie J. B. Calvello, Bryn Mawr, PA (US); David M. Zawrotny, Moorestown, NJ (US)

(73) Assignee: Bristol-Myers Squibb Pharma Company, Wilmington, DE (US)

( * ) Notice: Subject to any disclaimer, the term of this patent is extended or adjusted under 35 U.S.C. 154(b) by 0 days.

(21) Appl. No.: 09/595,250

(22) Filed: Jun. 15, 2000

Related U.S. Application Data

(60) Provisional application No. 60/139,321, filed on Jun. 15, 1999.

(51) Int. Cl.$^7$ .............. C07D 487/00; C07D 243/00; C07D 491/00; C07D 241/36; A61K 31/55

(52) U.S. Cl. .............. 514/219; 514/250; 540/494; 540/556; 544/343

(58) Field of Search .............. 540/556, 494; 514/219, 250; 544/343

(56) References Cited

U.S. PATENT DOCUMENTS

| | | | |
|---|---|---|---|
| 3,299,078 A | 1/1967 | Pachter | 260/296 |
| 3,813,392 A | 5/1974 | Sellstedt et al. | 260/250 R |
| 3,891,643 A | 6/1975 | Sellstedt et al. | 260/250 Q |
| 3,892,746 A | 7/1975 | Sellstedt et al. | 260/247.2 A |
| 3,914,421 A | 10/1975 | Rajogopalan | 424/248 |
| 4,013,652 A | 3/1977 | Rajagopalan | 260/244 R |
| 4,088,647 A | 5/1978 | Glushkov et al. | 544/343 |
| 4,115,577 A | 9/1978 | Rajagopalan | 424/256 |
| 4,183,936 A | 1/1980 | Rajagopalan | 424/256 |
| 4,219,550 A | 8/1980 | Rajagopalan | 424/246 |
| 4,238,607 A | 12/1980 | Rajagopalan | 544/14 |
| 4,997,831 A | 3/1991 | Bays et al. | 514/211 |
| 5,100,884 A | 3/1992 | Hamminga et al. | 514/183 |
| 5,223,625 A | 6/1993 | Van Wijngaarden et al. | 546/70 |
| 5,328,905 A | 7/1994 | Hamminga et al. | 514/214 |
| 5,512,575 A | 4/1996 | Jacobs et al. | 514/256 |
| 5,654,139 A | 8/1997 | Lappalainen et al. | 435/6 |
| 5,902,815 A | 5/1999 | Olney et al. | 514/285 |
| 5,908,830 A | 6/1999 | Smith et al. | 514/12 |
| 6,107,324 A | 8/2000 | Behan et al. | 514/406 |
| 6,140,509 A | 10/2000 | Behan et al. | 548/365.7 |
| 6,407,092 B1 | 6/2002 | Hester et al. | 514/215 |

FOREIGN PATENT DOCUMENTS

| | | |
|---|---|---|
| CA | 2011107 | 8/1991 |
| EP | 0725068 | 8/1996 |
| FR | 2213283 | 2/1974 |
| WO | WO0064899 | 11/2000 |

OTHER PUBLICATIONS

Bickerdike MJ, Vickers, SP, Dourish CT, (1999) 5–HT2C receptor modulation and the treatment of obesity. Diabetes, Obesity and Metabolism 1:207–214.

Tecott LH, et al. (1995) Eating disorder and epilepsy in mice lacking 5–HT2C serotonin receptors. Nature (London) 374:542–546.

Cryan JF, Lucki I, (2000) Antidepressant–like behavioral effects mediated by 5–hydroxtryptamine2C receptors. J. Pharmacol. Exper. Ther. 295:1120–1126.

Millan MJ, Peglion JL, Lavielle G, Perrin–Monneyron S, (1997) 5–HT2C receptors mediate penile erection in rats: actions of novel and selective agonists and antagonists. Eur. J. Pharmacol. 325:9–12.

Martin JR, et al. (1998) 5–HT2C receptor agonists: Pharmacological characteristics and therapeutic potential. J. Pharmacol. Exper. Ther. 286:913–924.

Meltzer HY. (1999) The role of serotonin in antipsychotic drug action. Neuropsychopharmacology 21(2):1065–1155.

Curzon et al, Appetite suppression by commonly used drugs depends on 5–HT receptors but not on 5–HT availability, TiPS, vol. 18, 1997; 21–25.

(List continued on next page.)

*Primary Examiner*—Bruck Kifle
(74) *Attorney, Agent, or Firm*—Scott K. Larsen; Maureen P. O'Brien

(57) ABSTRACT

The present invention is directed to certain novel compounds represented by structural Formula (I)

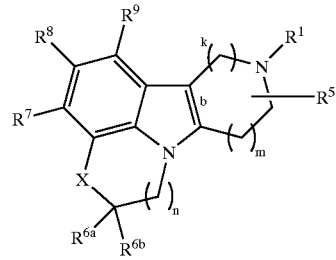

(I)

or pharmaceutically acceptable salt forms thereof, wherein $R^1$, $R^5$, $R^{6a}$, $R^{6b}$, $R^7$, $R^8$, $R^9$, X, b, k, m, and n, and the dashed lines are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

21 Claims, No Drawings

OTHER PUBLICATIONS

Mora et al, Role of 5–HT2A and 5–HT2C Receptor subtypes in the Two Types of Fear Generated by the Elevated T–Maze, Pharma. Biolchem. & Behavior, vol. 58, No. 4, 1997; 1051–1057.

Jenck et al, Antiaversive effects of 5HT2C receptor agonists and fluoxetine in a model of panic–like anxiety in rats, European Neuropsychopharmacology, 8, 1998; 161–168.

Leysen, Selective 5–HT2c agonists as potential antidepressants, Drugs, 1999, 2(2); 109–120.

Jenck et al, The role of 5–HT2c receptors in affective disorders, Exp. Opin. Invest. Drugs, 1998, 7(10); 1587–1599.

Kennett, 5–HT drugs and eating disorders, I Drugs, 1998, vol. 1, No. 4; 456–470.

Brewerton, Induction of migrainelike headaches by the serotonin agonist m–chlorophenylpiperazine, Clin. Pharmacol. Ther., 1988, 605–609.

Kahn et al, m–Chlorophenylpiperazine as a probe of serotonin function, Biol. Psychiatry, 1991; 30: 1139–1166.

Gibson et al, Evidence that mCPP–induced Anxiety in the Plus–maze is mediated by Postsynaptic 5–HT2c receptors but not by sympathomimetic effects, Neuropharmacology, vol. 33, No. 3, 4, 1994; 457–465.

SUBSTITUTED HETEROCYCLE FUSED GAMMA-CARBOLINES

This application claims the benefit of U.S. Provisional Application No. 60/139,321, filed Jun. 15, 1999.

FIELD OF THE INVENTION

The present invention is directed to certain novel compounds represented by structural Formula (I)

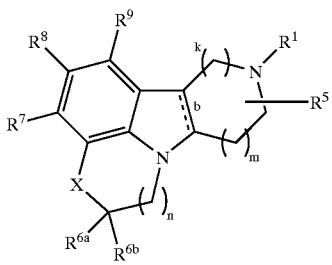

(I)

or pharmaceutically acceptable salt forms thereof, wherein $R^1$, $R^5$, $R^{6a}$, $R^{6b}$, $R^7$, $R^8$, $R^9$, X, b, k, m, and n, and the dashed lines are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

BACKGROUND OF THE INVENTION

There exists a substantial correlation for the relationship between 5-HT2 receptor modulation and a variety of diseases and therapies. To date, three subtypes of the 5-HT2 receptor class have been identified, 5-HT2A, 5-HT2B, and 5-HT2C. Prior to the early 1990's the 5-HT2C and 5-HT2A receptors were referred to as 5-HT1C and 5-HT2, respectively.

The agonism or antagonism of 5-HT2 receptors, either selectively or nonselectively, has been associated with the treatment of various central nervous system (CNS) disorders. Ligands possessing affinity for the 5-HT2 receptors have been shown to have numerous physiological and behavioral effects (Trends in Pharmacological Sciences, 11, 181, 1990). In the recent past the contribution of serotonergic activity to the mode of action of antidepressant drugs has been well documented. Compounds that increase the overall basal tone of serotonin in the CNS have been successfully developed as antidepressants. The serotonin selective reuptake inhibitors (SSRI) function by increasing the amount of serotonin present in the nerve synapse. These breakthrough treatments, however, are not without side effects and suffer from delayed onset of action (Leonard, J. Clin. Psychiatry, 54(suppl), 3, 1993). Due to the mechanism of action of the SSRIs, they effect the activity of a number of serotonin receptor subtypes. This non-specific modulation of the serotonin family of receptors most likely plays a significant role in the side effect profile. In addition, these compounds often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

There is ample evidence to support the role of selective 5-HT2 receptor ligands in a number of disease therapies. Modulation of 5-HT2 receptors has been associated with the treatment of schizophrenia and psychoses (Ugedo, L., et. al., Psychopharmacology, 98, 45, 1989). Mood, behavior and hallucinogenesis can be affected by 5-HT2 receptors in the limbic system and cerebral cortex. 5-HT2 receptor modulation in the hypothalamus can influence appetite, thermoregulation, sleep, sexual behavior, motor activity, and neuroendocrine function (Hartig, P., et.al., Annals New York Academy of Science, 149, 159). There is also evidence indicating that 5-HT2 receptors mediate hypoactivity, effect feeding in rats, and mediate penile erections (Pyschopharmacology, 101, 57, 1990).

Compounds exhibiting selectivity for the 5-HT2B receptor are useful in treating conditions such as tachygastria, hypermotility associated with irritable bowel disorder, constipation, dyspepsia, and other peripherally mediated conditions.

5-HT2A antagonists have been shown to be effective in the treatment of schizophrenia, anxiety, depression, and migraines (Koek, W., Neuroscience and Behavioral reviews, 16, 95, 1996). Aside from the beneficial antipsychotic effects, classical neuroleptic are frequently responsible for eliciting acute extrapyramidal side effects and neuroendocrine disturbances. These compounds generally possess signifcant dopamine D2 receptor affinity (as well as other nuisance receptor affinity) which frequently is associated with extra pyramidal symptoms and tardive dyskinesia, thus detracting from their efficacy as front line treatments in schizophrenia and related disorders. Compounds possessing a more favorable selectivity profile would represent a possible improvement for the treatment of CNS disorders.

U.S. Pat. Nos. 3,914,421; 4,013,652; 4,115,577; 4,183,936; and 4,238,607 disclose pyridopyrrolobenzheterocycles of formula:

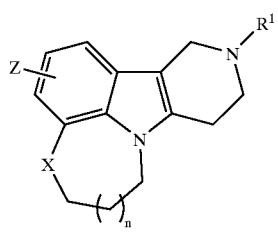

where X is O, S, S(=O), or $SO_2$; n is 0 or 1; $R^1$ is various carbon substituents, and Z is a monosubstituent of H, methyl, or chloro.

U.S. Pat. No. 4,219,550 discloses pyridopyrrolobenzheterocycles of formula:

[Structure diagram]

where X is O or S; $R^1$ is $C_{1-4}$ alkyl or cyclopropyl; $R^2$ is H, $CH_3$, $OCH_3$, Cl, Br, F, or $CF_3$; and (A) is —$CH_2$—, —$CH(CH_3)$—, or —$CH_2CH_2$—.

SUMMARY OF THE INVENTION

One object of the present invention is to provide novel compounds which are useful as agonists or antagonists of 5-HT2 receptors, more specifically 5-HT2A and 5-HT2C receptors, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility comprising administering to a host in need of such treatment a therapeutically effective amount of at least one of the compounds of the present invention or a pharmaceutically acceptable salt or prodrug form thereof. More specifically, the present invention provides a method for treating obesity anxiety, depression, or schizophrenia.

These and other objects, which will become apparent during the following detailed description, have been achieved by the inventors' discovery that compounds of Formula (I):

[Structure diagram of Formula (I)]

(I)

or pharmaceutically acceptable salt or prodrug forms thereof, wherein $R^1$, $R^5$, $R^{6a}$, $R_{6b}$, $R^7$, $R^8$, $R^9$, X, b, k, m, and n are defined below, are effective agonists or antagonists of 5-HT2 receptors.

DETAILED DESCRIPTION OF THE EMBODIMENTS

Thus, in a first embodiment, the present invention provides a novel compound of Formula (I):

[Structure diagram of Formula (I)]

(I)

or stereoisomers or pharmaceutically acceptable salt forms thereof, wherein:

b is a single bond or a double bond;

X is —$CHR^{10}$—, —C(=O)—, —O—, —S—, —S(=O)—, —$S(=O)_2$—, —$NR^{10A}$—, —C(=O)$NR^{10A}$—, or —$NR^{10A}$C(=O)—;

$R^1$ is selected from

H $C(=O)R^2$, $C(=O)OR^2$, $C_{1-8}$ alkyl, $C_{2-8}$ alkenyl, $C_{2-8}$ alkynyl, $C_{3-7}$ cycloalkyl, $C_{1-6}$ alkyl substituted with Z, $C_{2-6}$ alkenyl substituted with Z, $C_{2-6}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{1-3}$ alkyl substituted with Y, $C_{2-3}$ alkenyl substituted with Y, $C_{2-3}$ alkynyl substituted with Y, $C_{1-6}$ alkyl substituted with 0–2 $R^2$, $C_{2-6}$ alkenyl substituted with 0–2 $R^2$, $C_{2-6}$ alkynyl substituted with 0–2 $R^2$, aryl substituted with 0–2 $R^2$, and 5–6 membered heterocyclic ring system containing at least one heteroatom selected from the group consisting of N, O, and S, said heterocyclic ring system substituted with 0–2 $R^2$;

Y is selected from $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with z;

$C_{3-6}$ cycloalkyl substituted with —($C_{1-3}$ alkyl)-Z, aryl substituted with —($C_{1-3}$ alkyl)-Z, and 5–6 membered heterocyclic ring system containing at least one heteroatom selected from the group consisting of N, O, and S, said heterocyclic ring system substituted with —($C_{1-3}$ alkyl)-Z;

Z is selected from H,
- —CH(OH)R$^2$,
- —C(ethylenedioxy)R$^2$,
- —OR$^2$,
- —SR$^2$,
- —NR$^2$R$^3$,
- —C(O)R$^2$,
- —C(O)NR$^2$R$^3$,
- —NR$^3$C(O)R$^2$,
- —C(O)OR$^2$,
- —OC(O)R$^2$,
- —CH(=NR$^4$)NR$^2$R$^3$,
- —NHC(=NR$^4$)NR$^2$R$^3$,
- —S(O)R$^2$,
- —S(O)$_2$R$^2$,
- —S(O)$_2$NR$^2$R$^3$, and —NR$^3$S(O)$_2$R$^2$;

R$^2$, at each occurrence, is independently selected from
- C$_{1-4}$ alkyl,
- C$_{2-4}$ alkenyl,
- C$_{2-4}$ alkynyl,
- C$_{3-6}$ cycloalkyl,
- phenyl substituted with 0–5 R$^{42}$;
- C$_{3-10}$ carbocyclic residue substituted with 0–3 R$^{41}$, and
- 5–10 membered heterocyclic ring system containing from 1–4 heteroatoms selected from the group consisting of N, O, and S substituted with 0–3 R$^{41}$;

R$^3$, at each occurrence, is independently selected from
- H, C$_{1-4}$ alkyl, C$_{2-4}$ alkenyl, and C$_{2-4}$ alkynyl;
- alternatively, R$^2$ and R$^3$ join to form a 5- or 6-membered ring optionally substituted with —O— or —N(R$^4$)—;

R$^4$, at each occurrence, is independently selected from H and C$_{1-4}$ alkyl;

R$^5$ is H or C$_{1-4}$ alkyl;

R$^{6a}$ and R$^{6b}$, at each occurrence, are independently selected from
- H, —OH, —NR$^{46}$R$^{47}$, —CF$_3$, C$_{1-4}$ alkyl, C$_{2-4}$ alkenyl, C$_{2-4}$ alkynyl, C$_{1-4}$ alkoxy, C$_{1-4}$ haloalkyl, C$_{3-6}$ cycloalkyl, and
- aryl substituted with 0–3 R$^{44}$;

R$^7$ and R$^9$, at each occurrence, are independently selected from
- H, halo, —CF$_3$, —OCF$_3$, —OH, —CN, —NO$_2$, —NR$^{46}$R$^{47}$,
- C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
- C$_{3-10}$ cycloalkyl, substituted with 0–2 R$^{33}$,
- C$_{1-4}$ alkyl substituted with 0–2 R$^{11}$,
- C$_{3-10}$ carbocyclic residue substituted with 0–3 R$^{33}$, aryl substituted with 0–5 R$^{33}$,
- 5–10 membered heterocyclic ring system containing from 1–4 heteroatoms selected from the group consisting of N, O, and S substituted with 0–3 R$^{31}$;
- OR$^{12}$, SR$^{12}$, NR$^{12}$R$^{13}$, C(O)R$^{13}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;

R$^8$ is selected from
- H, halo, —CF$_3$, —OCF$_3$, —OH, —CN, —NO$_2$,
- C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
- C$_{3-10}$ cycloalkyl, substituted with 0–2 R$^{33}$,
- C$_{1-4}$ alkyl substituted with 0–2 R$^{11}$,
- C$_{3-10}$ carbocyclic residue substituted with 0–3 R$^{33}$,
- aryl substituted with 0–5 R$^{33}$,
- 5–10 membered heterocyclic ring system containing from 1–4 heteroatoms selected from the group consisting of N, O, and S substituted with 0–3 R$^{31}$;
- OR$^{12}$, SR$^{12}$, NR$^{12}$R$^{13}$, C(O)R$^{13}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;

R$^{10}$ is selected from H, —OH,
- C$_{1-6}$ alkyl substituted with 0–1 R$^{10B}$,
- C$_{2-6}$ alkenyl substituted with 0–1 R$^{10B}$,
- C$_{2-6}$ alkynyl substituted with 0–1 R$^{10B}$, and
- C$_{1-6}$ alkoxy;

R$^{10A}$ is selected from H,
- C$_{1-6}$ alkyl substituted with 0–1 R$^{10B}$,
- C$_{2-6}$ alkenyl substituted with 0–1 R$^{10B}$,
- C$_{2-6}$ alkynyl substituted with 0–1 R$^{10B}$, and
- C$_{1-6}$ alkoxy;

R$^{10B}$ is selected from
- C$_{1-4}$ alkoxy,
- C$_{3-6}$ cycloalkyl,
- C$_{3-10}$ carbocyclic residue substituted with 0–3 R$^{33}$,
- phenyl substituted with 0–3 R$^{33}$, and
- 5–6 membered heterocyclic ring system containing 1, 2, or 3 heteroatoms selected from the group consisting of N, O, and S substituted with 0–2 R$^{44}$;

R$^{11}$ is selected from
- H, halo, —CF$_3$, —CN, —NO$_2$,
- C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
- C$_{3-10}$ carbocyclic residue substituted with 0–3 R$^{33}$,
- aryl substituted with 0–5 R$^{33}$,
- 5–10 membered heterocyclic ring system containing from 1–4 heteroatoms selected from the group consisting of N, O, and S substituted with 0–3 R$^{31}$;
- OR$^{12}$, SR$^{12}$, NR$^{12}$R$^{13}$, C(O)R$^{13}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$; p0 R$^{12}$, at each occurrence, is independently selected from
- C$_{1-4}$ alkyl,
- C$_{2-4}$ alkenyl,
- C$_{2-4}$ alkynyl,
- C$_{3-6}$ cycloalkyl,
- phenyl substituted with 0–5 R$^{33}$;
- C$_{3-10}$ carbocyclic residue substituted with 0–3 R$^{33}$, and
- 5–10 membered heterocyclic ring system containing from 1–4 heteroatoms selected from the group consisting of N, O, and S substituted with 0–3 R$^{31}$;

R$^{13}$, at each occurrence, is independently selected from
- H, C$_{1-4}$ alkyl, C$_{2-4}$ alkenyl, and C$_{2-4}$ alkynyl;
- alternatively, R$^{12}$ and R$^{13}$ join to form a 5- or 6-membered ring optionally substituted with —O— or —N(R$^{14}$)—;

R$^{14}$, at each occurrence, is independently selected from H and C$_{1-4}$ alkyl;

R$^{31}$, at each occurrence, is independently selected from
- H, OH, halo, CF$_3$, SO$_2$R$^{45}$, NR$^{46}$R$^{47}$, and C$_{1-4}$ alkyl;

R$^{33}$, at each occurrence, is independently selected from

H, OH, halo, CN, $NO_2$, $CF_3$, $SO_2R^{45}$, $NR^{46}R^{47}$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, and $C_{1-4}$ alkyl-C(=O)NH—;

$R^{41}$, at each occurrence, is independently selected from

H, $CF_3$, halo, OH, $CO_2H$, $SO_2R^{45}$, $NR^{46}R^{47}$, $NO_2$, CN;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from

H, $CF_3$, halo, OH, $CO_2H$, $SO_2R^{45}$, $NR^{46}SO_2R^{45}$, $NR^{46}COR^{45}$, $NR^{46}R^{47}$, $NO_2$, CN, CH(=NH)$NH_2$, NHC(=NH)$NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0, 1, 2, or 3;

n is 0, 1, or 2;

provided when m is 0, then k is 1;

provided that when b is a double bond; n is 1 or 2; m is 1; k is 1; X is —O—, —S—, —S(=O)—, or —$SO_2$—; and the three substituents of $R^7$, $R^8$, and $R^9$, consist of i) three hydrogens, ii) two hydrogens and one chloro, or iii) two hydrogens and one methyl; then $R^1$ must contain the substituent Z or Y;

provided that when b is a double bond; n is 0 or 1; m is 1; k is 1; X is —$CH_2$—; and $R^1$ is hydrogen, $C_{1-6}$ alkyl or benzyl; then one of $R^7$, R8, and $R^9$, must be other than hydrogen, halo, $C_{1-6}$ alkyl, $C_{1-6}$ alkoxy or trifluoromethyl;

provided that when b is a single bond; n is 1 or 2; m is 1; k is 1; X is O or S; and $R^1$ is $C_{1-4}$ alkyl or cyclopropyl, then $R^8$ is a substituent other than H;

provided that when $R^6$ or $R^{6a}$ is $NH_2$, then X is not —CH($R^{10}$); and provided that when n=0, then $R^6$ or $R^{6a}$ is not $NH_2$ or —OH.

In another embodiment of the present invention,

X is —$CHR^{10}$—, —C(=O)—, —O—, —S—, —S(=O)—, —S(=O)$_2$—, —NH—, —C(=O)NH—, or —NHC(=O)—;

$R^1$ is selected from

H,

C(=O)$R^2$,

C(=O)O$R^2$, $C_{1-8}$ alkyl, $C_{2-8}$ alkenyl, $C_{2-8}$ alkynyl, $C_{3-7}$ cycloalkyl, $C_{1-6}$ alkyl substituted with Z, $C_{2-6}$ alkenyl substituted with Z, $C_{2-6}$ alkynyl substituted with Z, $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{1-3}$ alkyl substituted with Y, $C_{2-3}$ alkenyl substituted with Y, $C_{2-3}$ alkynyl substituted with Y, $C_{1-6}$ alkyl substituted with 0–2 $R^2$, $C_{2-6}$ alkenyl substituted with 0–2 $R^2$, $C_{2-6}$ alkynyl substituted with 0–2 $R^2$, aryl substituted with 0–2 $R^2$, and 5–6 membered heterocyclic ring system containing at least one heteroatom selected from the group consisting of N, O, and S, said heterocyclic ring system substituted with 0–2 $R^2$;

Y is selected from $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{3-6}$ cycloalkyl substituted with —($C_{1-3}$ alkyl)-Z, aryl substituted with —($C_{1-3}$ alkyl)-Z, and 5–6 membered heterocyclic ring system containing at least one heteroatom selected from the group consisting of N, O, and S, said heterocyclic ring system substituted with —($C_{1-3}$ alkyl)-Z;

Z is selected from H,

—CH(OH)$R^2$,

—C(ethylenedioxy)$R^2$,

—O$R^2$,

—S$R^2R^3$,

—N$R^2R^3$,

—C(O)$R^2$,

—C(O)N$R^2R^3$,

—$NR^3$C(O)$R^2$,

—C(O)O$R^2$,

—OC(O)$R^2$,

—CH(=$NR^4$)N$R^2R^3$,

—NHC(=$NR^4$)N$R^2R^3$,

—S(O)$R^2$,

—S(O)$_2R^2$,

—S(O)$_2$N$R^2R^3$, and —$NR^3$S(O)$_2R^2$;

$R^2$, at each occurrence, is independently selected from halo, $C_{1-3}$ haloalkyl, $C_{1-4}$ alkyl, $C_{2-4}$ alkenyl, $C_{2-4}$ alkynyl, $C_{3-6}$ cycloalkyl, aryl substituted with 0–5 $R^{42}$;

$C_{3-10}$ carbocyclic residue substituted with 0–3 $R^{41}$, and

5–10 membered heterocyclic ring system containing from 1–4 heteroatoms selected from the group consisting of N, O, and S substituted with 0–3 $R^{41}$;

$R^3$, at each occurrence, is independently selected from

H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H and $C_{1-4}$ alkyl;

$R^5$ is H or $C_{1-4}$ alkyl;

$R^{6a}$ and $R^{6b}$, at each occurrence, are independently selected from

H, —OH, —NR$^{46}$R$^{47}$, —CF$_3$, $C_{1-4}$ alkyl, $C_{2-4}$ alkenyl, $C_{2-4}$ alkynyl, $C_{1-4}$ alkoxy, $C_{1-4}$ haloalkyl, $C_{3-6}$ cycloalkyl, and aryl substituted with 0–3 $R^{44}$;

$R^7$ and $R^9$, at each occurrence, are independently selected from

H, halo, —CF$_3$, —OCF$_3$, —OH, —CN, —NO$_2$, —NR$^{46}$R$^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O) NHR$^{15}$;

$R^8$ is selected from

H, halo, —CF$_3$, —OCF$_3$, —OH, —CN, —NO$_2$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

$R^{10A}$ is selected from H, $C_{1-6}$ alkyl substituted with 0–1 $R^{10B}$, $C_{2-6}$ alkenyl substituted with 0–1 $R^{10B}$, $C_{2-6}$ alkynyl substituted with 0–1 $R^{10B}$, and $C_{1-6}$ alkoxy;

$R^{10B}$ is selected from $C_{1-4}$ alkoxy, $C_{3-6}$ cycloalkyl, $C_{3-10}$ carbocyclic residue substituted with 0–3 $R^{33}$, phenyl substituted with 0–3 $R^{33}$, and 5–6 membered heterocyclic ring system containing 1, 2, or 3 heteroatoms selected from the group consisting of N, O, and S substituted with 0–2 $R^{44}$;

$R^{11}$ is selected from

H, halo, —CF$_3$, —CN, —NO$_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

$R^{12}$ at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from

H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from

H, $C_{1-4}$ alkyl, $C_{2-4}$ alkenyl, and $C_{2-4}$ alkynyl;

$R^{16}$, at each occurrence, is independently selected from

H, OH, halo, CN, NO$_2$, CF$_3$, SO$_2$R$^{45}$, NR$^{46}$R$^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from

H, OH, halo, CF$_3$, SO$_2$R$^{45}$, NR$^{46}$R$^{47}$, and $C_{1-4}$ alkyl;

$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—,
$C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN, =O;
$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —C(=O) NH ($C_{1-4}$ alkyl), —$SO_2$($C_{1-4}$ alkyl) —C(=O)O($C_{1-4}$ alkyl), —C(=O)( $C_{1-4}$ alkyl), and —C(=O)H;

k is 1 or 2;
m is 0, 1, or 2;
n is 1, 2, or 3;
provided when m is 0 or 1 then k is 1 or 2;
provided when m is 2 then k is 1;
provided that when n=0, then $R^6$ or $R^{6a}$ is not $NH_2$ or —OH.

(2) In a preferred embodiment of the present invention, X is —$NR^{10A}$—, —C(=O)$NR^{10A}$—, or —$NR^{10A}$C(=O)—;

$R^1$ is selected from
H,
C(=O)$R^2$,
C(=O)O$R^2$,
$C_{1-8}$ alkyl,
$C_{2-8}$ alkenyl,
$C_{2-8}$ alkynyl,
$C_{3-7}$ cycloalkyl,
$C_{1-6}$ alkyl substituted with Z,
$C_{2-6}$ alkenyl substituted with Z,
$C_{2-6}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{1-3}$ alkyl substituted with Y,
$C_{2-3}$ alkenyl substituted with Y,
$C_{2-3}$ alkynyl substituted with Y,
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$,
aryl substituted with 0–2 $R^2$, and
5–6 membered heterocyclic ring system containing at least one heteroatom selected from the group consisting of N, O, and S, said heterocyclic ring system substituted with 0–2 $R^2$;

Y is selected from
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z; $C_{3-6}$ cycloalkyl substituted with ·($C_{1-3}$ alkyl)-Z, aryl substituted with ·($C_{1-3}$ alkyl)-Z, and 5–6 membered heterocyclic ring system containing at least one heteroatom selected from the group consisting of N, O, and S, said heterocyclic ring system substituted with ·($C_{1-3}$ alkyl)-Z;

Z is selected from H,
—CH(OH)$R^2$,
—C(ethylenedioxy)$R^2$,
—O$R^2$,
—S$R^2R^3$,
—C(O)$R^2$
—C(O)N$R^2R^3$,
—$NR^3$C(O)$R^2$,
—C(O)O$R^2$,
—OC(O)$R^2$,
—CH(=$NR^4$)N$R^2R^3$,
—NHC(=$NR^4$)N$R^2R^3$,
—S(O)$R^2$,
—S(O)$_2R^2$,
—S(O)$_2$N$R^2R^3$, and —$NR^3$S(O)$_2R^2$;

$R^2$, at each occurrence, is independently selected from
halo,
$C_{1-3}$ haloalkyl,
$C_{1-4}$ alkyl,
$C_{2-4}$ alkenyl,
$C_{2-4}$ alkynyl,
$C_{3-6}$ cycloalkyl,
aryl substituted with 0–5 $R^{42}$;
$C_{3-10}$ carbocyclic residue substituted with 0–3 $R^{41}$, and 5–10 membered heterocyclic ring system containing from 1–4 heteroatoms selected from the group consisting of N, O, and S substituted with 0–3 $R^{41}$;

$R^3$, at each occurrence, is independently selected from
H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H and $C_{1-4}$ alkyl;

$R^5$ is H or $C_{1-4}$ alkyl;

$R^{6a}$ and $R^{6b}$, at each occurrence, are independently selected from
H, —OH, —N$R^{46}R^{47}$, —$CF_3$, $C_{1-4}$ alkyl, $C_{2-4}$ alkenyl, $C_{2-4}$ alkynyl, $C_{1-4}$ alkoxy, $C_{1-4}$ haloalkyl, $C_{3-6}$ cycloalkyl, and
aryl substituted with 0–3 $R^{44}$;

$R^7$ and $R^9$, at each occurrence, are independently selected from
H, halo, —$CF_3$, —$OCF_3$, —OH, —CN, —$NO_2$, —N$R^{46}R^{47}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}CCO)R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$ $NR^{12}$C(O)$OR^{15}$, $NR^{12}$S(O)$_2R^{15}$, and $NR^{12}$C(O)$NHR^{15}$;

$R^8$ is selected from
H, halo, —$CF_3$, —$OCF_3$, —OH, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O) $NHR^{15}$;

$R^{10A}$ is selected from H,
$C_{1-6}$ alkyl substituted with 0–1 $R^{10B}$,
$C_{2-6}$ alkenyl substituted with 0–1 $R^{10B}$,
$C_{2-6}$ alkynyl substituted with 0–1 $R^{10B}$, and
$C_{1-6}$ alkoxy;

$R^{10B}$ is selected from
$C_{1-4}$ alkoxy,
$C_{3-6}$ cycloalkyl,
$C_{3-10}$ carbocyclic residue substituted with 0–3 $R^{33}$,
phenyl substituted with 0–3 $R^{33}$, and
5–6 membered heterocyclic ring system containing 1, 2, or 3 heteroatoms selected from the group consisting of N, O, and S substituted with 0–2 $R^{44}$;

$R^{11}$ is selected from
H, halo, —$CF_3$, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2$, $R^{12}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from
H, $C_{1-4}$ alkyl, $C_{2-4}$ alkenyl, and $C_{2-4}$ alkynyl;

$R^{16}$, at each occurrence, is independently selected from
H, OH, halo, CN, $NO_2$, $CF_3$, $SO_2R^{45}$, $NR^{46}R^{47}$, —C(=O)H,
$C_{1-4}$ alkyl, $C_{2-4}$ alkenyl, $C_{2-4}$ alkynyl, $C_{1-4}$ haloalkyl,
$C_{1-3}$ haloalkyl-oxy-, and $C_{1-3}$ alkyloxy-;

$R^{31}$, at each occurrence, is independently selected from
H, OH, halo, $CF_3$, $SO_2R^{45}$, $NR^{46}R^{47}$, and $C_{1-4}$ alkyl;

$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-,
$C_{1-4}$ alkyloxy-,
$C_{1-4}$ alkylthio-, $C_{1-4}$ alkyl-C(=O)—, $C_{1-4}$ alkyl-C(=O)NH—,
$C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN, =O;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, CH(=NH)$NH_2$, NHC(=NH)$NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —C(=O)NH($C_{1-4}$ alkyl), —$SO_2$($C_{1-4}$ alkyl), —C(=O)O($C_{1-4}$ alkyl), —C(=O)( $C_{1-4}$ alkyl), and —C(=O)H;

k is 1 or 2;

m is 0, 1, or 2;

n is 1, 2, or 3;

provided when m is 0 or 1 then k is 1 or 2;

provided when m is 2 then k is 1;

provided that when n=0, then $R^6$ or $R^{6a}$ is not $NH_2$ or —OH.

In a further preferred embodiment of the present invention,

X is —$NR^{10A}$—, —C(=O)NH—, or —NHC(=O)—;

$R^1$ is selected from
H,
C(=O)$R^2$,
C(=O)O$R^2$,
$C_{1-8}$ alkyl,
$C_{2-8}$ alkenyl,
$C_{2-8}$ alkynyl,
$C_{3-7}$ cycloalkyl,
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$,
aryl substituted with 0–2 $R^2$, and
5–6 membered heterocyclic ring system containing at least one heteroatom selected from the group consisting of N, O, and S, said heterocyclic ring system substituted with 0–2 $R^2$;

$R^2$, at each occurrence, is independently selected from
F, Cl, $CH_2F$, $CHF_2$, $CF_3$,
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^5$ is H, methyl, ethyl, propyl, or butyl;

$R^{6a}$ is selected from
H, —OH, —$NR^{46}R^{47}$, —$CF_3$,
$C_{1-4}$ alkyl, $C_{1-4}$ alkoxy, $C_{1-4}$ haloalkyl, and
aryl substituted with 0–3 $R^{44}$;

$R^{6b}$ is H;

$R^7$ and $R^9$, at each occurrence, are independently selected from
H, halo, —$CF_3$, —$OCF_3$, —OH, —CN, —$NO_2$, —$NR^{46}R^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^8$ is selected from
H, halo, —$CF_3$, —$OCF_3$, —OH, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{10A}$ is selected from H,
$C_{1-6}$ alkyl substituted with 0–1 $R^{10B}$,
$C_{2-6}$ alkenyl substituted with 0–1 $R^{10B}$, $C_{2-6}$ alkynyl substituted with 0–1 $R^{10B}$, and $C_{1-6}$ alkoxy;

$R^{10B}$ is selected from $C_{1-4}$ alkoxy, $C_{3-6}$ cycloalkyl, $C_{3-10}$ carbocyclic residue substituted with 0–3 $R^{33}$, phenyl substituted with 0–3 $R^{33}$, and 5–6 membered heterocyclic ring system containing 1, 2, or 3 heteroatoms selected from the group consisting of N, O, and S substituted with 0–2 $R^{44}$;

$R^{11}$ is selected from

H, halo, —$CF_3$, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from

H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from

H, $C^{1-4}$ alkyl, $C_{2-4}$ alkenyl, and $C_{2-4}$ alkynyl;

$R^{16}$, at each occurrence, is independently selected from

H, OH, halo, CN, $NO_2$, $CF_3$, $SO_2R^{45}$, $NR^{46}R^{47}$, —$C(=O)H$, $C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from

H, OH, halo, $CF_3$, $SO_2R^{45}$, $NR^{46}R^{47}$, and $C_{1-4}$ alkyl;

$R^{33}$, at each occurrence, is independently selected from

H, OH, halo, CN, $NO_2$, $CF_3$, $SO_2R^{45}$, $NR^{46}R^{47}$, —$C(=O)H$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-$C(=O)$—, $C_{1-4}$ alkyl-$C(=O)NH$—, $C_{1-4}$ alkyl-$OC(=O)$—, $C_{1-4}$ alkyl-$C(=O)O$—, $C_{3-6}$ cycloalkyl-oxy-, $C_{3-6}$ cycloalkylmethyl-oxy-;

$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from

H, $CF_3$, halo, OH, $CO_2H$, $SO_2R^{45}$, $NR^{46}R^{47}$, $NO_2$, CN;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from

H, $CF_3$, halo, OH, $CO_2H$, $SO_2R^{45}$, $NR^{46}R^{47}$, $NO_2$, CN, $CH(=NH)NH_2$, $NHC(=NH)NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0, 1, or 2; and n is 1, 2, or 3.

[4] In a more preferred embodiment of the present invention,

X is —$NR^{10A}$—;

$R^1$ is selected from

H, $C(=O)R^2$, $C(=O)OR^2$, $C_{1-6}$ alkyl, $C_{2-6}$ alkenyl, $C_{2-6}$ alkynyl, $C_{3-6}$ cycloalkyl, $C_{1-4}$ alkyl substituted with 0–2 $R^2$, $C_{2-4}$ alkenyl substituted with 0–2 $R^2$, and $C_{2-4}$ alkynyl substituted with 0–2 $R^2$;

$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{42}$;
  $C_{3-10}$ carbocyclic residue substituted with 0–3 $R^{41}$, and
  5–10 membered heterocyclic ring system containing from 1–4 heteroatoms selected from the group consisting of N, O, and S substituted with 0–3 $R^{41}$;
$R^5$ is H, methyl, ethyl, propyl, or butyl;
$R^{6a}$ is selected independently from
  H, —OH, —$NR^{46}R^{47}$, —$CF_3$, $C_{1-3}$ alkyl, and $C_{1-3}$ alkoxy;
$R^{6b}$ is H;
$R^7$ and $R^9$, at each occurrence, are independently selected from
  H, halo, —$CF_3$, —$OCF_3$, —OH, —CN, —$NO_2$, —$NR^{46}R^{47}$,
  $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{3-10}$ carbocyclic residue substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $SO(O)_2R^{12}$, $S(O)NR^{12}R^{13}$, $S(O)_2NR^{12}R^{13}$, $NR^{14}S(O)R^{12}$, and $NR^{14}S(O)_2R^{12}$;
$R^8$ is selected from
  H, halo, —$CF_3$, —$OCF_3$, —OH, —CN, —$NO_2$,
  $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{2-4}$ alkenyl substituted with 0–2 $R^{11}$,
  $C_{2-4}$ alkynyl substituted with 0–1 $R^{11}$,
  $C_{3-10}$ carbocyclic residue substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;
$R^{10A}$ is selected from H,
  $C_{1-4}$ alkyl substituted with 0–1 $R^{10B}$,
  $C_{2-4}$ alkenyl substituted with 0–1 $R^{10B}$,
  $C_{2-4}$ alkynyl substituted with 0–1 $R^{10B}$, and
  $C_{1-6}$ alkoxy;
$R^{10B}$ is selected from
  $C_{1-4}$ alkoxy,
  $C_{3-6}$ cycloalkyl,
  phenyl substituted with 0–3 $R^{33}$, and
  5–6 membered heterocyclic ring system containing 1, 2, or 3 heteroatoms selected from the group consisting of N, O, and S substituted with 0–2 $R^{44}$;
$R^{11}$ is selected from
  H, halo, —$CF_3$, —CN, —$NO_2$, $C_{1-6}$ alkyl,
  $C_{2-6}$ alkenyl, $C_{2-6}$ alkynyl, $C_{1-4}$ haloalkyl, $C_{1-6}$ alkoxy, $C_{3-10}$ cycloalkyl,
  $C_{3-10}$ carbocyclic residue substituted with 0–3 $R^{33}$,
  aryl substituted with 0–5 $R^{33}$,
  5-10 membered heterocyclic ring system containing from 1–4 heteroatoms selected from the group consisting of N, O, and S substituted with 0–3 $R^{31}$;
  $OR^{12}$, $SR^{12}$, $NR^{12}R^{13}$, C(O)H, $(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;
$R^{12}$, at each occurrence, is independently selected from
  $C_{1-4}$ alkyl substituted with 0–1 $R^{12a}$,
  $C_{2-4}$ alkenyl substituted with 0–1 $R^{12a}$,
  $C_{2-4}$ alkynyl substituted with 0–1 $R^{12a}$,
  $C_{3-6}$ cycloalkyl substituted with 0–3 $R^{33}$,
  phenyl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;
$R^{12a}$, at each occurrence, is independently selected from
  phenyl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;
$R^{13}$, at each occurrence, is independently selected from
  H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —$N(R^{14})$—;
alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;
$R^{14}$, at each occurrence, is independently selected from H, methyl, ethyl, propyl, and butyl;
$R^{15}$, at each occurrence, is independently selected from
  H, $C_{1-4}$ alkyl, $C_{2-4}$ alkenyl, and $C_{2-4}$ alkynyl;
$R^{16}$, at each occurrence, is independently selected from
  H, OH, F, Cl, CN, $NO_2$, $CF_3$, $SO_2R^{45}$, $NR^{46}R^{47}$, —C(=O)H,
  methyl, ethyl, methoxy, ethoxy, trifluoromethyl, and trifluoromethoxy;
$R^{31}$, at each occurrence, is independently selected from
  H, OH, halo, $CF_3$, $SO_2R^{45}$, $NR^{46}R^{47}$, and $C_{1-4}$ alkyl;
$R^{33}$, at each occurrence, is independently selected from
  H, OH, halo, CN, $NO_2$, $CF_3$, $SO_2R^{45}$, $NR^{46}R^{47}$, —C(=O)H,
  $C_{1-6}$ alkyl, $C_{2-6}$ alkenyl, $C_{2-6}$ alkynyl,
  $C_{3-6}$ cycloalkyl, $C_{1-4}$ haloalkyl, $C_{1-4}$ haloalkyl-oxy-,
  $C_{1-4}$ alkyloxy-,
  $C_{1-4}$ alkylthio-, $C_{1-4}$ alkyl-C(=O)—, $C_{1-4}$ alkyl-C(=O)NH—,
  $C_{1-4}$ alkyl-OC(=O)—,
  $C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN,
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;
$R^{44}$, at each occurrence, is independently selected from H, halo, —OH, $NR^{46}R^{47}$, $C_2H$, $SO_2R^{45}$, —$CF_3$, —$OCF_3$, —CN, —$NO_2$, $C_{1-4}$ alkyl, and $C_{1-4}$ alkoxy;
$R^{45}$ is $C_{1-4}$ alkyl;
$R^{46}$, at each occurrence, is independently selected from H and $C_{1-4}$ alkyl;
$R^{47}$, at each occurrence, is independently selected from H and $C_{1-4}$ alkyl;
k is 1 or 2;
m is 0 or 1; and
n is 1 or 2.

[5] In an even more preferred embodiment of the present invention,
X is —NH—;
$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;
$R^{6a}$ is H, methyl, ethyl, methoxy, —OH, or —$CF_3$;
$R^{6b}$ is H;
$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
H, halo, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;
alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from
H, OH, F, Cl, CN, $NO_2$, methyl, ethyl, methoxy, ethoxy, trifluoromethyl, and trifluoromethoxy;

$R^{31}$, at each occurrence, is independently selected from
H, OH, halo, $CF_3$, methyl, ethyl, and propyl;

$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—,
$C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN,
$C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $C_2H$, $SO_2R^{45}$, —$CF_3$, —$OCF_3$, —CN, —$NO_2$,
methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from
from H, methyl, ethyl, propyl, and butyl;

k is 1;
m is 1; and
n is 1 or 2.

[6] In another even more preferred embodiment of the present invention,

X is —NH—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
H, F, Cl, Br, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O) NHR^{15}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;
alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;
$R^{14}$, at each occurrence, is independently selected from H, methyl, ethyl, propyl, and butyl;
$R^{15}$, at each occurrence, is independently selected from H, methyl, ethyl, propyl, and butyl;
$R^{16}$, at each occurrence, is independently selected from
H, OH, F, Cl, CN, $NO_2$, methyl, ethyl, methoxy, ethoxy, trifluoromethyl, and trifluoromethoxy;
$R^{31}$, at each occurrence, is independently selected from
H, OH, halo, $CF_3$, methyl, ethyl, and propyl;
$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-,
$C_{1-4}$ alkyloxy-,
$C_{1-4}$ alkylthio-, $C_{1-4}$ alkyl-C(=O)—, $C_{1-4}$ alkyl-C(=O)NH—,
$C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;
$R^{41}$, at each occurrence, is independently selected from
H, $CF_3$, halo, OH, $C_2H$, $SO_2R^{45}$, $NR^{46}R^{47}$, $NO_2$, CN,
$C_{2-4}$ alkenyl, $C_{2-4}$ alkynyl, $C_{1-3}$ alkoxy, $C_{1-3}$ haloalkyl, and $C_{1-3}$ alkyl;
$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;
$R^{43}$ is cyclopropyl, cyclobutyl, cyclopentyl, cyclohexyl, phenyl, or pyridyl, each substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$,
methyl, ethyl, propyl, butyl, methoxy, ethoxy, propoxy, and butoxy;
$R^{45}$ is methyl, ethyl, propyl, or butyl;
$R^{46}$, at each occurrence, is independently selected from H, methyl, ethyl, propyl, and butyl;
$R^{47}$, at each occurrence, is independently selected from from H, methyl, ethyl, propyl, and butyl;
k is 1;
m is 1; and
n is 1 or 2.

[7] In another even more preferred embodiment of the present invention,
X is —NH—;
$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;
$R^2$ is $C_{3-6}$ cycloalkyl;
$R^5$ is H, methyl, ethyl, or propyl;
$R^{6a}$ is H, methyl, or ethyl;
$R^{6b}$ is H;
$R^7$ and $R^9$, at each occurrence, are independently selected from
H, F, Cl, —$CH_3$, —$OCH_3$, —$CF_3$, —$OCF_3$, —CN, and —$NO_2$,
$R^8$ is selected from
methyl substituted with $R^{11}$;
ethenyl substituted with $R^{11}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;
$R^{11}$ is selected from
phenyl-substituted with 0–5 fluoro;
2-($H_3CCH_2C$(=O))-phenyl-substituted with $R^{33}$;
2-($H_3CC$(=O))-phenyl-substituted with $R^{33}$;
2-(HC(=O))-phenyl-substituted with $R^{33}$;
2-($H_3CCH$(OH))-phenyl-substituted with $R^{33}$;
2-($H_3CCH_2CH$(OH))-phenyl-substituted with $R^{33}$;
2-($HOCH_2$)-phenyl-substituted wit h $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH$(OMe))-phenyl-substituted with $R^{33}$;
2-($H_3COC$(=O))-phenyl-substituted with $R^{33}$;
2-($HOCH_2CH$=CH)-phenyl-substituted with $R^{33}$;
2-((MeOC=O)CH=CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CS$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C$(=O))-phenyl-substituted with $R^{33}$;
4-(($H_3C)_2CHC$(=O))-phenyl-substituted with $R^{33}$;
4-($H_3CCH_2C$(=O))-phenyl-substituted with $R^{33}$;
4-($H_3CC$(=O))-phenyl-substituted with $R^{33}$;

4-($H_3CCH_2CH_2CH(OH)$)-phenyl-substituted with $R^{33}$;
4-(($H_3C)_2CHCH(OH)$)-phenyl-substituted with $R^{33}$;
4-($H_3CCH_2CH(OH)$)-phenyl-substituted with $R^{33}$;
4-($H_3CCH(OH)$)-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;
$R^{12}$ is selected from
phenyl-substituted with 0–5 fluoro;
2-($H_3CCH_2C(=O)$)-phenyl-substituted with $R^{33}$;
2-($H_3CC(=O)$)-phenyl-substituted with $R^{33}$;
2-($HC(=O)$)-phenyl-substituted with $R^{33}$;
5  2-($H_3CCH(OH)$)-phenyl-substituted with $R^{33}$;
2-($H_3CCH_2CH(OH)$)-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH(OMe)$)-phenyl-substituted with $R^{33}$;
2-($H_3COC(=O)$)-phenyl-substituted with $R^{33}$;
2-($HOCH_2CH=CH$)-phenyl-substituted with $R^{33}$;
2-(($MeOC=O)CH=CH$)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(choloro)-phenyl-substituted with $R^{33}$;
3-(NC)-phenyl-substituted with $R^{33}$;
3-($H_3CO$)-phenyl-substituted with $R^{33}$;
3-(floro)-phenyl-substituted with $R^{33}$;
3-(chloro)-phenyl-substituted with $R^{33}$;
4-(NC)-phenyl-substituted with $R^{33}$;
4-(fluoro)-phenyl-substituted with $R^{33}$;
4-(choloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C(=O)$)-phenyl-substituted with $R^{33}$;
4-(($H_3C)_2CHC(=O)$)-phenyl-substituted with $R^{33}$;
4-($H_3CCH_2C(=O)$)-phenyl-substituted with $R^{33}$;
4-($H_3CC(=O)$)-phenyl-substituted with $R^{33}$;
4-($H_3CCH_2CH_2CH(OH)$)-phenyl-substituted with $R^{33}$;
4-(($H_3C)_2CHCH(OH)$)-phenyl-substituted with $R^{33}$;
4-($H_3CCH_2CH(OH)$)-phenyl-substituted with $R^{33}$;
4-($H_3CCH(OH)$)-phenyl-substituted with $R^{33}$;
4-(cyclopropyloxy)-phenyl-substituted with $R^{33}$.;
4-(cyclobutyloxy)-phenyl-substituted with $R^{33}$; and
4-(cyclopentyloxy)-phenyl-substituted with $R^{33}$;
$R^{13}$ is H, methyl, or ethyl;
alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;
$R^{15}$ is H, methyl, ethyl, propyl, or butyl;
$R^{16}$, at each occurrence, is independently selected from
H, OH, F, Cl, CN, $NO_2$, methyl, ethyl, methoxy, ethoxy, trifluoromethyl, and trifluoromethoxy;
$R^{33}$, at each occurrence, is independently selected from
H, F, Cl, —$CH_3$, —$OCH_3$, —$CF_3$, —$OCF_3$, —CN, and —$NO_2$;
k is 1;
m is 1; and
n is 1 or 2.

[8] In an even more preferred embodiment of the present invention, the compound of Formula (I) is selected from Formula (I-a):

(I-a)

wherein:
b is a single bond or a double bond;
X is —$NR^{10A}$—;
$R^1$ is selected from
hydrogen, methyl, ethyl, n-propyl, n-butyl, s-butyl,
t-butyl, n-pentyl, n-hexyl, 2-propyl, 2-butyl, 2-pentyl,
2-hexyl, 2-methylpropyl, 2-methylbutyl, 2-methylpentyl,
2-ethylbutyl, 3-methylpentyl, 3-methylbutyl,
4-methylpentyl, 2-fluoroethyl, 2,2-difluoroethyl,
2,2,2-trifluoroethyl,
2-propenyl, 2-methyl-2-propenyl, trans-2-butenyl,
3-methyl-butenyl, 3-butenyl, trans-2-pentenyl,
cis-2-pentenyl, 4-pentenyl, 4-methyl-3-pentenyl,
3,3-dichloro-2-propenyl, trans-3-phenyl-2-propenyl,
cyclopropyl, cyclobutyl, cyclopentyl, cyclohexyl,
cyclopropylmethyl, cyclobutylmethyl, cyclopentylmethyl,
cyclohexylmethyl,
benzyl, 2-methylbenzyl, 3-methylbenzyl, 4-methylbenzyl,
2,5-dimethylbenzyl, 2,4-dimethylbenzyl, 3,5-dimethylbenzyl,
2,4,6-trimethyl-benzyl, 3-methoxy-benzyl, 3,5-dimethoxybenzyl, pentafluorobenzyl, 2-phenylethyl,
1-phenyl-2-propyl, 4-phenylbutyl, 4-phenylbenzyl,
2-phenylbenzyl,
(2,3-dimethoxy-phenyl)C(=O)—, (2,5-dimethoxyphenyl)C(=O)—, (3,4-dimethoxy-phenyl)C(=O)—,
(3,5-dimethoxy-phenyl)C(=O)—, cyclopropyl-C(=O)—, isopropyl-C(=O)—, ethyl-CO$_2$—, propyl-CO$_2$—, t-butyl-CO$_2$—, 2,6-dimethoxy-benzyl, 2,4-dimethoxy-benzyl, 2,4,6-trimethoxy-benzyl, 2,3-dimethoxy-benzyl, 2,4,5-trimethoxy-benzyl, 2,3,4-trimethoxy-benzyl, 3,4-dimethoxy-benzyl, 3,4,5-trimethoxy-benzyl, (4-fluoro-phenyl)ethyl, —CH=CH$_2$, —CH$_2$—CH=CH$_2$, —CH=CH—CH$_3$, —C≡—CH, —C≡C—CH$_3$, and

—CH$_2$—C≡CH;

$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, methylC(=O)—, ethylC(=O)—, propylC(=O)—, isopropylC(=O)—, butylC(=O)—, phenylC(=O)—, methylCO$_2$—, ethylCO$_2$—, propylCO$_2$—, isopropylCO$_2$—, butylCO$_2$—, phenylCO$_2$—, dimethylamino-S(=O)—, diethylamino-S(=O)—, dipropylamino-S(=O)—, di-isopropylamino-S(=O)—, dibutylamino-S(=O)—, diphenylamino-S(=O)—, dimethylamino-SO$_2$—, diethylamino-SO$_2$—, dipropylamino-SO$_2$—, di-isopropylamino-SO$_2$—, dibutylamino-SO$_2$—, diphenylamino-SO$_2$—, dimethylamino-C(=O)—, diethylamino-C(=O)—, dipropylamino-C(=O)—, di-isopropylamino-C(=O)—, dibutylamino-C(=O)—, diphenylamino-C(=O)—, 2-chlorophenyl, 2-fluorophenyl, 2-bromophenyl, 2-cyanophenyl, 2-methylphenyl, 2-trifluoromethylphenyl, 2-methoxyphenyl, 2-trifluoromethoxyphenyl, 3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl, 4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl, 2,3-dichlorophenyl, 2,3-difluorophenyl, 2,3-dimethylphenyl, 2,3-ditrifluoromethylphenyl, 2,3-dimethoxyphenyl, 2,3-ditrifluoromethoxyphenyl, 2,4-dichlorophenyl, 2,4-difluorophenyl, 2,4-dimethylphenyl, 2,4-ditrifluoromethylphenyl, 2,4-dimethoxyphenyl, 2,4-ditrifluoromethoxyphenyl, 2,5-dichlorophenyl, 2,5-difluorophenyl, 2,5-dimethylphenyl, 2,5-ditrifluoromethylphenyl, 2,5-dimethoxyphenyl, 2,5-ditrifluoromethoxyphenyl, 2,6-dichlorophenyl, 2,6-difluorophenyl, 2,6-dimethylphenyl, 2,6-ditrifluoromethylphenyl, 2,6-dimethoxyphenyl, 2,6-ditrifluoromethoxyphenyl, 3,4-dichlorophenyl, 3,4-difluorophenyl, 3,4-dimethylphenyl, 3,4-ditrifluoromethylphenyl, 3,4-dimethoxyphenyl, 3,4-ditrifluoromethoxyphenyl, 2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl, 2-chloro-4-CF$_3$-phenyl, 2-fluoro-3-chloro-phenyl, 2-chloro-4-CF$_3$-phenyl, 2-chloro-4-methoxy-phenyl, 2-methoxy-4-isopropyl-phenyl, 2-CF$_3$-4-methoxy-phenyl, 2-methyl-4-methoxy-5-fluoro-phenyl, 2-methyl-4-methoxy-phenyl, 2-chloro-4-CF$_3$O-phenyl, 2,4,5-trimethyl-phenyl, 2-methyl-4-chloro-phenyl, methyl-C(=O)NH—, ethyl-C(=O)NH—, propyl-C(=O)NH—, isopropyl-C(=O)NH—, butyl-C(=O)NH—, phenyl-C(=O)NH—,.

4-acetylphenyl, 3-acetamidophenyl, 4-pyridyl, 2-furanyl, 2-thiophenyl, 2-naphthyl;

2-Me-5-F-phenyl, 2-F-5-Me-phenyl, 2-MeO-5-F-phenyl,

2-Me-3-Cl-phenyl, 3-NO$_2$-phenyl, 2-NO$_2$-phenyl,

2-Cl-3-Me-phenyl, 2-Me-4-EtO-phenyl, 2-Me-4-F-phenyl,

2-Cl-6-F-phenyl, 2-Cl-4-(CHF$_2$)O-phenyl, 2,4-diMeO-6-F-phenyl, 2-CF$_3$-6-F-phenyl, 2-MeS-phenyl, 2,6-diCl-4-MeO-phenyl, 2,3,4-triF-phenyl, 2,6-diF-4-Cl-phenyl, 2,3,4,6-tetraF-phenyl, 2,3,4,5,6-pentaF-phenyl, 2-CF$_3$-4-EtO-phenyl, 2-CF$_3$-4-iPrO-phenyl, 2-CF$_3$-4-Cl-phenyl, 2-CF$_3$-4-F-phenyl, 2-Cl-4-EtO-phenyl, 2-Cl-4-iPrO-phenyl, 2-Et-4-MeO-phenyl, 2-CHO-4-MeO-phenyl, 2-CH(OH)Me-4-MeO-phenyl, 2-CH(OMe)Me-4-MeO-phenyl, 2-C(=O)Me-4-MeO-phenyl, 2-CH$_2$(OH)-4-MeO-phenyl, 2-CH$_2$(OMe)-4-MeO-phenyl, 2-CH(OH)Et-4-MeO-phenyl, 2-C(=O)Et-4-MeO-phenyl, (Z)-2-CH=CHC$_2$Me-4-MeO-phenyl, 2-CH$_2$CH$_2$CO$_2$Me-4-MeO-phenyl, (Z)-2-CH=CHCH$_2$(OH)-4-MeO-phenyl, (E)-2-CH=CHC$_2$Me-4-MeO-phenyl, (E)-2-CH=CHCH$_2$ (OH)-4-MeO-phenyl, 2-CH2CH$_2$OMe-4-MeO-phenyl, 2-F-4-MeO-phenyl, 2-Cl-4-F-phenyl, (2-Cl-phenyl)-CH=CH—, (3-Cl-phenyl)-CH=CH—, (2,6-diF-phenyl)-CH=CH—, —CH$_2$CH=CH$_2$, phenyl-CH=CH—, (2-Me-4-MeO-phenyl)-CH=CH—, cyclohexyl, cyclopentyl, cyclohexylmethyl, —CH$_2$CH$_2$CO$_2$Et, —(CH$_2$)$_3$CO$_2$Et, —(CH$_2$)$_4$CO$_2$Et, benzyl, 2-F-benzyl, 3-F-benzyl, 4-F-benzyl, 3-MeO-benzyl, 3-OH-benzyl, 2-MeO-benzyl, 2-OH-benzyl, 2-CO$_2$Me-3-MeO-phenyl,
2-Me-4-CN-phenyl, 2-Me-3-CN-phenyl, 2-CF$_3$-4-CN-phenyl,
3-CHO-phenyl, 3-CH$_2$(OH)-phenyl, 3-CH$_2$(OMe)-phenyl,
3-CH$_2$(NMe$_2$)-phenyl, 3-CN-4-F-phenyl,
3-CONH$_2$-4-F-phenyl, 2-CH$_2$(NH$_2$)-4-MeO-phenyl-,
phenyl-NH—, (4-F-phenyl)-NH—, (2,4-diCl-phenyl)-NH—,
phenyl-C(=O)NH—, benzyl-NH—, (2-Me-4-MeO-phenyl)-NH—,
(2-F-4-MeO-phenyl)-NH—, (2-Me-4-F-phenyl)-NH—,
phenyl-S—, —NMe$_2$, 1-pyrrolidinyl, and
—N(tosylate)$_2$,
provided that two of R$^7$, R$^8$, and R$^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;
R$^{10A}$ is selected from hydrogen, methyl, ethyl, benzyl and 4-fluorobenzyl;
m is 1; and
n is 1 or 2.

[9] In an even more preferred embodiment of the present invention, the compound of Formula (I) is selected from Formula (IV):

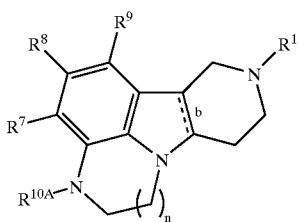

(IV)

wherein:
b is a single bond, wherein the bridge hydrogens are in a cis position;
R$^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, —CH=CH$_2$, —CH$_2$—CH=CH$_2$, —CH=CH—CH$_3$, —C≡CH, —C≡C—CH$_3$,
and —CH$_2$—C≡H;
R$^7$ and R$^9$, at each occurrence, are independently selected from hydrogen, fluoro, methyl, trifluoromethyl, and methoxy;
R$^8$ is selected from
hydrogen, fluoro, chloro, bromo, cyano, methyl, ethyl, propyl, isopropyl, butyl, t-butyl, nitro,
trifluoromethyl, methoxy, ethoxy, isopropoxy, trifluoromethoxy, phenyl,
methylC(=O)—, ethylC(=O)—, propylC(=O)—, isopropylC(=O)—,
butylC(=O)—, phenylC(=O)—,
methylCO$_2$—, ethylCO$_2$—, propylCO$_2$—, isopropylCO$_2$—,
butylCO$_2$—, phenylCO$_2$—,
dimethylamino-S(=O)—, diethylamino-S(=O)—,
dipropylamino-S(=O)—, di-isopropylamino-S(=O)—,
dibutylamino-S(=O)—, diphenylamino-S(=O)—,
dimethylamino-SO$_2$—, diethylamino-SO$_2$—,
dipropylamino-SO$_2$—di-isopropylamino-SO$_2$—,
dibutylamino-SO$_2$—,
diphenylamino-SO$_2$—,
dimethylamino-C(=O)—, diethylamino-C(=O)—,
dipropylamino-C(=O)—, di-isopropylamino-C(=O)—,
dibutylamino-C(=O)—, diphenylamino-C(=O)—,
2-chlorophenyl, 2-fluorophenyl, 2-bromophenyl, 2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl,
4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl,
2,3-dichlorophenyl, 2,3-difluorophenyl, 2,3-dimethylphenyl,
2,3-ditrifluoromethylphenyl, 2,3-dimethoxyphenyl, 2,3-ditrifluoromethoxyphenyl,
2,4-dichlorophenyl, 2,4-difluorophenyl, 2,4-dimethylphenyl,
2,4-ditrifluoromethylphenyl, 2,4-dimethoxyphenyl, 2,4-ditrifluoromethoxyphenyl,
2,5-dichlorophenyl, 2,5-difluorophenyl, 2,5-dimethylphenyl,
2,5-ditrifluoromethylphenyl, 2,5-dimethoxyphenyl, 2,5-ditrifluoromethoxyphenyl,
2,6-dichlorophenyl, 2,6-difluorophenyl, 2,6-dimethylphenyl,
2,6-ditrifluoromethylphenyl, 2,6-dimethoxyphenyl, 2,6-ditrifluoromethoxyphenyl,
3,4-dichlorophenyl, 3,4-difluorophenyl, 3,4-dimethylphenyl,
3,4-ditrifluoromethylphenyl, 3,4-dimethoxyphenyl, 3,4-ditrifluoromethoxyphenyl,
2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl,
2-chloro-4-CF$_3$-phenyl, 2-fluoro-3-chloro-phenyl, 2-chloro-4-CF$_3$-phenyl, 2-chloro-4-methoxy-phenyl,
2-methoxy-4-isopropyl-phenyl, 2-CF$_3$-4-methoxy-phenyl,
2-methyl-4-methoxy-5-fluoro-phenyl,
2-methyl-4-methoxy-phenyl, 2-chloro-4-CF$_3$O-phenyl,
2,4,5-trimethyl-phenyl, 2-methyl-4-chloro-phenyl,
methyl-C(=O)NH—, ethyl-C(=O)NH—, propyl-C(=O)NH—, isopropyl-C(=O)NH—, butyl-C(=O)NH—, phenyl-C(=O)NH—,
4-acetylphenyl, 3-acetamidophenyl, 4-pyridyl, 2-furanyl, 2-thiophenyl, 2-naphthyl;
2-Me-5-F-phenyl, 2-F-5-Me-phenyl, 2-MeO-5-F-phenyl, 2-Me-3-Cl-phenyl, 3-NO$_2$-phenyl, 2-NO$_2$-phenyl,
2-Cl-3-Me-phenyl, 2-Me-4-EtO-phenyl, 2-Me-4-F-phenyl,
2-Cl-6-F-phenyl, 2-Cl-4-(CHF$_2$)0-phenyl,
2,4-diMeo-6-F-phenyl, 2-CF$_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF$_3$-4-EtO-phenyl, 2-CF$_3$-4-iPrO-phenyl,
2-CF$_3$-4-Cl-phenyl, 2-CF$_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH(OH)Me-4-MeO-phenyl,
2-CH(OMe)Me-4-MeO-phenyl, 2-C(=O)Me-4-MeO-phenyl,
2-CH$_2$(OH)-4-MeO-phenyl, 2-CH$_2$(OMe)-4-MeO-phenyl,
2-CH(OH)Et-4-MeO-phenyl, 2-C(=O)Et-4-MeO-phenyl,
(Z)-2-CH=CHCO$_2$Me-4-MeO-phenyl,
2-CH$_2$CH$_2$CO$_2$Me-4-MeO-phenyl,
(Z)-2-CH=CHCH$_2$(OH)-4-MeO-phenyl,
(E)-2-CH=CHCO$_2$Me-4-MeO-phenyl,
(E)-2-CH=CHCH$_2$(OH)-4-MeO-phenyl,
2-CH$_2$CH$_2$OMe-4-MeO-phenyl,
2-F-4-MeO-phenyl, 2-Cl-4-F-phenyl,
(2-Cl-phenyl)-CH=CH—, (3-Cl-phenyl)-CH=CH—,
(2,6-diF-phenyl)-CH=CH—, —CH$_2$CH=CH$_2$,
phenyl-CH=CH—, (2-Me-4-MeO-phenyl)-CH=CH—,
cyclohexyl, cyclopentyl, cyclohexylmethyl,
—CH$_2$CH$_2$CO$_2$Et, —(CH$_2$)$_3$CO$_2$Et, —(CH$_2$)$_4$CO$_2$Et,
benzyl, 2-F-benzyl, 3-F-benzyl, 4-F-benzyl,
3-MeO-benzyl, 3-OH-benzyl, 2-MeO-benzyl,
2-OH-benzyl, 2-CO$_2$Me-3-MeO-phenyl,
2-Me-4-CN-phenyl, 2-Me-3-CN-phenyl, 2-CF$_3$-4-CN-phenyl,
3-CHO-phenyl, 3-CH$_2$(OH)-phenyl, 3-CH$_2$(OMe)-phenyl,
3-CH$_2$(NMe$_2$)-phenyl, 3-CN-4-F-phenyl,
3-CONH$_2$-4-F-phenyl, 2-CH$_2$(NH$_2$)-4-MeO-phenyl—,
phenyl-NH—, (4-F-phenyl)-NH—, (2,4-diCl-phenyl)-NH—,
phenyl-C(=O)NH—, benzyl-NH—, (2-Me-4-MeO-phenyl)-NH—,
(2-F-4-MeO-phenyl)-NH—, (2-Me-4-F-phenyl)-NH—, phenyl-S—, —NMe$_2$, 1-pyrrolidinyl, and —N(tosylate)$_2$;
R$^{10A}$ is selected from hydrogen, methyl, ethyl, 4-fluorobenzyl and benzyl; and p0 n is 1 or 2.

[10] In another preferred embodiment of the present invention,
X is —NR$^{10A}$—, —C(=O)NR$^{10A}$—, or —NR$^{10A}$C(=O)—;
R$^1$ is selected from
  C$_{1-6}$ alkyl substituted with Z,
  C$_{2-6}$ alkenyl substituted with Z,
  C$_{2-6}$ alkynyl substituted with Z,
  C$_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  C$_{1-6}$ alkyl substituted with 0–2 R$^2$,
  C$_{2-6}$ alkenyl substituted with 0–2 R$^2$,
  C$_{2-6}$ alkynyl substituted with 0–2 R$^2$,
  aryl substituted with 0–2 R$^2$, and
  5–6 membered heterocyclic ring system containing at least one heteroatom selected from the group consisting of N, O, and S, said heterocyclic ring system substituted with 0–2 R$^2$;
Z is selected from H,
  —CH(OH)R$^2$,
  —C(ethylenedioxy)R$^2$,
  —OR$^2$,
  —SR$^2$,
  —NR$^2$R$^3$,
  —C(O)R$^2$,
  —C(O)NR$^2$R$^3$,
  —NR3C(O)R$^2$,
  —C(O)OR$^2$,
  —OC(O)R$^2$,
  —CH(=NR$^4$)NR$^2$R$^3$,
  —NHC(=NR$^4$)NR$^2$R$^3$,
  —S(O)R$^2$,
  —S(O)$_2$R$^2$,
  —S(O)$_2$NR$^2$R$^3$, and —NR$^3$S(O)$_2$R$^2$;
R$^2$, at each occurrence, is independently selected from
  —C$_{1-4}$ alkyl,
  C$_{2-4}$ alkenyl,
  C$_{2-4}$ alkynyl,
  C$_{3-6}$ cycloalkyl,
  aryl substituted with 0–5 R$^{42}$;
  C$_{3-10}$ carbocyclic residue substituted with 0–3 R$^{41}$, and
  5–10 membered heterocyclic ring system containing from 1–4 heteroatoms selected from the group consisting of N, O, and S substituted with 0–3 R$^{41}$;
R$^3$, at each occurrence, is independently selected from
  H, C$_{1-4}$ alkyl, C$_{2-4}$ alkenyl, C$_{2-4}$ alkynyl, and
  C$_{1\ 1-4}$ alkoxy;
alternatively, R$^2$ and R$^3$ join to form a 5- or 6-membered ring optionally substituted with —O— or —N(R$^4$)—;
R$^4$, at each occurrence, is independently selected from H, methyl, ethyl, propyl, and butyl;
R$^5$ is H, methyl, ethyl, propyl, or butyl;

$R^{6a}$ is selected from
  H, —OH, —NR$^{46}$R$^{47}$, —CF$_3$,
  $C_{1-4}$ alkyl, $C_{2-4}$ alkenyl, $C_{2-4}$ alkynyl, $C_{1-4}$ alkoxy, $C_{1-4}$ haloalkyl, $C_{3-6}$ cycloalkyl, and
  aryl substituted with 0–3 R$^{44}$;
$R^{6b}$ is H;
$R^7$, $R^8$, and $R^9$, at each occurrence, are independently selected from
  H, halo, —CF$_3$, —OCF$_3$, —OH, —CN, —NO$_2$, —NR$^{46}$R$^{47}$,
  $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
  $C_{1-4}$ alkyl substituted with 0–2 R$^{11}$,
  $C_{3-10}$ carbocyclic residue substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$, S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;
$R^{10A}$ is selected from H,
  $C_{1-6}$ alkyl substituted with 0–1 R$^{10B}$,
  $C_{2-6}$ alkenyl substituted with 0–1 R$^{10B}$,
  $C_{2-6}$ alkynyl substituted with 0–1 R$^{10B}$, and
  $C_{1-6}$ alkoxy;
$R^{10B}$ is selected from
  $C_{1-4}$ alkoxy,
  $C_{3-6}$ cycloalkyl,
  $C_{3-10}$ carbocyclic residue substituted with 0–3 R$^{33}$,
  phenyl substituted with 0–3 R$^{33}$, and
  5–6 membered heterocyclic ring system containing 1, 2, or 3 heteroatoms selected from the group consisting of N, O, and S substituted with 0–2 R$^{44}$;
$R^{11}$ is selected from
  H, halo, —CF$_3$, —CN, —NO$_2$,
  $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
  $C_{3-10}$ carbocyclic residue substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, CO)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S()$_2$NR$^{12}$R$^{13}$, NR$^{14}$S(O)R$^{12}$, and NR$^{14}$S(O)$_2$R$^{12}$;
$R^{12}$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 R$^{33}$;
  $C_{3-10}$ carbocyclic residue substituted with 0–3 R$^{33}$, and
  5–10 membered heterocyclic ring system containing from 1–4 heteroatoms selected from the group consisting of N, O, and S substituted with 0–3 R$^{31}$;
$R^{13}$, at each occurrence, is independently selected from
  H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N(R$^{14}$)—;
$R^{14}$, at each occurrence, is independently selected from H and $C_{1-4}$ alkyl;
$R^{31}$, at each occurrence, is independently selected from
  H, OH, halo, CF$_3$, SO$_2$R$^{45}$, NR$^{46}$R$^{47}$, methyl, ethyl, and propyl;
$R^{33}$, at each occurrence, is independently selected from
  H, OH, halo, CN, NO$_2$, CF$_3$, SO$_2$R$^{45}$, NR$^{46}$R$^{47}$,
  $C_{1-3}$ alkyl, $C_{2-3}$ alkenyl, $C_{2-3}$ alkynyl, $C_{3-5}$ cycloalkyl, $C_{1-3}$ haloalkyl, $C_{1-3}$ haloalkyl-oxy, $C_{1-3}$ alkyloxy-, $C_{1-3}$ alkylthio-, $C_{1-3}$ alkyl-C(=O)—, and $C_{1-3}$ alkyl-C(=O)NH—;
$R^{41}$, at each occurrence, is independently selected from
  H, CF$_3$, halo, OH, CO$_2$H, SO$_2$R$^{45}$, NR$^{46}$R$^{47}$, NO$_2$, CN, =O,
  $C_{2-8}$ alkenyl, $C_{2-8}$ alkynyl, $C_{1-4}$ alkoxy, $C_{1-4}$ haloalkyl
  $C_{1-4}$ alkyl substituted with 0–1 R$^{43}$,
  aryl substituted with 0–3 R$^{42}$, and
  5–10 membered heterocyclic ring system containing from 1–4 heteroatoms selected from the group consisting of N, O, and S substituted with 0–3 R$^{44}$;
$R^{42}$, at each occurrence, is independently selected from
  H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
  $C_{2-6}$ alkenyl, $C_{2-6}$ alkynyl, $C_{1-4}$ alkoxy, $C_{1-4}$ haloalkyl, $C_{3-6}$ cycloalkyl,
  $C_{1-4}$ alkyl substituted with 0–1 R$^{43}$,
  aryl substituted with 0–3 R$^{44}$, and
  5–10 membered heterocyclic ring system containing from 1–4 heteroatoms selected from the group consisting of N, O, and S substituted with 0–3 R$^{44}$;
$R^{43}$ is $C_{3-6}$ cycloalkyl or aryl substituted with 0–3 R$^{44}$;
$R^{44}$, at each occurrence, is independently selected from H, halo, —OH, NR$^{46}$R$^{47}$, C$_2$H, SO$_2$R$^{45}$, —CF$_3$, —OCF$_3$, —CN, —NO$_2$,
  $C_{1-4}$ alkyl, and $C_{1-4}$ alkoxy;
$R^{45}$ is $C_{1-4}$ alkyl;
$R^{46}$, at each occurrence, is independently selected from H and $C_{1-4}$ alkyl;
$R^{47}$, at each occurrence, is independently selected from H, $C_{1-4}$ alkyl, —C(=O)NH($C_{1-4}$ alkyl), —SO$_2$($C_{1-4}$ alkyl), —SO2(phenyl), —C(=O)O($C_{1-4}$ alkyl), —C(=O)($C_{1-4}$ alkyl),
  and —C(=O)H;
$R^{48}$, at each occurrence, is independently selected from H, $C_{1-4}$ alkyl, —C(=O)NH($C_{1-4}$ alkyl), —C(=O)O($C_{1-4}$ alkyl),
  —C(=O)($C_{1-4}$ alkyl), and —C(=O)H;
k is 1 or 2;
m is 0, 1, or 2; and
n is 1 or 2.
[11] In a further preferred embodiment of the present invention,
X is —NR$^{10A}$—;
$R^1$ is selected from
  $C_{2-5}$ alkyl substituted with Z,
  $C_{2-5}$ alkenyl substituted with Z,
  $C_{2-5}$ alkynyl substituted with Z,
  $C_{3-6}$ cycloalkyl substituted with Z, aryl substituted with Z, 5–6 membered heterocyclic ring system containing at least one heteroatom selected from the group consisting of N, O, and S, said heterocyclic ring system substituted with Z;

$C_{1-5}$ alkyl substituted with 0–2 $R^2$, $C_{2-5}$ alkenyl substituted with 0–2 $R^2$, and $C_{2-5}$ alkynyl substituted with 0–2 $R^2$;

Z is selected from H,
CH(OH)$R^2$,
—C(ethylenedioxy)$R^2$,
—O$R^2$,
—S$R^2$,
—N$R^2R^3$,
—C(O)$R^2$,
—C(O)N$R^2R^3$,
—N$R^3$C(O)$R^2$,
—C(O)O$R^2$,
—OC(O)$R^2$,
—CH(=N$R^4$)N$R^2R^3$,
—NHC(=N$R^4$)N$R^2R^3$,
—S(O)$R^2$,
—S(O)$_2R^2$,
—S(O)$_2$N$R^2R^3$, and —N$R^3$S(O)$_2R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
aryl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from
H, $C_{1-4}$ alkyl, $C_{2-4}$ alkenyl, $C_{2-4}$ alkynyl, and
$C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H, methyl, ethyl, propyl, and butyl;

$R^5$ is H, methyl, or ethyl;

$R^{6a}$ is selected from
H, —OH, —N$R^{46}R^{47}$, —CF$_3$,
$C_{1-4}$ alkyl, $C_{2-4}$ alkenyl, $C_{2-4}$ alkynyl, $C_{1-4}$ alkoxy, $C_{1-4}$ haloalkyl, and $C_{3-6}$ cycloalkyl;

$R^{6b}$ is H;

$R^7$, $R^8$, and $R^9$, at each occurrence, are independently selected from
H, halo, —CF$_3$, —OCF$_3$, —OH, —OCH$_3$, —CN, —NO$_2$, —N$R^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$ C(O)N$R^{12}R^{13}$, N$R^{14}$C(O)$R^{12}$, C(O)O$R^{12}$, OC(O)$R^{12}$, CH(=N$R^{14}$) N$R^{12}R^{13}$, NHC(=N$R^{14}$)N$R^{12}R^{13}$, S(O)$R^{12}$, S(O)$_2R^{12}$, S(O)$_2$N$R^{12}R^{13}$, N$R^{14}$S(O)$_2R^{12}$, N$R^{14}$S(O)$R^{12}$, N$R^{14}$S (O)$_2R^{12}$, N$R^{12}$C(O)$R^{15}$, N$R^{12}$C(O)O$R^{15}$, N$R^{12}$S(O) $_2R^{15}$, and N$R^{12}$C(O)NHR$^{15}$;

$R^{10A}$ is selected from H,
$C_{1-6}$ alkyl substituted with 0–1 $R^{10B}$,
$C_{2-6}$ alkenyl substituted with 0–1 $R^{10B}$,
$C_{2-6}$ alkynyl substituted with 0–1 $R^{10B}$, and
$C_{1-6}$ alkoxy;

$R^{10B}$ is selected from
$C_{1-4}$ alkoxy,
$C_{3-6}$ cycloalkyl,
$C_{3-6}$ carbocyclic residue substituted with 0–3 $R^{33}$,
phenyl substituted with 0–3 $R^{33}$, and
5–6 membered heterocyclic ring system containing 1, 2, or 3 heteroatoms selected from the group consisting of N, O, and S substituted with 0–2 $R^{44}$;

$R^{11}$ is selected from
H, halo, —CF$_3$, —OCF$_3$, —OH, —OCH$_3$, —CN, —NO$_2$, —N$R^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, N$R^{12}R^{13}$, C(O)H, C(O)$R^{12}$ C(O)N$R^{12}R^{13}$, N$R^{14}$C(O)$R^{12}$, C(O)O$R^{12}$, OC(O)$R^{12}$, CH(=N$R^{14}$) N$R^{12}R^{13}$, NHC(=N$R^{14}$)N$R^{12}R^{13}$, S(O)$R^{12}$, S(O)$_2R^{12}$, S(O)$_2$N$R^{12}R^{13}$, and N$R^{14}$S(O)$_2R^{12}$;

$R^{12}$ at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

$R^{14}$, at each occurrence, is independently selected from H and $C_{1-4}$ alkyl;

$R^{31}$, at each occurrence, is independently selected from
H, OH, halo, CF$_3$, methyl, and ethyl;

$R^{33}$, at each occurrence, is independently selected from
H, OH, halo, CN, NO$_2$, CF$_3$, methyl, and ethyl;

$R^{41}$, at each occurrence, is independently selected from
H, CF$_3$, halo, OH, CO$_2$H, SO$_2R^{45}$, N$R^{46}R^{47}$, NO$_2$, CN, =O,
$C_{2-8}$ alkenyl, $C_{2-8}$ alkynyl, $C_{1-4}$ alkoxy, $C_{1-4}$ haloalkyl,
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $C_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-3}$ alkyl;

$R^{47}$, at each occurrence, is independently selected from H, $C_{1-4}$ alkyl, —C(=O)NH($C_{1-4}$ alkyl), —$SO_2$($C_{1-4}$ alkyl), —SO2(phenyl), —C(=O)O($C_{1-4}$ alkyl), —C(=O)( $C_{1-4}$ alkyl)
and —C(=O)H;

$R^{48}$, at each occurrence, is independently selected from H, $C_{1-4}$ alkyl, —C(=O)NH($C_{1-4}$ alkyl), —C(=O)O($C_{1-4}$ alkyl),
—C(=O)( $C_{1-4}$ alkyl), and —C(=O)H;

k is 1 or 2;
m is 0, 1, 2; and
n is 1 or 2.

[12] In more preferred embodiment of the present invention,
X is —$NR^{10A}$—;
$R^1$ is selected from
$C_{2-4}$ alkyl substituted with Z,
$C_{2-4}$ alkenyl substituted with Z,
$C_{2-4}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{2-4}$ alkyl substituted with 0–2 $R^2$, and
$C_{2-4}$ alkenyl substituted with 0–2 $R^2$;

Z is selected from H,
—CH(OH)$R^2$,
—C(ethylenedioxy)$R^2$,
—$OR^2$,
—$SR^2$,
—$NR^2R^3$,
—C(O)$R^2$,
—C(O)$NR^2R^3$,
—$NR^3C(O)R^2$,
—C(O)$OR^2$,
—S(O)$R^2$,
—S(O)$_2R^2$,
—S(O)$_2NR^2R^3$, and —$NR^3S(O)_2R^2$;

$R^2$, at each occurrence, is independently selected from
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from
H, $C_{1-4}$ alkyl, $C_{2-4}$ alkenyl, $C_{2-4}$ alkynyl, and $C_{1-4}$ alkoxy;
alternatively, $R^2$ and $R^3$ join to form a 5- or 6-membered ring optionally substituted with —O——or —N($R^4$)—;

$R^4$, at each occurrence, is independently selected from H, methyl, ethyl, propyl, and butyl;

$R^5$ is H;

$R^{6a}$ is selected from H, —OH, —$CF_3$, methyl, ethyl, propyl, butyl, methoxy, and, ethoxy;

$R^{6b}$ is H;

$R^7$, $R^8$, and $R^9$, at each occurrence, are independently selected from
H, halo, —$CF_3$, —$OCF_3$, —OH, —$OCH_3$, —CN, —$NO_2$, $C_{1-4}$ alkyl, $C_{1-4}$ haloalkyl, $C_{1-4}$ alkoxy, ($C_{1-3}$ haloalkyl)oxy, and
$C_{1-4}$ alkyl substituted with 0–2 $R^{11}$;

$R^{10A}$ is selected from H, $C_{1-6}$ alkyl, $C_{1-4}$ alkoxy, and $C_{1-2}$ alkyl substituted with 0–1 $R^{10B}$;

$R^{10B}$ is $C_{3-6}$ cycloalkyl or
phenyl substituted with 0–3 $R^{33}$;

$R^{11}$ is selected from
H, halo, —$CF_3$, —$OCF_3$, —OH, —$OCH_3$, —CN, —$NO_2$, $C_{1-4}$ alkyl, $C_{1-4}$ haloalkyl, $C_{1-4}$ alkoxy, and ($C_{1-3}$ haloalkyl)oxy;

$R^{33}$, at each occurrence, is independently selected from
H, OH, halo, $CF_3$, and methyl;

$R^{41}$, at each occurrence, is independently selected from
H, $CF_3$, halo, OH, $CO_2H$, $SO_2R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$ haloalkyl,
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $C_2H$, $SO_2R^{45}$, $SR^{45}$, $NR^{46}R^{47}$, $OR^{48}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$,
methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from
H, methyl, ethyl, n-propyl, 1-propyl, n-butyl, i-butyl, —C(=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O) (methyl),
—C(=O)(ethyl), and —C(=O)H;
$R^{48}$, at each occurrence, is independently selected from
H, methyl, ethyl, n-propyl, i-propyl, —C(=O)NH (methyl), —C(=O)NH(ethyl), —C(=O)O(methyl), —C(=O)O(ethyl), —C(=O)(methyl), —C(=O)(ethyl), and —C(=O)H;
k is 1;
m is 0, 1, or 2; and
n is 1 or 2.

[13] In an even more preferred embodiment of the present invention,
X is —NH—;
$R^1$ is selected from
ethyl substituted with Z,
propyl substituted with Z,
butyl substituted with Z,
propenyl substituted with Z,
butenyl substituted with Z,
ethyl substituted with $R^2$,
propyl substituted with $R^2$,
butyl substituted with $R^2$,
propenyl substituted with $R^2$, and
butenyl substituted with $R^2$;
Z is selected from H,
—CH(OH)$R^2$,
—O$R^2$,
—S$R^2$,
—N$R^2R^3$,
—C(O)$R^2$,
—C(O)N$R^2R^3$,
—N$R^3$C(O)$R^2$,
—C(O)O$R^2$,
—S(O)$R^2$,
—S(O)$_2R^2$,
—S(O)$_2$N$R^2R^3$, and —N$R^3$S(O)$_2R^2$;
$R^2$, at each occurrence, is independently selected from
phenyl substituted with 0–3 $R^{42}$;
naphthyl substituted with 0–3 $R^{42}$;
cyclopropyl substituted with 0–3 $R^{41}$;
cyclobutyl substituted with 0–3 $R^{41}$;
cyclopentyl substituted with 0–3 $R^{41}$;
cyclohexyl substituted with 0–3 $R^{41}$;
pyridyl substituted with 0–3 $R^{41}$;
indolyl substituted with 0–3 $R^{41}$;
indolinyl substituted with 0–3 $R^{41}$;
benzimidazolyl substituted with 0–3 $R^{41}$;
benzotriazolyl substituted with 0–3 $R^{41}$;
benzothienyl substituted with 0–3 $R^{41}$;
benzofuranyl substituted with 0–3 $R^{41}$;
phthalimid-1-yl substituted with 0–3 $R^{41}$;
inden-2-yl substituted with 0–3 $R^{41}$;
2,3-dihydro-1H-inden-2-yl substituted with 0–3 $R^{41}$;
indazolyl substituted with 0–3 $R^{41}$;
tetrahydroquinolinyl substituted with 0–3 $R^{41}$; and
tetrahydro-isoquinolinyl substituted with 0–3 $R^{41}$;
$R^3$, at each occurrence, is independently selected from
H, methyl, and ethyl;

$R^5$ is H;
$R^{6a}$ is selected from H, —OH, methyl, and methoxy;
$R^{6b}$ is H;
$R^7$, $R^8$, and $R^9$, at each occurrence, are independently selected from H, F, Cl, methyl, ethyl, methoxy, —CF$_3$, and —OCF$_3$;
$R^{41}$, at each occurrence, is independently selected from
H, F, Cl, Br, OH, CF$_3$, NO$_2$, CN, =O, methyl, ethyl, propyl, butyl, methoxy, and ethoxy;
$R^{42}$, at each occurrence, is independently selected from
H, F, Cl, Br, OH, CF$_3$, SO$_2R^{45}$, S$R^{45}$, N$R^{46}R^{47}$, O$R^{48}$, NO$_2$, CN, =O, methyl, ethyl, propyl, butyl, methoxy, and ethoxy;
$R^{45}$ is methyl, ethyl, propyl, or butyl;
$R^{46}$, at each occurrence, is independently selected from H, methyl, ethyl, propyl, and butyl;
$R^{47}$, at each occurrence, is independently selected from
H, methyl, ethyl, n-propyl, i-propyl, n-butyl, i-butyl, —C(=O)NH(methyl), —C(=O)NH(ethyl), —SO$_2$(methyl), —SO$_2$(ethyl), —SO$_2$(phenyl), —C(=O)O(methyl),—C(=O)O(ethyl), —C(=O) (methyl),
—C(=O)(ethyl), and —C(=O)H;
$R^{48}$, at each occurrence, is independently selected from
H, methyl, ethyl, n-propyl, i-propyl, —C(=O)NH (methyl), —C(=O)NH(ethyl), —C(=O)O(methyl), —C(=O)O(ethyl), —C(=O)(methyl), —C(=O) (ethyl), and —C(=O)H;
k is 1;
m is 0, 1, or 2; and
n is 1 or 2.

[14] In another even more preferred embodiment of the present invention, the compound of Formula (I) is selected from Formula (I-a):

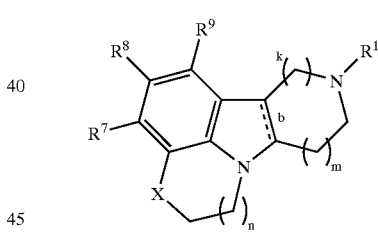

(I-a)

wherein:
b is a single bond or a double bond;
X is —N$R^{10A}$—;
$R^1$ is selected from
—(CH$_2$)$_3$C(=O)(4-fluoro-phenyl),
—(CH$_2$)$_3$C(=O)(4-bromo-phenyl),
—(CH$_2$)$_3$C(=O)(4-methyl-phenyl),
—(CH$_2$)$_3$C(=O)(4-methoxy-phenyl),
—(CH$_2$)$_3$C(=O)(4-(3,4-dichloro-phenyl)phenyl),
—(CH$_2$)$_3$C(=O)(3-methyl-4-fluoro-phenyl),
—(CH$_2$)$_3$C(=O)(2,3-dimethoxy-phenyl),
—(CH$_2$)$_3$C(=O)(phenyl),
—(CH$_2$)$_3$C(=O)(4-chloro-phenyl),
—(CH$_2$)$_3$C(=O)(3-methyl-phenyl),
—(CH$_2$)$_3$C(=O)(4-t-butyl-phenyl),
—(CH$_2$)$_3$C(=O)(3,4-difluoro-phenyl),
—(CH$_2$)$_3$C(=O)(2-methoxy-5-fluoro-phenyl),
—(CH$_2$)$_3$C(=O)(4-fluoro-1-naphthyl),
—(CH$_2$)$_3$C(=O)(benzyl), —(CH$_2$)$_3$ C(=O)(4-pyridyl),
—(CH$_2$)$_3$C(=O)(3-pyridyl),
—(CH$_2$)$_3$CH(OH)(4-fluoro-phenyl),
—(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O)(4-fluoro-phenyl),
—(CH$_2$)$_3$ SO$_2$(3-fluoro-phenyl),
—(CH$_2$)$_3$ SO$_2$(4-fluoro-phenyl),
—(CH$_2$)$_3$O(4-fluoro-phenyl),
—(CH$_2$)$_3$O(phenyl),
—(CH$_2$)$_3$O(3-pyridyl),
—(CH$_2$)$_3$O(4-pyridyl),
—(CH$_2$)$_3$O(2-NH$_2$-phenyl),
—(CH$_2$)$_3$O(2-NH$_2$-5-F-phenyl),
—(CH$_2$)$_3$O($^2$-NH$_2$-4-F-phenyl),
—(CH$_2$)$_3$O(2-NH$_2$-3-F-phenyl),
—(CH$_2$)$_3$O(2-NH$_2$-4-Cl-phenyl),
—(CH$_2$)$_3$O($^2$-NH$_2$-4-OH-phenyl),
—(CH$_2$)$_3$O(2-NH$_2$-4-Br-phenyl),
—(CH$_2$)$_3$O(2-NHC(=O)Me-4-F-phenyl),
—(CH$_2$)$_3$O(2-NHC(=O)Me-phenyl)
—(CH$_2$)$_3$NH(4-fluoro-phenyl),
—(CH$_2$)$_3$N(methyl)(4-fluoro-phenyl),
—(CH$_2$)$_3$C$_2$(ethyl),
—(CH$_2$)$_3$C(=O)N(methyl)(methoxy),
—(CH$_2$)$_3$C(=O)NH(4-fluoro-phenyl),
—(CH$_2$)$_2$NHC(=O)(phenyl),
—(CH$_2$)$_2$NMeC(=O)(phenyl),
—(CH$_2$)$_2$NHC(=O)(2-fluoro-phenyl),
—(CH$_2$)$_2$NMeC(=O)(2-fluoro-phenyl),
—(CH$_2$)$_2$NHC(=O)(4-fluoro-phenyl),
—(CH$_2$)$_2$NMeC(=O)(4-fluoro-phenyl),
—(CH$_2$)$_2$NHC(=O)(2,4-difluoro-phenyl),
—(CH$_2$)$_2$NMeC(=O)(2,4-difluoro-phenyl),
—(CH$_2$)$_3$(3-indolyl),
—(CH$_2$)$_3$(1-methyl-3-indolyl),
—(CH$_2$)$_3$(1-indolyl),
—(CH$_2$)$_3$(1-indolinyl)
—(CH$_2$)$_3$(1-benzimidazolyl)
—(CH$_2$)$_3$(1H-1,2,3-benzotriazol-1-yl),
—(CH$_2$)$_3$(1H-1,2,3-benzotriazol-2-yl),
—(CH$_2$)$_2$(1H-1,2,3-benzotriazol-1-yl),
—(CH$_2$)$_2$(1H-1,2,3-benzotriazol-2-yl),
—(CH$_2$)$_3$(3,4 dihydro-1(2H)-quinolinyl),
—(CH$_2$)$_2$C(=O)(4-fluoro-phenyl),
—(CH$_2$)$_2$C(=O)NH(4-fluoro-phenyl),
—CH$_2$CH$_2$(3-indolyl),
—CH$_2$CH$_2$(1-phthalimidyl),
—(CH$_2$)$_4$C(=O)N(methyl)(methoxy),
—(CH$_2$)$_4$CO$_2$(ethyl),
—(CH$_2$)$_4$C(=O)(phenyl),
—(CH$_2$)$_4$(cyclohexyl),
—(CH$_2$)$_3$CH(phenyl)$_2$,
—CH$_2$CH$_2$CH=C(phenyl)$_2$, —CH$_2$CH$_2$CH=CMe(4-F-phenyl),
—(CH$_2$)$_3$CH (4-fluoro-phenyl)$_2$,
—(CH$_2$CH$_2$CH=C(4-fluoro-phenyl)$_2$,
—(CH$_2$)$_2$ (2,3-dihydro-1H-inden-2-yl) ,
—(CH$_2$)$_3$C(=O)(2-NH$_2$-phenyl),
—(CH$_2$)$_3$C(=O)(2-NH$_2$-5-F-phenyl),
—(CH$_2$)$_3$C(=O)(2-NH$_2$-4-F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$C(=O)(2-NH$_2$-4-OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-Cl-1H-indazol-3-yl),
—(CH$_2$)$_3$(6-Br-1H-indazol-3-yl),
—(CH$_2$)$_3$C(=O)(2-NHMe-phenyl),
—(CH$_2$)$_3$(1-benzothien-3-yl),
—(CH$_2$)$_3$(6-F-1H-indol-1-yl)
—(CH$_2$)$_3$(5-F-1H-indol-1-yl),
—(CH$_2$)$_3$(6-F-2,3-dihydro-1H-indol-1-yl),
—(CH$_2$)$_3$(5-F-2,3-dihydro-1H-indol-1-yl),
—(CH$_2$)$_3$(6-F-1H-indol-3-yl),
—(CH$_2$)$_3$ (5-F-1H-indol-3-yl),
—(CH$_2$ )$_3$(5-F-1H-indol-3-yl),
—(CH$_2$)$_3$(5-F-1H-indol-3-yl),
—(CH$_2$)$_3$ (9H-purin-9-yl),
—(CH$_2$)$_3$(7H-purin-7-yl),
—(CH$_2$)$_3$(6-F-1H-indazol-3-yl),
—(CH$_2$)$_3$C(=O)(2-NHSO$_2$Me-4-F-phenyl),
—(CH$_2$)$_3$C(=O)(2-NHC(=O)Me-4-F-phenyl),
—(CH$_2$)$_3$C(=O)(2-NHC(=O)Me-phenyl),
—(CH$_2$)$_3$C(=O)(2-NHCO$_2$Et-4-F-phenyl),
—(CH$_2$)$_3$C(=O)(2-NHC(=O)NHEt-4-F-phenyl),
—(CH$_2$)$_3$C(=O)(2-NHCHO-4-F-phenyl),
—(CH$_2$)$_3$C(=O)(2-OH-4-F-phenyl),
—(CH$_2$)$_3$C(=O)(2-MeS-4-F-phenyl),
—(CH$_2$)$_3$C(=O)(2-NHSO$_2$Me-4-F-phenyl),
—(CH$_2$)$_2$C(Me)CO$_2$Me,
—(CH$_2$)$_2$C(Me)CH(OH)(4-F-phenyl)$_2$,
—(CH$_2$)$_2$C(Me)CH(OH)(4-Cl-phenyl)$_2$,
—(CH$_2$)$_2$C(Me)C(=O)(4-F-phenyl),
—(CH$_2$)$_2$C(Me)C(=O)(2-MeO-4-F-phenyl),
—(CH$_2$)$_2$C(Me)C(=O)(3-Me-4-F-phenyl),
—(CH$_2$)$_2$C(Me)C(=O)(2-Me-phenyl),
—(CH$_2$)$_2$C(Me)C(=O)phenyl,

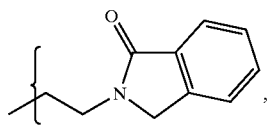,

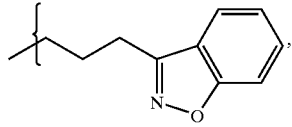,

45

-continued

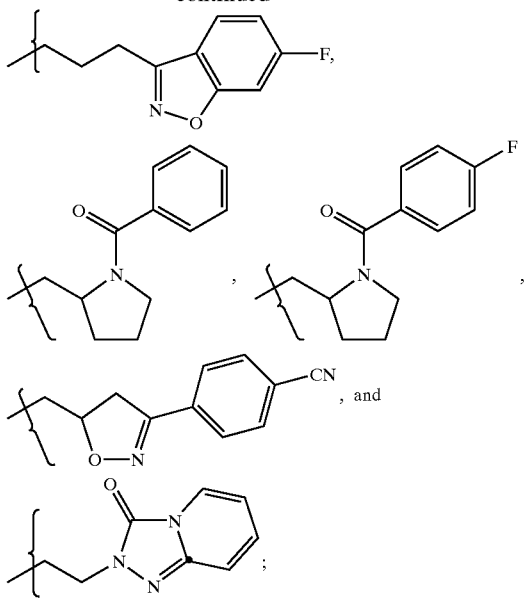

R⁷, R⁸, and R⁹, at each occurrence, are independently selected from
  hydrogen, fluoro, chloro, bromo, cyano, methyl, ethyl, propyl, isopropyl, butyl, t-butyl, nitro,
  trifluoromethyl, methoxy, ethoxy, isopropoxy, trifluoromethoxy, phenyl, benzyl,
  HC(=O)—, methylC(=O)—, ethylC(=O)—, propylC(=O)—,
  isopropylC(=O)—, n-butylC(=O)—, isobutylC(=O)—,
  secbutylC(=O)—, tertbutylC(=O)—, phenylC(=O)—,
  methylC(=O)NH—, ethylC(=O)NH —, propylC(=O)NH—,
  isopropylC(=O)NH—, n-butylC(=O)NH—, isobutylC(=O)NH—,
  secbutylC(=O)NH—, tertbutylC(=O)NH—, phenylC(=O)NH—,
  methylamino-, ethylamino-, propylamino-, isopropylamino-,
  n-butylamnino-, isobutylamino-, secbutylamino-,
  tertbutylamino-, phenylamino-,
provided that two of substituents R⁷, R⁸ and R⁹, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy;
R¹⁰ᴬ is selected from hydrogen, methyl, ethyl, propyl, isopropyl, butyl, benzyl, 2-chlorobenzyl, 2-fluorobenzyl, 2-bromobenzyl, 2-methylbenzyl, 2-trifluoromethylbenzyl, 2-methoxybenzyl, 2-trifluoromethoxybenzyl, 3-chlorobenzyl, 3-fluorobenzyl, 3-bromobenzyl, 3-methylbenzyl, 3-trifluoromethylbenzyl, 3-methoxybenzyl, 3-trifluoromethoxybenzyl, 4-chlorobenzyl, 4-fluorobenzyl, 4-bromobenzyl, 4-methylbenzyl, 4-trifluoromethylbenzyl, 4-methoxybenzyl, and 4-trifluoromethoxybenzyl;
k is 1 or 2;
m is 1 or 2; and
n is 1 or 2.

46

[15] In another even more preferred embodiment of the present invention, the compound of Formula (I) is selected from Formula (IV-a):

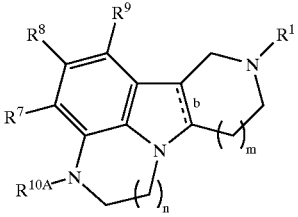

(IV-a)

wherein:
b is a single bond, wherein the bridge hydrogens are in a cis position;
R¹ is selected from
  —(CH$_2$)$_3$C(=O)(4-fluoro-phenyl),
  —(CH$_2$)$_3$C(=O)(4-bromo-phenyl),
  —(CH$_2$)$_3$C(=O)(4-methyl-phenyl),
  —(CH$_2$)$_3$C(=O)(4-methoxy-phenyl),
  —(CH$_2$)$_3$C(=O)(4-(3,4-dichloro-phenyl)phenyl),
  —(CH$_2$)$_3$C(=O)(3-methyl-4-fluoro-phenyl),
  —(CH$_2$)$_3$C(=O)(2,3-dimethoxy-phenyl),
  —(CH$_2$)$_3$C(=O)(phenyl),
  —(CH$_2$)$_3$C(=O)(4-chloro-phenyl),
  —(CH$_2$)$_3$C(=O)(3-methyl-phenyl),
  —(CH$_2$)$_3$C(=O)(4-t-butyl-phenyl),
  —(CH$_2$)$_3$C(=O)(3,4-difluoro-phenyl),
  —(CH$_2$)$_3$C(=O)(2-methoxy-5-fluoro-phenyl),
  —(CH$_2$)$_3$C(=O)(4-fluoro-1-naphthyl),
  —(CH$_2$)$_3$C(=O)(benzyl),
  —(CH$_2$)$_3$C(=O)(4-pyridyl),
  —(CH$_2$)$_3$C(=O)(3-pyridyl),
  —(CH$_2$)$_3$CH(OH)(4-fluoro-phenyl),
  —(CH$_2$)$_3$CH(OH)(4-pyridyl),
  —(CH$_2$)$_3$CH(OH)(2,3-dimethoxy-phenyl),
  —(CH$_2$)$_3$S(3-fluoro-phenyl),
  —(CH$_2$)$_3$S(4-fluoro-phenyl),
  —(CH$_2$)$_3$S(=O)(4-fluoro-phenyl),
  —(CH$_2$)$_3$SO$_2$(3-fluoro-phenyl),
  —(CH$_2$)$_3$SO$_2$(4-fluoro-phenyl),
  —(CH$_2$)$_3$O(4-fluoro-phenyl),
  —(CH$_2$)$_3$O(phenyl)
  —(CH$_2$)$_3$NH(4-fluoro-phenyl),
  —(CH$_2$)$_3$N(methyl)(4-fluoro-phenyl),
  —(CH$_2$)$_3$CO$_2$(ethyl),
  —(CH$_2$)$_3$C(=O)N(methyl)(methoxy),
  —(CH$_2$)$_3$C(=O)NH(4-fluoro-phenyl),
  —(CH$_2$)$_2$NHC(=O)(phenyl),
  —(CH$_2$)$_2$NMeC(=O)(phenyl),
  —(CH$_2$)$_2$NHC(=O)(2-fluoro-phenyl),
  —(CH$_2$)$_2$NMeC(=O)(2-fluoro-phenyl) ,
  —(CH$_2$)$_2$NHC(=O)(4-fluoro-phenyl),
  —(CH$_2$)$_2$NMeC(=O)(4-fluoro-phenyl)
  —(CH$_2$)$_2$NHC(=O)(2,4-difluoro-phenyl),
  —(CH$_2$)$_2$NMeC(=O)(2,4-difluoro-phenyl),
  —(CH$_2$)$_3$(3-indolyl), —(CH₂)₃(1-methyl-3-indolyl)
—(CH₂)₃(1-indolyl),
—(CH₂)₃(1-indolinyl),
—(CH₂)₃(1-benzimidazolyl),
—(CH₂)₃(1H-1,2,3-benzotriazol-1-yl),
—(CH₂)₃(1H-1,2,3-benzotriazol-2-yl),
—(CH₂)₂(1H-1,2,3-benzotriazol-1-yl)
—(CH₂)₂(1H-1,2,3-benzotriazol-2-yl),
—(CH₂)₂(3,4 dihydro-1(2H)-quinolinyl),
—(CH₂)₂C(=O)(4-fluoro-phenyl),
—(CH₂)₂C(=O)NH(4-fluoro-phenyl)
—CH₂CH₂(3-indolyl),
—CH₂CH₂(1-phthalimidyl) ,
—(CH₂)₄C(=O)N(methyl)(methoxy),
—(CH₂)₄C₂(ethyl),
—(CH₂)₄C(=O)(phenyl),
—(CH₂)₄(cyclohexyl),
—(CH₂)₃CH(phenyl)₂,
—CH₂CH₂CH=C(phenyl)₂,
—CH₂CH₂CH=CMe(4-F-phenyl),
—(CH₂)₃CH(4-fuoro-phenyl)₂,
—CH₂CH₂CH=C(4-fluoro-phenyl)₂,
—(CH₂)₂(2,3-dihydro-1H-inden-2-yl),
—(CH₂)₃C(=O)(2-NH₂-phenyl),
—(CH₂)₃C(=O)(2-NH₂-5-F-phenyl),
—(CH₂)₃C(=O)(2-NH₂-4-F-phenyl),
—(CH₂)₃C(=O)(2-NH₂-3-F-phenyl),
—(CH₂)₃C(=O)(2-NH₂-4-Cl-phenyl),
—(CH₂)₃C(=O)(2-NH₂-4-OH-phenyl),
—(CH₂)₃C(=O)(2-NH₂-4-Br-phenyl),
—(CH₂)₃(1H-indazol-3-yl),
—(CH₂)₃(5-F-1H-indazol-3-yl),
—(CH₂)₃(7-F-1H-indazol-3-yl),
—(CH₂)₃(6-Cl-1H-indazol-3-yl) ,
—(CH₂)₃(6-Br-1H-indazol-3-yl),
—(CH₂)₃C(=O)(2-NHMe-phenyl),
—(CH₂)₃(1-benzothien-3-yl),
—(CH₂)₃(6-F-1H-indol-1-yl),
—(CH₂)₃(5-F-1H-indol-1-yl) ,
—(CH₂)₃(6-F-2,3-dihydro-1H-indol-1-yl),
—(CH₂)₃(5-F-2,3-dihydro-1H-indol-1-yl),
—(CH₂)₃(6-F-1H-indol-3-yl),
—(CH₂)₃(5-F-1H-indol-3-yl),
—(CH₂)₃(5-F-1H-indol-3-yl),
—(CH₂)₃(9H-purin-9-yl),
—(CH₂)₃(7H-purin-7-yl),
—(CH₂)₃(6-F-1H-indazol-3-yl),
—(CH₂)₃C(=O)(2-NHSO₂Me-4-F-phenyl),
—(CH₂)₃C(=O)(2-NHC(=O)Me-4-F-phenyl),
—(CH₂)₃C(=O)(2-NHC(=O)Me-4-F-phenyl),
—(CH₂)₃C(=O)(2-NHCO₂Et-4-F-phenyl),
—(CH₂)₃C(=O)(2-NHC(=O)NHEt-4-F-phenyl),
—(CH₂)₃C(=O)(2-NHCHO-4-F-phenyl),
—(CH₂)₃(=O)(2-OH-4-F-phenyl),
—(CH₂)₃C(=O)(2-MeS-4-F-phenyl),
—(CH₂)₃C(=O)(2-NHSO₂Me-4-F-phenyl), —(CH₂)₂C(Me)CO₂Me,
—(H₂)₂C(Me)CH(OH)(4-F-phenyl)₂,
—(CH₂)₂C(Me)CH(OH)(4-Cl-phenyl)₂,
—(CH₂)₂C(Me)C(=O)(4-F-phenyl)₂,
—(CH₂)₂C(Me)C(=O)(2-MeO-4-F-phenyl),
—(CH₂)₂C(Me)C(=O)(3-Me-4-F-phenyl),
—(CH₂)₂C(Me)C(=O)(2-Me-phenyl),
—(CH₂)₂C(Me)C(=O)phenyl,

[structures shown]

, and

[structure shown];

$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, methylC(=O)—, ethylC(=O)—, propylC(=O)—, isopropylC(=O)—, methylC(=O)NH—, ethylC(=O)NH—, propylC(=O)NH—, isopropylC(=O)NH, methylamino-, ethylamino-, propylamino-, and isopropylamino-,
provided that two of substituents $R^7$, $R^8$, and $R^9$, are independently selected from hydrogen, fluoro, chloro, methyl, trifluoromethyl, methoxy, and trifluoromethoxy;
$R^{10A}$ is selected from hydrogen, methyl, ethyl, propyl, isopropyl, butyl, benzyl, 2-chlorobenzyl, 2-fluorobenzyl, 2-bromobenzyl, 2-methylbenzyl, 2-trifluoromethylbenzyl, 2-methoxybenzyl, 2-trifluoromethoxybenzyl, 3-chlorobenzyl, 3-fluorobenzyl, 3-bromobenzyl, 3-methylbenzyl, 3-trifluoromethylbenzyl, 3-methoxybenzyl, 3-trifluoromethoxybenzyl, 4-chlorobenzyl, 4-fluorobenzyl, 4-bromobenzyl, 4-methylbenzyl, 4-trifluoromethylbenzyl, 4-methoxybenzyl, and 4-trifluoromethoxybenzyl;

m is 1 or 2; and n is 1 or 2.

In an even further more preferred embodiment of the present invention, are compounds of Formula (I) selected from Table 1.

In a second embodiment, the present invention provides a pharmaceutical composition comprising a compound of Formula (I) and a pharmaceutically acceptable carrier.

In a third embodiment, the present invention provides a method for the treatment a central nervous system disorder comprising administering to a host in need of such treatment a therapeutically effective amount of a compound of Formula (I), or a pharmaceutically acceptable salt thereof, wherein the compound is a 5HT2a antagonist or a 5HT2c agonist.

In a preferred embodiment the compound is a 5HT2a antagonist.

In another preferred embodiment the compound is a 5HT2c agonist.

In a more preferred embodiment the present invention provides a method for the treatment central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility comprising administering to a host in need of such treatment a therapeutically effective amount of a compound of Formula (I).

In a further preferred embodiment the central nervous system disorder comprises obesity.

In another further preferred embodiment the central nervous system disorder comprises schizophrenia.

In another further preferred embodiment the central nervous system disorder comprises depression.

In another further preferred embodiment the central nervous system disorder comprises anxiety.

In a fourth embodiment the present invention provides novel compounds of Formula (I) or pharmaceutically acceptable salt forms thereof for use in therapy.

In a fifth embodiment the present invention provides the use of novel compounds of Formula (I) or pharmaceutically acceptable salt forms thereof for the manufacture of a medicament for the treatment of central nervous system disorders including obesity, anxiety, depression, psychosis, schizophrenia, sleep disorders, sexual disorders, migraine, conditions associated with cephalic pain, social phobias, and gastrointestinal disorders.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The numbering of the tetracyclic ring-system present in the compounds of Formula (I), as defined by nomenclature known to one skilled in the art, is shown for two examples in Formula (I'), when k is 1, m is 1, and n is 1; and in Formula (I''), when k is 1, m is 1, and n is 2:

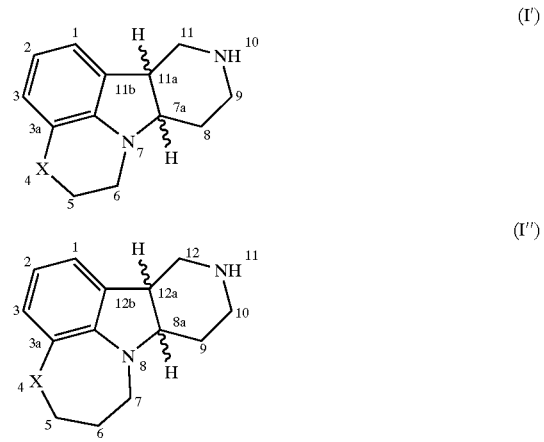

The tetracyclic ring-system present in compounds of Formula (I) occur as "cis" or "trans" isomers when the carbon-carbon bond b in Formula (I) is a single bond. As such, the terms "cis" and "trans", in conjunction with the tetracyclic ring structure, refer to the configuration of hydrogen atoms on carbon atoms 7a and 11a in Formula (I') or, for example, on carbon atoms 8a and 12a in Formula (I''), above. When both hydrogens are on the same side of the mean plane determined by the octahydro tetracyclic moiety then the configuration is designated "cis", if not, the configuration is designated "trans". It is understood that the above example is for demonstrative puproses only and not intended to limit the scope of the tetracyclic ring-system present in compounds of Formula (I). As such, it is understood that one skilled in the art of organic chemistry can apply the above numbering system to other values of k, m, and n in the scope of compounds of Formula (I) to deterine the appropriate numbering. Additional Examples of the numbering of the tetracyclic ring-system are further provided below in the synthetic Examples. Lastly, it is understood that the use of "cis" or "trans" in the identification of the tetracyclic ring-system is not meant to construe the configuration of any other cis or trans geometric isomer in the molecule, for example, cis or trans butene.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^2$) occurs more than one time in any constituent or formula for a compound, its definition at each occurrence is independent of its definition at every other occurrence. Thus, for example, if a group is shown to be substituted with 0–2 $R^2$, then said group may optionally be substituted with up to two $R^2$ groups and $R^2$ at each occurrence is selected independently from the definition of $R^2$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$-$C_6$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration and one or more carbon-carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$-$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" is represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

As used herein, the term "bicyclic heterocyclic ring system" is intended to mean a stable 9- to 10-membered bicyclic heterocyclic ring formed from the substituent $R^{12}R^{13}$, which is partially unsaturated or unsaturated (aromatic), and which consists of carbon atoms, a nitrogen atom, and 1 or 2 additional heteroatoms independently selected from the group consisting of N, O and S. The additional nitrogen or sulfur heteroatoms may optionally be oxidized. The heterocyclic ring is attached to its pendant group by the nitrogen atom of the group $NR^{12}R^{13}$ and for which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. The term "bicyclic heterocyclic ring system" is intended to be a subset of the term "heterocyclic ring system". Preferred examples of a 9- to 10- membered bicyclic heterocyclic ring system are benzimidazolyl, benzimidazolinyl, benzoxazolinyl, dihydrobenzthiazolyl, dihydrodioxobenzthiazolyl, benzisoxazolinyl, 1H-indazolyl, indolyl, indolinyl, isoindolinyl, tetrahydro-isoquinolinyl, tetrahydro-quinolinyl, and benzotriazolyl.

Additionally, a subclass of preferred heterocycles are heterocycles which function as an isostere of a cyclic but non-heterocyclic substitutent such as —$CH_2$—C(=O)-phenyl. Preferred examples of such heterocycles include, but are not limited to, benzimidazolyl, benzofuranyl, benzothiophenyl, benzoxazolyl, benzthiazolyl, benzisoxazolyl, furanyl, imidazolinyl, 1H-indazolyl, indolinyl, isoindolinyl, isoquinolinyl, oxazolyl, piperidinyl, pyrazinyl, pyridinyl, pyrimidinyl, quinolinyl, thiazolyl, thiophenyl, and 1,2,3-triazolyl.

As used herein, the term "aryl", or aromatic residue, is intended to mean an aromatic moiety containing the specified number of carbon atoms, such as phenyl, pyridinyl and naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

Throughout the details of the invention, the following abbreviations are used with the following meanings:

| Reagents: | |
|---|---|
| MCPBA | m-chloroperoxybenzoic acid |
| DIBAL | diisobutyl aluminum hydride |
| $Et_3N$ | triethylamine |
| TFA | trifluoroacetic acid |
| LAH | lithium aluminum hydride |
| NBS | N-bromo succinimide |
| Red-Al | Sodium bis(2-methoxyethoxy)aluminum hydride |
| $Pd_2dba_3$ | Tris(dibenzylideneacetone)dipalladium(0) |
| ACE-Cl | 2-chloroethylchloroformate |
| Solvents: | |
| THF | tetrahydrofuran |
| MeOH | methanol |
| EtOH | ethanol |
| EtOAc | ethyl acetate |
| HOAc | acetic acid |
| DMF | dimethyl formamide |
| DMSO | dimethyl sulfoxide |
| DME | dimethoxyethane |
| $Et_2O$ | diethylether |
| iPrOH | isopropanol |
| MEK | methyl ethyl ketone |
| Others: | |
| Ar | aryl |
| Ph | phenyl |
| Me | methyl |
| Et | ethyl |
| NMR | nuclear magnetic resonance |
| MHz | megahertz |
| BOC | tert-butoxycarbonyl |
| CBZ | benzyloxycarbonyl |
| Bn | benzyl |
| Bu | butyl |
| Pr | propyl |

| | |
|---|---|
| cat. | catalytic |
| mL | milliliter |
| nM | nanometer |
| ppm | part per million |
| mmol | millimole |
| mg | milligram |
| g | gram |
| TLC | thin layer chromatography |
| HPLC | high pressure liquid chromatography |
| RPM | revolutions per minute |
| rt | room temperature |
| aq. | aqueous |
| sat. | saturated |

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The preparation of compounds of Formula (I) of the present invention may be carried out in a convergent or sequential synthetic manner. Detailed synthetic preparations of the compounds of Formula (I) are shown in the following reaction schemes. The skills required in preparation and purification of the compounds of Formula (I) and the intermediates leading to these compounds are known to those in the art. Purification procedures include, but are not limited to, normal or reverse phase chromatography, crystallization, and distillation.

Several methods for the preparation of the compounds of the present invention are illustrated in the schemes and examples shown below. The substitutions are as described and defined above.

Compounds of Formula (I) of this invention may be prepared as shown in Scheme 1. Thus, preparation of an aryl hydrazine (III) is accomplished, for example, by treatment of a corresponding substituted aniline (II) with $NaNO_2$ followed by reduction of the N-nitroso intermediate with a reducing agent such as LAH or zinc and an organic acid, such as acetic acid or trifluoroacetic acid at low temperature. Assembly of the core tetracyclic intermediate indole (V) is accomplished by Fischer indole cyclization of the aryl hydrazine and a suitably substituted ketone (i.e. (IV)) by methods described by, but not limited to, R. J. Sundberg, "Indoles, Best Synthetic Methods" 1996, Academic Press, San Diego, Calif. For example, treatment of the aryl hydrazine (III) as the free base or the corresponding mineral acid salt with the ketone (IV) ($R^1$=H, Bn, CBZ, $CO_2$Et, etc) in an alcoholic solvent in the presence of mineral acid affords the indoles (V) as the free bases (after treatment with aq. NaOH). Reduction of the indoles 0to the corresponding cis or trans substituted dihydroindoles is accomplished by, for example, treatment with hydrogen in the presence of a catalyst such as platinum oxide or palladium on carbon, or with a metal such as zinc and a mineral acid such as hydrochloric acid, or with sodium and liquid ammonia, or with borane-amine complex such as borane-triethylamine in tetrahydofuran, or preferably by treatment with $NaCNBH_3$ in an acid such as acetic or trifluoroacetic acid.

The corresponding enantiomers can be isolated by separation of the racemic mixture of (I) on a chiral stationary phase column utilizing normal or reverse phase HPLC techniques, the details of which are described in the examples. Alternatively, a diastereomeric mixture of (I) can be prepared by treatment of (I, $R^1$=H) with an appropriate chiral acid (or suitably activated derivative), for example dibenzoyl tartrate or the like (see, for example, Kinbara, K., et. al., *J. Chem . Soc., Perkin Trans.* 2, 1996, 2615; and Tomori, H., et. al., *Bull. Chem. Soc. Jpn.,* 1996, 3581). The diastereomers would then be separated by traditional techniques (i.e. silica chromatography, crystallization, HPLC, etc) followed by removal of the chiral auxiliary to afford enantiomerically pure (I).

In the cases where the carboline nitrogen has been protected (VI) (i.e. $R^1$=Boc, Bn, CBZ, $CO_2$R), it may be removed under a variety of conditions as described in Greene, T. W., Wuts, P. G. W., "Protective Groups in Organic Synthesis, 2nd Edition", John Wiley and Sons, Inc., New York, pages 309–405, 1991. The free secondary amine could then be alkylated, for example, by treatment with a suitably substituted alkyl halide ($R^1$Cl, or $R^1$I) and a base to afford additional compounds of type (I), as described, for example, by Glennon, R. A., et. al., *Med. Chem. Res.,* 1996, 197.

SCHEME 1

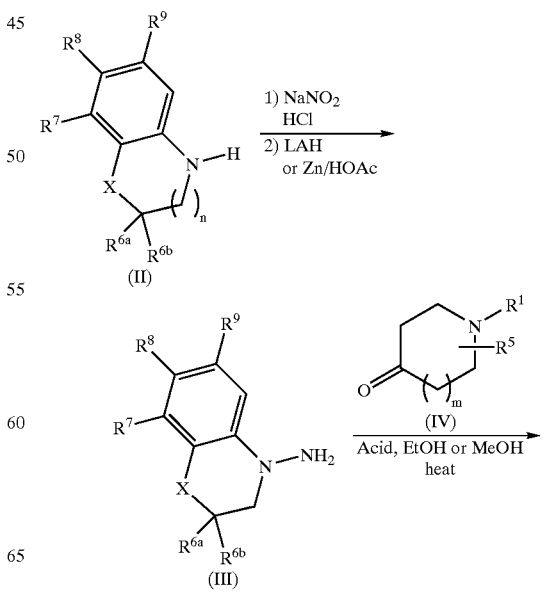

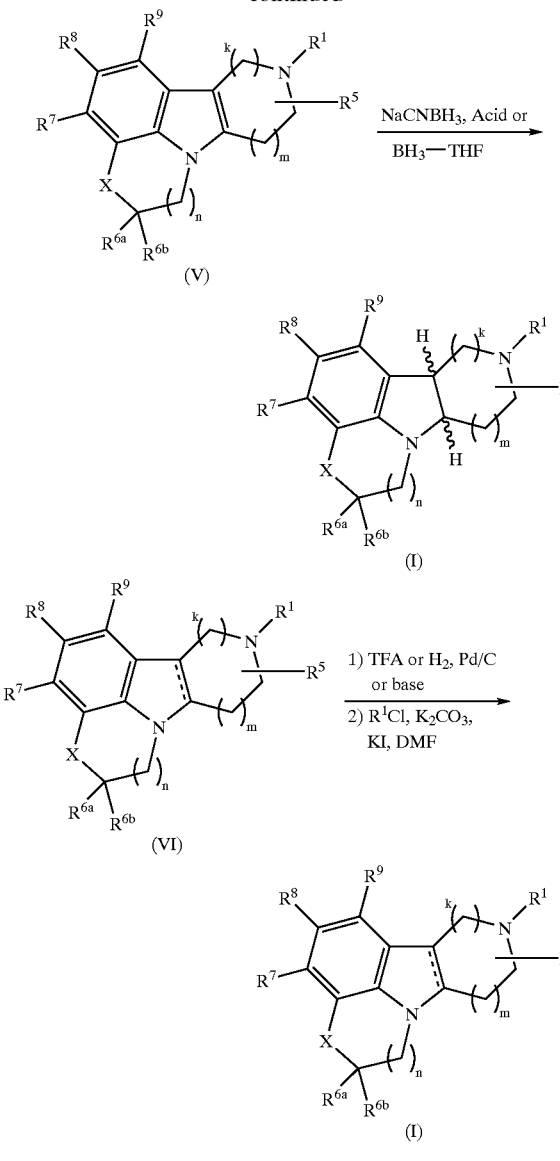

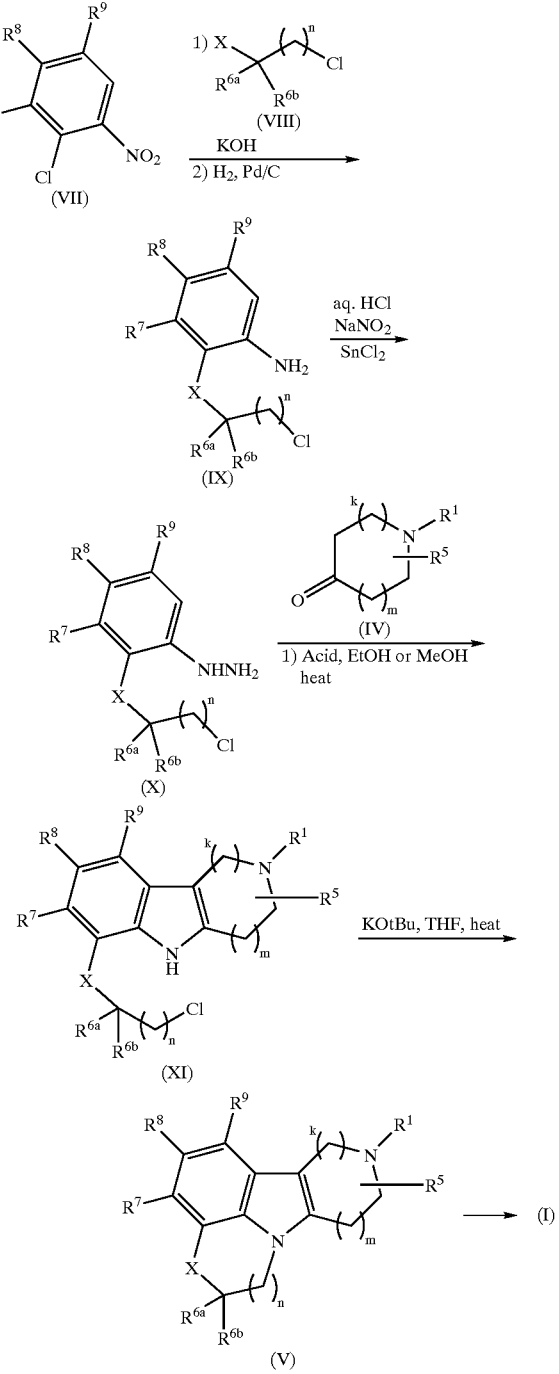

t-butoxide in a solvent such as DME or THF affords the tetracyclic indole intermediates (V). These indoles can also be reduced to the corresponding cis or trans indolines (I) as described previously in Scheme 1.

SCHEME 2

Alternatively, compounds of Formula (I) can be prepared as described in Scheme 2. Treatment of an ortho halonitrobenzene compound (VII) with a nucleophilic alkyl halide (X=OH, SH, NHR, (VIII)) (as described by Kharasch, N., Langford, R. B., *J. Org. Chem.*, 1963, 1903) and a suitable base followed by subsequent reduction of the corresponding nitroaryl derivative to the aniline (IX). The reduction may be accomplished with a variety of reducing agents, for example, LAH, $SnCl_2$, $NaBH_4$, $N_2H_4$, etc. or with hydrogen in the presence of a suitable catalyst, such as palladium on carbon, or platinum oxide, etc., (see Hudlicky, M., "Reductions in Organic Chemistry", Ellis Horwood, Ltd., Chichester, UK, 1984). Formation of the aryl hydrazine (X) may be accomplished as described previously in Scheme 1 or more directly by treatment of the aniline (IX) with aq. hydrochloric acid, stannous chloride and $NaNO_2$ at room temperature (see, Buck, J. S., Ide, W. S., *Org. Syn., Coll. Vol.*, 2, 1943, 130). This primary aryl hydrazine (X) can then be cyclized under Fischer indole cyclization conditions as detailed above for compound (V), to afford the indole (XI) as the corresponding salt. Upon treatment of the indole (XI) with a base such potassium hydroxide or potassium Still another related route to compounds of Formula (I) is shown in Scheme 3. Initiating the synthesis with a nitrobenzene derivative such as (XII), this approach allows for a variety of derivatization. More highly substituted nitrobenzenes can be obtained by traditional synthetic manipulation (i.e. aromatic substitution) and are known by those in the art (see Larock, R. C., *Comprehensive Organic Transformations*, VCH Publishers, New York, 1989): Treatment of nitrobenzene derivative with a reducing agent such as LAH, etc., as described previously (see Hudlicky, et. al.), affords the corresponding aniline intermediate. Subsequent formation of the hydrazine followed by Fischer indole cyclization with a suitably functionalized ketone as described above (i.e. Scheme 1, (III) to (V)) affords the g-carboline indole (XIII). At this point the fused ring may be appended by condensation of a haloalkyl carboxylic acid or a related activated carboxylic acid (i.e. acid chloride, mixed anhydride, etc.) such as (XIV). Reduction of the resultant heterocyclic carbonyl may be effected with various reducing agents, for example, sodium borohydride, diisobutyl aluminum hydride and the like (see Larock, R. C., *Comprehensive Organic Transformations,* VCH Publishers, New York, 1989 and/or Hudlicky, M., "Reductions in Organic Chemistry", Ellis Horwood, Ltd., Chichester, UK, 1984) to afford the tetracyclic indoles (V). Further reduction of the indole (V) to the indolines (I) is as described previously in Scheme 1.

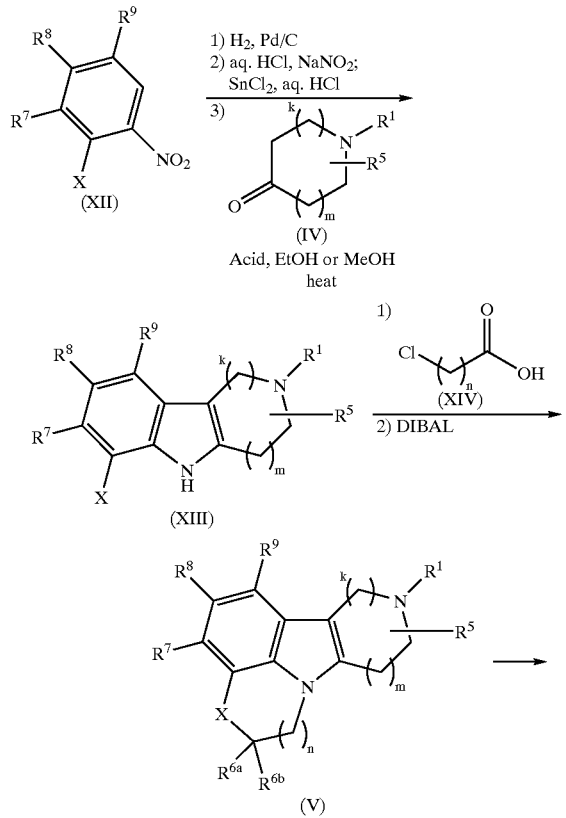

Preparation of the aniline precursors (II) to the Fischer indole cyclizations is shown in Scheme 4. Treatment of a suitably ortho-functionalized aniline (XVI) with a chloroalkyl carboxylic acid or ester (or equivalent substrate, i.e. acrylic acid, acryloyl chloride, etc.) and concomitant condensation, followed by reduction of the resultant heterocyclic carbonyl with a reducing agent such as LAH, DIBAL, or Red-Al affords the fused heterocyclic benzene derivatives (II). More diverse intermediates of (II) may be obtained by formation of the ortho substitiuted aniline from the corresponding ortho substituted nitobenzenes and concomitant reduction of the nitro moiety as described above. Furthermore, aromatic substitution of the fluoro (or other halo derived nitrobenzene) functionality of (XV) for an oxygen, or sulphur moiety is accomplished, for example, by treatment of (XV) with a nucleophile, such as sodium sulfide or an alcohol, followed by formation of the requisite thiophenol or phenol, respectively, using standard techniques known by those in the art (see Larock, R. C., *Comprehensive Organic Transformations,* VCH Publishers, New York, 1989, page 481). Reduction of the nitro as before affords the substituted anilines (XVI).

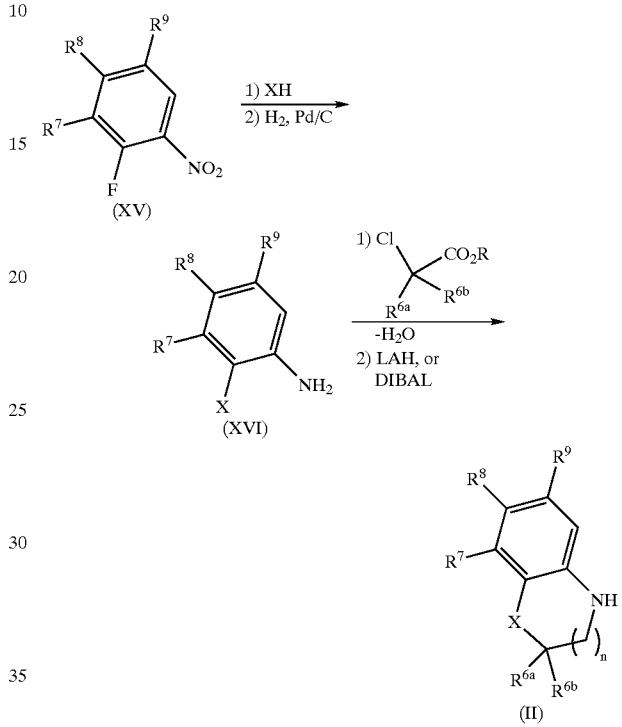

An alternate approach to the substituted fused anilines (II) is shown in Scheme 5. Treatment of the phenol (X=OH), thiophenol (X=SH), or other nucleophilically aromatic substituted derivative (XVII) with, for example, a haloalkyl carboxylic acid (or equivalent activated haloalkylcarboxylic acid, (i.e. acid halide, mixed anhydride, acrylic acid, acryloyl chloride, etc.), affords the derivative (XVIII) which when treated under Friedel-Crafts acylation conditions (see Ed. G. A. Olah, "Friedel-Crafts and Related Reactions", J. Wiley and Sons, New York, 1964, Vol 3, Pts 1 and 2 or Chem. Rev., 1955, 229, or Olah, G. A., "Friedel-Crafts Chemistry", Wiley Interscience, New York, 1973, for varying conditions and protocols), i.e. strong Lewis acids (AlCl$_3$, FeCl$_3$, etc.), affords the cyclic alkylphenones (XIX). Incorporation of the nitrogen functionality can be accomplished in several ways. For example, Schmidt rearrangement (as described by Smith, P. A. S., *J. Am. Chem. Soc.,* 1948, 320) is effected by treatment of the carbonyl derivative (XIX) with NaN$_3$ and methanesulfonic acid to afford the bicyclic lactam (XX). Alternatively, this transformation may be carried out under Hoffmann rearrangement protocol (see, for example, Dike, S. Y., et. al., *Bioorg. Med. Chem. Lett.,* 1991, 383), by initial formation of the oxime derivative of (XXI) by treatment with hydroxylamine hydrochloride. Subsequent rearrangement to the lactam is efficiently accomplished by heating in polyphosphoric acid to afford the lactam (XX). Reduction of the lactam (XX) can be accomplished with a variety of reducing agents, for example, DIBAL, Red-Al and the like to afford the aniline (II).

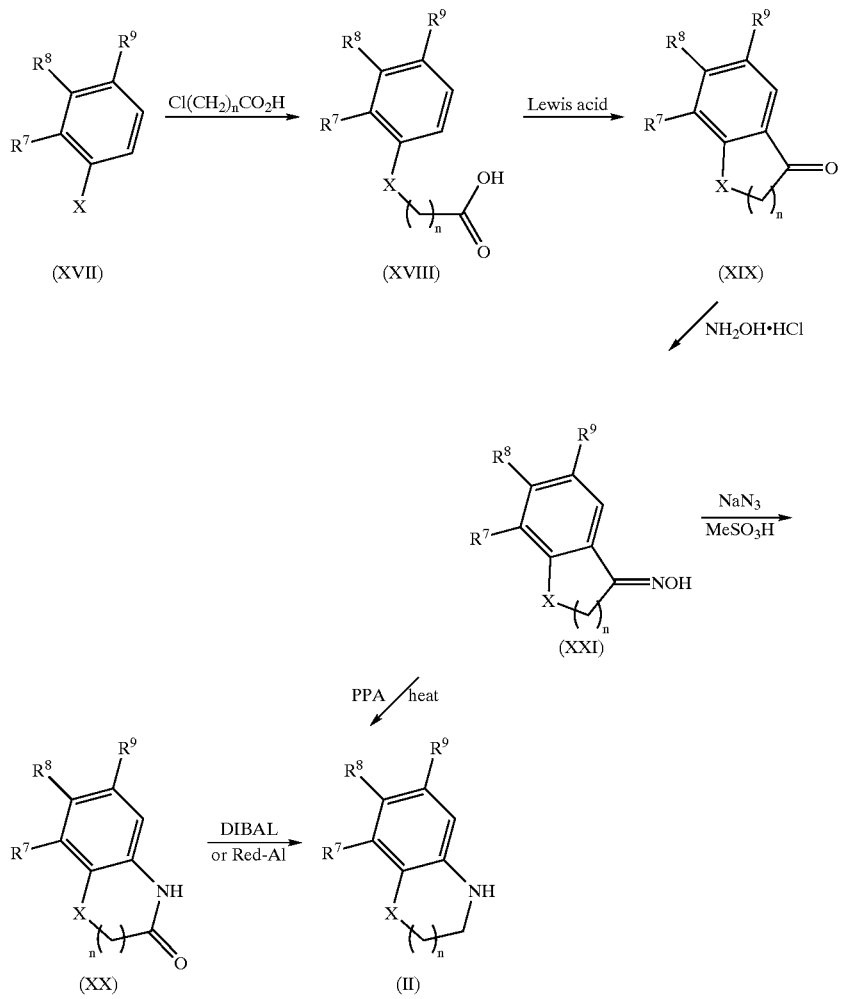

SCHEME 5

The preparation of compounds of Formula (I) with additional diversity of functionalization of the aromatic A ring of the tetracycle is shown in Scheme 6 and Scheme 7 and described here. Due to the nature of the synthetic route of Scheme 1 to derivatives of Formula (I), compounds with halogen substituents on the A-ring are difficult to prepare. However, bromination of the indolines (I, $R^8$=H) when the amine is protected, for example, with the Boc or CBZ protecting groups, with, for example, NBS in DMF affords the $R^8$ brominated derivatives (XXII). These activated aryl derivatives (XXII) act as excellent counterparts for a number of important synthetic transformations.

For example, biaryl coupling is accomplished under Suzuki coupling protocol. For a review and leading references of palladium catalyzed cross coupling reactions, see Miyaura, N., Suzuki, A., Chem. Rev., 1995, 2457. One such procedure entails treatment of the aryl bromide (XXII) with a functionalized aryl boronic acid (XXIII) in the presence of a catalytic Pd(0) species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd(0) catalyst, and a base such as $Na_2CO_3$ or $Et_3N$ in a suitable solvent such as DMF, toluene, THF, DME or the like, to afford the indolines (XXIV). Alternatively formation of the indole boronic acid from the bromine derivative (XXII) (i.e. (I, $R^8$=B(OH)$_2$)) would allow for greater diversity in the subsequent coupling of this indole boronic acid with commercially available haloaromatic derivatives in a similar Suzuki coupling strategy as-described above to afford the indolines (XXIV).

SCHEME 6

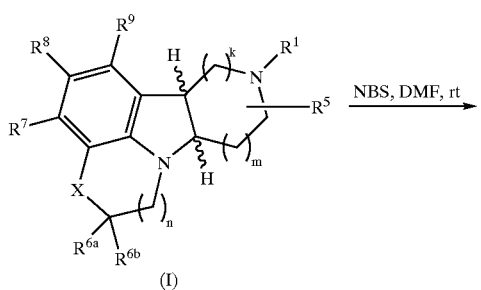

(I)

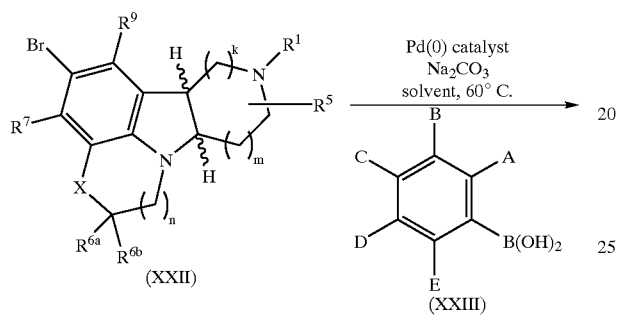

(XXII) (XXIII)

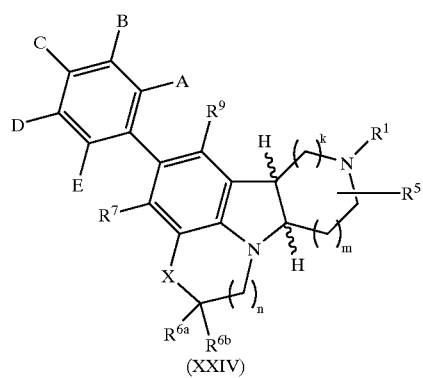

(XXIV)

Similarly biaryl coupling of the bromine derivatives (XXV), readily obtained by the synthetic sequence exemplified in Scheme 2, (starting with the suitably functionalized bromo nitrobenzenes (II)), is shown in Scheme 7. This approach allows for the preparation of biaryl indoles as well as the corresponding indoline derivatives. Protection of the amine functionality must be carried out if $R^1$=H (see Greene et.al for protections of amines). This is readily accomplished, for example, by treatment of bromo derivatives (XXV) with $(Boc)_2O$ in aqueous sodium hydroxide and dioxane. Subsequent Suzuki coupling with a variety of aryl boronic acids is carried out as described above in Scheme 6, to afford the biaryl adducts (XXVI). This protocol is amenable to $R^7$, $R^8$, and $R^9$ bromide, iodide, triflates, and/or diazo derivatives (see Miyaura, N., Suzuki, A., *Chem. Rev.,* 1995, 2457, for a review of aryl couplings).

SCHEME 7

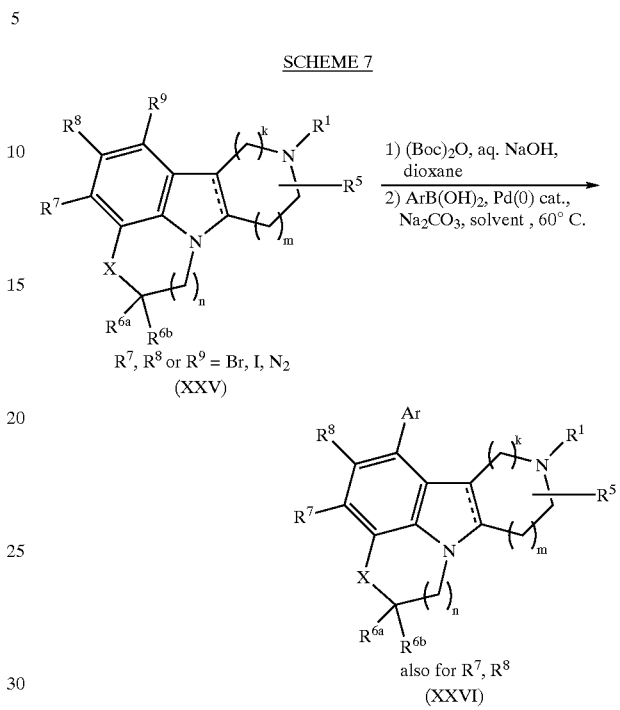

$R^7$, $R^8$ or $R^9$ = Br, I, $N_2$
(XXV)

also for $R^7$, $R^8$
(XXVI)

Furthermore and as an extension of this approach to a rapid preparation of a large array of biaryl indole and indoline derivatives, these bromide derivatives (XXV) can be bound to a solid support and the Suzuki couplings can be carried out on solid support (see XXVIII) as illustrated in Scheme 8. Towards that end treatment of indoline (XXV) with TFA in $CH_2Cl_2$, to remove the Boc protecting group, followed extraction from aqueous base provides the free amine (XXXVII). The free amine can be loaded onto a suitable solid support such as (XXVIII) using conditions well known to those skilled in the art. Thus, p-nitrophenylchloroformate Wang resin (XXVIII) which can be obtained commercially from sources such as Novabiochem, Inc. is swollen in a suitable solvent such as N-methyl pyrrolidinone and treated with 1.5 equiv. of amine to afford the functionalized resin (XXIX). Suzuki couplings are then carried out in array format by treatment of resins (XXIX) with a suitable palladium source such as $Pd(PPh_3)_4$ or $Pd(dppf)Cl_2$ and a suitable base such as 2M aqueous $K_2CO_3$ or $Na_2CO_3$ or triethylamine with an excess (typically 5 equivalents) of an aryl boronic acid (procedures for solid-phase Suzuki and other palladium couplings are well-known by those in the art, see for instance L. A. Thompson and J. A. .Ellman, *Chem. Rev.* 1996, 96, (1), 555–600). The coupling may be repeated to ensure complete conversion to the desired coupled product. Cleavage from the solid support by treatment with TFA affords the corresponding indoles and indolines (XXX) as their TFA salts.

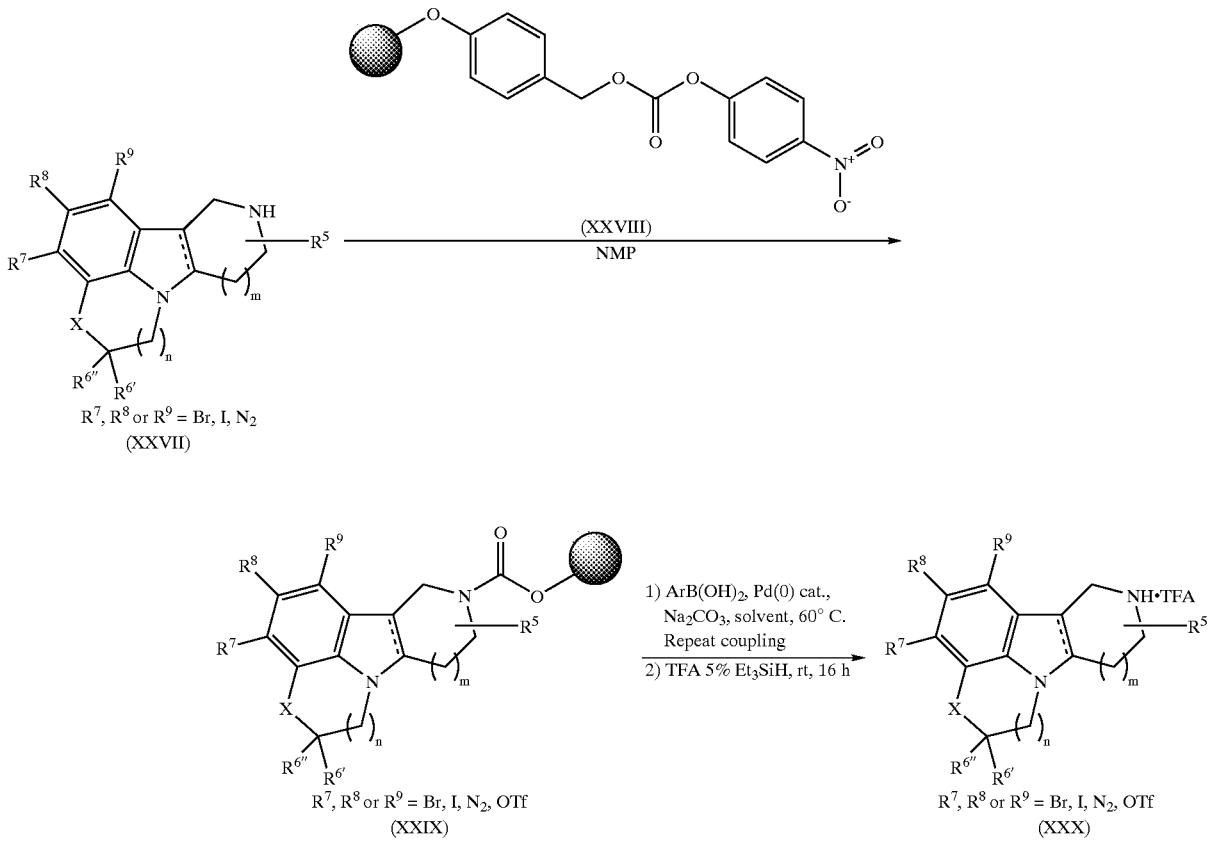

SCHEME 8

In addition, there exists a wide range of procedures and protocols for functionalizing haloaromatics, aryldiazonium and aryltriflate compounds. These procedures are well known by those in the art and described, for example, by Stanforth, S. P., Tetrahedron, 1998, 263; Buchwald, S. L., et. al., *J. Am. Chem. Soc.,* 1998, 9722; Stille, J. K., et. al., *J. Am. Chem. Soc.,* 1984, 7500. Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York, 1995.

One such method to prepare compounds of Formula (I) with substituted $R^1$ sidechains in a more direct manner is shown in Scheme 9. Alkylation of the indole or indoline derivatives (I, $R^1$=H) with a haloalkyl ester, such as $ClCH_2(CH_2)_pCO_2Me$, in the presence of NaI or KI and a base such as $K_2CO_3$, $Na_2CO_3$ or the like, in dioxane or THF or other such solvent while heating (see Glennon, R. A., et. al., *Med. Chem. Res.,* 1996, 197) affords the $R^1$ alkylated esters. Subsequent formation of the activated amides (XXXI) is accomplished by treatment of the ester with N,O-dimethylhydroxylamine hydrochloride and a Lewis acid such as trimethylaluminum or triethylaluminum in toluene (see, for example, Golec, J. M. C., et. al., *Tetrahedron,* 1994, 809) at 0° C. Treatment of the amide (XXXI) with a variety of organometallic agents, such as Grignard reagents $R^{1a}MgBr$, alkyl and aryl lithium reagents etc. (see Sibi, M. P., et. al., *Tetrahedron Lett.,* 1992, 1941; and more generally House, H. O., *Modern Synthetic Reactions,* W. A. Benjamin, Inc., Menlo Park, Calif., 1972), in a suitable solvent such as THF, ether, etc. at low temperatures affords the substituted ketones (XXXII).

SCHEME 9

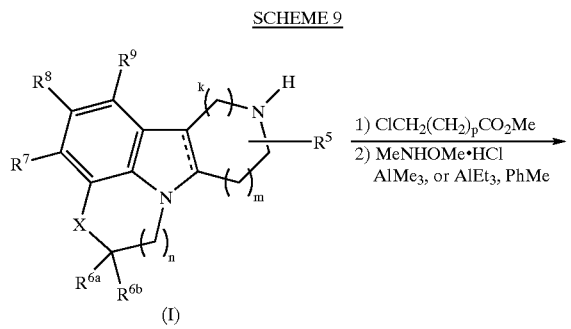

(I)

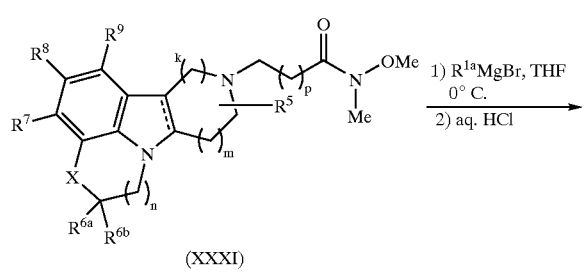

(XXXI)

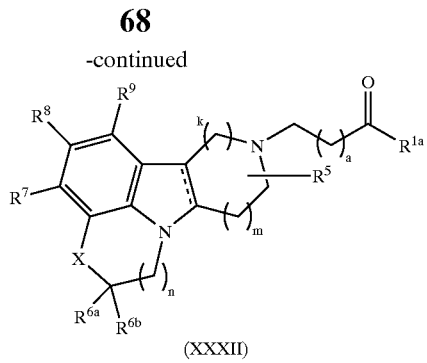

(XXXII)

Preparation of compounds of Formula (I) where m=0, k=1 is outlined in Scheme 10 and described here. Fischer indole cyclization of the previously described hydrazine (III) with a known protected 2,3-dioxopyrolidine (Carlson, E. H., et. al., *J. Org. Chem.*, 1956, 1087) under a variety of typical cyclization conditions affords the tetracyclic indole (XXXIII). The reduction may be accomplished with a variety of reducing agents, for example, LAH, DIBAL, etc., to yield the pyrole fused indole (XXXIV). This derivative can then be deprotected and subsequently alkylated as described previously (see Greene, T. W., Wuts, P. G. W., "Protective Groups in Organic Synthesis, 2nd Edition", John Wiley and Sons, Inc., New York, 1991, and Scheme 1), to give the $R^1$ alkylated indole analogs (XXXV). Alternatively, reduction of the indole to the indoline, as described previously (see Scheme 1), followed by deprotection of the benzyl group to give (XXXVI) and alkylation gives access to the corresponding $R^1$ alkylated indoline derivatives (XXXVII). All the previously described methods to functionalize the aromatic ring, and to afford derivatives of varying $R^1$ sidecahins are applicable to these cores.

SCHEME 10

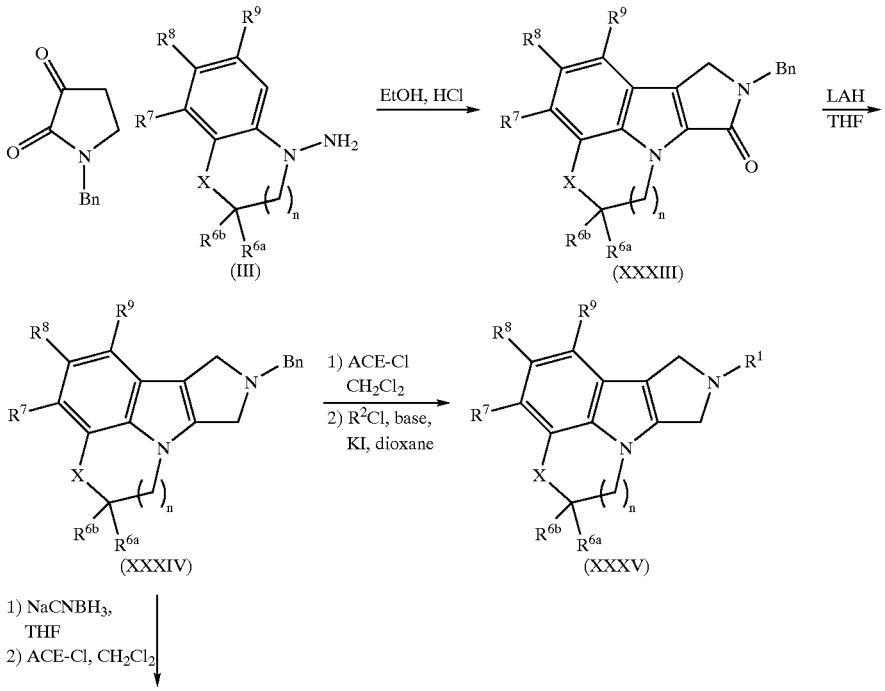

-continued

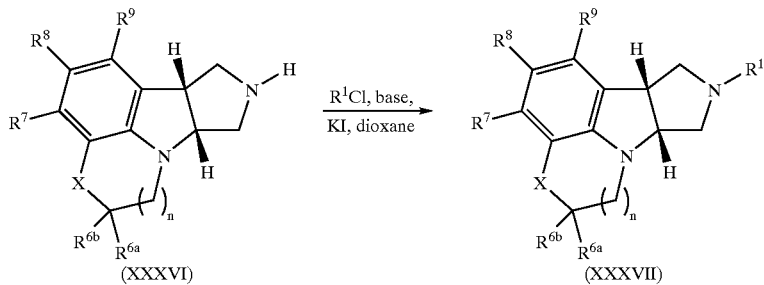

(XXXVI) → (XXXVII)

Reagents: R¹Cl, base, KI, dioxane

EXAMPLES

Chemical abbreviations used in the Examples are defined above. The detailed processes for preparing the compounds of Formula (I) are illustrated by the following Examples. It is, however, understood that this invention is not limited to the specific details of these examples. The Examples as set forth below are intended to demonstrate the scope of the invention but are not intended to limit the scope of the invention. Proton nuclear magnetic resonance spectra ($^1$H NMR) were measured in chloroform-d (CDCl$_3$) unless otherwise specified and the peaks are reported in parts per million (ppm) downfield from tetramethylsilane (TMS). The coupling patterns are reported as follows: s, singlet; d, doublet; dd, doublet of doublets; t, triplet; q, quartet; m, multiplet; bs, broad singlet; bm, broad multiplet.

Example 4 ethyl 1-fluoro-6,7,9,12-tetrahydro-5H-pyrido[4,3-b][1,4]thiazepino[2,3,4-hi]indole-11(10H)-carboxylate Step A:

p-Fluorothiophenol (5 g, 40 mmol) and β-propiolactone (2.8 g, 40 mmol) were dissolved in THF (36 mL of freshly distilled) and then placed in an ice bath. 95% sodium hydride (1 g, 42.9 mmol) was added in small portions over 1 hour. The reaction was allowed to stir at 0° C. for 2 hours, then placed in the freezer overnight. The reaction was quenched with ice chips and then acidified with concentrated hydrogen chloride until a pH of 2. The product was extracted with ethyl acetate (1×200 mL) and dichloromethane (2×200 mL), dried (sodium sulfate) and concentrated to give 3-[(4-fluorophenyl)sulfanyl]propanoic acid (7.08 g, 89%). $^1$H NMR (CDCl$_3$, 300 MHz): δ 7.42–7.35 (m, 2H), 7.02 (t, 2H, J=8.6 Hz), 4.35 (t, 1H, J=6.2 Hz), 3.10 (t, 2H, J=7.3 MHz), 2.63 (t, 2H, J=7.3 Hz) ppm.

Step B:

3-[(4-fluorophenyl)sulfonyl]propanoic acid (3 g, 15 mmol) was dissolved in dichloromethane (30 mL) and cooled to 0° C. in an ice bath. Oxalyl chloride (10 mL) was added slowly, dimethyl formamide (1 drop) was added and the reaction mixture was stirred at 0° C. for 0.5 hours. At which point the reaction was concentrated under reduced pressure to a residue, then resuspended in dichloromethane and cooled to 0° C. in an ice bath, CS$_2$ (1 mL) was added and AlCl$_3$ (4 g, 15 mmol) was added slowly. The reaction mixture was then allowed to warm to room temperature and stirred over night. Ice chips and water (250 mL) were added and stirred. Concentrated hydrogen chloride was added until pH of 2, and extracted with dichloromethane (3×150 mL). Organics were combined, washed with brine (1×100 mL) and water (1×100 mL), dried (sodium sulfate), and concentrated to a yellow solid. The solid was purified by flash column chromatography on 100 g silica gel, eluting 10% ethyl acetate in hexanes to give 6-fluoro-2,3-dihydro-4H-1-benzothiopyran-4-one (2.55 g, 93%). $^1$H NMR (CDCl$_3$, 300 MHz): δ 7.80–7.76 (m, 1H), 7.27–7.23 (m, 2H), 7.15–7.09 (m, 1H), 3.23 (t, 2H, J=6.4 Hz), 2.97 (t, 2H, J=6.4 Hz) ppm.

Step C:

6-fluoro-2,3-dihydro-4H-1-benzothiopyran-4-one (100 mg, 0.54 mmol) was dissolved in acetic acid (0.5 mL, 1.1 eq), sodium azide (71.2 mg, 1.1 mmol) was added and mixture was heated to 50° C. Sulfuric acid (0.13 mL, 4.3 eq) was added slowly and stirred at 50° C. for 1.5 hours. Ice chips (150 mg) were added and a green solid precipitated, this was filtered, washed with water and dried to give 7-fluoro-2,3-dihydro-1,5-benzothiazepin-4(5H)-one (80 mg, 24%). $^1$H NMR (CDCl$_3$, 300 MHz): δ 7.77 (s-broad, 1H), 7.69 (t, 1H, J=7.3 Hz), 6.94–6.82 (m, 2H), 3.42 (t, 2H, J=7 Hz), 2.63 (t, 2H, J=6.7 Hz) ppm.

Step D: #

7-fluoro-2,3-dihydro-1,5-benzothiazepin-4(5H)-one (76 mg, 0.38 mmol) dissolved in toluene (1 mL) and cooled to 0° C. in an ice bath. Red-Al (275 mL, 0.91mmol) was added and then the reaction allowed to warm to room temperature. The reaction was heated at reflux for 1.5 hours. 1 N sodium hydoxide was added slowly until pH>10, this was stirred for 10 minutes, extracted with dichloromethane (3×25 mL), washed with water, and dried (sodium sulfate). The concentrated organics were purified by preparative thin layer chromatography on silica gel and eluted with 50% ethyl acetate in hexanes to give 7-fluoro-2,3,4,5-tetrahydro-1,5-benzothiazepine (30.8 mg, 93%). $^1$H NMR (CDCl$_3$, 300 MHz): δ 7.32 (t, 1H, J=7.5 Hz), 6.53–6.42 (m, 2H), 4.09 (s-broad, 1H), 3.31–3.27 (m, 2H), 2.83–2.79 (m, 2H), 2.11–2.04 (m, 2H) ppm.

Step E:

7-fluoro-2,3,4,5-tetrahydro-1,5-benzothiazepine (423 mg, 2.3 mmol) was dissolved in acetic acid (1.15 mL)at 0° C. in an ice bath. 2.7 M aqueous sodium nitrite (1 mL) was added and this was stirred over night. Water was added (100 mL) and extracted with dichloromethane (3×50 mL), the organics were combined and concentrated to give 7-fluoro-5-nitroso-2,3,4,5-tetrahydro-1,5-benzothiazepine (449 mg, 92%). $^1$H NMR (CDCl$_3$, 300 MHz): δ 7.43 (t, 1H, J=7.1 Hz), 7.30 (dd, 1H, J=9.1 Hz, J=9.2 MHz), 7.26–7.00 (m, 1H), 4.18 (t, 2H, J=5.8 Hz), 2.86 (t, 2H, J=7.2 Hz), 2.17–2.04 (m, 2H) ppm.

Step F:

7-fluoro-5-nitroso-2,3,4,5-tetrahydro-1,5-benzothiazepine (449 mg, 2.11 mmol) was suspended in THF (1 mL of freshly distilled) and cooled to 0° C. in an ice bath. Lithium aluminum hydride (80 mg, 2.11 mmol) was added in a portion-wise fashion. The flask was removed from the ice bath and allowed to warm to room temperature and was stirred for 2 hours. Water (0.08 mL) was added and stirred for 10 minutes. 15% sodium hydroxide (0.08 mL) was added stirred for 10 minutes. Water (0.024 mL) was added and stirred for 10 minutes. The reaction was extracted with dichloromethane (2×25 mL). The organics were concentrated to a residue, then taken up in minimal amount of dichloromethane and then hydrogen chloride in ether (1 M) was added until precipatation formed, the precipatate was filtered off to give 7-fluoro-3,4-dihydro-1,5-benzothiazepin-5(2H)-amine (471 mg, 95%). $^1$H NMR (CD$_3$OD, 300 MHz): δ 7.59 (t, 1H, J=7.5 Hz), 7.28 (d, 1H, J=9.9 Hz), 7.00 (t, 1H, J=8.2 Hz), 3.52 (t, 1H, J=7.5 Hz), 2.92–2.86 (m, 1H), 2.72–2.70 (m, 2H), 2.40–2.31 (m, 1H), 2.2–2.18 (m, 2H) ppm.

Step G:

7-fluoro-3,4-dihydro-1,5-benzothiazepin-5(2H)-amine (470 mg, 2 mmol), 1-carbethoxy-4-piperidone (0.3 mL, 2mmol), and ethanol (11 mL) were all combined and heated to reflux overnight. The reaction was concentrated to a residue and purified by flash column chromatography on 20 g of silica, eluting with (1%, 2%, 3%, and 10%) methanol in dichloromethane to give the title compound (115 mg, 54%). $^1$H NMR (CDCl$_3$, 300 MHz): δ 6.84 (t, 1H, J=6.4 Hz), 6.50 (t, 1H, J=6 Hz), 4.72 (s-broad, 2H), 4.47 (t, 2H, J=5.8 Hz), 4.20–4.13 (m, 2H), 3.82 (s-broad, 2H), 3.27 (t, 2H, J=6.7 Hz), 2.69 (s-broad, 2H), 2.27 (q, 2H, J=6.1 Hz), 1.36 (t, 3H, J=6.9 Hz) ppm. Mass Spec (ESI): 335 (base M+H).

Example 196

8-[4-(4-fluorophenyl)-4-oxobutyl]-7,8,9,10-tetrahydro-1H-pyrido[3',4':4,5]pyrrolo[1,2,3-de]quinoxalin-2(3H)-one 7,8,9,10-hexahydro-2-oxo-1H-pyrido[3',4':4,5]-pyrrolo[1,2,3-de]quinoxalin-2(3H)-one (108 mg, 0.48 mmol) was dissolved in 1.2 mL of MEK. KI (80 mg, 0.48 mmol) and K$_2$CO$_3$ (193 mg, 1.40 mmol), and 4-chloro-4'-fluorobutyrophenone (124 mg, 0.62 mmol) were added. The suspension was refluxed for 48 hrs and then cooled to rt. The suspension was filtered and the residue was washed with CH$_2$Cl$_2$ (5mL). The solution was concentrated in vacuo. The residue was purified by column chromatography (10% MeOH—CH$_2$Cl$_2$) to afford the title compound (20.1 mg, 11%) as a white amorphous solid. $^1$H NMR (CDCl$_3$, 300 MHz) δ 7.90–7.94 (m, 2 H), 7.00–7.05 (m, 3H), 6.84–6.89 (m, 1H), 6.42 (d, 1H, 7.0 Hz), 4.74 (s, 2H), 3.66 (s, 2H), 3.00 (t, 2H, 6.9 Hz), 2.78–2.90 (m, 2H), 2.50–2.77 (m, 4H), 1.90–2.05 (m, 2H) ppm. MS (ESI): 392.2 (base, M+H).

Example 197

4-((8aS,12aR)-6,7,9,10,12,12a-hexahydro-5H-pyrido[4,3-b][1,4]thiazepino[2,3,4-hi]indol-11(8aH)-yl)-1-(4-methylphenyl)-1-butanone hydrochloride General Procedure A:

To a suspension of (8aS,12aR)-6,7,8a,9,10,11,12,12a-octahydro-5H-pyrido[4,3-b][1,4]thiazepino[2,3,4-hi]indole 0.5 mmol) in 1,4-dioxane (3 mL) was added the corresponding chlorobutyrophenone (0.5–1.0 mmol), potassium iodine (100 mg) and potassium carbonate (300 mg). The reaction mixture was heated at reflux for 2 days. The solvent was removed under reduced pressure. The residue was treated with water (50 mL) and extracted with diethyl ether ( 3×50 mL). The ether extract was washed with brine (150 mL), dried over MgSO$_4$, filtered and concentrated to a residue. The residue was purified by flash column chromatography (Silica gel, CH$_2$Cl$_2$:CH$_3$OH 9:1). The product was dissolved in ether (2 mL) and stirred at 0° C. for 10 minutes, added 1N HCl in ether (0.5 mL) at 0° C. The white crystalline solid was collected by filtration to give the title compound in 50–90 % yield.

General procedure B:

To a suspension of (8aS,12aR)-6,7,8a,9,10,11,12,12a-octahydro-5H-ptrido[4,3-b][1,4]thiazepino[2,3,4-hi]indole 0.5 mmol) in 1,4-dioxane (3 mL) was added the corresponding alkyl halide (0.5–1.0 mmol), potassium iodine (100 mg) and triethylamine (1.5 mmol). The reaction mixture was heated at reflux for 2 days. The solvent was removed under reduced pressure. The residue was treated with water (50 mL) and extracted with diethyl ether ( 3×50 mL). The ether extract was washed with brine (150 mL), dried over MgSO$_4$, filtered and concentrated to a residue. The residue was purified by flash column chromatography (Silica gel, CH$_2$Cl$_2$:CH$_3$OH 9:1). The product was dissolved in ether (2 mL) and stirred at 0° C. for 10 minutes, added 1N HCl in ether (0.5 mL) at 0° C. The white crystalline solid was collected by filtration to give the title compound in 50–90 % yield.

The title compound was prepared from addition of 4-chloro-4'-methylbutyrophenone to (8aS,12aR)-6,7,8a,9,10,11,12,12a-octahydro-5H-ptrido[4,3-b][1,4]thiazepino[2,3,4-hi]indole following General procedure A above. $^1$H NMR (300 MHz, CDCl$_3$) δ 7.86 (d, J=8.0 Hz, 2H), 7.25 (d, J=8.0 Hz, 2H), 6.94 (d, J=7.7 Hz, 1H), 6.84 (d, J=7.3 Hz, 1H), 6.61 (dd, J=7.7 Hz, 7.3 Hz, 1H), 3.72–3.86 (m, 2H), 3.44–3.59 (m, 2H), 3.22–3.27 (m, 1H), 2.98–3.14 (m, 7H), 2.41 (s, 3H), 2.68–2.84 (m, 2H), 1.89–2.16 (m, 6H) ppm. MS-ESI: 407 [MH]$^+$ Example 203

(8aS,12aR)-11-[3-(4-fluorophenoxy)propyl]-6,7,8a,9,10,11,12,12a-octahydro-5H-pyrido[4,3-b][1,4]thiazepino[2,3,4-hi]indole hydrochloride The title compound was prepared from addition of 3-chloro-1-(4-fluorophenoxy)propane to (8aS,12aR)-6,7,8a,9,10,11,12,12a-octahydro-5H-ptrido[4,3-b][1,4]thiazepino[2,3,4-hi]indole following General procedure A of Example 197. $^1$H NMR (300 MHz, CDCl$_3$) δ 6.91–7.00 (m, 3H), 6.79–6.87 (m, 3H), 6.62 (dd, J=7.7 Hz, 7.3 Hz, 1H), 3.97 (t, J=6.2, 2H), 3.70–3.87 (m, 1H), 3.50–3.60 (m, 1H), 3.18–3.31 (m, 2H), 2.90–3.12 (m, 2H), 2.70–2.80 (m, 2H), 2.40–2.62 (m, 2H), 2.22–2.38 (m, 1H), 1.90–2.11 (m, 7H) ppm. MS-ESI: 399 [MH]$^+$ Example 210

4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-pyridinyl)-1-butanone hydrochloride The title compound was prepared from addition of the of 4-chloro-1-(4-pyridyl)butan-1-one to 3-methyl-2,3,6b,7,8,9,10,10a-octahydro-1H-pyrido[3',4':4,5]pyrrolo[1,2,3-de]quinoxaline following General procedure A of Example 197. $^1$H NMR (300 MHz, CDCl$_3$) δ 8.79 (dd, J=4.4 Hz, 1.8 Hz, 2H), 7.74 (dd, J=4.4 Hz, 1.4 Hz, 2H), 6.64 (dd, J=7.4 Hz, 7.6 Hz, 1H),6.49 (d, J=6.9 Hz, 1H), 6.39 (d, J=7.7 Hz, 1H), 3.54–3.62 (m, 1H), 3.23–3.31 (m, 2H), 3.13–3.17 (m, 1H), 2.95–3.03 (m, 2H), 2.85 (s, 3H), 2.76–2.84 (m, 2H), 2.57–2.60 (m, 1H), 2.31–2.41 (m, 1H), 2.22 (td, J=11.7 Hz, 2.9 Hz, 1H), 1.92–2.02 (m, 3H),1.83–1.88 (m, 1H), 1.66–1.76 (m, 2H) ppm. MS (CI, NH$_3$) m/e 376 (base, M+H$^+$).

The title compound was separated into the corresponding enantiomers by chiral chromatographic separation. (Chiralpak AD column, methanol/ethanol 50/50): $^1$H NMR (300 MHz, CDCl$_3$) δ 8.79 (dd, J=4.4 Hz, 1.8 Hz, 2H), 7.74

(dd, J=4.4 Hz, 1.4 Hz, 2H), 6.64 (dd, J=7.4 Hz, 7.6 Hz, 1H),6.49 (d, J=6.9 Hz, 1H), 6.39 (d, J=7.7 Hz, 1H), 3.54–3.62 (m, 1H), 3.23–3.31 (m, 2H), 3.13–3.17 (m, 1H), 2.95–3.03 (m, 2H), 2.85 (s, 3H), 2.76–2.84 (m, 2H), 2.57–2.60 (m, 1H), 2.31–2.41 (m, 1H), 2.22 (td, J=11.7 Hz, 2.9 Hz, 1H), 1.92–2.02 (m, 3H),1.83–1.88 (m, 1H), 1.66–1.76 (m, 2H) ppm. MS (CI, $NH_3$) m/e 376 (base, $M+H^+$).

Example 211

(6bR,10aS)-2,3,6b,7,8,9,10,10a-octahydro-1H-pyrido[3',4':4,5]pyrrolo[1,2,3-de]quinoxaline Step A:

The procedure described in Example 4, Steps E through G, was utilized to prepare ethyl-2-oxo-2,3,9,10-tetrahydro-1H-pyrido[3',4':4,5]-pyrrolo[1,2,3-de]quinoxaline-8(7H)-carboxylate from the corresponding amine, 1,3,4-trihydroquinoxalin-2-one, and ethyl 4-oxopiperidinecarboxylate. This indole (5.74 g, 19.2 mmol) was dissolved in TFA (100 mL). The reaction was cooled to 0° C. $NaCNBH_3$ (3.96 g, 63.0 mmol) was added in small portions over 30 min, keeping the temperature less than 5° C. The reaction was stirred at r.t. for 4 hr. Ice was added to the reaction flask, and the reaction was basified with 50% NaOH until pH=12. Water (80 mL) was added to dissolve the precipitate. The reaction was extracted with $CHCl_3$ (3×200 mL). The combined organic layers were washed with brine, dried, and concentrated to afford ethyl (6bR,10aS)-2-oxo-2,3,6b,9,10,10a-hexahydro-1H-pyrido[3',4':4,5]pyrrolo[1,2,3-de]quinoxaline-8(7H)-carboxylate (4.41 g, 77%). $^1$H NMR ($CDCl_3$, 300 MHz) δ 8.45 bs, 1H), 6.86 (d, J=7.4 Hz, 1H), 6.74 (dd, J=7.7 Hz, 7.7 Hz, 1H), 6.63 (d, J=7.3 Hz, 1H), 4.15 (q, J=7.0 Hz, 2H), 3.89–3.993 (m, 2H), 3.41–3.47 (m, 2H), 3.33–3.41 (m, 2H), 3.12–3.31 (m, 1H), 2.69–2.75 (m, 2H), 1.90–1.92 (m, 2H), 1.28 (t, J=7.3 Hz, 3H) ppm. MS-APcI: 302 $[MH]^+$ Step B:

To ethyl-(6bR,10aS)-2-oxo-2,3,6b,9,10,10a-hexahydro-1H-pyrido[3',4':4,5]pyrrolo[1,2,3-de]quinoxaline-8(7H)-carboxylate (4.41 g, 14.6 mmol) was added 1M $BH_3$ THF complex solution (36.6 mL). The reaction was heated under reflux for 5 hr. After the reaction cooled down to r.t, 6N HCl (40 mL) was added dropwise with chilling. The reaction solution was heated under reflux for 30 minutes. After cooled down to r.t., 1N NaOH was added to adjust the pH to 8. The reaction was extracted with $CH_2Cl_2$ (2×200 mL). The combined organic layers were washed with brine, dried over $MgSO_4$, and concentrated to afford ethyl (6bR,10aS)-2,3,6b,9,10,10a-hexahydro-1H-pyrido[3',4':4,5]pyrrolo[1,2,3-de]quinoxaline-8(7H)-carboxylate (4.10 g, 98%). The product was used in next step without further purification. MS-APcI: 288 $[MH]^+$ Step C:

To ethyl (6bR,10aS)-2,3,6b,9,10,10a-hexahydro-1H-pyrido[3',4':4,5]pyrrolo[1,2,3-de]quinoxaline-8(7H)-carboxylate (4.10 g, 14.3 mmol) was added n-butanol (18.0 mL) and KOH powder (3.0 g). The reaction was heated at 119° C. in a sealed tube for 18 hr. The solvent was removed under reduced pressure. To the residue was added water (30 mL) extracted with $CH_2Cl_2$ (3×50 mL). The combined organic layers were washed with brine, dried over $MgSO_4$, and concentrated to afford the title compound as a pale yellow oil (2.70 g, 78%). MS-ESI: 216 $[MH]^+$ Example 212

4-((6bR,10aS)-2,3,6b,9,10,10a-hexahydro-1H-pyrido[3',4':4,5]pyrrolo[1,2,3-de]quinoxalin-8(7H)-yl)-1-(4-fluorophenyl)-1-butanone Step A:

To 2,3,6b,7,8,9,10,10a-octahydro-1H-pyrido[3',4':4,5]pyrrolo[1,2,3-de]quinoxaline (2.70 g, 10.8 mmol) was added 1N NaOH (40.0 mL) and dioxane (40.0 mL). $Boc_2O$ was added in small portions in 30 minute at 0° C. The reaction was stirred at r.t. for 18 hr. The reaction was extracted with $CH_2Cl_2$ (3×150 mL). The combined organic layers were washed with brine, dried over $MgSO_4$, and concentrated to afford a residue which was purified by flash column chromatography (Hexane/Ethyl acetate: 50/50) to afford tert-butyl-2,3,6b,9,10,10a-hexahydro-1H-pyrido[3',4':4,5]pyrrolo[1,2,3-de]quinoxaline-8(7H)-carboxylate. The racemate could be separated by Chiralcel OD column (5 cm×50 cm, 20 u; IPA/Hexane: 8%) to afford the corresponding enantiomers.

Step B:

To either of the enantiomers of tert-butyl-2,3,6b,9,10,10a-hexahydro-1H-pyrido[3',4':4,5]pyrrolo[1,2,3-de]quinoxaline-8(7H)-carboxylate (790 mg, 2.25 mmol) were added 20% $TFA/CH_2Cl_2$ (5 mL), stirred at r.t. overnight. The solution was concentrated to a residue to afford the TFA salt in 99% yield. To this indoline TFA salt (493.5 mg, 1.5 mmol) was added triethylamine (0.4 mL), $K_2CO_3$ (300 mg) KI (100 mg) and 1,4-dioxane (6 mL). 4-Chloro-4'-fluorobutyrophenone (3.37 mmol) was then added and the mixture was heated at 103° C. in a sealed tube for 2.4 hr. The solvent was removed under reduced pressure. To the residue was added water (30 mL) extracted with $CH_2Cl_2$ (3×50 mL). The combined organic layers were washed with brine, dried over $MgSO_4$, and concentrated to a residue. The residue was purified by flash column chromatography to afford the title compound (280 mg, 53% yield). $^1$H NMR ($CDCl_3$, 300 MHz) δ 7.97–8.02 ( m, 2H), 7.09–7.15 (m, 2H), 6.51–6.61 (m, 2H), 6.38 (dd, J=7.3 Hz, J=1.4 Hz, 1H), 3.64–3.72 (m, 2H), 3.26–3.49 (m, 2H), 3.13–3.24 (m, 2H), 2.99–3.04 (m, 2H), 2.91–2.97 (m, 1H), 2.61–2.79 (m, 2H), 2.43–2.53 (m, 2H), 2.34–2.43 (m, 1H), 1.95–2.13 (m, 4H) ppm. MS-ESI: 380 $[MH]^+$ Example 217

(6bR,10aS)-8-[3-(6-fluoro-1,2-benzisoxazol-3-yl)propyl]-3-methyl-2,3,6b,7,8,9,10,10a-octahydro-1H-pyrido[3',4':4,5]pyrrolo[1,2,3-de]quinoxaline hydrochloride Step A:

To a cold boron trifluoride etherate (280 mmol) solution was added 3-fluorophenol or phenol (89 mmol) and 4-chlorobutyryl chloride (178 mmol). The resulting solution was stirred at 130° C. for 18 hours. The reaction mixture was cooled and poured into ice water (100 mL). After stirring for 10 minutes, the water mixture was extracted with ether (3×100 mL). The ether layer was washed with brine (100 mL), dried over $MgSO_4$, filtered and concentrated to a residue to afford 4-chloro-1-(4-fluoro-2-hydroxyphenyl)butan-1-one and 4-chloro-1-(2-hydroxyphenyl)butan-1-one in 52%-67% yield, which was used in the following step without further purification.

Step B:

To pyridine (25 mL) was added the corresponding ketone from Step A (46.5 mmol) and hydroxylamine hydrochloride (53.5 mmol). The resultant mixture was stirred at ambient temperature overnight and then poured into dilute HCl (100 mL). The mixture was stirred for 5 minutes and extracted with ether (3×50 mL). The ether layer was dried over MgSO₄, filtered and concentrated to a residue to afford (1E)-4-chloro-1-(4-fluoro-2-hydroxyphenyl)-1-butanone oxime and (1E)-4-chloro-1-(2-hydroxyphenyl)-1-butanone oxime in 99% yield, which were used in the following step without further purification.

Step C:

To acetic anhydride (10 mL) was added the corresponding oxime from Step B (40.0 mmol). The reaction mixture was heated at 60° C. for 2 hours, then poured into ether (10 mL). The mixture was washed with sat. NaHCO₃ solution (4×10 mL), then with brine (10 mL). The organic layer was separated, dried over MgSO₄, filtered and concentrated to afford 2-[(1E)-N-(acetyloxy)-4-chlorobutanimidoyl]-5-fluorophenyl acetate and 2-[(1E)-N-(acetyloxy)-4-chlorobutanimidoyl]phenyl acetate in 61%-75% yield.

Step D:

To the corresponding bis-acylated derivatives from Step C (5.2 mmol) in ethanol (4 mL) was added KOH (14.4 mmol). The reaction mixture was refluxed for 2 hours, cooled down to rt, added ethyl acetate (10 mL), washed with brine (10 mL), dried over MgSO₄, filtered and concentrated to a residue. The residue was purified by silica gel flash column chromatography (Ethyl acetate/Hexane: 3:7) to afford 3-(3-chloropropyl)-6-fluoro-1,2-benzisoxazole and 3-(3-chloropropyl)-1,2-benzisoxazole in 32% yield.

Step E:

The title compound was prepared from addition of 3-(3-chloropropyl)-6-fluoro-1,2-benzisoxazole from Step D and (6bR,10aS)-3-methyl-2,3,6b,7,8,9,10,10a-octahydro-1H-pyrido[3',4':4,5]pyrrolo[1,2,3-de]quinoxaline following General procedure A, Example 197. ¹H NMR (300 MHz, CDCl3) δ 7.63 (dd, J=8.8 Hz, 4.7 Hz, 1H), 7.20–7.24 (m, 1H), 7.03–7.10 (m, 1H), 6.65 (dd, J=7.7 Hz, 7.7 Hz, 1H), 6.50 (d, J=7.3 Hz, 1H), 6.41 (d, J=7.3 Hz), 3.73–3.77 (m, 1H), 3.55–3.62 (m, 1H), 3.21–3.32 (m, 3H), 2.91–3.10 (m, 3H), 2.86 (s, 3H), 2.75–2.82 (m, 2H), 2.54–2.63 (m, 1H), 2.41–2.48 (m, 1H), 1.95–2.11 (m, 6H) ppm. MS (CI, NH₃) m/e 407 (base, M+H⁺).

Example 218

(6bR,10aS)-8-[3-(1,2-benzisoxazol-3-yl)propyl]-3-methyl-2,3,6b,7,8,9,10,10a-octahydro-1H-pyrido[3',4':4,5]pyrrolo[1,2,3-de]quinoxaline hydrochloride The title compound was prepared from addition 3-(3-chloropropyl)-1,2-benzisoxazole from Step D Example 22 and (6bR,10aS)-3-methyl-2,3,6b,7,8,9,10,10a-octahydro-1H-pyrido[3',4':4,5]pyrrolo[1,2,3-de]quinoxaline following the General procedure A of Example 197. ¹H NMR (300 MHz, CDCl₃) δ 7.59–7.62 (m, 1H), 7.46–7.50 (m, 2H), 7.20–7.25 (m, 1H), 6.57 (dd, J=7.7 Hz, 7.3 Hz, 1H), 6.43 (d, J=6.9 Hz, 1H), 6.33 (d, J=7.3 Hz), 3.48–3.52 (m, 1H), 3.06–3.25 (m, 4H), 2.94–2.99 (m, 2H), 2.70–2.89 (m, 4H), 2.79 (s, 3H), 2.20–2.65 (m, 3H), 1.92–2.07 (m, 4H) ppm. MS (CI, NH₃) m/e 389 (base, M+H⁺).

Example 255

(6bR,10aS)-3-methyl-2,3,6b,7,8,9,10,10a-octahydro-1H-pyrido[3',4':4,5]pyrrolo[1,2,3-de]quinoxaline The procedure described in Example 4, Steps E through G, was utilized to prepare ethyl 2,3,9,10-tetrahydro-2-oxo-1H-pyrido[3',4':4,5]-pyrrolo[1,2,3-de]quinoxaline-8(7H)-carboxylate from the corresponding amine, 1,3,4-trihydroquinoxalin-2-one, and ethyl 4-oxopiperidinecarboxylate Step A:

Sodium cyanoborohydride (4.0 g, 65 mmol) was added, in small portions, to a vigorously stirred solution of ethyl 2,3,9,10-tetrahydro-2-oxo-1H-pyrido[3',4':4,5]-pyrrolo[1,2,3-de]quinoxaline-8(7H)-carboxylate (11.97 g, 40 mmol) in trifluoroacetic acid (125 mL) cooled in an ice-water bath, under nitrogen. After the addition was complete, the mixture was stirred for 30 min and then poured slowly into ammonium hydroxide (300 mL) containing ice followed by the addition of enough 1N sodium hydroxide to make the mixture basic. The mixture was extracted with dichloromethane (2×) and the extract was washed with water, dried over magesium sulfate, and evaporated to dryness to yield 10.89 g (90%) of ethyl (6bR,10aS)-2-oxo-2,3,6b,9,10,10a-hexahydro-1H-pyrido[3',4':4,5]pyrrolo[1,2,3-de]quinoxaline-8(7H)-carboxylate as an off-white powder, m.p. 167–168° C. (dec., sinters at 70° C.). ¹H NMR (CDCl₃, 300 MHz) δ 1.28 (t, J=7 Hz, 3H), 1.81–1.95 (m, 2H), 3.13–3.22 (m,1H), 3.23–3.39 (m, 1H), 3.44 (d, J=14.7 Hz, 1H), 3.41–3.51(m, 1H), 3.80–3.95 (m, 1H), 3.98 (d, J=14.7 Hz, 2H), 4.16 (q, 2H), 6.59 (d, J=7.7 Hz, 1H), 6.74 (t, J=7.7 Hz, 1H), 6.83 (d, J=7.7 Hz, 1H), 8.17 (s, 1H) ppm. MS (CI): 302 (M+H⁺).

Step B:

Sodium hydride (900 mg of 60% dispersion in oil; 22.5 mmol) was washed with hexane, and suspended in anhydrous dimethylformamide (5 mL). The suspension was added to a stirred solution of ethyl (6bR, 10aS)-2-oxo-2,3,6b,9,10,10a-hexahydro-1H-pyrido[3',4':4,5]pyrrolo[1,2,3-de]quinoxaline-8(7H)-carboxylate (6.02 g, 20 mmol) in anhydrous dimethylformamide (50 mL) under nitrogen. After gas evolution had subsided, the mixture was cooled in ice-water bath and treated with iodomethane (3.55 g., 25 mmol). The mixture was stirred at room temperature for 1 h and then concentrated. The residue was treated with water and extracted with dichloromethane (2×) and the extract was washed with brine, dried over magnesium sulfate and evaporated to dryness to yield 5.48 g (87%) of ethyl (6bR,10aS)-3-methyl-2-oxo-2,3,6b,9,10,10a-hexahydro-1H-pyrido[3',4':4,5]pyrrolo[1,2,3-de]quinoxaline-8(7H)-carboxylate as a tan solid, m.p. 149–151° C. (dec.). [M+H] calc. 316; found 316. ¹H NMR (CDCl₃, 300MHz) δ 1.28 (t, J=7.3 Hz, 3H), 1.85 to 1.93 (m,1H), 2.65 to 2.82 (m, 1H),3.08 to 3.25 (m, 1H), 3.25 to 3.40 (m, 1H),3.30–3.50 (m, 1H), 3.34 (s, 3H), 3.42 (d, J=14.3 Hz, 1H), 3.85 to 4.0 (m,1H), 4.02 (d, J=14.3 Hz, 1H, 4.15 (q, J=7.2 Hz, 4H), 6.76 (d, J=8.1 Hz, 1H), 6.83 (t, J=7.3 Hz, 1H), 6.90 (d, J=7.3 Hz, 1H). MS (CI): 316 (M+H⁺).

Step C:

A solution of borane in tetrahydrofuran (1M, 33 mL, 33 mmol) was added dropwise to a stirred solution of ethyl (6bR, 10aS)-3-methyl-2-oxo-2,3,6b,9,10,10a-hexahydro-1H-pyrido[3',4':4,5]pyrrolo[1,2,3-de]quinoxaline-8(7H)-carboxylate (5.24 g, 16.6 mmol) in anhydrous tetrahydrofuran (25 mL) under nitrogen. After the addition was complete, the mixture was stirred and heated at reflux for 1 h, cooled and treated with 6N hydrochloric acid (15 mL). It was then heated under reflux for 30 min, cooled and evaporated to dryness under reduced pressure. The residue was dissolved in a minimum quantity of water and the solution basified with 1N sodium hydroxide and extracted with dichloromethane (2×). The extract was washed with water, dried over magnesium sulfate, and concentrated to yield 4.65 g (93%) of ethyl (6bR,10aS)-3-methyl-2,3,6b,9,10,10a-hexahydro-1H-pyrido[3',4':4,5]pyrrolo[1,2,3-de]quinoxaline-8(7H)-carboxylate as a viscous liquid. ¹H NMR (CDCl₃, 300 MHz) δ 1.28 (t, J=7 Hz, 3H), 1.68–1.78 (m, 1H), 1.78–1.93 (m, 2H), 2.81–2.90 (m, 2H), 2.86 (s, 3H), 3.05–3.26 (m, 2H), 3.26–3.38 (m, 2H), 3.56–3.75 (m, 2H), 3.79–3.87 (m, 1H), 4.16 (q, J=7 Hz, 2H), 6.41 (d, J=8.1 Hz, 1H), 6.61 (d, J=8.1 Hz, 1H), 6.67 (t, J=8.1 Hz, 1H) ppm. MS (CI): 302 (M+H$^+$).

Step D:

Powdered potassium hydroxide (10.0 g) was added to a stirred solution of ethyl (6bR, 10aS)-3-methyl-2,3,6b,9,10,10a-hexahydro-1H-pyrido[3',4':4,5]pyrrolo[1,2,3-de]quinoxaline-8(7H)-carboxylate (4.52 g, 15.0 mmol) in warm 1-butanol (50 mL) and the resulting mixture was heated under reflux for 5 h. It was then evaporated under reduced pressure and the residue treated with water and extracted with dichloromethane (2×). The extract was washed with water, dried over magnesium sulfate and concentrated to yield 3.27 g (95%) of the title compound as a viscous liquid. $^1$H NMR (CDCl$_3$, 300 MHz) δ 1.74–1.93 (m, 4H), 2.57–2.71 (m, 1H), 2.80–2.95 (m, 3H), 2.87 (s, 3H), 2.95–3.12 (m, 2H), 3.26–3.38 (m, 3H), 3.55–3.64 (m, 1H), 6.41 (d, J=7.3 Hz, 1H), 6.51 (d, J=7.3 Hz, 1H), 6.65 (t, J=7.3 Hz, 1H) ppm. MS (CI): 230 (M+H$^+$)

Example 256

(6bR,10aS)-3-ethyl-2,3,6b,7,8,9,10,10a-octahydro-1H-pyrido[3',4':4,5]pyrrolo[1,2,3-de]quinoxaline Utilizing the material from Example 255 Step A, the title compound was prepared in analogous fashion using ethyl iodide as the alkyl halide and following the procedure of Step B-D of Example 255, as a light brown amorphous solid. $^1$H NMR (CDCl$_3$, 300 MHz) δ 1.15 (t, 3H), 1.70–2.01 (m, 3H), 2.65–2.70 (t, J=9.6 Hz, 3H), 2.70–2.95 (m,2H), 2,95–3.13 (m, 2H), 3.13–3.72 (m, 5H), 3.60–3.95 (m, 1H), 6.39 (d, J=8.0 Hz, 1H), 6.47 (d, J=7,4 Hz, 1H), 6,64 (t, J=7.3 Hz), 1H) ppm. MS (CI): 244 (M+H$^+$).

Step B:

Ethyl (6bR,10aS)-3-ethyl-2-oxo-2,3,6b,9,10,10a-hexahydro-1H-pyrido[3',4':4,5]pyrrolol[1,2,3-de]quinoxaline-8(7H)-carboxylate. Viscous brown liquid. Yield 70%. MS (CI) 330 (M+H$^+$).

Step C:

Ethyl (6bR,10aS)-3-ethyl-2,3,6b,9,10,10a-hexahydro-1H-pyrido[3',4':4,5]pyrrolol[1,2,3-de]quinoxaline-8(7H)-carboxylate. Viscous brown liquid. Yield 70%. MS (CI): 316 (M+H$^+$).

Example 257

(6bR,10aS)-3-propyl-2,3,6b,7,8,9,10,10a-octahydro-1H-pyrido[3',4':4,5]pyrrolo[1,2,3-de]quinoxaline Step A:

Utilizing the material from Example 255 Step A, the title compound was prepared in analogous fashion using propyl iodide as the alkyl halide and following the procedure of Step B-D of Example 255, as an amorphous tan solid. $^1$H NMR (CDCl$_3$, 300 MHz) δ 0.94 (t, 2H), 1.40–2.01 (m, 6H), 2.65–2.70 (t, J=9.6 Hz, 2H), 2.70–2.95 (m, 2H), 2.95–3.45 (m, 7H)), 3.3.60–3.95 (m, 1H), 6.37(d, J=7.7 Hz, 1H), 6.46 (d, J=7.0 Hz, 1H), 6.64 (t, J=7.6 Hz) ppm. MS (CI): 258 (M+H$^+$).

Step B:

Ethyl (6bR,10aS)-3-propyl-2-oxo-2,3,6b,9,10,10a-hexahydro-1H-pyrido[3',4':4,5]pyrrolol[1,2,3-de]quinoxaline-8(7H)-carboxylate. Viscous brown liquid. Yield 72%. MS (CI) 344 (M+H$^+$).

Step C:

Ethyl (6bR,10aS)-3-propyl-2,3,6b,9,10,10a-hexahydro-1H-pyrido[3',4':4,5]pyrrolol[1,2,3-de]quinoxaline-8(7H)-carboxylate. Light brown viscous liquid. Yield 69%. MS (CI): 330 (M+H$^+$).

Example 258

(6bR,10aS)-3-isopropyl-2,3,6b,7,8,9,10,10a-octahydro-1H-pyrido[3',4':4,5]pyrrolo[1,2,3-de]quinoxaline Step A:

Utilizing the material from Example 255 Step A, the title compound was prepared in analogous fashion using isopropyl iodide as the alkyl halide and following the procedure of Step B-D of Example 255, as a viscous brown liquid. $^1$H NMR (CDCl$_3$, 300 MHz) δ 1.18 (d, 6H), 1.60–1.67 (m, 1H), 1.71–1.94 (m, 2H), 2.63–2.75 (m, 2H), 2.81–2.95 (m, 2H), 2.99–3.20 (m, 2H), 3.30–3.55 (m, 3H), 3.99–4.12 (m, 1H), 6.45 (d, J=7.4 Hz, 2H), 6.65 (t, J=7.3 Hz, 1H) ppm. MS (CI): 258 (M+H$^+$).

Step B:

Ethyl (6bR,10aS)-3-isopropyl-2-oxo-2,3,6b,9,10,10a-hexahydro-1H-pyrido[3',4':4,5]pyrrolol[1,2,3-de]quinoxaline-8(7H)-carboxylate. Viscous brown liquid. Yield 69%. MS (CI) 344 (M+H$^+$).

Step C:

Ethyl (6bR,10aS)-3-isopropyl-2,3,6b,9,10,10a-hexahydro-1H-pyrido[3',4':4,5]pyrrolol[1,2,3-de]quinoxaline-8(7H)-carboxylate. Viscous brown liquid. Yield 97%. MS (CI): 330 (M+H$^+$).

Example 259

(6bR,10aS)-3-butyl-2,3,6b,7,8,9,10,10a-octahydro-1H-pyrido[3',4':4,5]pyrrolo[1,2,3-de]quinoxaline Step A:

Utilizing the material from Example 255 Step A, the title compound was prepared in analogous fashion using n-butyl iodide as the alkyl halide and following the procedure of Step B-D of Example 255, as a viscous brown liquid. $^1$H NMR (CDCl$_3$, 300 Mhz) δ 0.95 (t, 3H), 1.30–1.45 (m, 2H), 1.50–1.65 (m, 2H), 1.95–2.15 (m, 2H), 2.65–2.80 (m, 2H), 2.65–2.80 (m, 2H), 2.85–3.08 (m, 1H), 3.08–3.22 (m, 3H), 3.22–3.40 (m, 6H), 3.68–3.78 (m, 1H), 6.38 (d, J=7.1 Hz), 6.46 (d, J=7.1 Hz, 1H), 6.66 (t, J=7.7 Hz, 1H) ppm. MS (CI): 436 (M+H$^+$).

Step B:

Ethyl (6bR,10aS)-3-butyl-2-oxo-2,3,6b,9,10,10a-hexahydro-1H-pyrido[3',4':4,5]pyrrolol[1,2,3-de]quinoxaline-8(7H)-carboxylate. Viscous brown liquid. Yield 82%. MS(CI): 358 (M+H$^+$).

Step C:

Ethyl (6bR,10aS)-3-butyl-2,3,6b,9,10,10a-hexahydro-1H-pyrido[3',4':4,5]pyrrolol[1,2,3-de]quinoxaline-8(7H)-carboxylate. Viscous brown liquid. Yield 92%. MS (CI): 344 (M+H$^+$).

Example 260

(6bR,10aS)-3-benzyl-2,3,6b,7,8,9,10,10a-octahydro-1H-pyrido[3',4':4,5]pyrrolo[1,2,3-de]quinoxaline Step A:

Utilizing the material from Example 255 Step A, the title compound was prepared in analogous fashion using benzyl iodide as the alkyl halide and following the procedure of Step B-D of Example 255, as a viscous liquid. $^1$H NMR (CDCl$_3$, 300 MHz) δ 1.60–2.0 (m, 2H), 2.55–2.95(m, 4H), 2.95–3.15 (m, 2H), 3.20–3.45 (m, 3H), 4,40 (q, J=16.1 Hz, 2H), 6.41 (d, J=7.1 Hz, 1H), 6.51 (d, J=7.1 Hz, 1H), 6.62 (t, J=7.1 Hz, 1H), 7.20–7.40 (m, 5H) ppm. MS (CI): 306 (M+H$^+$).

Step B:

Ethyl (6bR,10aS)-3-benzyl-2-oxo-2,3,6b,9,10,10a-hexahydro-1H-pyrido[3',4':4,5]pyrrolo1[1,2,3-de]quinoxaline-8(7H)-carboxylate. Viscous brown liquid. Yield 80%. MS (CI) 392 (M+H$^+$).

Step C:

Ethyl (6bR,10aS)-3-benzyl-2,3,6b,9,10,10a-hexahydro-1H-pyrido[3',4':4,5]pyrrolo1[1,2,3-de]quinoxaline-8(7H)-carboxylate. Viscous brown liquid. Yield 85%. MS (CI): 378 (M+H$^+$).

Example 261

4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone A mixture of 3-methyl-2,3,6b,7,8,9,10,10a-octahydro-1H-pyrido[3',4':4,5]pyrrolo[1,2,3-de]quinoxaline (3.20 g, 14 mmol), 4-chloro-4'-fluoro-butyrophenone (4.21 g, 21 mmol), triethylamine (3 mL), potassium iodide (3.48 g, 21 mmol), dioxane (25 mL), and toluene (25 mL) was stirred and refluxed for 15 h under an atmosphere of nitrogen and then evaporated under reduced pressure to remove the volatiles. The residue was triturated with a small volume of dichloromethane and decanted from the insoluble material. The process was repeated two more times and the combined dichloromethane solutions was added to 0.5N solution of hydrogen chloride in ether(200 mL). The salt that separated was filtered off, washed with ether, dissolved immediately in a minimum quantity of water and the solution extracted with ether. The ether extract was discarded and aqueous layer basified with 10% aqueous sodium hydroxide. The resulting mixture was extracted with dichloromethane (2×) and the extract dried over magnesium sulfate and stripped of the solvent under reduced pressure to yield 4.15 g (75%) of a highly viscous brown liquid. $^1$H NMR (CDCl$_3$, 300 MHz) δ 1.79–2.13 (m, 6H), 2.21–2.32 (m, 1H), 2.32–2.44 (m, 2H), 2.60–2.71 (m, 1H), 2.75–2.92 (m, 2H), 2.86 (s, 3H), 2.98 (t, J=7.3Hz, 2H), 3.04–3.16 (m, 1H), 3.16–3.35 (m, 2H), 3.55–3.64 (m, 1H), 6.39 (d, J=8.1 Hz, 1H), 6.50 (d, J=8.1 Hz, 1H), 6.64 (t, J=7.7 Hz, 1H), 7.12 (t, 2H), 8.01 (m, 2H) ppm. MS (CI): 394 (M+H$^+$).

The above compound was resolved into its enantiomers on chiral HPLC column. 4-((6bS,10aR)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone. Viscous tan liquid. [a]$^D$=−36.8° (c=0.886, CHCl$_3$). MS (CI): 394 (M+H$^+$).

4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone. Viscous tan liquid. [a]$^D$=+33.6° (c=0.646, CHCl$_3$). MS (CI): 394 (M+H$^+$).

Example 262

4-((6bR,10aS)-3-ethyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone Treatment of (6bR,10aS)-3-ethyl-2,3,6b,7,8,9,10,10a-octahydro-1H-pyrido[3',4':4,5]pyrrolo[1,2,3-de]quinoxaline according to the procedure of Example 261 afforded the title compound in good yield as a viscous brown liquid. $^1$H NMR (300 MHz, CDCl$_3$) δ 1.15 (t, J=7.0 Hz, 3H), 1.75–2.03 (m, 5H), 2.20 to 2.30 (m, 1H), 2.30–2.42 (m,2H), 2.63 to 2.77 (m, 3H), 2.77 to 2.87 (m,1H), 2.98 (t, J=7.0 HZ, 2H), 3.04–3.43 (m, 5H), 3.64–3.72 (m, 1H0, 6.30 (d, J=7.7 Hz, 1H), (6.47 d, J=7.7 Hz, 1H), 6.64 (d, J=7.7 Hz, 1H), 7.12 (t, J=8.5 Hz, 2H), 7.98 to 8.03 (m, 2H) ppm. MS (CI): 408 (M+H$^+$).

Example 263

4-((6bR,10aS)-3-isopropyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone Treatment of (6bR,10aS)-3-isopropyl-2,3,6b,7,8,9,10,10a-octahydro-1H-pyrido[3',4':4,5]pyrrolo[1,2,3-de]quinoxaline according to the procedure of Example 261 afforded the title compound in good yield as a viscous, brown liquid. $^1$H NMR (CDCl$_3$, 300 MHz) δ 1.18 (d, J=6.6 Hz, 6H), 1.82–1.84 (m, 5H), 2.21–2.29 (m, 1H), 2.29–2.41 (m, 2H), 2.64–2.68 (m, 2H), 2.79–2.87 (m, 1H), 2.98 (t, J=7.3 Hz, 2H), 3.03–3.17 (m, 2H), 3.21–3.45 (m, 3H), 4.03 (dt, J=6.6, 2.3 Hz, 1H), 6.45 (d, J=6.2 Hz, 2H), 6.64 (t, J=7.7 Hz, 1H), 7.12 (t, J=8.3 Hz, 2H), 8.0–8.03 (m, 2H) ppm. MS(CI): 422 (M+H$^+$).

Example 264

4-((6bR,10aS)-3-benzyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone Treatment of (6bR,10aS)-3-benzyl-2,3,6b,7,8,9,10,10a-octahydro-1H-pyrido[3',4':4,5]pyrrolo[1,2,3-de]quinoxaline according to the procedure of Example 261 afforded the title compound in good yield as a viscous brown liquid. Yield 23%. $^1$H NMR (CDCl$_3$, 300 MHz,) δ 1.84–2.05 (m, 5H), 2.20–2.31 (m, 1H), 2.31–2.43 (m, 2H), 2.64–2.72 (m ,1H), 2.72–2.80 (m, 1H), 2.80–2.89 (m, 1H), 2.99 (t, J=7.3 Hz, 2H), 3.06–3.14 (m, 1H), 3.14–3.26 (m, 1H), 3.26–3.34 (m, 2H), 3.65–3.74 (m, 1H), 4,43 (q, J=16.5 Hz, 2H), 6.40 (d, J=8.0 Hz, 1H), 6.50 (d, J=7.0 Hz, 1H), ) 6.61 (t, J=8.1 Hz, 1H), 7.13 (t, J=8.5 Hz, 2H) 7.20–7.35 (m, 5H), 8.00–8.03 (m, 2H) ppm. MS (CI): 470 (M+H$^+$).

Example 269

(6bR,10aS)-8-[3-(4-fluorophenoxy)propyl]-3-methyl-2,3,6b,7,8,9,10,10a-octahydro-1H-pyrido[3',4':4,5]pyrrolo[1,2,3-de]quinoxaline Treatment of (6bR,10aS)-3-methyl-2,3,6b,7,8,9,10,10a-octahydro-1H-pyrido[3',4':4,5]pyrrolo[1,2,3-de]quinoxaline according to the procedure of Example 203 afforded the title compound in good yield as a viscous liquid. Yield 30%. $^1$H NMR (CDCl$_3$, 300 MHz): δ 1.85–2.10 (m, 5H), 2.20–2.40 (m, 1H)2.40–2.60 (m, 2H), 2.66–2.78 (m, 1H), 2.78–2.95 (m, 2H), 2.87 (t, 3H), 3.10–3.35 (m, 4H), 3.55–3.70 (m, 1H), 3.97 (t, J 6.2 Hz, 2H), 6.40 (d, J=7.7 Hz, 1H), 6.52 (d, J=7.3 Hz, 1H), 6.65 (t, J=7.7 Hz, 1H), 6.79–6.90 (m, 2H), 6.96 (t, J=8.5 Hz, 2H) ppm. MS (CI): 382 (M+H$^+$).

Example 274

(6bR,10aS)-5-(2,4-dichlorophenyl)-3-methyl-2,3,6b,7,8,9,10,10a-octahydro-1H-pyrido[3',4':4,5]pyrrolo[1,2,3-de]quinoxaline To a solution of tert-butyl (6bR,10aS)-5-(2,4-dichlorophenyl)-3-methyl-2-oxo-2,3,6b,9,10,10a-hexahydro-1H-pyrido[3',4':4,5]pyrrolo[1,2,3-de]quinoxaline-8(7H)-carboxylate (100 mg, 0.21 mmol) in THF (5.0 mL), BH$_3$-THF (1M in THF) (0.82 mL, 0.82 mmol) was added dropwise. After addition was completed, the resulting reaction mixture was refluxed for 4 h, cooled to room temperature, and quenched cautiously with water (1.0 mL). The mixture was evaporated to dryness under reduced pressure and the residue obtained was treated with o-xylene (10 mL) and 1-octene (5 mL) and heated at reflux for 4 h. The reaction mixture was cooled to room temperature and concentrated to dryness under reduced pressure to give tert-butyl (6bR,10aS)-5-(2,4-dichlorophenyl)-3-methyl-2,3, 6b,9,10,10a-hexahydro-1H-pyrido[3',4':4,5]pyrrolo[1,2,3-de]quinoxaline-8(7H)-carboxylate as a white solid (50 mg, 58%).

The hydrochloride salt of the title compound was prepared from tert-butyl (6bR,10aS)-5-(2,4-dichlorophenyl)-3-methyl-2,3,6b,9,10,10a-hexahydro-1H-pyrido[3',4':4,5]pyrrolo[1,2,3-de]quinoxaline-8(7H)-carboxylate (50 mg) using the deprotection procedures described in Example 275, Step B. The salt formed was free-based with 6 N NaOH to give the title compound (31 mg, 80%). $^1$H NMR (CD$_3$OD, 300 MHz) δ 1.80–1.90 (m, 1H), 1.96–2.10 (m, 1H), 2.50 (m, 2H), 2.76–2.90 (m, 5H), 2.93–3.1 (m, 2H), 3.20–3.50 (m, 4H), 3.50–3.60 (m, 2H), 6.40 (d, 1H), 6.5 (d, 1H), 7.22–7.32 (m, 2H), 7.44 (d, 1H) ppm. MS-CI m/z=374 [C$_{20}$H$_{21}$Cl$_2$N$_3$+H]$^+$ Example 275

(6bR,10aS)-5-(2,4-dichlorophenyl)-2,3,6b,7,8,9,10, 10a-octahydro-1H-pyrido[3',4':4,5]pyrrolo[1,2,3-de] quinoxaline hydrochloride Step A:

Typical Procedure for Suzuki Coupling: The corresponding bromo-indoline (1.0 equiv), the boronic acid (1.5–2 equivs) and barium hydroxide (1.5 equivs) were stirred into a solution of water and DME, then heated at 60° C. while bubbling through a stream of Argon gas for 20 min.

The reaction mixture was then cooled to room temperature and Pd(PPh$_3$)$_2$Cl$_2$ (2.5–5 mol %) and PPh$_3$ (3 equivs based on Pd source) were quickly added and refluxing resumed for 4 hours. When the reaction was completed as shown by TLC, ethyl acetate was added and the mixture was filtered through a Celite bed. Organic layer was separated, dried over sodium sulfate and concentrated under reduced pressure to a yellow oil. This residue was purified on a flash column eluting with 10% EtOAc/Hexanes to give the desired product.

Tert-butyl (6bR, 10aS)-5-(2,4-dichlorophenyl)-2,3,6b,9, 10,10a-hexahydro-1H-pyrido[3',4':4,5]pyrrolo[1,2,3-de] quinoxaline-8(7H)-carboxylate (37 mg, 60%) was prepared via coupling of tert-butyl (6bR, 10aS)-5-bromo-2,3,6b,9,10, 10a-hexahydro-1H-pyrido[3',4':4,5]pyrrolo[1,2,3-de] quinoxaline-8(7H)-carboxylate (50 mg, 0.13 mmol) with 2,4-dichlorophenyl boronic acid (74 mg, 0.39 mmol) as illustrated above using the general procedure for Suzuki coupling. $^1$H NMR (CDCl$_3$, 300 MHz) δ 1.46 (s, 9H), 1.82–1.96 (m, 2H), 2.74–2.82 (m, 1H), 2.99–3.05 (m, 1H), 3.16–3.22 (m, 2H), 3.33–3.39 (m, 1H), 3.43–3.50 (m, 1H), 3.52–3.57 (m, 1H), 3.62–3.69 (m, 1H), 3.43–3.50 (m, 1H), 3.52–3.57 (m, 1H), 3.62–3.69 (m, 1H), 3.71–3.79 (m, 1H), 3.80–3.85 (m, 1H), 3.89–4.14 (m, 1H), 6.44 (s, 1H), 6.59 (s, 1H), 7.22 (s, 2H), 7.42 (s, 1H) ppm.

Step B:

General procedure for removal of Boc protecting group: The indoline (100–150 mg) is mixed with cold ethanolic hydrochloric acid (4M) (5 mL), and the solution is stirred for 10 min at 0° C. The solvent is removed under reduced pressure and the residue is disolved in hot acetonitrile with a small amount of methanol. Upon cooling to room temperature, the desired salt is obtained as a crystalline material.

(6bR,10aS)-5-(2,4-dichlorophenyl)-2,3,6b,7,8,9,10,10a-octahydro-1H-pyrido[3',41:4,5]pyrrolo[1,2,3-de] quinoxaline hydrochloride (57 mg, 78%) was formed from tert-butyl (6bR, 10aS)-5-(2,4-dichlorophenyl)-2,3,6b,9,10, 10a-hexahydro-1H-pyrido[3',4':4,5]pyrrolo[1,2,3-de] quinoxaline-8(7H)-carboxylate (110 mg) using the deprotection procedure described above to afford the title compound. $^1$H NMR (CD$_3$OD, 300 MHz) δ 1.80–1.92 (m, 1H), 1.96–2.10 (m, 1H), 2.5–2.69 (m, 2H), 2.76–2.90 (m, 2H), 2.97–3.1 (m, 2H), 3.35–3.50 (m, 4H), 3.57–3.70 (m, 2H), 6.40 (d, 1H), 6.5 (d, 1H), 7.22–7.32 (m, 2H), 7.44 (d, 1H) ppm. MS-CI m/z=361 [C$_{19}$H$_{19}$Cl$_2$N$_3$+H]$^+$ Example 276

4-((6bR,10aS)-5-bromo-3-methyl-2,3,6b,9,10,10a-hexahydro-1H-pyrido[3',4':4,5]pyrrolo[1,2,3-de] quinoxalin-8(7H)-yl)-1-(4-fluorophenyl)-1-butanone Typical procedure for alkylation of carbolines: A mixture of indoline hydrochloride (188 mg, 0.7 mmol) in dioxane (4 mL) was treated with Hunig's base (10 equivs) and heated to reflux for 15 min. To the cooled reaction mixture was added 4-chloro-4'-fluoro-butyrophenone (5 equivs), KI (0.9 equivs), then the whole mixture was refluxed for 48 h. The reaction was then diluted with chloroform (20 mL) and extracted once with saturated solution of ammonium chloride (10 mL) and twice with ice-cold water (100 mL). The organic layer was dried over sodium sulfate and concentrated to dryness under reduced pressure. The residue was purified by flash chromatography eluting with a gradient of hexane/ethylacetate (e.g. 96:4 to 50:50), following with a gradient methanol/dichloromethane (e.g. 1:99 to 3:97) to give the desired product.

The title compound (271 mg, 95%) was obtained from the alkylation of the (6bR,10aS)-5-bromo-3-methyl-2,3,6b,7,8, 9,10,10a-octahydro-1H-pyrido[3',4':4,5]pyrrolo[1,2,3-de] quinoxaline hydrochloride (200 mg, 0.65 mmol) with 4-chloro-4'-fluorobutyrophenone (0.53 mL, 3.24 mmol) using the general procedure described above. $^1$H NMR (CDCl$_3$, 300 MHz) δ 2.00–1.30 (m, 4H), 1.82–2.40 (m, 4H), 2.66–2.80 (m, 2H), 2.86 (s, 3H), 3.07–3.37 (m, 4H), 3.55–3.70 (m, 7H), 6.07 (s, 1H), 6.12 (s, 1H), 7.10–7.19 (m, 2H), 7.92–8.10 (m, 2H) ppm. MS -CI/EI m/z=473 [C$_{24}$H$_{27}$BrFN$_3$O+H]

Example 277

4-((6bR,10aR)-5-methoxy-3-methyl-2,3,6b,9,10,10a-hexahydro-1H-pyrido[3',4':4,5]pyrrolo[1,2,3-de] quinoxalin-8(7H)-yl)-1-(4-fluorophenyl)-1-butanone The title compound (2.0 mg, 52%) was obtained from the alkylation of the optically pure (6bR,10aR)-5-methoxy-3-methyl-2,3,6b,7,8,9,10,10a-octahydro-1H-pyrido[3',4':4,5] pyrrolo[1,2,3-de]quinoxaline hydrochloride (4.2 mg) with 4-chloro-4'-fluorobutyrophenone (5.0 equiv) using the general procedure described in Example 276. $^1$H NMR (CDCl$_3$, 300 MHz) δ 1.42–1.79 (m, 4H), 1.92–2.50 (m, 4H), 2.66–2.79 (m, 2H), 286 (s, 3H), 3.07–3.32 (m, 4H), 3.55–3.75 (m, 7H), 6.07 (s, 1H), 6.12(s, 1H), 7.06–7.21 (m, 2H), 7.92–8.10 (m, 2H) ppm. MS-CI/EI m/z=424 [C$_{25}$H$_{30}$FN$_3$O$_2$+H]

Example 278

(8aS,12aR)-2-(2,4-dichlorophenyl)-4,5,6,7,8a,9,10, 11,12,12a-decahydro[1,4]diazepino[3,2,1-hi]pyrido [4,3-b]indole hydrochloride

Step A:

To a solution of tert-butyl 6-nitro-1,3,4,5-tetrahydro-2H-pyrido[4,3-b]indole-2-carboxylate (15.6 g, 49.15 mmol) in ethanol (250 mL) was added a spatula tip of 10% Pd/C. The reaction mixture was shaken under a hydrogen atmosphere (15 psi, Parr apparatus) for 2 h. Upon removal from the Parr apparatus, the reaction mixture was filtered through Celite. The Celite was washed with ethanol and the combined filtrates were concentrated in vacuo to give tert-butyl 6-amino-1,3,4,5-tetrahydro-2H-pyrido[4,3-b]indole-2-carboxylate, quantitatively as a white solid: $^1$H NMR (CDCl$_3$, 500 MHz) δ 1.42–1.67 (m, 9H), 2.74–2.85 (m, 2H), 3.58 (brs, 2H), 3.79 (brs, 2H), 4.60 (brs, 2H), 6.53–6.56 (m, 1H), 6.89–6.99 (m, 2H), 7.77 (brs, 1H) ppm.

Step B:

To a solution of tert-butyl 6-amino-1,3,4,5-tetrahydro-2H-pyrido[4,3-b]indole-2-carboxylate (4.62 g, 16.08 mmol) in benzene (100 mL) was added a catalytic amount of DMAP. An inert atmosphere was created and chloropropionyl chloride (2)(1.68 mL) was added dropwise to the reaction mixture. After stirring at room temperature for 20 min, the reaction mixture was transferred to a separatory funnel containing 50% solution of sodium bicarbonate and was extracted with CH$_2$Cl$_2$ (3×250 mL). The combined organics were dried over Na$_2$SO$_4$ and concentrated in vacuo to give tert-butyl 6-[(3-chloropropanoyl)amino]-1,3,4,5-tetrahydro-2H-pyrido[4,3-b]indole-2-carboxylate as a white solid in 99% yield: $^1$H NMR (DMSO, 500 MHz) δ 1.38–1.53 (m, 9H), 2.75–2.99 (m, 2H), 3.65–3.78 (m, 4H), 3.88–3.97 (m, 2H), 4.53 (brs, 2H), 6.88–6.96 (m, 1H), 7.15–7.22 (m, 1H), 7.31–7.37 (m, 1H), 9.72 (brs, 1H), 10.44 (brs, 1H) ppm.

Step C:

To a suspension of NaH (95%) (100 mg, 3.96 mmol) in DMF (4 mL), stirring under an N$_2$ atmosphere at 0° C., was added dropwise a solution of tert-butyl 6-[(3-chloropropanoyl) amino]-1,3,4,5-tetrahydro-2H-pyrido[4,3-b]indole-2-carboxylate (500 mg, 1.32 mmol) and TBAI (cat.) in DMF (4 mL). The reaction was heated to 70° C. for 6 h then stirred at room temperature for 14 h. The mixture was quenched by slow transfer of the reaction mixture to a separatory funnel containing a saturated solution of sodium bicarbonate. The mixture was extracted with Et$_2$O (3×25 mL). The combined organics were concentrated in vacuo and the resulting residue was recrystallized from CH$_3$CN to give tert-butyl 5-oxo-4,5,6,7,9,12-hexahydro[1,4]diazepino [3,2,1-hi]pyrido[4,3-b]indole-11(10H)-carboxylate: $^1$H NMR (CDCl$_3$, 500 MHz) δ 1.49 (brs, 9H), 2.78 (brs, 2H), 3.02–3.07 (m, 2H), 3,84 (brs, 2H), 4.24–4.28 (m, 2H), 4.62 (brs, 2H), 6.66 (d, 1H, J=7.9 Hz), 7.02 (t, 1H, J=7.9 Hz), 7.19 (d, 1H, J=7.9 Hz), 7.80 (brs, 1H) ppm.

Step D:

To a solution of tert-butyl 5-oxo-4,5,6,7,9,12-hexahydro [1,4]diazepino[3,2,1-hi]pyrido[4,3-b]indole-11(10H)-carboxylate (914 mg, 2.68 mmols) in TFA (25 mL) stirring at −20° C. was added NaCNBH$_3$ (675 mg, 10.71 mmols) in 5 portions. The reaction was then stirred at −10° C. for 2 h. The yellow reaction solution was quenched by the dropwise addition of 6 N HCl (50 mL) followed by refluxing for 35 min. After cooling to room temperature, the reaction mixture was made basic by slowly pouring it into a solution of K$_2$CO$_3$. The mixture was transferred to a separatory funnel and extracted with CH$_2$Cl$_2$ (3×250 mL). The combined organics were dried over Na$_2$SO$_4$ and concentrated in vacuo and purified by column chromatography to give tert-butyl (8aS,12aR)-5-oxo-4,5,6,7,9,10,12,12a-octahydro [1,4]diazepino[3,2,1-]pyrido[4,3-b]indole-11(8aH)-carboxylate. $^1$H NMR (CDCl$_3$, 300 MHz) δ 1.49 (brs, 9H), 1.81–1.94 (m, 2H), 2.77–3.94 (m, 10H), 6.58–6.69 (m, 2H), 6.83 (d, 1H, J=6.7 Hz), 7.87 (s, 1H) ppm.

Step E:

To a solution of tert-butyl (8aS,12aR)-5-oxo-4,5,6,7,9,10, 12,12a-octahydro[1,4]diazepino[3,2,1-hi]pyrido[4,3-b] indole-11(8aH)-carboxylate (449 mg, 1.31 mmols) in DMF (6 mL1), stirring under a N$_2$ atmosphere at −10° C., was added N-bromosuccinimide (243 mg, 1.37 mmols). After 1 h, the brominated compound was precipitated by the addition of crushed ice. The reaction mixture was allowed to warm to room temperature and the solid collected by vacuum filtration. The white solid was washed with H$_2$O at 0° C. and dried under vacuum to give tert-butyl (8aS, 12aR)-2-bromo-5-oxo-4,5,6,7,9,10,12,12a-octahydro[1,4] diazepino[3,2,1-hi]pyrido[4,3-b]indole-11(8aH)-carboxylate in 65% yield: $^1$H NMR (CDCl$_3$, 500 MHz) δ 1.40–1.53 (m, 9H), 1.80–1.94 (m, 2H), 2.76–2,92 (m, 2H), 3.19–3.89 (m, 8H), 6.71 (s, 1H), 6.93 (s, 1H), 7.35 (brs, 1H) ppm.

Step F:

General lactam reduction procedure: To a solution of the lactam (approx 100 mg) in THF (5.0 mL), BH$_3$-THF (1M in THF) (4 equivs) is added dropwise. After addition is complete, the resulting reaction mixture is refluxed for 4 h, cooled to room temperature, and quenched cautiously with water (1.0 mL). The mixture is evaporated to dryness under reduced pressure and the residue obtained is treated with o-xylene (10 mL) and 1-octene (5 mL) and heated at reflux for 4 h. The reaction mixture is cooled to room temperature and concentrated to dryness under reduced pressure to give the desired target as a solid.

Tert-butyl (8aS, 12aR)-2-bromo-4,5,6,7,9,10,12,12a-octahydro[1,4]diazepino[3,2,1-hi]pyrido[4,3-b]indole-11 (8aH)-carboxylate (188 mg, 100%) was prepared from the reduction of tert-butyl (8aS, 12aR)-2-bromo-5-oxo-4,5,6,7, 9,10,12,12a-octahydro[1,4]diazepino[3,2,1-hi]pyrido[4,3-b] indole-11(8aH)-carboxylate from Step E (179 mg, 0.82 mmol) using the procedure illustrated above. 1H NMR (CDCl$_3$, 500 MHz) δ0.85–0.95 (m, 2H), 1.30–1.62 (m, 9H), 1.76–2.01 (m, 3H), 2.32–2.46 (m, 1H), 2.77–2.84 (m, 1H), 3.32–3.49 (m, 4H), 3.56–3.98 (m, 3H), 6.64 (s, 1H), 6.72 (s,1H) ppm.

Step G:

Tert-butyl (8aS, 12aR)-2-(2,4-dichlorophenyl)-4,5,6,7,9, 10,12,12a-octahydro[1,4]diazepino[3,2,1-hi]pyrido[4,3-b] indole-11(8aH)-carboxylate (48 mg, 42%) was prepared via coupling of tert-butyl (8aS, 12aR)-2-bromo-4,5,6,7,9,10,12, 12a-octahydro[1,4]diazepino[3,2,1-hi]pyrido[4,3-b]indole-11(8aH)-carboxylate (85 mg, 0.21 mmol) with 2,4-dichlorophenyl boronic acid (60 mg, 0.31 mmol) as illustrated by the general procedure described in Example275 Step A. This material was used without further purification in the subsequent step. tert-butyl (8aS, 12aR)-2-(2,4-dichlorophenyl)-4,5,6,7,9,10,12,12a-octahydro[1,4] diazepino[3,2,1-hi]pyrido[4,3-b]indole-11(8aH)-carboxylate (35 mg) was deprotected using the procedure described in Example 275 Step B to afford the title compound (20 mg, 63%). $^1$H NMR (DMSO, 500 MHz) δ 1.59–1.76 (m, 1H), 1.79–2.78 (m, 4H), 2.81–5.0 (m, 9H), 6.82–7.20 (m, 2H), 7.32–7.44 (m, 1H), 7.47–7.53 (m, 1H), 7.65–7.75 (m, 1H), 8.81–9.23 (m, 2H) ppm. MS-CI; m/z= 376[C$_{20}$H$_{21}$Cl$_2$N$_3$+H]$^+$.

Example 279

(8aS,12aR)-2-(4-methoxy-2-methylphenyl)-4,5,6,7, 8a,9,10,11,12,12a-decahydro[1,4]diazepino[3,2,1-hi] pyrido [4,3-b]indole hydrochloride

Tert-butyl (8aS, 12aR)-2-(4-methoxy-2-methylphenyl)-4, 5,6,7,9,10,12,12a-octahydro[1,4]diazepino[3,2,1-hi]pyrido

[4,3-b]indole-11(8aH)-carboxylate (48 mg, 52%) was prepared via coupling of the tert-butyl (8aS, 12aR)-2-bromo-4,5,6,7,9,10,12,12a-octahydro[1,4]diazepino[3,2,1-hi]pyrido[4,3-b]indole-11(8aH)-carboxylate (85 mg, 0.21 mmol) with 2-methyl-4-methoxyphenyl boronic acid (53 mg, 0.31 mmol) using the general procedure described in Example275 Step A. This material was used without further purification in the subsequent step.

Tert-butyl (8aS, 12aR)-2-(4-methoxy-2-methylphenyl)-4,5,6,7,9,10,12,12a-octahydro[1,4]diazepino[3,2,1-hi]pyrido[4,3-b]indole-11(8aH)-carboxylate (38 mg) was deprotected using the procedure described in Example 275 Step B to afford the title compound (22 mg, 61%). $^1$H NMR (DMSO, 500 MHz) δ 1.86–1.97 (m, 1H), 2.07–2.18 (m, 2H), 2.22 (s, 3H), 2.35–2.48 (m, 2H), 2.62–2.70 (m, 1H), 2.86–2.93 (m, 1H), 3.17–3.71 (m, 9H), 3.79 (s, 3H), 6.71–6.82 (m, 4H), 7.02–7.07 (m, 1H) ppm. MS-CI; m/z=350 [$C_{22}H_{27}N_3O$+H]$^+$.

Example 280

(8aS,12aR)-2-(2,4-dichlorophenyl)-6,7,8a,9,10,11,12,12a-octahydro[1,4]diazepino[3,2,1-hi]pyrido[4,3-b]indol-5(4H)-one hydrochloride Tert-butyl (8aS, 12aR)-2-(2,4-dichlorophenyl)-4-methyl-5-oxo-4,5,6,7,9,10,12,12a-octahydro[1,4]diazepino[3,2,1-hi]pyrido[4,3-b]indole-11(8aH)-carboxylate (223 mg, 48%) was prepared via coupling of tert-butyl (8aS, 12aR)-2-bromo-4-methyl-5-oxo-4,5,6,7,9,10,12,12a-octahydro[1,4]diazepino[3,2,1-hi]pyrido[4,3-b]indole-11(8aH)-carboxylate (404 mg, 0.96 mmol) with 2,4-dichlorophenyl boronic acid (275 mg, 1.44 mmol) using the general procedure described in Example 275 Step A. $^1$H NMR (CDCl$_3$, 500 MHz) δ 1.41 (brs, 9H), 1.85–1.98 (m, 2H) 2.83–2.96 (m, 2H), 3.18–3.46 (m, 4H), 3.46–3.54 (m, 2H), 3.76 (d, 1H, J=1.6 Hz), 3.83 (brs, 1H), 6.63 (s, 1H), 6.92 (s, 1H), 7.18–7.27 (m, 2H), 7.39 (s, 1H), 7.45 (s, 1H)

Tert-butyl (8aS, 12aR)-2-(2,4-dichlorophenyl)-4-methyl-5-oxo-4,5,6,7,9,10,12, 12a-octahydro[1,4]diazepino[3,2,1-hi]pyrido[4,3-b]indole-11(8aH)-carboxylate (75 mg) was deprotected using the procedure described in Example 275 Step B to afford the title compound. (52 mg, 83%) $^1$H NMR (CD3OD, 300 MHz) δ 2.06–2.19 (m, 1H), 2.27–2.36 (m, 1H), 2.80–2.92 (m, 4H), 3.16–3.34 (m, 3H), 3.37–3.59 (m, 4H), 3.68–3.74 (m, 1H), 6.94 (d, 1H, J=3.3 Hz), 7.04 (d, 1H, J=3.3 Hz), 7.29–7.38 (m 2H), 7.53 (d, 1H, J=1.7 Hz) ppm. MS-CI; m/z 389 [$C_{20}H_{19}Cl_2N_3O$+H]$^+$.

Example 281

(6bS,11aS)-3-methyl-2,3,7,8,9,10,11,11a-octahydro-1-H,6bH-azepino[4',5':4,5]pyrrolo[1,2,3-de]uinoxaline Step A:

o-Nitrophenyl hydrazine (5.22 g, 34 mmol) and azepin-3-one 2 (5.09 g, 34 mmol) were dissolved in 60 mL of CF$_3$CH$_2$OH. The solution was refluxed for 1 hr. The reaction was cooled to rt and concentrated. The organic solid was transferred to a sealed tube, and 100 mL of conc HCl were added. The mixture was heated to 80° C. for 18 hrs. The reaction was then cooled to 0° C. and ice chips were added to the reaction vessel. The reaction was basified with 50% NaOH until the pH=14. Dioxane (100 mL) and Boc2O (8.18 g, 3.7 mmol) were added. This solution was stirred at rt for 18 hrs. The reaction was then concentrated. Brine (50 mL) and CHCl$_3$ were added to the residue and the biphasic mixture was stirred for 10 min. The layers were separated, and the aqueous phase was re-extracted with CHCl$_3$ (2×30 mL). The combined organic layers were washed with brine, dried, and concentrated to afford 7.8 g of a brown residue. This crude product was purified by column chromatography (1–2% MeOH/CH$_2$Cl$_2$) to afford tert-butyl 7-nitro-1,4,5,6-tetrahydroazepino[4,5-b]indole-3(2H)-carboxylate (5.87 g, 52%) as an amorphous solid. $^1$H NMR (CDCl$_3$, 300 MHz) δ 9.45 (1H, bs), 8.07 (1H, bd, J=8.1 Hz), 7.7–7.9 (1H, m), 7.13–7.19 (1H, m), 3.69–3.73 (4H, m), 2.9–3.11 (4H, m), 1.50 (9H, s) ppm.

Step B:

NaH was suspended in DMF (2 mL) at 0° C. tert-butyl 7-nitro-1,4,5,6-tetrahydroazepino[4,5-b]indole-3(2H)-carboxylate (462 mg, 1.4 mmol) was added as a solution in DMF (4mL) drop-wise. The reaction was heated to 40° C. for 10 min was the cooled back to 0° C. Bromoethyl acetate was added drop-wise. The reaction was warmed to rt and stirred for 3 hrs. Brine (20 mL) and EtOAc (20 mL) were added to the reaction and stirred for 10 min. The layers were separated. The aqueous layer was re-extracted with EtOAc (2×20 mL). The combined organic layers were washed with brine, dried, and concentrated to afford 498 mg of a brown viscous oil. This crude product was purified by column chromatography (30% EtOAc/hexane) to afford tert-butyl 6-(2-ethoxy-2-oxoethyl)-7-nitro-1,4,5,6-tetrahydroazpino[4,5-b]indole-3(2H)-carboxylate as an orange amorphous solid (453 mg, 53%). $^1$H NMR (CDCl$_3$, 300 MHz) δ 7.80 (1H, d, J=7.7 Hz), 7.10–7.75 (1H, m), 7.11–7.16 (1H, m), 4.82 (2H, s), 4.25 (2H, q, J=7.0 Hz), 3.6–3.9 (4H, m), 2.8–3.1 (4H, m), 1.48 (9H, s), 1.30 (3H, t, J=7.0 Hz) ppm.

Step C:

Tert-butyl 6-(2-ethoxy-2-oxoethyl)-7-nitro-1,4,5,6-tetrahydroazpino[4,5-b]indole-3(2H)-carboxylate (146 mg, 0.35 mmol) was added to EtOH (15 mL). The reaction flask was evacuated and shaken on a Parr shaker at 55 psi of H$_2$. After 18 hrs, the reaction was disassembled and was filtered over a cake of Celite. The supernatant was concentrated to afford 115 mg of a black material, which was purified by column chromatography. tert-butyl 2-oxo-2,3,7,8,10,11-hexahydro-1H,9H-azepino[4'5':4,5]pyrrolo[1,2,3-de]quinoxaline-9-carboxylate (93.6 mg, 78%) was isolated as a white amorphous solid. $^1$H NMR (CDCl$_3$, 300 MHz) δ 7.96 (1H, bs), 7.11–7.17 (1H, m), 6.92–6.98 (1H, s), 6.50 (1H, s), 4.86 (2H, s), 3,68–3.73 (4H, m), 2.91–3.05 (4H, m) 1.59 (9H, s) ppm.

Step D:

Tert-butyl 2-oxo-2,3,7,8,10,11-hexahydro-1H,9H-azepino[4'5':4,5]pyrrolo[1,2,3-de]quinoxaline-9-carboxylate (501.4 mg, 1.5 mmol) was dissolved in DMF (5mL). The solution was cooled to 0° C. NaH (44.5 mg, 1.76 mmol) was added. The reaction was warmed to 50° C. for 45 min. The reaction was cooled back to 0° C., and excess MeI was added. The reaction was then stirred at 0° C. for 2 hrs. The reaction was quenched with a saturated aqueous solution of NH$_4$Cl. The reaction was extracted with EtOAc (3×15 mL). The combined organic layers were washed with brine, dried, and concentrated to afford 558 mg of a brown oil. This crude product was purified by column chromatography (2–5% MeOH/CH$_2$Cl$_2$) to afford tert-butyl 3-methyl-2-oxo-2,3,7,8,10,11-hexahydro-1H,9H-azepino[4'5':4,5]pyrrolo[1,2,3-de]quinoxaline-9-carboxylate (152.9 mg, 29%) as a white amorphous solid. $^1$H NMR (CDCl$_3$, 300 MHz) δ 7.14–7.18 (1H, m), 6.99–7.04 (1H, m), 6.63 (1H, d, J=7.3 Hz), 4.88 (2H, s), 3.63–3.74 (4H, m), 3.46 (3H, s), 2.89–2.99 (4H, m), 1.59 (9H, m) ppm.

Step E:

Tert-butyl 3-methyl-2-oxo-2,3,7,8,10,11-hexahydro-1H,9H-azepino[4'5':4,5]pyrrolo[1,2,3-de]quinoxaline-9-carboxylate (153.3 mg, 0.6 mmol) was dissolved in THF (20 mL). 1M BH$_3$THF (2.1 mL, 2.1 mmol) was added dropwise. The reaction was refluxed for 2 hours and then subsequently cooled to rt. 5M HCl (12 mL) was added drop-wise. After the bubbling ceased, the reaction was heated to reflux for 30 min, after which it was cooled to 0° C. 50% NaOH was added drop-wise until the pH=14. The reaction mixture was extracted with CHCl$_3$ (3×20 mL). The combined organic layers were washed with brine, dried, and concentrated to afford a 190 mg light-brown oil. This crude material was dissolved in dioxane (4 mL) and 1M NaOH (2mL), and then BOc$_2$O (143 mg, 6.6 mmol) was added. The solution was stirred for 18 hrs, and then it was concentrated. EtOAc (20 mL) and brine (20 mL) were added to the residue and stirred for 10 min. The layers were separated, and the aqueous was re-extracted with EtOAc (2×20 mL). The combined organic layers were washed with brine, dried, and concentrated to afford 220 mg of a brown oil. This crude product was purified by column chromatography (30% acetone/hexane) to afford (120 mg, 58%) of tert-butyl (6bS,11aS)-3-methyl-2,3,6b,7,8,10,11,11a-octahydro-1H,9H-azepino[4',5':4,5]pyrrolo[1,2,3-de]quinoxaline-9-carboxylate as a clear oil. $^1$H NMR (CDCl$_3$, 300 MHz) δ 6.55–6.7 (1H, m), 6.4–6.5 (1H, m), 6.37 (1H, d, J=7.7 Hz), 3.1–3.7 (9H, m), 3.8–3.9 (4H, m), 1.7–2.1 (4H, m), 1.46 (9H, s) ppm.

Step F:

Tert-butyl (6bS,11aS)-3-methyl-2,3,6b,7,8,10,11,11a-octahydro-1H,9H-azepino[4',5':4,5]pyrrolo[1,2,3-de]quinoxaline-9-carboxylate (115 mg, 0.33 mmol) was dissolved in 20% TFA (3 mL) in CH$_2$Cl$_2$ at rt. The reaction was stirred at rt for 2.5 hrs. Ice chips were added to the reaction, an then it was basified with 50% NaOH until pH=14. Brine (5 mL) was added and then the reaction was extracted with CH$_2$Cl$_2$ (2×10 mL). The combined organic layers were washed with brine, dried, and concentrated to afford the title compound (84.1 mg, 103%) as a viscous oil. $^1$H NMR (CDCl$_3$, 300 MHz) δ 6.59–6.64 (1H, m), 6.48 (1H, d, J=7.3 Hz), 6.37 (1H, d, J=7.7 Hz), 3.4–3.7 (4H, m), 2.6–3.3 (10H, m), 1.7–2.2 (4H, m) ppm. MS (ESI): 244.2 (base, M+H)

Example 282

4-(3-methyl-2,3,6b,7,8,10,11,11a-octahydro-1H,9H-azepino[4',5':4,5]pyrrolo[1,2,3-de]quinoxalin-9-yl)-1-(4-fluorophenyl)-1-butanone 3-Methyl-2,3,7,8,9,10,11,11a-octahydro-1H,6bH-azepino[4',5':4,5]pyrrolo[1,2,3-de]quinoxaline (72 mg, 0.3 mmol), 4-chloro-4'-flourobutyrophenone (119 mg, 0.6 mmol), KI (49 mg, 0.3 mmol), and DIEA (383 mg, 3 mmol) were added to dioxane (2.5 mL). The suspension was stirred at 96° C. for 18 hrs. The reaction was cooled to rt and then concentrated. The residue was purified by column chromatography (5–10 % MeOH/CH$_2$Cl$_2$), to afford the title compound (37.5 mg, 31%) as an oil. The enantiomers of the title compound were separated on a Chiracel OD column using 8% EtOH-Hexane as the eluent. 1H NMR (CDCl$_3$, 300 MHz) δ 7.9–8.1 (2H, m), 7.1–7.2 (2H, m), 6.6–6.7 (1H, m), 6.3–6.5 (2H, m), 2.7–3.8 (19 H, m), 1.9–2.3 (4H, m) ppm. MS (ESI): 408.3 (base, M+H)

Example 283

(+/−)-1,1,3-Trimethyl-2,3,6b,7,8,9,10,10a-octahydro-1H-pyrido[3',4':4,5]pyrrolo[1,2,3-de]quinoxaline Step A:

To a solution of ethyl 2-oxo-2,3,9,10-tetrahydro-1H-pyrido[3',4':4,5]pyrrolo[1,2,3-de]quinoxaline-8(7H)-carboxylate (from Example 211, Step A) (360 mg, 1.2 mmol) in DMF (20 mL) at rt was added NaH (172 mg, 4.8 mmol), MeI (0.25 mL, 4.0 mmol) and stirred at 25° C. for 6 hours. The solution was diluted with water (30 mL) and extracted with EtOAc (2×30 mL). The combined extracts were dried over magnesium sulfate, concentrated, and purified by flash chromatography to afford ethyl 1,1,3-trimethyl-2-oxo-2,3,9,10-tetrahydro-1H-pyrido[3',4':4,5]pyrrolo[1,2,3-de]quinoxaline-8(7H)-carboxylate (370 mg, 90%) as an oil. MS [M+H]$^+$342. $^1$H NMR (CDCl$_3$, 300 MHz): δ 7.12 (d, 1H, J=7.7 Hz), 7.01 (t, 1H, J=7.7 Hz), 6.63 (d, 1H, J=7.7 Hz), 4.69 (s, 2H), 4.23 (m, 2H), 3.86 (m, 2H), 3.43 (s, 3H), 3.01 (m, 2H), 1.81 (s, 6H), 1.24 (t, 3H, J=7.3 Hz) ppm.

Step B:

To a solution of ethyl 1,1,3-trimethyl-2-oxo-2,3,9,10-tetrahydro-1H-pyrido[3',4':4,5]pyrrolo[1,2,3-de]quinoxaline-8(7H)-carboxylate (240 mg, 0.7 mmol) in THF (20 mL) at 25° C. was added BH$_3$/THF complex (0.7 mL, 0.7 mmol). The mixture was stirred at 80° C. for 5 hours then cooled to rt and added 6N HCl (10 mL) with stirred for another 1 hr. About 30 mL of H$_2$O was added and then was extracted with EtOAc (2×30 mL). The combined extracts were dried over magnesium sulfate, concentrated, and purified by flash chromatography to give ethyl-1,1,3-trimethyl-2,3,9,10-tetrahydro-1H-pyrido[3',4':4,5]pyrrolo[1,2,3-de]quinoxaline-8(7H)-carboxylate as an oil (152 mg, 66%). MS [M+H]$^+$327. $^1$H NMR (CDCl$_3$, 300 MHz) δ 7.01 (t, 1H, J=7.7 Hz), 6:97 (d, 1H, J=7.7 Hz), 6.41 (d, 1H, J=7.7 Hz), 4.68 (s, 2H), 4.23 (m, 2H), 3.84 (m, 2H), 3.11 (m, 2H), 2.99 (s, 3H), 1.54 (s, 6H), 1.27 (t, 3H, J=7.3 Hz) ppm.

Step C:

To a solution of ethyl-1,1,3-trimethyl-2,3,9,10-tetrahydro-1H-pyrido[3',4':4,5]pyrrolo[1,2,3-de]quinoxaline-8(7H)-carboxylate (69 mg, 0.21 mmol) in TFA (2 mL) at 0° C. was added NaBH$_3$CN (53 mg, 0.84 mmol). The mixture was stirred at rt for 4 hours, and then removed the TFA by N$_2$. About 10 mL of H$_2$O was added and then was extracted with EtOAc (2×10 mL). The combined extracts were dried over magnesium sulfate and concentrated to afford ethyl-1,1,3-trimethyl-2,3,6b,9,10,10a-hexahydro-1H-pyrido[3',4':4,5]pyrrolo[1,2,3-de]quinoxaline-8(7H)-carboxylate as an oil which was used for the next reaction (45 mg, 65%). MS [M+H]+330.

Step D:

To a solution of ethyl 1,1,3-trimethyl-2,3, 6b,9,10,10a-hexahydro-1H-pyrido[3',4':4,5]pyrrolo[1,2,3-de]quinoxaline-8(7H)-carboxylate (8 mg, 0.02 mmol) in n-butanol (5 mL) at rt was added KOH (50 mg, 0.89 mmol) and stirred at 120° C. for 20 hours. The solution was diluted with water (10 mL) and extracted with EtOAc (2×20 mL). The combined extracts were dried over magnesium sulfate and concentrated to afford the title compound (5 mg, 81%). MS [M+H]+258.

Example 284

(+/−)-1-(4-Fluorophenyl)-4-(1,1,3-trimethyl-2,3,6b,9,10,10a-hexahydro-1H-pyrido[3',4':4,5]pyrrolo[1,2,3-de]quinoxalin-8(7H)-yl)-1-butanone

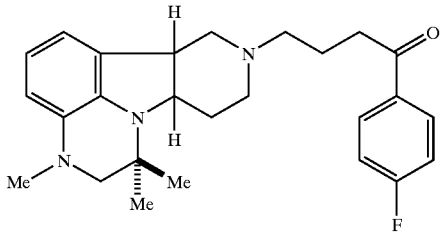

To a solution of 1,1,3-trimethyl-2,3,6b,7,8,9,10,10a-octahydro-1H-pyrido[3',4':4,5]pyrrolo[1,2,3-de]quinoxaline (from Example 283) (82 mg, 0.32 mmol) in dioxane (10 mL) at rt was added 4-chloro-1-(4-fluorophenyl)butan-1-one (83 mg, 0.42 mmol), $K_2CO_3$ (100 mg), KI (30 mg) and stirred at 25° C. for 24 hours. The solution was diluted with water (30 mL) and extracted with EtOAc (2×30 mL). The combined extracts were dried over magnesium sulfate, concentrated, and purified by flash chromatography to afford the title compound (58 mg, 43%). MS [M+H]+422. $^1$H NMR (CDCl$_3$, 300 MHz): δ 8.01 (m, 2H), 7.15 (t, 2H, J=7.7 Hz), 6.65 (t, 1H, J=7.7 Hz), 6.51 (d, 1H, J=7.0 Hz), 6.43 (d, 1H, J=7.0 Hz), 3.63 (m, 1H), 3.25 (d, 1H, J=11 Hz), 3.09 (m, 2H), 2.89 (s, 3H), 2.63 (m, 2H), 2.25 (m, 2H), 2.17 (m, 2H), 1.31 (s, 3H), 1.12 (s, 3H) ppm. This racemate was then separated into its corresponding enantiomers by HPLC utilizing a Chiralcel AD column with 50% Ethanol/Methanol solvent system.

Example 285

(+/−)-1,3-Dimethyl-2,3,6b,7,8,9,10,10a-octahydro-1H-pyrido[3',4':4,5]pyrrolo[1,2,3-de]quinoxaline

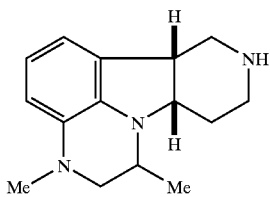

Step A:

To a solution of ethyl 2-oxo-2,3,9,10-tetrahydro-1H-pyrido[3',4':4,5]pyrrolo[1,2,3-de]quinoxaline-8(7H)-carboxylate (from Example 211, StepA) (500 mg, 1.6 mmol) in DMF (20 mL) at rt was added NaH (147 mg, 3.6 mmol), MeI (0.25 mL, 4.0 mmol) and stirred at 25° C. for 3 hours. The solution was diluted with water (30 mL) and extracted with EtOAc (2×30 mL). The combined extracts were dried over magnesium sulfate, concentrated, and purified by flash chromatography to afford ethyl 1,3-dimethyl-2-oxo-2,3,9,10-tetrahydro-1H-pyrido[3',4':4,5]pyrrolo[1,2,3-de]quinoxaline-8(7H)-carboxylate (350 mg, 64%) as an oil. MS [M+H]+328. $^1$H NMR (CDCl$_3$, 300 MHz): δ 7.18 (d, 1H, J=7.7 Hz), 7.01 (t, 1H, J=7.7 Hz), 6.63 (d, 1H, J=7.7 Hz), 4.90 (m, 1H), 4.51 (m, 1H), 3.20 (m, 5H), 3.49 (m, 1H), 3.42 (s, 3H), 2.91 (m, 1H), 2.80 (m, 1H), 1.61 (d, 3H, J=7.0), 1.28 (t, 3H, J=7.3 Hz) ppm.

Step B:

Following the procedure of example 283 Steps B–D to afford the title compound. MS [M+H]+258.

Example 286

4-(1,3-Dimethyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone

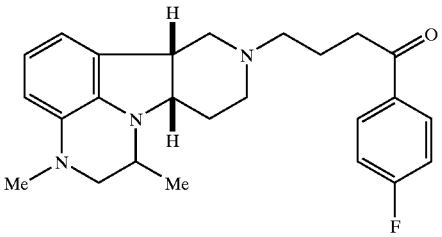

The title compound was prepared in a manner similar to that described for Example 284, utilizing 1,3-dimethyl-2,3,6b,7,8,9,10,10a-octahydro-1H-pyrido[3',4':4,5]pyrrolo[1,2,3-de]quinoxaline from Example 285. The product was obtained as colorless oil. MS [M+H]+408. $^1$H NMR (CDCl$_3$, 300 MHz): δ 7.89 (m, 2H), 7.15 (t, 2H, J=8.4 Hz), 6.62 (t, 1H, J=7.3 Hz), 6.51 (d, 1H, J=7.4 Hz), 6.39 (d, 1H, J=7.4 Hz), 3.63 (m, 1H), 3.52 (m, 4H), 3.15 (m, 4H), 3.86 (s, 3H), 3.65 (m, 4H), 2.17 (m, 2H), 1.81 (m, 1H), 1.21 (m, 1H), 1.13 (d, 3H, J=6.2 Hz) ppm. This racemate was then separated into its corresponding enantiomers by HPLC utilizing a Chiralcel AD column with 90% Acetonitrile/2-Propanol solvent system.

Example 287

4-(1,3-dimethyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone

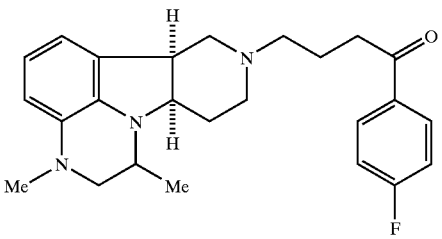

The title compound was prepared in a manner similar to that described for Example 284, utilizing 1,3-dimethyl-2,3,6b,7,8,9,10,10a-octahydro-1H-pyrido[3',4':4,5]pyrrolo[1,2,3-de]quinoxaline from Example 285. The product was obtained as colorless oil. MS [M+H]+408. $^1$H NMR (CDCl$_3$, 300 MHz): δ 8.00 (m, 2H), 7.15 (m, 2H), 6.62 (t, 1H, J=7.3 Hz), 6.51 (d, 1H, J=7.4 Hz), 6.39 (d, 1H, J=7.4 Hz), 3.63 (t, 1H, J=5.2 Hz), 3.60 (m, 1H), 3.40 (m, 4H), 3.25 (m, 4H), 2.82 (s, 3H), 2.60 (m, 4H), 2.17 (m, 2H), 1.81 (m, 1H), 1.13 (d, 3H, J=6.2 Hz) ppm. This racemate was then separated into its corresponding enantiomers by HPLC utilizing a Chiralcel AD column with 90% Acetonitrile/2-Propanol solvent system.

Example 288

(+/−)-5-(2,4-dichlorophenyl)-2-methyl-2,3,6b,7,8,9,10,10a-octahydro-1H-pyrido[3',4':4,5]pyrrolo[1,2,3-de]quinoxaline Step A:

To a solution of tert-butyl 6-amino-1,3,4,5-tetrahydro-2H-pyrido[4,3-b]indole-2-carboxylate (7 g, 24.3 mmol) in $CH_2Cl_2$ (40 mL) at rt was added saturated $K_2CO_3$ (30 mL), ethyl chloroformate (2.4 mL, 4.0 mmol) and stirred at 25° C. for 0.5 hour. The solution was diluted with water (30 mL) and extracted with $CH_2Cl_2$ (2×30 mL). The combined extracts were dried over magnesium sulfate, and concentrated to afford tert-butyl 6-[(ethoxycarbonyl)amino]-1,3,4,5-tetrahydro-2H-pyrido[4,3-b]indole-2-carboxylate (8.7 g, 100%) as an crude oil. MS [M+H]$^+$360.

Step B:

To a solution of tert-butyl 6-[(ethoxycarbonyl)amino]-1,3,4,5-tetrahydro-2H-pyrido[4,3-b]indole-2-carboxylate (8.7 g, 24.3 mmol) in $CH_2Cl_2$ (40 mL) at rt was added TFA (20 mL) and stirred at rt for 3 hours before the solvent was removed by the nitrogen stream. The solution was diluted with water (30 mL) and extracted with $CH_2Cl_2$ (2×30 mL). The combined extracts were dried over magnesium sulfate, and concentrated to afford an crude residue that was re-dissolved in $CH_2Cl_2$ (40 mL) followed by saturated $K_2CO_3$ (30 mL), ethyl chloroformate (2.4 mL, 4.0 mmol) and stirred at 25° C. for 0.5 hour. The solution was diluted with water (30 mL) and extracted with $CH_2Cl_2$ (2×30 mL). The combined extracts were dried over magnesium sulfate, concentrated, and purified by flash chromatography to afford ethyl 6-[(ethoxycarbonyl)amino]-1,3,4,5-tetrahydro-2H-pyrido[4,3-b]indole-2-carboxylate (4.5 g, 67%) as a clear oil. MS [M+H]$^+$332. $^1$H NMR (CDCl$_3$, 300 MHz): δ 7.00 (t, 1H, J=7.7 Hz), 6.82 (m, 1H), 6.71 (m, 1H), 4.62 (s, 2H), 4.02–4.31 (m, 4H), 3.82 (t, 1H, J=5.5 Hz), 2.82 (t, 1H, J=5.5 Hz), 1.20–1.24 (m, 6H) ppm.

Step C:

To a solution of ethyl 6-[(ethoxycarbonyl)amino]-1,3,4,5-tetrahydro-2H-pyrido[4,3-b] indole-2-carboxylate (4.5 g, 13.6 mmol) in $CH_2Cl_2$ (40 mL) at 0° C. was added TFA (20 mL) followed by NaCNBH$_3$ (1.8 g, 27 mmol) and stirred at rt for 3 hours before the solvent was removed by the nitrogen stream. To the resulting residue were added $CH_2Cl_2$ (40 mL) and 6N HCl (20 mL) and stirred for 0.5 hour. The solution was diluted with water (20 mL), 1N NaOH (30 mL) and extracted with $CH_2Cl_2$ (2×30 mL). The combined extracts were dried over magnesium sulfate, concentrated, and purified by flash chromatography to afford ethyl 6-[(ethoxycarbonyl)amino]-1,3,4,4a,5,9b-hexahydro-2H-pyrido[4,3-b]indole-2-carboxylate (3.6 g, 80%) as a clear oil. MS [M+H]$^+$334. $^1$H NMR (CDCl$_3$, 300 MHz): δ 6.97 (d, 1H, J=7.3 Hz), 6.85 (d, 1H, J=7.3 Hz), 6.72 (t, 1H, J=7.3 Hz), 4.05 (m, 4H), 3.41 (m, 4H), 1.92 (m, 2H), 1.20–1.24 (m, 6H) ppm.

Step D:

To a solution of ethyl 6-[(ethoxycarbonyl)amino]-1,3,4,4a,5,9b-hexahydro-2H-pyrido[4,3-b]indole-2-carboxylate (2.2 g, 6.6 mmol) in DMF (20 mL) at 0° C. was added NaH (660 mg, 16.5 mmol), DMAP (878 mg, 7.2 mmol), acetyl chloride (0.6 mL, 7.2 mmol) and stirred at rt for 16 hours. The solution was diluted with water (30 mL), and extracted with EtOAc (2×30 mL). The combined extracts were dried over magnesium sulfate, concentrated, and purified by flash chromatography to afford diethyl 1-oxo-6b,9,10,10a-tetrahydro-1H-pyrido[3',4':4,5]pyrrolo[1,2,3-de]quinoxaline-3,8(2H,7H)-dicarboxylate (1.1 g, 57%) as a clear oil. MS [M+H]$^+$374. $^1$H NMR (CDCl$_3$, 300 MHz): δ 6.75 (t, 1H, J=7.7 Hz), 6.59 (m, 1H), 6.45 (m, 1H), 4.05 (m, 1H), 3.60–4.00 (m, 7H), 3.40 (m, 1H), 3.00 (m, 3H), 1.92 (m, 2H), 0.91 (m, 1H), 0.85 (m, 6H) ppm.

Step E:

To a solution of diethyl 1-oxo-6b,9,10,10a-tetrahydro-1H-pyrido[3',4':4,5]pyrrolo[1,2,3-de]quinoxaline-3,8(2H,7H)-dicarboxylate (360 mg, 0.97 mmol) in DMF (20 mL) at 0° C. was added NaH (193 mg, 4.8 mmol), MeI (0.3 mL, 4.8 mmol)- and stirred at rt for 16 hours. The solution was diluted with water (20 mL), and extracted with EtOAc (2×20 mL). The combined extracts were dried over magnesium sulfate, concentrated to afford diethyl 2-methyl-1-oxo-6b,9,10,10a-tetrahydro-1H-pyrido[3',4':4,5]pyrrolo[1,2,3-de]quinoxaline-3,8(2H,7H)-dicarboxylate (300 mg, 80%) as a crude oil. MS [M+H]$^+$388.

Step F:

To a solution of diethyl 2-methyl-1-oxo-6b,9,10,10a-tetrahydro-1H-pyrido[3',4':4,5]pyrrolo[1,2,3-de]quinoxaline-3,8(2H,7H)-dicarboxylate (300 mg, 0.77 mmol) in THF (10 mL) at rt was added BH$_3$THF complex (3.8 mL, 3.8 mmol) and refluxed for 5 hours. At rt 6N HCl (10 mL) was added and stirred for 0.5 hour before the solution was diluted with water (20 mL), and extracted with EtOAc (2×20 mL). The combined extracts were dried over magnesium sulfate, concentrated, and purified by flash chromatography to afford diethyl 2-methyl-6b,9,10,10a-tetrahydro-1H-pyrido[3',4':4,5]pyrrolo[1,2,3-de]quinoxaline-3,8(2H,7H)-dicarboxylate (200 mg, 69%) as a clear oil. MS [M+H]$^+$374.

Step G:

To a solution of diethyl 2-methyl-6b,9,10,10a-tetrahydro-1H-pyrido[3',4':4,5]pyrrolo[1,2,3-de]quinoxaline-3,8(2H,7H)-dicarboxylate (40 mg, 0.1 mmol) in DMF (10 mL) at 0° C. was added NBS (20 mg, 0.11 mmol) and stirred at 0° C. for 2 hours. The solution was diluted with water (10 mL), and extracted with EtOAc (2×20 mL). The combined extracts were dried over magnesium sulfate, concentrated, and purified by flash chromatography to afford diethyl 5-bromo-2-methyl-6b,9,10,10a-tetrahydro-1H-pyrido[3',4':4,5]pyrrolo[1,2,3-de]quinoxaline-3,8(2H,7H)-dicarboxylate (40 mg, 88%) as a clear oil. MS [M+H]$^+$454.

Step H:

To a solution of diethyl 5-bromo-2-methyl-6b,9,10,10a-tetrahydro-1H-pyrido[3',4':4,5]pyrrolo[1,2,3-de]quinoxaline-3,8(2H,7H)-dicarboxylate (100 mg, 0.22 mmol) in DMF (10 mL) was added 2,4-dichlorophenyl boronic acid (63 mg, 0.33 mmol) and Na$_2$CO$_3$ (58 mg, 0.55 mmol, in 0.4 mL of H$_2$O). The mixture was degassed with a stream of nitrogen for 20 min and then there was added Pd(PPh$_3$)$_4$ (35 mg, 0.03 mmol) and the mixture was stirred at 100° C. for 16 h. The reaction was allowed to cool to ambient temperature and was diluted with ethyl acetate, washed with saturated aqueous sodium bicarbonate and brine, dried (MgSO$_4$), filtered through Celite and concentrated in vacuo. The residue was purified by flash chromatography (elution with hexanes/ethyl acetate) to afford diethyl 5-(2,4-dichlorophenyl)-2-methyl-6b,9,10,10a-tetrahydro-1H-pyrido[3',4':4,5]pyrrolo[1,2,3-de]quinoxaline-3,8(2H,7H)-dicarboxylate (30 mg, 29% yield) MS [M+H]+517.

Step I:

To a solution of diethyl 5-(2,4-dichlorophenyl)-2-methyl-6b,9,10,10a-tetrahydro-1H-pyrido[3',4':4,5]pyrrolo[1,2,3-de]quinoxaline-3,8(2H,7H)-dicarboxylate (30 mg, 0.06 mmol) in 10 mL of n-BuOH was added KOH (33 mg, 0.6 mmol) and stirred at 120° C. for 16 h. The reaction was allowed to cool to ambient temperature and was diluted with ethyl acetate, washed with water (10 mL). The organic layer was collected and washed with 1N HCl (10 mL) and water (10 mL). This time the aqueous layer was collected and neutralized with saturated aqueous sodium bicarbonate and extracted with EtOAc (2×20 mL). The combined extracts were dried over magnesium sulfate, concentrated to afford 5-(2,4-dichlorophenyl)-2-methyl-2,3,6b,7,8,9,10,10a-octahydro-1H-pyrido[3',4':4,5]pyrrolo[1,2,3-de]quinoxaline (10 mg, 45%) as a solid. MS [M+H]$^+$374.

Utility

The compounds of the present invention have therapeutic utility for illnesses or disorders involving the neurotransmitter serotonin (5-hydroxy tryptamine or 5-HT) and either agonism or antagonism of 5-HT2 receptors, as demonstrated by the assays described below. Therapeutic utility for these illnesses or disorders could involve numerous biological processes affected by serotonin including, but not limited to, appetite, mood, sleep, sexual activity, and arterial constriction. These biological processes may also be important to numerous central nervous system (CNS) disorders including those related to the affective disorders of depression, anxiety, psychosis, and schizophrenia, as well as, disorders of food intake such as anorexia, bulemia, and obesity. The compounds of the present invention potentially have therapeutic utility in other conditions in which serotonin has been implicated, such as migraine, attention deficit disorder or attention deficit hyperactivity disorder, addictive behavior, and obsessive-compulsive disorder, as well as, conditions associated with cephalic pain, social phobias, and gastrointestinal disorders such as dysfunction of the gastrointestinal tract motility. Lastly, compounds of the present invention potentially have therapeutic utility in neurodegenerative diseases and traumatic conditions represented by the examples of Alzheimer's disease and brain/spinal cord trauma.

The pharmacological analysis of each compound for either antogonism or agonism of at 5-HT2A and 5-HT2C receptors consisted of in vitro and in vivo studies. In vitro analyses included Ki determinations at 5-HT2A and 5-HT2C receptors and an assessment of functional (i.e., agonism or antagonism) activity at each receptor class by IP3 hydrolysis assays. Additional receptor assays were conducted to evaluate receptor specificity of 5-HT2A and 5-HT2C receptors over monoamine and nuisance receptors (e.g. histamine, dopamine, and muscarinic). A compound is considered active as a 5-HT2A antagonist or a 5-HT2C agonist if it has an IC$_{50}$ value or a K$_i$ value of less than about 1 micromolar; preferably less than about 0.1 micromolar; more preferably less than about 0.01 micromolar. Compounds of the invention have been shown to have an IC$_{50}$ value of less than about 1 micromolar for 5-HT2A antagonism or a 5-HT2C agonism.

In vivo assays assessed compound activity in a variety of behavioral paradigms including quipazine head twitch, acute and chronic feeding models, anxiety and depression models (learned-helplessness, elevated plus maze, Geller-Siefter, conditioned taste aversion, taste reactivity, satiety sequence). In aggregate, these models reflect activity as a 5-HT2A antagonist (quipazine head twitch, depression models) or 5-HT2C agonist (feeding models, anxiety models, depression models) and provide some indication as to bioavailability, metabolism and pharmacokinetics.

Radioligand binding experiments were conducted on recombinant human 5-HT2A and 5-HT2C receptors expressed in HEK293E cells. The affinities of compounds of the present invention to bind at these receptors is determined by their capacity to compete for [$^{125}$I]-1-(2,5-dimethoxy-4-iodophenyl)-2-amino-propane (DOI) binding at the 5-HT2A or 5-HT2C. General references for binding assays include 1) Lucaites V L, Nelson D L, Wainscott D B, Baez M (1996) Receptor subtype and density determine the coupling repertoire of the 5-HT2 receptor subfamily. Life Sci., 59(13):1081–95. J Med Chem 1988 January; 31(1):5–7; 2) Glennon R A, Seggel M R, Soine W H, Herrick-Davis K, Lyon R A, Titeler M (1988) [125I]-1-(2,5-dimethoxy-4-iodophenyl)-2-amino-propane: an iodinated radioligand that specifically labels the agonist high-affinity state of 5-HT2 serotonin receptors. J Med. Chem. 31(1):5–7 and 3) Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2):328–35.

The functional properties of compounds (efficacy and potency) were determined in whole cells expressing 5-HT2A or 5-HT2C receptors by assessing their ability to stimulate or inhibit receptor-mediated phosphoinositol hydrolysis. The procedures used are described below.

In Vitro Binding Assays

Stable Expression of 5-HT2A and 5-HT2C Receptors in HEK293E Cells

Stable cell lines were generated by transfecting 293EBNA cells with plasmids containing human 5-HT2A, 5-HT2B, or 5-HT2C (VNV edited isoform) cDNA using calcium phosphate. These plasmids also contained the cytomegalovirus (CMV) immediate early promoter to drive receptor expression and EBV or iP for their maintenance as an extrachromosomal element, and the hph gene from E. Coli to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% CO$_2$) for 10 days. The 5-HT2A cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately 1×108 cells) expressing the 5-HT2A or 5-HT2C receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., Ill.) using bovine serum albumin as the standard. Radioligand Binding Assays for the 5-HT2A and 5-HT2C Receptors Radioligand binding studies were conducted to determine the binding affinities (KI values) of compounds for the human recombinant 5-HT2A, 5-HT2B, and 5-HT2C receptors (Fitzgerald et al., 1999). Assays were conducted in disposable polypropylene 96-well plates (Costar Corp., Cambridge, Mass.) and were initiated by the addition of 5-HT2A, 5-HT2B, or 5-HT2C membrane homogenate in tissue buffer (10–30 (g/well) to assay buffer (50 mM Tris HCl, 0.5 mM EDTA, 10 mM pargyline, 10 mM MgSO$_4$, 0.05 % ascorbic acid, pH 7.5) containing [$^{125}$I]DOI for the 5-HT2A and 5-HT2C receptors (0.3–0.5 nM, final) or [$^3$H] LSD (2–2.5 nM, final) for the 5-HT2B receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (cell harvestor; Inotech Biosystems Inc., Lansing, Mich.) over GFF glass-fiber filters that had been pre-soaked in 0.3% polyethyleneimine. Filters were washed in ice-cold 50 mM Tris HCl buffer (pH 7.5) and then counted in a gamma counter for the 5-HT2A and 5-HT2C assays, or by liquid scintillation spectroscopy for the 5-HT2B assay.

Phosphoinositide Hydrolysis Studies

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT2A, 5-HT2B, or 5-HT2C receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/ml hygromycin B, and 250 (g/ml G418. Following a 24–48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16–18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Data analyses

The equilibrium apparent dissociation constants (Ki's) from the competition experiments were calculated using an iterative nonlinear regression curve-fitting program (GraphPad Prism; San Diego, Calif). For the PI hydrolysis experiments, EC50's were calculated using a one-site 'pseudo' Hill model: y=((Rmax-Rmin)/(1+R/EC50)nH))+Rmax where R=response (DeltaGraph, Monterey, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

In Vivo Experiments for Serotonergic Ligands

Preclinical Efficacy, Potency, and Side Effect Liability.
a) Anti-Serotonin Efficacy.
Antagonism of Quipazine-Induced Head Twitch in Rat. Quipazine, an agonist at 5-HT receptors, produces a characteristic head twitch response in rats. 5-HT receptor antagonists effectively antagonize this 5-HT agonist-induced behavioral effect (Lucki et al., 1984). Accordingly, the quipazine-induced head twitch model in rat can function as an in vivo behavioral correlate to 5-HT receptor binding. Compounds are administered 30 minutes before behavioral testing (and 25 minutes before quipazine), and a dose-related antagonism of the quipazine response is determined.
b) Antipsychotic Efficacy.
Inhibition of the Conditioned Avoidance Response (CAR) in Rat. Rats are trained to consistently avoid (by climbing onto a pole suspended from the ceiling of the test chamber) an electric foot shock (0.75 mA) delivered to the grid floor of the testing chamber. All antipsychotic drugs effectively inhibit this conditioned avoidance response (Arnt, 1982). The ability of a compound to inhibit this response is used to determine the antipsychotic efficacy of potential drug candidates.
c) Extrapyramidal Side Effect Liability
Induction of Catalepsy in Rat. Typical antipsychotic drugs produce extrapyramidal side effects (EPS) at clinically effective doses. The most widely accepted preclinical indicator of EPS liability in humans is a drug-induced catalepsy syndrome in rat (Costall and Naylor, 1975), a condition whereby the animal will remain immobile in an externally imposed posture (analogous to a catatonic stupor in humans). Rats are tested for induction of catalepsy in a dose-response test after oral administration of compounds.
d) CNS penetration; In vivo Brain Receptor Occupancy.
In Vivo Binding. To determine the level of in vivo receptor occupancy, an in vivo receptor binding protocol is used. This procedure uses an appropriate radioligand to label the receptor of interest. For example, to measure both Dopamine D2 and 5-HT2A receptors in vivo, one can use $^3$H-N-methyl spiperone ($^3$H -NMSP), (Frost, et. al. 1987) The procedure uses rats (or mice) fasted overnight. To measure the effects of compounds on the receptors of interest, compounds are dosed, usually p.o. for example in 2 microliters/gram body weight in 0.25% Methocel suspension. The radiolabeled compound (in this example, $^3$H-NMSP) is administered by i.v. tail vein injection (10 microcuries label/200 gram rat). Time course experiments are used to determine the optimal time of binding for both the radiolabeled and unlabeled compound. These optimal time frames are used for all subsequent dose-response experiments. After the appropriate time frame of compound/radioligand exposure, the animals are sacrificed and the relevant brain regions dissected (frontal cortex for 5-HT2A and striatum for D2 receptors) and examined for their content of radioactivity. The level of non-specific binding is determined by examining a brain region known not to contain the receptor of interest (in this case the cerebellum) or by administering an excess of compound known pharmacologically to interact with the receptor.

REFERENCES

Arnt, J. Acta Pharmacol. et Toxicol. 1982: 51, 321–329.
Berridge M. J., Downes P. C. , Hanley M. R. (1982) Lithium amplifies agonist-dependent phosphotidyinositol response in brain and salivary glands. Biochem. J., 206, 587–595.
Costall, B and Naylor, R J. Psychopharmacology. 1975: 43, 69–74.
Egan C. T., Herrick-Davis K., Miller K., Glennon R. A., and Teitler M. (1998) Agonist activity of LSD and lisuride at cloned 5-HT2A and 5-HT2C receptors. Psychopharmacology, 136, 409–414.
Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT2A and 5-HT2C receptors: evidence favoring the ternary complex and two-state models of agonist action. J. Neurochem., 72, 2127–2134.

Frost, J. J., Smith, A. C., Kuhar, M. J., Dannals, R. F., Wagner, H. N., 1987, In Vivo Binding of 3H-N-Methylspiperone to Dopamine and Serotonin Receptors. Life Sciences, 40:987–995.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301–308.

Lucki, I, Nobler, M. S., Frazer, A., 1984, Differential actions of serotonin antagonists on two behavioral models of serotonin receptor activation in the rat. J. Pharmacol. Exp. Ther. 228(1):133–139.

Dosage and Formulation

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences,* supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 ml contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

The Tables below provide representative Examples, the synthesis of which are described above, of the the compounds of Formula (I) of the present invention.

TABLE 1

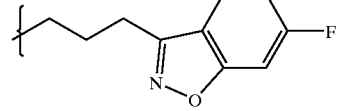

| Ex # | X | n | k | R7 | R8 | R9 | b | R1 |
|---|---|---|---|---|---|---|---|---|
| 196 | NHCO | 1 | 1 | H | H | H | dbl | —(CH$_2$)$_3$C(═O)(4-F-phenyl) |
| 210 | NMe | 2 | 1 | H | H | H | sgl | —(CH$_2$)$_3$C(═O)(4-pryidyl) |
| 211 | NH | 2 | 1 | H | H | H | sgl | H |
| 212 | NH | 2 | 1 | H | H | H | sgl | —(CH$_2$)$_3$C(═O)(4-F-phenyl) |
| 217 | NMe | 2 | 1 | H | H | H | sgl | (6-F-benzisoxazol-3-yl)propyl |
| 218 | NMe | 2 | 1 | H | H | H | sgl | (benzisoxazol-3-yl)propyl |
| 255 | NMe | 2 | 1 | H | H | H | sgl | H |
| 256 | NEt | 2 | 1 | H | H | H | sgl | H |
| 257 | NPr | 2 | 1 | H | H | H | sgl | H |
| 258 | N(i-Pr) | 2 | 1 | H | H | H | sgl | H |
| 259 | N(n-Bu) | 2 | 1 | H | H | H | sgl | H |
| 260 | N(CH$_2$Ph) | 2 | 1 | H | H | H | sgl | H |
| 261 | NMe | 2 | 1 | H | H | H | sgl | —(CH$_2$)$_3$C(═O)(4-F-phenyl) |
| 262 | NEt | 2 | 1 | H | H | H | sgl | —(CH$_2$)$_3$C(═O)(4-F-phenyl) |
| 263 | N(i-Pr) | 2 | 1 | H | H | H | sgl | —(CH$_2$)$_3$C(═O)(4-F-phenyl) |
| 264 | N(CH$_2$Ph) | 2 | 1 | H | H | H | sgl | —(CH$_2$)$_3$C(═O)(4-F-phenyl) |
| 269 | NMe | 2 | 1 | H | H | H | sgl | —(CH$_2$)$_3$O(4-F-phenyl) |
| 274 | NMe | 2 | 1 | H | 2,4-diCl-phenyl | H | sgl | H |
| 275 | NH | 2 | 1 | H | 2,4-diCl-phenyl | H | sgl | H |
| 276 | NMe | 2 | 1 | H | Br | H | sgl | —(CH$_2$)$_3$C(═O)(4-F-phenyl) |
| 277 | NMe | 2 | 1 | H | MeO | H | sgl | —(CH$_2$)$_3$C(═O)(4-F-phenyl) |
| 278 | NMe | 2 | 1 | H | 2,4-diCl-phenyl | H | sgl | H |
| 279 | NH | 3 | 1 | H | 4-MeO-2-Me-phenyl | H | sgl | H |
| 280 | NHCO | 2 | 1 | H | 2,4-diCl-phenyl | H | sgl | H |
| 281 | NMe | 2 | 2 | H | H | H | sgl | H |
| 282 | NMe | 2 | 2 | H | H | H | sgl | —(CH$_2$)$_3$C(═O)(4-F-phenyl) |
| 283 | NHCH(Me) | 1 | 1 | H | 2,4-diCl-phenyl | H | sgl | H |

TABLE 2

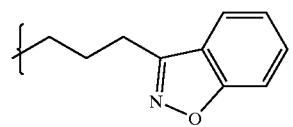

| Ex # | R7 | R8 | R9 | b | R1 |
|---|---|---|---|---|---|
| 4 | H | H | F | dbl | —CO$_2$Et |
| 5 | H | H | F | dbl | H |

TABLE 2-continued

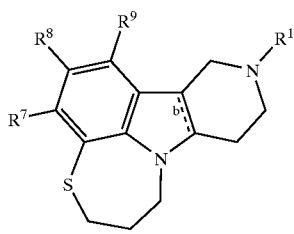

| Ex # | R7 | R8 | R9 | b | R1 |
|---|---|---|---|---|---|
| 6 | H | H | Me | dbl | H |
| 7 | H | H | Me | dbl | —CO$_2$-tBu |
| 8 | H | H | Me | sgl | H |
| 9 | H | H | H | sgl | H |
| 10 | H | H | NO$_2$ | dbl | H |
| 11 | H | H | NO$_2$ | sgl | H |
| 12 | Cl | H | H | dbl | H |
| 13 | Cl | H | H | sgl | H |
| 14 | Me | H | H | dbl | H |
| 15 | Me | H | H | sgl | H |
| 18 | H | H | Br | dbl | H |
| 19 | H | H | Br | sgl | H |
| 25 | H | H | H | sgl | —C(=O)(3,4-diMeO-phenyl) |
| 26 | H | H | H | sgl | —C(=O)(2,5-diMeO-phenyl) |
| 27 | H | H | H | sgl | —C(=O)(3,5-diMeO-phenyl) |
| 28 | H | H | H | sgl | 2,6-diMeO-benzyl |
| 29 | H | H | H | sgl | 2,4-diMeO-benzyl |
| 30 | H | H | H | sgl | 2,4,6-triMeO-benzyl |
| 31 | H | H | H | sgl | 2,3-diMeO-benzyl |
| 32 | H | H | H | sgl | 2,4,5-triMeO-benzyl |
| 33 | H | H | H | sgl | cyclohexylmethyl |
| 34 | H | H | H | sgl | 2,3,4-triMeO-benzyl |
| 35 | H | H | H | sgl | 3,4-diMeO-benzyl |
| 36 | H | H | H | sgl | 3,4,5-triMeO-benzyl |
| 39 | H | H | H | sgl | —CO$_2$Et |
| 40 | H | —C(=O)CH$_3$ | H | sgl | —CO$_2$Et |
| 41 | H | —NHC(=O)CH$_3$ | H | sgl | —CO$_2$Et |
| 42 | H | H | H | sgl | —CH$_2$CH$_2$(4-F-phenyl) |
| 43 | H | H | H | sgl | Et |
| 44 | H | H | H | sgl | Pr |
| 45 | H | H | H | sgl | butyl |
| 46 | H | H | H | sgl | pentyl |
| 47 | H | H | H | sgl | hexyl |
| 48 | H | H | H | sgl | 2-propyl |
| 49 | H | H | H | sgl | 2-butyl |
| 50 | H | H | H | sgl | 2-pentyl |
| 51 | H | H | H | sgl | 2-hexyl |
| 52 | H | H | H | sgl | 2-Me-propyl |
| 53 | H | H | H | sgl | 2-Me-butyl |
| 54 | H | H | H | sgl | 2-Me-pentyl |
| 55 | H | H | H | sgl | 2-Et-butyl |
| 56 | H | H | H | sgl | 3-Me-pentyl |
| 57 | H | H | H | sgl | 3-Me-butyl |
| 58 | H | H | H | sgl | 4-Me-pentyl |
| 59 | H | H | H | sgl | cyclopropylmethyl |
| 60 | H | H | H | sgl | cyclobutylmethyl |
| 61 | H | H | H | sgl | cyclohexylmethyl |
| 62 | H | H | H | sgl | 2-propenyl |
| 63 | H | H | H | sgl | 2-Me-2-propenyl |
| 64 | H | H | H | sgl | trans-2-butenyl |
| 65 | H | H | H | sgl | 3-Me-butenyl |
| 66 | H | H | H | sgl | 3-butenyl |
| 67 | H | H | H | sgl | trans-2-pentenyl |
| 68 | H | H | H | sgl | cis-2-pentenyl |
| 69 | H | H | H | sgl | 4-pentenyl |
| 70 | H | H | H | sgl | 4-Me-3-pentenyl |
| 71 | H | H | H | sgl | 3,3-diCl-2-propenyl |
| 72 | H | H | H | sgl | benzyl |
| 73 | H | H | H | sgl | 2-Me-benzyl |
| 74 | H | H | H | sgl | 3-Me-benzyl |
| 75 | H | H | H | sgl | 4-Me-benzyl |
| 76 | H | H | H | sgl | 2,5-diMe-benzyl |
| 77 | H | H | H | sgl | 2,4-diMe-benzyl |
| 78 | H | H | H | sgl | 3,5-diMe-benzyl |
| 79 | H | H | H | sgl | 2,4,6-triMe-benzyl |

TABLE 2-continued

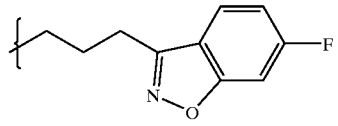

| Ex # | R7 | R8 | R9 | b | R1 |
|---|---|---|---|---|---|
| 80 | H | H | H | sgl | 3-MeO-benzyl |
| 81 | H | H | H | sgl | 3,5-diMeO-benzyl |
| 82 | H | H | H | sgl | pentafluorobenzyl |
| 83 | H | H | H | sgl | 2-phenylethyl |
| 84 | H | H | H | sgl | 1-phenyl-2-propyl |
| 85 | H | H | H | sgl | trans-3-phenyl-2-propenyl |
| 86 | H | H | H | sgl | 4-phenylbutyl |
| 87 | H | H | H | sgl | 4-phenylbenzyl |
| 88 | H | H | H | sgl | 2-phenylbenzyl |
| 169 | H | Me | H | sgl | H |
| 170 | H | CN | H | sgl | H |
| 171 | H | Et | H | sgl | H |
| 175 | H | H | H | dbl | Me |
| 176 | H | H | H | sgl | Me |
| 177 | H | H | H | sgl | H |
| 178 | Cl | H | H | sgl | —$(CH_2)_3C(=O)$(4-F-phenyl) |
| 179 | Me | H | H | sgl | —$(CH_2)_3C(=O)$(4-F-phenyl) |
| 180 | H | H | H | sgl | —$(CH_2)_3S$(3-F-phenyl) |
| 181 | H | H | H | sgl | —$(CH_2)_3CH(OH)$(4-F-phenyl) |
| 186 | H | H | H | sgl | —$(CH_2)_3C(=O)$(4-F-phenyl) |
| 187 | H | MeO | H | sgl | —$(CH_2)_3C(=O)$(4-F-phenyl) |
| 192 | H | H | H | sgl | —$(CH_2)_3C(=O)$(4-Br-phenyl) |
| 193 | H | H | H | sgl | —$(CH_2)_3SO_2$(3-F-phenyl) |
| 194 | H | H | H | sgl | —$(CH_2)_3C(=O)$(4-(3,4-diCl-phenyl)phenyl) |
| 197 | H | H | H | sgl | —$(CH_2)_3C(=O)$(4-Me-phenyl) |
| 198 | H | H | H | sgl | —$(CH_2)_3C(=O)$(4-F-phenyl) |
| 199 | H | H | H | sgl | —$(CH_2)_3C(=O)$(4-MeO-phenyl) |
| 200 | H | H | H | sgl | —$(CH_2)_3C(=O)$(4-F-phenyl) |
| 201 | H | H | H | sgl | —$(CH_2)_3SO_2$(4-F-phenyl) |
| 202 | H | H | H | sgl | —$(CH_2)_3S(=O)$(4-F-phenyl) |
| 203 | H | H | H | sgl | —$(CH_2)_3O$(4-F-phenyl) |
| 204 | H | H | H | sgl | —$(CH_2)_3O$(phenyl) |
| 205 | H | H | H | sgl | —$(CH_2)_3S$(4-F-phenyl) |
| 206 | H | H | H | sgl | —$(CH_2)_3NH$(4-F-phenyl) |
| 207 | H | H | H | sgl | —$(CH_2)_3N(CH_3)$(4-F-phenyl) |
| 208 | H | H | H | sgl | —$(CH_2)_3C(=O)$(4-pyridyl) |
| 209 | H | H | H | sgl | —$(CH_2)_3C(=O)$(3-pyridyl) |
| 214 | H | H | H | sgl | 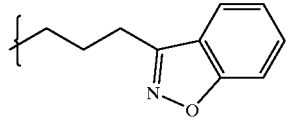 |
| 215 | H | H | H | sgl | |
| 219 | H | H | H | sgl | —$(CH_2)_3CO_2Et$ |
| 220 | H | H | H | sgl | —$(CH_2)_4CO_2Et$ |
| 221 | H | H | H | sgl | —$(CH_2)_3C(=O)N(CH_3)(OCH_3)$ |
| 222 | H | H | H | sgl | —$(CH_2)_4C(=O)N(CH_3)(OCH_3)$ |
| 223 | H | H | H | sgl | —$(CH_2)_3C(=O)$(3-Me-4-F-phenyl) |
| 224 | H | H | H | sgl | —$(CH_2)_3C(=O)$(phenyl) |
| 225 | H | H | H | sgl | —$(CH_2)_3C(=O)$(4-Cl-phenyl) |
| 226 | H | H | H | sgl | —$(CH_2)_3C(=O)$(3-Me-phenyl) |
| 227 | H | H | H | sgl | —$(CH_2)_3C(=O)$(4-tBu-phenyl) |
| 228 | H | H | H | sgl | —$(CH_2)_3C(=O)$(3,4-diF-phenyl) |
| 229 | H | H | H | sgl | —$(CH_2)_3C(=O)$(2-MeO-5-F-phenyl) |
| 230 | H | H | H | sgl | —$(CH_2)_4C(=O)$(phenyl) |
| 231 | H | H | H | sgl | —$(CH_2)_3C(=O)$(4-F-1-naphthyl) |

TABLE 2-continued

| Ex # | R7 | R8 | R9 | b | R1 |
|---|---|---|---|---|---|
| 232 | H | H | H | sgl | —(CH$_2$)$_3$C(=O)(benzyl) |
| 233 | H | H | H | sgl | —(CH$_2$)$_2$C(=O)NH(4-F-phenyl) |
| 234 | H | H | H | sgl | —(CH$_2$)$_3$C(=O)NH(4-F-phenyl) |
| 235 | H | H | H | sgl | —(CH$_2$)$_3$CH(OH)(4-F-phenyl) |
| 236 | H | H | H | sgl | —(CH$_2$)$_3$CH(OH)(4-pyridyl) |
| 237 | H | H | H | sgl | —(CH$_2$)$_3$CH(OH)(2,3-diMeO-phenyl) |
| 238 | H | H | H | sgl | —(CH$_2$)$_3$C(=O)(2,3-diMeO-phenyl) |
| 239 | H | H | H | sgl | —(CH$_2$)$_4$(cyclohexyl) |
| 240 | H | H | H | sgl | —(CH$_2$)$_3$CH(phenyl)$_2$ |
| 241 | H | H | H | sgl | —CH$_2$CH$_2$CH=C(phenyl)$_2$ |
| 242 | H | H | H | sgl | —(CH$_2$)$_3$CH(4-F-phenyl)$_2$ |
| 243 | H | H | H | sgl | —CH$_2$CH$_2$CH=C(4-F-phenyl)$_2$ |
| 244 | H | H | H | sgl | —(CH$_2$)$_2$NHC(=O)(phenyl) |
| 245 | H | H | H | sgl | —(CH$_2$)$_2$NHC(=O)(2-F-phenyl) |
| 246 | H | H | H | sgl | —(CH$_2$)$_2$NHC(=O)(4-F-phenyl) |
| 247 | H | H | H | sgl | —(CH$_2$)$_3$(3-indolyl) |
| 248 | H | H | H | sgl | —(CH$_2$)$_3$(1-Me-3-indolyl) |
| 249 | H | H | H | sgl | —CH$_2$CH$_2$(3-indolyl) |
| 250 | H | H | H | sgl | —(CH$_2$)$_3$(1-indolyl) |
| 251 | H | H | H | sgl | —(CH$_2$)$_3$(1-indolinyl) |
| 252 | H | H | H | sgl | —(CH$_2$)$_3$(1-benzimidazolyl) |
| 253 | H | H | H | sgl | (N-propyl phthalimide) |
| 254 | H | H | H | sgl | (N-propyl isoindolinone) |
| 268 | H | F | H | sgl | —(CH$_2$)$_3$C(=O)(4-F-phenyl) |
| 271 | H | H | H | sgl | H |
| 273 | H | F | H | sgl | H |
| S274 | Br | H | H | sgl | H |
| S275 | 2,6-diF-phenyl | H | H | sgl | H |
| S276 | 2-Me-4-MeO-phenyl | H | H | sgl | H |
| S277 | 4-CF$_3$-phenyl | H | H | sgl | H |
| S278 | 2,3-diCl-phenyl | H | H | sgl | H |
| S279 | 2,4-diCl-phenyl | H | H | sgl | H |
| S280 | 2-Cl-4-CF$_3$-phenyl | H | H | sgl | H |
| S281 | CN | H | H | sgl | H |
| S282 | CN | Br | H | sgl | H |
| S283 | benzyl | H | H | sgl | H |
| 284 | CHO | H | H | sgl | H |
| 285 | CO$_2$H | H | H | sgl | H |
| 286 | H | H | H | sgl | —(CH$_2$)$_2$NHC(=O)(2,4-diF-phenyl) |
| 287 | H | H | H | sgl | —(CH$_2$)$_2$NMeC(=O)-phenyl |
| 288 | H | H | H | sgl | —(CH$_2$)$_2$NMeC(=O)(2-F-phenyl) |
| 289 | H | H | H | sgl | —(CH$_2$)$_2$NMeC(=O)(2,4-diF-phenyl) |
| 290 | H | H | H | sgl | —(CH$_2$)$_2$NMeC(=O)(4-F-phenyl) |
| 291 | H | H | H | sgl | —(CH$_2$)$_3$(1H-1,2,3-benzotriazol-1-yl) |
| 292 | H | H | H | sgl | —(CH$_2$)$_3$(1H-1,2,3-benzotriazol-2-yl) |

TABLE 2-continued

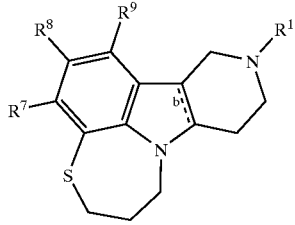

| Ex # | R7 | R8 | R9 | b | R1 |
|---|---|---|---|---|---|
| 293 | H | H | H | sgl | 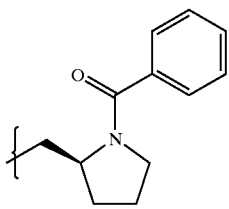 |
| 294 | H | H | H | sgl | 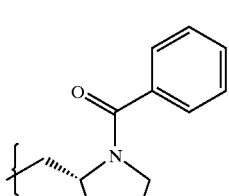 |
| 295 | H | H | H | sgl | 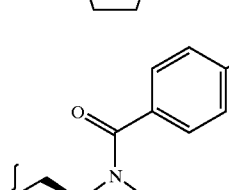 |
| 296 | H | H | H | sgl | —$(CH_2)_2$(1H-1,2,3-benzotriazol-1-yl) |
| 297 | H | H | H | sgl | 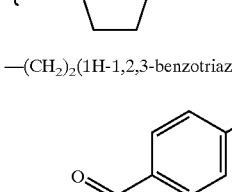 |
| 298 | H | H | H | sgl | —$(CH_2)_2$(1H-1,2,3-benzotriazol-1-yl) |
| 299 | H | H | H | sgl | —$(CH_2)_3$(3,4-dihydro-1(2H)-quinolinyl) |
| 300 | H | H | H | sgl | —$CH_2CH_2CH$=$CMe$-(4-F-phenyl) |
| 301 | H | H | H | sgl | —$(CH_2)_2$(2,3-dihydro-1H-inden-2-yl) |
| 302 | H | H | H | sgl | —$(CH_2)_3C$(=O)(2-$NH_2$-phenyl) |
| 303 | H | H | H | sgl | —$(CH_2)_3C$(=O)(2-$NH_2$-phenyl) |
| 304 | H | H | H | sgl | —$(CH_2)_3C$(=O)(2-$NH_2$-5-F-phenyl) |
| 305 | H | H | H | sgl | —$(CH_2)_3C$(=O)(2-$NH_2$-3-F-phenyl) |
| 306 | H | H | H | sgl | —$(CH_2)_3C$(=O)(2-$NH_2$-4-Cl-phenyl) |
| 307 | H | H | H | sgl | —$(CH_2)_3C$(=O)(2-$NH_2$-4-OH-phenyl) |
| 308 | H | H | H | sgl | —$(CH_2)_3C$(=O)(2-$NH_2$-4-Br-phenyl) |
| 309 | H | H | H | sgl | —$(CH_2)_3$(1H-indazol-3-yl) |
| 310 | H | H | H | sgl | —$(CH_2)_3$(5-F-1H-indazol-3-yl) |
| 311 | H | H | H | sgl | —$(CH_2)_3$(7-F-1H-indazol-3-yl) |
| 312 | H | H | H | sgl | —$(CH_2)_3$(6-Cl-1H-indazol-3-yl) |
| 313 | H | H | H | sgl | —$(CH_2)_3$(6-Br-1H-indazol-3-yl) |
| 314 | H | H | H | sgl | —$(CH_2)_3C$(=O)(2-NHMe-phenyl) |
| 315 | H | H | H | sgl | —$(CH_2)_3$(1-benzothien-3-yl) |

TABLE 2-continued

| Ex # | R7 | R8 | R9 | b | R1 |
|---|---|---|---|---|---|
| 355 | H | H | H | sgl | [2-(3-oxo-2H-[1,2,4]triazolo[4,3-a]pyridin-2-yl)ethyl substituent] |
| 356 | H | H | H | sgl | —(CH$_2$)$_3$(6-F-1H-indol-1-yl) |
| 357 | H | H | H | sgl | —(CH$_2$)$_3$(5-F-1H-indol-1-yl) |
| 358 | H | H | H | sgl | —(CH$_2$)$_3$(6-F-2,3-dihydro-1H-indol-1-yl) |
| 359 | H | H | H | sgl | —(CH$_2$)$_3$(5-F-2,3-dihydro-1H-indol-1-yl) |
| 360 | H | H | H | sgl | —(CH$_2$)$_3$(6-F-1H-indol-3-yl) |
| 361 | H | H | H | sgl | —(CH$_2$)$_3$(6-F-1H-indol-3-yl) |
| 362 | H | H | H | sgl | —(CH$_2$)$_3$(5-F-1H-indol-3-yl) |
| 363 | H | H | H | sgl | —(CH$_2$)$_3$(5-F-1H-indol-3-yl) |
| 364 | H | H | H | sgl | —(CH$_2$)$_3$(9H-purin-9-yl) |
| 365 | H | H | H | sgl | —(CH$_2$)$_3$(7H-purin-7-yl) |
| 366 | H | H | H | sgl | [5-(4-cyanophenyl)-4,5-dihydroisoxazol-3-yl methyl substituent] |
| 367 | H | H | H | sgl | —(CH$_2$)$_3$(6-F-1H-indazol-3-yl) |
| 368 | H | H | H | sgl | —(CH$_2$)$_3$(6-F-1H-indazol-3-yl) |
| 369 | H | H | H | sgl | —(CH$_2$)$_3$(6-F-1H-indazol-3-yl) |
| 370 | H | H | H | sgl | —(CH$_2$)$_3$C(=O)(2-NH$_2$-4-F-phenyl) |
| 371 | H | H | H | sgl | —(CH$_2$)$_3$C(=O)(2-NH$_2$-4-F-phenyl) |
| 372 | H | H | H | sgl | —(CH$_2$)$_3$C(=O)(2-NHSO$_2$Me-4-F-phenyl) |
| 373 | H | H | H | sgl | —(CH$_2$)$_3$C(=O)(2-NHC(=O)Me-4-F-phenyl) |
| 374 | H | H | H | sgl | —(CH$_2$)$_3$C(=O)(2-NHC(=O)Me-4-F-phenyl) |
| 375 | H | H | H | sgl | —(CH$_2$)$_3$C(=O)(2-NHCO$_2$Et-4-F-phenyl) |
| 376 | H | H | H | sgl | —(CH$_2$)$_3$C(=O)(2-NHC(=O)NHEt-4-F-phenyl) |
| 377 | H | H | H | sgl | —(CH$_2$)$_3$C(=O)(2-NHCHO)-4-F-phenyl) |
| 378 | H | H | H | sgl | —(CH$_2$)$_3$C(=O)(2-OH-4-F-phenyl) |
| 379 | H | H | H | sgl | —(CH$_2$)$_3$C(=O)(2-MeS-4-F-phenyl) |
| 442 | H | H | H | sgl | —(CH$_2$)$_3$C(=O)(2-NHSO$_2$Me-4-F-phenyl) |
| 485 | H | H | H | sgl | —(CH$_2$)$_2$C(Me)CO$_2$Me |
| 486 | H | H | H | sgl | —(CH$_2$)$_2$C(Me)C(=O)(4-F-phenyl)$_2$ |
| 487 | H | H | H | sgl | —(CH$_2$)$_2$C(Me)C(OH)(4-Cl-phenyl)$_2$ |
| 489 | H | H | H | sgl | —(CH$_2$)$_2$C(Me)C(=O)(4-F-phenyl) |
| 490 | H | H | H | sgl | —(CH$_2$)$_2$C(Me)C(=O)(2-MeO-4-F-phenyl) |
| 491 | H | H | H | sgl | —(CH$_2$)$_2$C(Me)C(=O)(3-Me-4-F-phenyl) |
| 492 | H | H | H | sgl | —(CH$_2$)$_2$C(Me)C(=O)(2-Me-phenyl) |
| 493 | H | H | H | sgl | —(CH$_2$)$_2$C(Me)C(=O)phenyl |
| 591 | Cl | H | H | sgl | —(CH$_2$)$_3$C(=O)(2-NH$_2$-4-F-phenyl |

TABLE 2A

| Ex# | R7 | R8 | R9 | b | R1 |
|---|---|---|---|---|---|
| 115 | H | H | Br | dbl | —CO$_2$-tBu |
| 116 | H | H | 2,3-diCl-phenyl | dbl | —CO$_2$-tBu |
| 117 | H | H | 3,4-diCl-phenyl | dbl | —CO$_2$-tBu |
| 118 | H | H | 2-Cl-4-CF$_3$-phenyl | dbl | —CO$_2$-tBu |
| 119 | H | H | 2,3-diCl-phenyl | dbl | H |
| 120 | H | H | 3,4-diCl-phenyl | dbl | H |
| 121 | H | H | 2-Cl-4-CF$_3$-phenyl | dbl | H |
| 122 | H | H | 2,3-diCl-phenyl | sgl | H |
| 123 | H | H | 3,4-diCl-phenyl | sgl | H |
| 124 | H | H | 2-Cl-4-CF$_3$-phenyl | sgl | H |
| 125 | H | H | Br | sgl | —CO$_2$-tBu |
| 126 | H | H | 2,6-diF-phenyl | sgl | —CO$_2$-tBu |
| 127 | H | H | 2,6-diF-phenyl | sgl | H |
| 128 | H | 2,4-diCl-phenyl | H | sgl | H |
| 129 | H | phenyl | H | sgl | H |
| 130 | H | 4-F-phenyl | H | sgl | H |
| 131 | H | 4-Cl-phenyl | H | sgl | H |
| 132 | H | 2-Cl-phenyl | H | sgl | H |
| 133 | H | 2-MeO-phenyl | H | sgl | H |
| 134 | H | 2-Cl-4-CF$_3$-phenyl | H | sgl | H |
| 135 | H | 2,4-diMe-phenyl | H | sgl | H |
| 136 | H | 2-Cl-4-MeO-phenyl | H | sgl | H |
| 137 | H | 4-iPr-phenyl | H | sgl | H |
| 138 | H | 4-Bu-phenyl | H | sgl | H |
| 139 | H | 2-Me-4-MeO-5-F-phenyl | H | sgl | H |
| 140 | H | 2-Me-4-MeO-phenyl | H | sgl | H |
| 141 | H | 2-Cl-4-CF$_3$O-phenyl | H | sgl | H |
| 142 | H | 2,4,5-triMe-phenyl | H | sgl | H |
| 143 | H | 3-Cl-phenyl | H | sgl | H |
| 144 | H | 4-Me-phenyl | H | sgl | H |
| 145 | H | 2-Me-4-Cl-phenyl | H | sgl | H |
| 146 | H | 2,5-diCl-phenyl | H | sgl | H |
| 147 | H | 2-MeO-4-iPr-phenyl | H | sgl | H |
| 148 | H | 2,6-diCl-phenyl | H | sgl | H |
| 149 | H | 2,6-diF-phenyl | H | sgl | H |
| 150 | H | 2-CF$_3$—4-MeO-phenyl | H | sgl | H |
| 151 | H | 2-CF$_3$-phenyl | H | sgl | H |
| 152 | H | 4-pyridyl | H | sgl | H |
| 153 | H | 2-furanyl | H | sgl | H |
| 154 | H | 2-thiophenyl | H | sgl | H |
| 155 | H | 4-F-phenyl | H | sgl | H |
| 156 | H | 2,3-diCl-phenyl | H | sgl | H |
| 157 | H | 4-Et-phenyl | H | sgl | H |
| 158 | H | 2,4-diMeO-phenyl | H | sgl | H |
| 159 | H | 2-F-3-Cl-phenyl | H | sgl | H |
| 160 | H | 4-MeO-phenyl | H | sgl | H |
| 161 | H | 4-MeS-phenyl | H | sgl | H |
| 162 | H | 4-CN-phenyl | H | sgl | H |
| 163 | H | 3-CF$_3$-phenyl | H | sgl | H |
| 164 | H | 2-MeO-phenyl | H | sgl | H |
| 165 | H | 2-naphthyl | H | sgl | H |
| 166 | H | 4-acetylphenyl | H | sgl | H |
| 167 | H | 3-acetamidophenyl | H | sgl | H |
| 168 | H | 2,4-diCl-phenyl | H | sgl | Me |
| 316 | H | 2,3-diMe-phenyl | H | sgl | H |
| 317 | H | 2-Me-5-F-phenyl | H | sgl | H |
| 318 | H | 2-F-5-Me-phenyl | H | sgl | H |
| 319 | H | 2-MeO-5-F-phenyl | H | sgl | H |
| 320 | H | 2-Me-3-Cl-phenyl | H | sgl | H |
| 321 | H | 3-NO$_2$-phenyl | H | sgl | H |
| 322 | H | 2-NO$_2$-phenyl | H | sgl | H |
| 323 | H | 2-Cl-3-Me-phenyl | H | sgl | H |
| 324 | H | 2-MeO-phenyl | H | sgl | H |
| 325 | H | 2,3-diCl-phenyl | H | sgl | H |

TABLE 2A-continued

| Ex# | R7 | R8 | R9 | b | R1 |
|---|---|---|---|---|---|
| 326 | H | 2-Cl-4-CF$_3$-phenyl | H | sgl | H |
| 327 | H | 2-Me-4-EtO-phenyl | H | sgl | H |
| 328 | H | 2-Me-4-F-phenyl | H | sgl | H |
| 329 | H | 4-Bu-phenyl | H | sgl | H |
| 330 | H | 2-CF$_3$-phenyl | H | sgl | H |
| 331 | H | 2-Cl-6-F-phenyl | H | sgl | H |
| 332 | H | 2-Cl-4-(CHF$_2$)O-phenyl | H | sgl | H |
| 333 | H | 4-CF$_3$-phenyl | H | sgl | H |
| 334 | H | 4-Me-phenyl | H | sgl | H |
| 335 | H | 4-CF$_3$O-phenyl | H | sgl | H |
| 336 | H | 2,4-diMeO-6-F-phenyl | H | sgl | H |
| 337 | H | 2-Me-phenyl | H | sgl | H |
| 338 | H | 2-CF$_3$-6-F-phenyl | H | sgl | H |
| 339 | H | 2-MeS-phenyl | H | sgl | H |
| 340 | H | 2,4,6-triF-phenyl | H | sgl | H |
| 341 | H | 2,4,6-triCl-phenyl | H | sgl | H |
| 342 | H | 2,6-diCl-4-MeO-phenyl | H | sgl | H |
| 343 | H | 2,3,4-triF-phenyl | H | sgl | H |
| 344 | H | 2,6-diF-4-Cl-phenyl | H | sgl | H |
| 345 | H | 2,3,4,6-tetraF-phenyl | H | sgl | H |
| 346 | H | 2,3,4,5,6-pentaF-phenyl | H | sgl | H |
| 347 | H | 2,6-diCF$_3$-phenyl | H | sgl | H |
| 348 | H | 2-CF$_3$O-phenyl | H | sgl | H |
| 349 | H | 2-CF$_3$-4-EtO-phenyl | H | sgl | H |
| 350 | H | 2-CF$_3$-4-iPrO-phenyl | H | sgl | H |
| 351 | H | 2-naphtyl | H | sgl | H |
| 352 | H | 2-CF$_3$-4-Cl-phenyl | H | sgl | H |
| 353 | H | 2-CF$_3$-4-F-phenyl | H | sgl | H |
| 354 | H | 2,4-diF-phenyl | H | sgl | Me |
| 380 | H | 2-Cl-4-EtO-phenyl | H | sgl | H |
| 381 | H | 2-Cl-4-iPrO-phenyl | H | sgl | H |
| 382 | H | 2-Et-4-MeO-phenyl | H | sgl | H |
| 383 | H | 2-CHO-4-MeO-phenyl | H | sgl | H |
| 384 | H | 2-CH(OH)Me-4-MeO-phenyl | H | sgl | H |
| 385 | H | 2-CH(OMe)Me-4-MeO-phenyl | H | sgl | H |
| 386 | H | 2-C(=O)Me-4-MeO-phenyl | H | sgl | H |
| 387 | H | 2-CH$_2$(OH)-4-MeO-phenyl | H | sgl | H |
| 388 | H | 2-CH$_2$(OMe)-4-MeO-phenyl | H | sgl | H |
| 389 | H | 2-CH(OH)Et-4-MeO-phenyl | H | sgl | H |
| 390 | H | 2-C(=O)Et-4-MeO-phenyl | H | sgl | H |
| 391 | H | (Z)-2-CH=CHCO$_2$Me-4-MeO-phenyl | H | sgl | H |
| 392 | H | 2-CH$_2$CH$_2$CO$_2$Me-4-MeO-phenyl | H | sgl | H |
| 393 | H | (Z)-2-CH=CHCH$_2$(OH)-4-MeO-phenyl | H | sgl | H |
| 394 | H | (E)-2-CH=CHCO$_2$Me-4-MeO-phenyl | H | sgl | H |
| 395 | H | (E)-2-CH=CHCH$_2$(OH)-4-MeO-phenyl | H | sgl | H |

TABLE 2A-continued

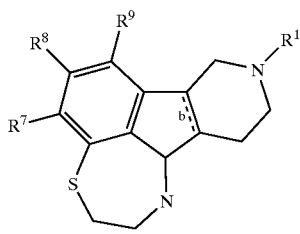

| Ex# | R7 | R8 | R9 | b | R1 |
|---|---|---|---|---|---|
| 396 | H | 2-CH$_2$CH$_2$OMe-4-MeO-phenyl | H | sgl | H |
| 397 | H | 2-F-4-MeO-phenyl | H | sgl | H |
| 403 | H | 2-Cl-4-F-phenyl | H | sgl | H |
| 405 | H | (2-Cl-phenyl)-CH=CH— | H | sgl | H |
| 406 | H | (3-Cl-phenyl)-CH=CH— | H | sgl | H |
| 407 | H | (2,6-diF-phenyl)-CH=CH— | H | sgl | H |
| 410 | H | cyclohexyl | H | sgl | H |
| 411 | H | cyclopentyl | H | sgl | H |
| 412 | H | cyclohexylmethyl | H | sgl | H |
| 413 | H | —CH$_2$CH$_2$CO$_2$Et | H | sgl | H |
| 414 | H | —(CH$_2$)$_3$CO$_2$Et | H | sgl | H |
| 415 | H | —(CH$_2$)$_4$CO$_2$Et | H | sgl | H |
| 416 | H | —CH$_2$CH=CH$_2$ | H | sgl | H |
| 417 | H | Pr | H | sgl | H |
| 418 | H | benzyl | H | sgl | H |
| 419 | H | 2-F-benzyl | H | sgl | H |
| 420 | H | 3-F-benzyl | H | sgl | H |
| 421 | H | 4-F-benzyl | H | sgl | H |
| 422 | H | 3-MeO-benzyl | H | sgl | H |
| 423 | H | 3-OH-benzyl | H | sgl | H |
| 424 | H | 2-MeO-benzyl | H | sgl | H |
| 425 | H | 2-OH-benzyl | H | sgl | H |
| 426 | H | 2-CO$_2$Me-3-MeO-phenyl | H | sgl | H |
| 427 | H | 2,6-diF-phenyl | H | sgl | H |
| 428 | H | phenyl-CH=CH— | H | sgl | H |
| 429 | H | (2-Me-4-MeO-phenyl)—CH=CH= | H | sgl | H |
| 430 | H | —NMe$_2$ | H | sgl | H |
| 431 | H | 1-pyrrolidinyl | H | sgl | H |
| 432 | H | —NTs$_2$ | H | sgl | H |
| 433 | H | MeO | H | sgl | H |
| 445 | H | 2-Me-4-MeO-phenyl | Me | sgl | H |
| 446 | H | 2-CF$_3$-4-MeO-phenyl | Me | sgl | H |
| 458 | Me | 2-CF$_3$-4-MeO-phenyl | H | sgl | H |
| 459 | Me | 2,4-diCl-phenyl | H | sgl | H |
| 460 | H | 3-CN-phenyl | H | sgl | H |
| 461 | H | 2-Me-4-CN-phenyl | H | sgl | H |
| 462 | H | 2-Me-3-CN-phenyl | H | sgl | H |
| 463 | H | 2-CN-phenyl | H | sgl | H |
| 464 | H | 2-CF$_3$-4-CN-phenyl | Me | sgl | H |
| 465 | H | 3-CHO-phenyl | Me | sgl | H |
| 466 | H | 3-CH$_2$(OH)-phenyl | Me | sgl | H |
| 467 | H | 3-CH$_2$(OMe)-phenyl | Me | sgl | H |
| 468 | H | 3-CH$_2$(NMe$_2$)-phenyl | Me | sgl | H |
| 469 | H | 3-CN-4-F-phenyl | Me | sgl | H |
| 470 | H | 3-CONH$_2$-4-F-phenyl | Me | sgl | H |
| 580 | NH$_2$ | H | H | sgl | H |
| 581 | H | phenyl-NH— | H | sgl | H |
| 582 | phenyl-NH— | H | H | sgl | H |
| 583 | H | (4-F-phenyl)—NH— | H | sgl | H |
| 584 | H | (2,4-diCl-phenyl)—NH— | H | sgl | H |
| 585 | H | phenyl-C(=O)NH— | H | sgl | H |
| 586 | H | benzyl-NH— | H | sgl | H |
| 587 | H | phenyl-S— | H | sgl | H |
| 588 | MeO | H | H | sgl | H |
| 589 | H | 2-CH$_2$(NH$_2$)-4-MeO-phenyl- | H | sgl | H |
| 590 | H | 2-Me-4-MeO-phenyl- | H | sgl | H |
| 592 | H | (2-Me-4-MeO-phenyl)—NH— | H | sgl | H |

TABLE 2A-continued

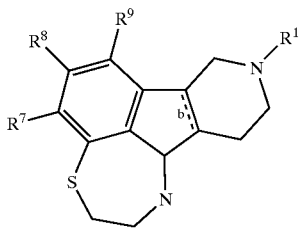

| Ex# | R7 | R8 | R9 | b | R1 |
|---|---|---|---|---|---|
| 593 | H | (2-F-4-MeO-phenyl)—NH— | H | sgl | H |
| 595 | H | (2-Me-4-F-phenyl)—NH— | H | sgl | H |

TABLE 3

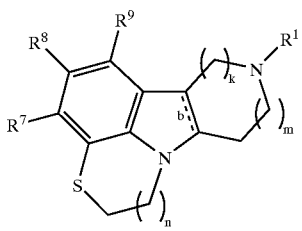

| Ex# | n | k | m | R7 | R8 | R9 | b | R1 |
|---|---|---|---|---|---|---|---|---|
| 471 | 2 | 2 | 1 | H | H | H | sgl | H |
| 472 | 2 | 2 | 1 | H | H | H | sgl | —(CH$_2$)$_3$C(=O)(4-F-phenyl) |
| 473 | 2 | 2 | 1 | H | H | H | sgl | —(CH$_2$)$_3$O(4-F-phenyl) |
| 474 | 2 | 2 | 1 | H | H | H | sgl | —(CH$_2$)$_3$(6-F-benzisoxazol-3-yl) |
| 475 | 2 | 2 | 1 | H | H | H | sgl | —(CH$_2$)$_3$C(=O)(4-pyridyl) |
| 476 | 2 | 3 | 0 | H | H | H | sgl | H |
| 477 | 2 | 3 | 0 | H | H | H | sgl | —(CH$_2$)$_3$C(=O)(4-F-phenyl) |
| 478 | 2 | 3 | 0 | H | H | H | sgl | —(CH$_2$)$_2$(6-F-benzisoxazol-3-yl) |
| 483 | 2 | 2 | 1 | H | Br | H | sgl | —(CH$_2$)$_3$C(=O)(4-F-phenyl) |
| 484 | 2 | 2 | 1 | H | Br | H | sgl | —(CH$_2$)$_3$O(4-F-phenyl) |
| 488 | 1 | 2 | 1 | H | Br | H | sgl | —CO$_2$-tBu |

TABLE 3A

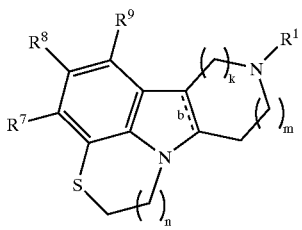

| Ex# | n | k | m | R7 | R8 | R9 | b | R1 |
|---|---|---|---|---|---|---|---|---|
| 479 | 2 | 2 | 1 | H | 2,4-diCl-phenyl | H | sgl | H |
| 480 | 2 | 2 | 1 | H | 2-Cl-4-MeO-phenyl | H | sgl | H |
| 481 | 2 | 2 | 1 | H | 2-Me-4-MeO-phenyl | H | sgl | H |
| 482 | 2 | 2 | 1 | H | Br | H | sgl | H |
| 497 | 1 | 1 | 1 | H | 2-Cl-phenyl | H | sgl | H |
| 498 | 1 | 1 | 1 | H | 3-Cl-phenyl | H | sgl | H |
| 499 | 1 | 1 | 1 | H | 3-F-phenyl | H | sgl | H |
| 500 | 1 | 1 | 1 | H | 4-Cl-phenyl | H | sgl | H |
| 501 | 1 | 1 | 1 | H | 4-F-phenyl | H | sgl | H |
| 502 | 1 | 1 | 1 | H | 2,3-diCl-phenyl | H | sgl | H |

TABLE 3A-continued

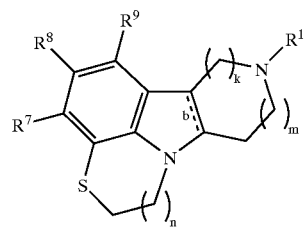

| Ex# | n | k | m | R7 | R8 | R9 | b | R1 |
|---|---|---|---|---|---|---|---|---|
| 503 | 1 | 1 | 1 | H | 2,3-diF-phenyl | H | sgl | H |
| 504 | 1 | 1 | 1 | H | 3,5-diCl-phenyl | H | sgl | H |
| 505 | 1 | 1 | 1 | H | 3,5-diF-phenyl | H | sgl | H |
| 506 | 1 | 1 | 1 | H | 3,4-diCl-phenyl | H | sgl | H |
| 507 | 1 | 1 | 1 | H | 3,4-diF-phenyl | H | sgl | H |
| 508 | 1 | 1 | 1 | H | 3-Cl-4-F-phenyl | H | sgl | H |
| 509 | 1 | 1 | 1 | H | 2-F-4-Cl-phenyl | H | sgl | H |

TABLE 4

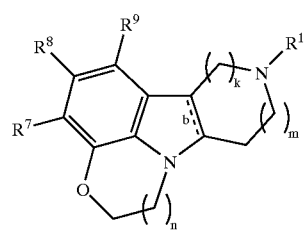

| Ex# | n | k | m | R7 | R8 | R9 | b | R1 |
|---|---|---|---|---|---|---|---|---|
| 172 | 2 | 1 | 1 | H | H | H | sgl | H |
| 173 | 1 | 1 | 1 | H | 2,4-diCl-phenyl | H | sgl | H |
| 174 | 1 | 1 | 1 | H | 2-Cl-4-MeO-phenyl | H | sgl | H |
| 436 | 1 | 1 | 1 | H | 2-Cl-phenyl | H | sgl | H |
| 497 | 1 | 1 | 1 | H | 2-Cl-phenyl | H | sgl | H |
| 498 | 1 | 1 | 1 | H | 3-Cl-phenyl | H | sgl | H |
| 499 | 1 | 1 | 1 | H | 3-F-phenyl | H | sgl | H |
| 500 | 1 | 1 | 1 | H | 4-Cl-phenyl | H | sgl | H |
| 501 | 1 | 1 | 1 | H | 4-F-phenyl | H | sgl | H |
| 502 | 1 | 1 | 1 | H | 2,3-diCl-phenyl | H | sgl | H |
| 503 | 1 | 1 | 1 | H | 2,3-diF-phenyl | H | sgl | H |
| 504 | 1 | 1 | 1 | H | 3,5-diCl-phenyl | H | sgl | H |
| 505 | 1 | 1 | 1 | H | 3,5-diF-phenyl | H | sgl | H |
| 506 | 1 | 1 | 1 | H | 3,4-diCl-phenyl | H | sgl | H |
| 507 | 1 | 1 | 1 | H | 3,4-diF-phenyl | H | sgl | H |
| 508 | 1 | 1 | 1 | H | 3-Cl-4-F-phenyl | H | sgl | H |

TABLE 4-continued

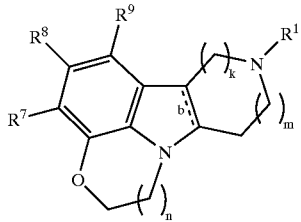

| Ex# | n | k | m | R7 | R8 | R9 | b | R1 |
|---|---|---|---|---|---|---|---|---|
| 509 | 1 | 1 | 1 | H | 2-F-4-Cl-phenyl | H | sgl | H |
| 510 | 1 | 1 | 1 | H | 2-Cl-4-F-phenyl | H | sgl | H |
| 511 | 1 | 1 | 1 | H | 2,5-diCl-phenyl | H | sgl | H |
| 512 | 1 | 1 | 1 | H | 2,6-diCl-phenyl | H | sgl | H |
| 513 | 1 | 1 | 1 | H | 2-CF$_3$-phenyl | H | sgl | H |
| 514 | 1 | 1 | 1 | H | 4-CF$_3$-phenyl | H | sgl | H |
| 515 | 1 | 1 | 1 | H | 2,4-diCF$_3$-phenyl | H | sgl | H |
| 516 | 1 | 1 | 1 | H | 2-Cl-4-CF$_3$-phenyl | H | sgl | H |
| 517 | 1 | 1 | 1 | H | 2-MeO-phenyl | H | sgl | H |
| 518 | 1 | 1 | i | H | 2,4-diMeO-phenyl | H | sgl | H |
| 519 | 1 | 1 | 1 | H | 2-MeO-5-iPr-phenyl | H | sgl | H |
| 520 | 1 | 1 | 1 | H | 3-NO$_2$-phenyl | H | sgl | H |
| 521 | 1 | 1 | 1 | H | 2-CHO-phenyl | H | sgl | H |
| 522 | 1 | 1 | 1 | H | 2-CH(Me)(OH)-phenyl | H | sgl | H |
| 523 | 1 | 1 | 1 | H | 2-CH$_2$(OH)-phenyl | H | sgl | H |
| 524 | 1 | 1 | 1 | H | 2-CHO-4-MeO-phenyl | H | sgl | H |
| 525 | 1 | 1 | 1 | H | 2-OH-phenyl | H | sgl | H |
| 526 | 1 | 1 | 1 | H | 2-CF$_3$-4-EtO-phenyl | H | sgl | H |
| 527 | 1 | 1 | 1 | H | 2-CF$_3$-4-iPrO-phenyl | H | sgl | H |
| 532 | 1 | 1 | 1 | H | 2-Me-4-MeO-phenyl | H | sgl | H |
| 533 | 1 | 1 | 1 | H | 2-CF$_3$-4-MeO-phenyl | H | sgl | H |
| 534 | 1 | 2 | 1 | H | 3,4,5-triMeO-phenyl | H | sgl | H |
| 535 | 1 | 2 | 1 | H | 1-naphthyl | H | sgl | H |
| 536 | 1 | 2 | 1 | H | 3-MeO-phenyl | H | sgl | H |
| 537 | 1 | 2 | 1 | H | 2,4-diCl-phenyl | H | sgl | H |
| 538 | 1 | 1 | 2 | H | H | H | sgl | H |
| 541 | 2 | 1 | 1 | H | H | H | dbl | H |
| 542 | 2 | 1 | 1 | H | H | H | sgl | H |
| 543 | 2 | 1 | 1 | H | 2,6-diF-phenyl | H | sgl | H |
| 545 | 1 | 2 | 1 | H | H | H | sgl | H |
| 547 | 2 | 1 | 1 | H | 2-CF$_3$-4-MeO-phenyl | H | sgl | H |
| 548 | 2 | 1 | 1 | H | 2-Me-4-MeO-phenyl | H | sgl | H |
| 549 | 2 | 1 | 1 | H | 2-Cl-4-CF$_3$-phenyl | H | sgl | H |
| 550 | 2 | 1 | 1 | H | 2,3-diCl-phenyl | H | sgl | H |
| 551 | 2 | 1 | 1 | H | 2,4-diMeO-phenyl | H | sgl | H |
| 552 | 2 | 1 | 1 | H | 3,4-diMeO-phenyl | H | sgl | H |
| 553 | 2 | 1 | 1 | H | 2,4-diCl-phenyl | H | sgl | H |
| 554 | 2 | 1 | 1 | H | 3,4-diCl-phenyl | H | sgl | H |
| 555 | 2 | 1 | 1 | H | 2,5-diCl-phenyl | H | sgl | H |
| 556 | 2 | 1 | 1 | H | 2-CF$_3$-phenyl | H | sgl | H |
| 557 | 2 | 1 | 1 | H | 2-Me-phenyl | H | sgl | H |
| 558 | 2 | 1 | 1 | H | 2-Cl-phenyl | H | sgl | H |
| 559 | 2 | 1 | 1 | H | 3-F-phenyl | H | sgl | H |
| 560 | 2 | 1 | 1 | H | phenyl | H | sgl | H |
| 561 | 2 | 1 | 1 | H | 2-CF$_3$-4-EtO-phenyl | H | sgl | H |
| 562 | 2 | 1 | 1 | H | 2-CF$_3$-4-iPrO-phenyl | H | sgl | H |
| 563 | 2 | 1 | 1 | H | 2-MeO-4-iPr-phenyl | H | sgl | H |
| 564 | 2 | 1 | 1 | H | 2-F-4-Cl-phenyl | H | sgl | H |
| 565 | 2 | 1 | 1 | H | 2-Cl-4-MeO-phenyl | H | sgl | H |
| 566 | 2 | 1 | 1 | H | 2-CHO-phenyl | H | sgl | H |
| 567 | 2 | 1 | 1 | H | 2-CHO-4-MeO-phenyl | H | sgl | H |
| 568 | 2 | 1 | 1 | H | 2-CH$_2$(OH)-4-MeO-phenyl | H | sgl | H |
| 569 | 2 | 1 | 1 | H | 2-CH$_2$(OH)-phenyl | H | sgl | H |
| 570 | 2 | 1 | 1 | H | 2-CF$_3$-4-NHMe-phenyl | H | sgl | H |
| 571 | 2 | 1 | 1 | H | 2-CF$_3$-4-NH$_2$-phenyl | H | sgl | H |
| 572 | 2 | 1 | 1 | H | 2-C(=O)Me-phenyl | H | sgl | H |
| 573 | 2 | 1 | 1 | H | 2-C(=O)Me-4-MeO-phenyl | H | sgl | H |

TABLE 4-continued

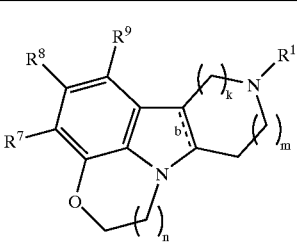

| Ex# | n | k | m | R7 | R8 | R9 | b | R1 |
|---|---|---|---|---|---|---|---|---|
| 574 | 2 | 1 | 1 | H | 2-CH(Me)(OH)-phenyl | H | sgl | H |
| 575 | 2 | 1 | 1 | H | 2-CH(Me)(OH)-4-MeO-phenyl | H | sgl | H |
| 576 | 2 | 1 | 1 | H | 2-CF$_3$-4-OH-phenyl | H | sgl | H |
| 577 | 2 | 1 | 1 | H | 2-CF$_3$-4-O(C=O)Me-phenyl | H | sgl | H |

TABLE 4A

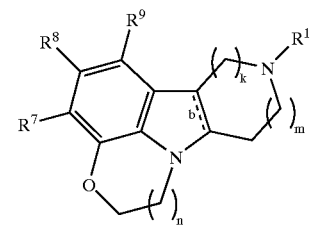

| Ex# | n | k | m | R7 | R8 | R9 | b | R1 |
|---|---|---|---|---|---|---|---|---|
| 182 | 1 | 1 | 1 | H | H | H | sgl | —(CH$_2$)$_3$C(=O)(4-F-phenyl) |
| 266 | 1 | 1 | 1 | H | H | Me | sgl | —(CH$_2$)$_3$C(=O)(4-F-phenyl) |
| 270 | 1 | 1 | 1 | H | H | H | sgl | —(CH$_2$)$_3$O(4-F-phenyl) |
| 272 | 1 | 1 | 1 | H | H | H | sgl | H |
| 494 | 1 | 1 | 1 | H | H | H | sgl | —(CH$_2$)$_3$C(=O)(2-NH$_2$-phenyl) |
| 495 | 1 | 1 | 1 | H | H | H | sgl | —(CH$_2$)$_3$C(=O)(2-NH$_2$-phenyl) |
| 496 | 1 | 1 | 1 | H | H | H | sgl | —(CH$_2$)$_3$(1H-indazol-3-yl) |
| 528 | 1 | 1 | 1 | H | H | H | sgl | —(CH$_2$)$_3$(6-F-1H-indazol-3-yl) |
| 529 | 1 | 1 | 1 | H | H | H | sgl | —(CH$_2$)$_3$C(=O)(2-NH$_2$-4-F-phenyl) |
| 530 | 1 | 1 | 1 | H | H | H | sgl | —(CH$_2$)$_3$C(=O)(2-NH$_2$-4-F-phenyl) |
| 531 | 1 | 1 | 1 | H | H | H | sgl | —(CH$_2$)$_3$C(=O)(2-OH-4-F-phenyl) |
| 539 | 1 | 2 | 1 | H | H | H | sgl | —(CH$_2$)$_3$O(4-F-phenyl) |
| 540 | 1 | 1 | 1 | H | H | H | sgl | —(CH$_2$)$_3$(6-F-1,2-benzisoxazol-3-yl) |
| 544 | 2 | 1 | 1 | H | H | H | sgl | —(CH$_2$)$_3$C(=O)(4-F-phenyl) |
| 546 | 1 | 2 | 1 | H | H | H | sgl | —(CH$_2$)$_3$C(=O)(4-F-phenyl) |

TABLE 5

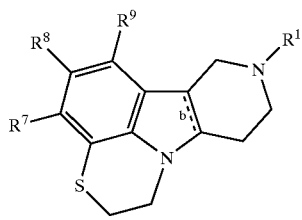

| Ex# | R7 | R8 | R9 | b | R1 |
|---|---|---|---|---|---|
| 183 | H | H | $CF_3$ | dbl | —$(CH_2)_3CH(OH)$(4-F-phenyl) |
| 184 | H | H | $CF_3$ | dbl | —$(CH_2)_3C(OCH_2CH_2O)$(4-F-phenyl) |
| 185 | H | H | $CF_3$ | sgl | —$(CH_2)_4$(4-F-phenyl) |
| 188 | H | H | H | sgl | —$(CH_2)_3C(=O)$(4-F-phenyl) |
| 195 | H | H | $CF_3$ | dbl | —$(CH_2)_3C(=O)$(4-F-phenyl) |
| 213 | H | $CH_3$ | H | sgl | —$(CH_2)_3C(=O)$(4-F-phenyl) |
| 438 | H | H | H | sgl | —$(CH_2)_3C(=O)$(2-$NH_2$-phenyl) |
| 439 | H | H | H | sgl | —$(CH_2)_3C(=O)$(2-$NH_2$-phenyl) |
| 440 | H | H | H | sgl | —$(CH_2)_3C(=O)$(2-$NH_2$-4-F-phenyl) |
| 441 | H | H | H | sgl | —$(CH_2)_3C(=O)$(2-$NH_2$-4-F-phenyl) |
| 456 | H | H | H | sgl | —$(CH_2)_3C(=O)$(4-F-phenyl) |
| 457 | H | H | H | sgl | —$(CH_2)_3C(=O)$(4-F-phenyl) |

TABLE 5A

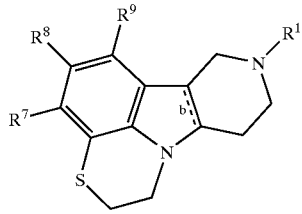

| Ex# | R7 | R8 | R9 | b | R1 |
|---|---|---|---|---|---|
| 443 | 2,3-diCl-phenyl | H | H | sgl | H |
| 444 | 2,3-diF-phenyl | H | H | sgl | H |
| 447 | 2,6-diCl-phenyl | H | H | sgl | H |
| 452 | 2-Me-4-MeO-phenyl | H | H | sgl | H |
| 453 | 2-Cl-6-F-phenyl | H | H | sgl | H |

TABLE 5A-continued

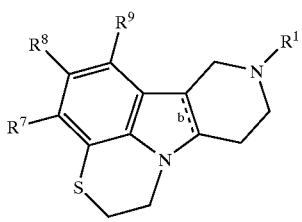

| Ex# | R7 | R8 | R9 | b | R1 |
|---|---|---|---|---|---|
| 454 | 2,6-diF-phenyl | H | H | sgl | H |
| 455 | 2,4-diCl-phenyl | H | H | sgl | H |

TABLE 6

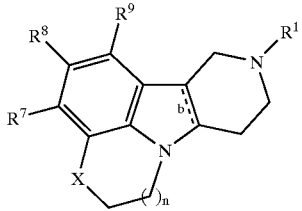

| Ex# | X | n | R7 | R8 | R9 | b | R1 |
|---|---|---|---|---|---|---|---|
| 398 | $SO_2$ | 2 | H | 2,4-diCl-phenyl | H | sgl | H |
| 399 | $SO_2$ | 2 | H | 2,6-diF-phenyl | H | sgl | H |
| 400 | $SO_2$ | 2 | H | 2-Cl-phenyl | H | sgl | H |
| 401 | $SO_2$ | 2 | H | 2-F-4-MeO-phenyl | H | sgl | H |
| 402 | $SO_2$ | 2 | H | 2-Me-4-MeO-phenyl | H | sgl | H |
| 404 | SO | 2 | H | 2-Cl-4-F-phenyl | H | sgl | H |
| 434 | SO | 2 | H | 2,4-diCl-phenyl | H | sgl | H |
| 435 | SO | 2 | H | 2-Me-4-MeO-phenyl | H | sgl | H |
| 448 | $SO_2$ | 1 | H | H | H | sgl | H |
| 449 | SO | 1 | H | H | H | sgl | H |
| 450 | $SO_2$ | 1 | H | 2-$CF_3$-4-MeO-phenyl | H | sgl | H |
| 451 | $SO_2$ | 1 | H | 2,4-diCl-phenyl | H | sgl | H |

TABLE 7

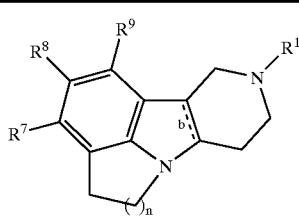

| Ex# | n | R7 | R8 | R9 | b | R1 |
|---|---|---|---|---|---|---|
| 1 | 1 | H | H | H | dbl | H |
| 2 | 1 | H | H | H | dbl | cycPropyl |
| 3 | 1 | H | H | H | sgl | H |

TABLE 7-continued

| Ex# | n | R7 | R8 | R9 | b | R1 |
|---|---|---|---|---|---|---|
| 16 | 2 | H | H | H | dbl | H |
| 17 | 2 | H | H | H | sgl | H |
| 37 | 1 | H | H | H | sgl | —C(=O)cycPropyl |
| 38 | 1 | H | H | H | sgl | —C(=O)iPropyl |
| 89 | 1 | H | 2-Cl-phenyl | H | sgl | —$CO_2$-tButyl |
| 90 | 1 | H | 2,4-diCl-phenyl | H | sgl | —$CO_2$-tButyl |
| 91 | 1 | H | 3,4-diCl-phenyl | H | sgl | —$CO_2$-tButyl |
| 92 | 1 | H | 2,3-diCl-phenyl | H | sgl | —$CO_2$-tButyl |
| 93 | 1 | H | 2-Cl-4-$CF_3$-phenyl | H | sgl | —$CO_2$-tButyl |
| 94 | 1 | H | 2-Cl-4-MeO-phenyl | H | sgl | —$CO_2$-tButyl |
| 95 | 1 | H | 2-MeO-4-iPr-phenyl | H | sgl | —$CO_2$-tButyl |
| 96 | 1 | H | 3-F-phenyl | H | sgl | —$CO_2$-tButyl |
| 97 | 1 | H | 2,4-diMeO-phenyl | H | sgl | —$CO_2$-tButyl |
| 98 | 1 | H | 2-Cl-phenyl | H | sgl | H |
| 99 | 1 | H | 2,4-diCl-phenyl | H | sgl | H |
| 100 | 1 | H | 3,4-diCl-phenyl | H | sgl | H |
| 101 | 1 | H | 2,3-diCl-phenyl | H | sgl | H |
| 102 | 1 | H | 2-Cl-4-$CF_3$-phenyl | H | sgl | H |
| 103 | 1 | H | 2-Cl-4-MeO-phenyl | H | sgl | H |
| 104 | 1 | H | 2-MeO-4-iPr-phenyl | H | sgl | H |
| 105 | 1 | H | 3-F-phenyl | H | sgl | H |
| 106 | 1 | H | 2,4-diMeO-phenyl | H | sgl | H |
| 107 | 2 | H | H | H | sgl | —$CO_2$-tButyl |
| 108 | 2 | H | Br | H | sgl | —$CO_2$-tButyl |
| 109 | 2 | H | 2,3-diCl-phenyl | H | sgl | —$CO_2$-tButyl |
| 110 | 2 | H | 3,4-diCl-phenyl | H | sgl | —$CO_2$-tButyl |
| 111 | 2 | H | 2-Cl-4-$CF_3$-phenyl | H | sgl | —$CO_2$-tButyl |
| 112 | 2 | H | 2,3-diCl-phenyl | H | sgl | H |
| 113 | 2 | H | 3,4-diCl-phenyl | H | sgl | H |
| 114 | 2 | H | 2-Cl-4-$CF_3$-phenyl | H | sgl | H |
| 189 | 1 | H | 2-Cl-phenyl | H | sgl | —$(CH_2)_3$C(=O)(4-F-phenyl) |
| 190 | 1 | H | 2,4-diCl-phenyl | H | sgl | —$(CH_2)_3$C(=O)(4-F-phenyl) |
| 191 | 2 | H | H | H | sgl | —$(CH_2)_3$C(=O)(4-F-phenyl) |
| 265 | 1 | H | H | H | sgl | —$(CH_2)_3$C(=O)(4-F-phenyl) |
| C274 | 1 | H | 2-F-4-MeO-phenyl | H | sgl | H |
| C275 | 1 | H | 2-$CF_3$-4-EtO-phenyl | H | sgl | —$CO_2$-tButyl |
| C276 | 1 | H | 2-$CF_3$-4-EtO-phenyl | H | sgl | H |
| C277 | 1 | H | 2-F-4-Cl-phenyl | H | sgl | —$CO_2$-tButyl |
| C278 | 1 | H | 2-F-4-Cl-phenyl | H | sgl | H |
| C279 | 1 | H | 2-$CF_3$-4-iPrO-phenyl | H | sgl | —$CO_2$-tButyl |
| C280 | 1 | H | 2-$CF_3$-4-iPrO-phenyl | H | sgl | H |
| C281 | 1 | H | 2-$CF_3$-4-MeO-phenyl | H | sgl | —$CO_2$-tButyl |
| C282 | 1 | H | 2-$CF_3$-4-MeO-phenyl | H | sgl | H |
| C283 | 1 | H | phenyl | H | sgl | —$CO_2$-tButyl |
| 284 | 1 | H | phenyl | H | sgl | H |
| 285 | 1 | H | 2-Me-phenyl | H | sgl | —$CO_2$-tButyl |
| 286 | 1 | H | 2-Me-phenyl | H | sgl | H |
| 287 | 1 | H | 2-$CF_3$-phenyl | H | sgl | —$CO_2$-tButyl |
| 288 | 1 | H | 2-$CF_3$-phenyl | H | sgl | H |
| 289 | 1 | H | 3,4-diMeO-phenyl | H | sgl | —$CO_2$-tButyl |
| 290 | 1 | H | 3,4-diMeO-phenyl | H | sgl | H |
| 291 | 1 | H | 2,5-diCl-phenyl | H | sgl | —$CO_2$-tButyl |
| 292 | 1 | H | 2,5-diCl-phenyl | H | sgl | H |
| 293 | 1 | H | 3,5-diCl-phenyl | H | sgl | —$CO_2$-tButyl |
| 294 | 1 | H | 3,5-diCl-phenyl | H | sgl | H |
| 295 | 1 | H | 2-iPr-4-MeO-phenyl | H | sgl | —$CO_2$-tButyl |
| 296 | 1 | H | 2-iPr-4-MeO-phenyl | H | sgl | H |
| 297 | 1 | H | 2-Me-4-MeO-5-F-phenyl | H | sgl | —$CO_2$-tButyl |
| 298 | 1 | H | 2-Me-4-MeO-5-F-phenyl | H | sgl | H |
| 299 | 1 | H | 2-Me-4-MeO-phenyl | H | sgl | —$CO_2$-tButyl |

TABLE 7-continued

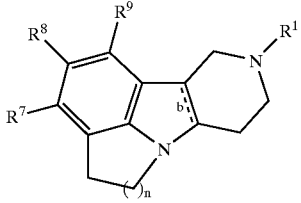

| Ex# | n | R7 | R8 | R9 | b | R1 |
|---|---|---|---|---|---|---|
| 300 | 1 | H | 2-Me-4-MeO-phenyl | H | sgl | H |
| 301 | 1 | H | 2-Cl-4-MeO-phenyl | H | sgl | —$CO_2$-tButyl |
| 302 | 1 | H | 2-Cl-4-MeO-phenyl | H | sgl | H |
| 303 | 1 | H | 2-Me-4-Cl-phenyl | H | sgl | —$CO_2$-tButyl |
| 304 | 1 | H | 2-Me-4-Cl-phenyl | H | sgl | H |
| 305 | 1 | H | 2-CHO-4-MeO-phenyl | H | sgl | H |
| 306 | 1 | H | 2,6-diCl-phenyl | H | sgl | H |
| 307 | 1 | H | 2-$CF_3$-4-MeNH-phenyl | H | sgl | H |
| 308 | 1 | H | 2-$CF_3$-4-$NH_2$-phenyl | H | sgl | H |
| 309 | 1 | H | 2-$CH_3$CH(OH)-4-MeO-phenyl | H | sgl | H |
| 310 | 3 | H | H | H | sgl | H |
| 311 | 3 | H | H | H | sgl | —$CO_2$-tButyl |
| 312 | 3 | H | H | H | sgl | H |
| 313 | 3 | H | H | H | sgl | H |
| 314 | 3 | H | Br | H | sgl | —$CO_2$-tButyl |
| 315 | 3 | H | 2,4-diCl-phenyl | H | sgl | H |
| 316 | 3 | H | 2,3-diCl-phenyl | H | sgl | H |
| 317 | 3 | H | 3,4-diCl-phenyl | H | sgl | H |
| 318 | 3 | H | 3,5-diCl-phenyl | H | sgl | H |
| 319 | 3 | H | 2,5-diCl-phenyl | H | sgl | H |
| 320 | 3 | H | 2,6-diCl-phenyl | H | sgl | H |
| 321 | 3 | H | 2-Cl-phenyl | H | sgl | H |
| 322 | 3 | H | 3-Cl-phenyl | H | sgl | H |
| 323 | 3 | H | 4-Cl-phenyl | H | sgl | H |
| 324 | 3 | H | 2,6-diF-phenyl | H | sgl | H |
| 325 | 3 | H | 2,6-diF-phenyl | H | sgl | H |
| 326 | 3 | H | 2,3-diF-phenyl | H | sgl | H |
| 327 | 3 | H | 3,4-diF-phenyl | H | sgl | H |
| 328 | 3 | H | 3-F-phenyl | H | sgl | H |
| 329 | 3 | H | 2-Cl-4-$CF_3$-phenyl | H | sgl | H |
| 330 | 3 | H | 2-Cl-4-MeO-phenyl | H | sgl | H |
| 331 | 3 | H | 2-F-4-MeO-phenyl | H | sgl | H |
| 332 | 3 | H | 2-Me-4-MeO-phenyl | H | sgl | H |
| 333 | 3 | H | 2-$CF_3$-4-MeO-phenyl | H | sgl | H |
| 334 | 3 | H | 2-$CF_3$-phenyl | H | sgl | H |
| 335 | 3 | H | 2-$CF_3$-4-iPrO-phenyl | H | sgl | H |
| 336 | 3 | H | 2,4-di$CF_3$-phenyl | H | sgl | H |
| 337 | 3 | H | 2-$CF_3$-4-F-phenyl | H | sgl | H |
| 338 | 3 | H | 2-$CF_3$-4-$NH_2$-phenyl | H | sgl | H |
| 339 | 3 | H | 2-$CF_3$-4-MeNH-phenyl | H | sgl | H |
| 340 | 3 | H | 2-CHO-phenyl | H | sgl | H |
| 341 | 3 | H | 2-$CH_2$(OH)-phenyl | H | sgl | H |
| 342 | 3 | H | 2-CHO-4-MeO-phenyl | H | sgl | H |
| 343 | 3 | H | 2-$CH_2$(OH)-4-MeO-phenyl | H | sgl | H |
| 344 | 3 | H | 2-Me-4-CN-phenyl | H | sgl | H |
| 345 | 3 | H | 2-$CH_3$CH(OH)-4-MeO-phenyl | H | sgl | H |
| 346 | 2 | H | Br | H | sgl | —$CO_2$-tButyl |
| 347 | 2 | H | 2,4-diCl-phenyl | H | sgl | H |
| 348 | 2 | H | 3,4-diCl-phenyl | H | sgl | H |
| 349 | 2 | H | 3,5-diCl-phenyl | H | sgl | H |
| 350 | 2 | H | 2,5-diCl-phenyl | H | sgl | H |
| 351 | 2 | H | 2,6-diCl-phenyl | H | sgl | H |
| 352 | 2 | H | 2-Cl-phenyl | H | sgl | H |
| 353 | 2 | H | 3-Cl-phenyl | H | sgl | H |
| 354 | 2 | H | 4-Cl-phenyl | H | sgl | H |
| 355 | 2 | H | 2,6-diF-phenyl | H | sgl | H |
| 356 | 2 | H | 2,6-diF-phenyl | H | sgl | Me |
| 357 | 2 | H | 2,3-diF-phenyl | H | sgl | H |
| 358 | 2 | H | 3,4-diF-phenyl | H | sgl | H |
| 359 | 2 | H | 3-F-phenyl | H | sgl | H |
| 360 | 2 | H | 2-Cl-4-MeO-phenyl | H | sgl | H |
| 361 | 2 | H | 2-F-4-MeO-phenyl | H | sgl | H |
| 362 | 2 | H | 2-Me-4-MeO-phenyl | H | sgl | H |

TABLE 7-continued

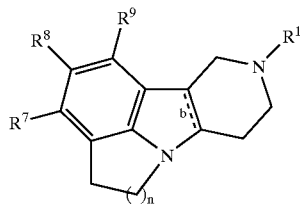

| Ex# | n | R7 | R8 | R9 | b | R1 |
|---|---|---|---|---|---|---|
| 363 | 2 | H | 2-$CF_3$-4-MeO-phenyl | H | sgl | H |
| 364 | 2 | H | 2-$CF_3$-4-MeO-phenyl | H | dbl | H |
| 365 | 2 | H | 2-$CF_3$-4-OH-phenyl | H | sgl | H |
| 366 | 2 | H | 2-$CF_3$-phenyl | H | sgl | H |
| 367 | 2 | H | 2-$CF_3$-4-iPrO-phenyl | H | sgl | H |
| 368 | 2 | H | 2,4-di$CF_3$-phenyl | H | sgl | H |
| 369 | 2 | H | 2-$CF_3$-4-F-phenyl | H | sgl | H |
| 370 | 2 | H | 2-$CF_3$-4-$NH_2$-phenyl | H | sgl | H |
| 371 | 2 | H | 2-$CF_3$-4-MeNH-phenyl | H | sgl | H |
| 372 | 2 | H | 4-CN-2-Me-phenyl | H | sgl | H |
| 373 | 2 | H | 2-CHO-phenyl | H | sgl | H |
| 374 | 2 | H | 2-$CH_2$(OH)-phenyl | H | sgl | H |
| 375 | 2 | H | 2-CHO-4-MeO-phenyl | H | sgl | H |
| 376 | 2 | H | 2-$CH_2$(OH)-4-MeO-phenyl | H | sgl | H |
| 377 | 3 | H | 2-$CF_3$-4-EtO-phenyl | H | sgl | H |
| 378 | 2 | H | 2-$CF_3$-4-EtO-phenyl | H | sgl | H |
| 379 | 3 | H | 2-Me-3-Cl-phenyl | H | sgl | H |
| 380 | 2 | H | 2-Me-3-Cl-phenyl | H | sgl | H |
| 381 | 2 | H | 2-Me-5-F-phenyl | H | sgl | H |
| 382 | 2 | H | 2,3-diCl-phenyl | H | sgl | Pr |
| 383 | 2 | H | 2,3-diCl-phenyl | H | sgl | Pr |
| 384 | 2 | H | 2,3-diCl-phenyl | H | sgl | Bu |
| 385 | 2 | H | 2,3-diCl-phenyl | H | sgl | Bu |
| 386 | 2 | H | 2,3-diCl-phenyl | H | sgl | 4-pentenyl |
| 387 | 2 | H | 2,3-diCl-phenyl | H | sgl | 3-Me-2-butenyl |
| 388 | 2 | H | 2,4-diCl-phenyl | H | sgl | Pr |
| 389 | 2 | H | 2,4-diCl-phenyl | H | sgl | Bu |
| 390 | 2 | H | 2,4-diCl-phenyl | H | sgl | 4-pentenyl |
| 391 | 2 | H | 2,4-diCl-phenyl | H | sgl | 3-Me-2-butenyl |
| 392 | 2 | H | 2,4-diCl-phenyl | H | sgl | cyclobutylmethyl |
| 393 | 2 | H | 2-$CF_3$-4-MeO-phenyl | H | sgl | Me |
| 394 | 2 | H | 2-$CF_3$-4-MeO-phenyl | H | sgl | Et |
| 395 | 2 | H | 2-$CF_3$-4-MeO-phenyl | H | sgl | Pr |
| 396 | 2 | H | 2-$CF_3$-4-MeO-phenyl | H | sgl | Bu |
| 397 | 2 | H | 2-$CF_3$-4-MeO-phenyl | H | sgl | 4-pentenyl |
| 398 | 2 | H | 2-$CF_3$-4-MeO-phenyl | H | sgl | 3-Me-2-butenyl |
| 399 | 2 | H | 2-$CF_3$-4-MeO-phenyl | H | sgl | 2-F-ethyl |
| 400 | 2 | H | 2-$CF_3$-4-MeO-phenyl | H | sgl | 2,2-diF-ethyl |
| 401 | 2 | H | 2-$CF_3$-4-MeO-phenyl | H | sgl | cyclobutylmethyl |
| 402 | 2 | H | H | H | sgl | —$(CH_2)_3$C(=O)(4-F-phenyl) |
| 403 | 2 | H | H | H | sgl | —$(CH_2)_3$C(=O)(4-F-phenyl) |
| 403 | 2 | H | H | H | sgl | —$(CH_2)_3$C(=O)(4-F-phenyl) |
| 404 | 2 | H | H | H | sgl | —$(CH_2)_3$C(=O)(2-$NH_2$-phenyl) |
| 405 | 2 | H | H | H | sgl | —$(CH_2)_3$C(=O)(2-$NH_2$-phenyl) |
| 406 | 2 | H | H | H | sgl | —$(CH_2)_3$C(4-F-phenyl) |
| 407 | 2 | H | H | H | sgl | —$(CH_2)_3$C(=O)(4-pyridyl) |

TABLE 7-continued

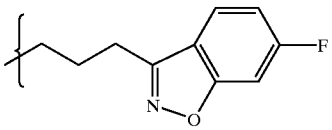

| Ex# | n | R7 | R8 | R9 | b | R1 |
|---|---|---|---|---|---|---|
| 408 | 2 | H | H | H | sgl | [3-(6-F-benzisoxazol-3-yl)propyl] |
| 409 | 2 | H | H | H | sgl | [3-(6-F-benzisoxazol-3-yl)propyl] |
| 410 | 2 | H | H | H | dbl | —(CH$_2$)$_3$C(=O)(4-F-phenyl) |
| 411 | 3 | H | H | H | sgl | —(CH$_2$)$_3$C(=O)(4-F-phenyl) |
| 412 | 3 | H | H | H | sgl | —(CH$_2$)$_3$C(=O)(4-F-phenyl) |
| 413 | 3 | H | H | H | sgl | —(CH$_2$)$_3$C(=O)(4-F-phenyl) |
| 414 | 3 | H | H | H | sgl | —(CH$_2$)$_3$C(=O)(2-NH$_2$-4-F-phenyl) |
| 415 | 2 | H | H | H | sgl | —(CH$_2$)$_3$C(=O)(2-NH$_2$-4-F-phenyl) |
| 416 | 2 | H | H | H | sgl | —(CH$_2$)$_3$C(=O)(2-NH$_2$-4-F-phenyl) |
| 417 | 2 | H | H | H | sgl | —(CH$_2$)$_3$C(=O)(2-NH$_2$-4-F-phenyl) |

TABLE 8

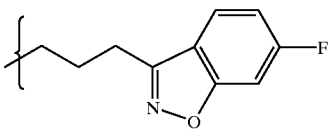

| Ex# | n | k | m | R7 | R8 | R9 | b | R1 |
|---|---|---|---|---|---|---|---|---|
| 418 | 2 | 2 | 1 | H | H | H | dbl | H |
| 419 | 2 | 2 | 1 | H | H | H | sgl | H |
| 420 | 2 | 2 | 1 | H | H | H | sgl | —(CH$_2$)$_3$C(=O)(4-F-phenyl) |
| 421 | 2 | 2 | 1 | H | H | H | sgl | —(CH$_2$)$_3$C(=O)(2-NH$_2$-4-F-phenyl) |
| 422 | 3 | 2 | 1 | H | H | H | dbl | H |
| 423 | 3 | 2 | 1 | H | H | H | sgl | H |
| 424 | 3 | 2 | 1 | H | H | H | sgl | —(CH$_2$)$_3$C(=O)(4-F-phenyl) |
| 425 | 3 | 2 | 1 | H | H | H | sgl | —(CH$_2$)$_3$C(=O)(2-NH$_2$-4-F-phenyl) |
| 434 | 2 | 1 | 2 | H | H | H | sgl | H |
| 435 | 2 | 1 | 2 | H | H | H | sgl | —CO$_2$-tButyl |
| 436 | 2 | 1 | 2 | H | Br | H | sgl | —CO$_2$-tButyl |
| 437 | 2 | 1 | 2 | H | 2-CF$_3$-4-MeO-phenyl | H | sgl | H |

TABLE 9

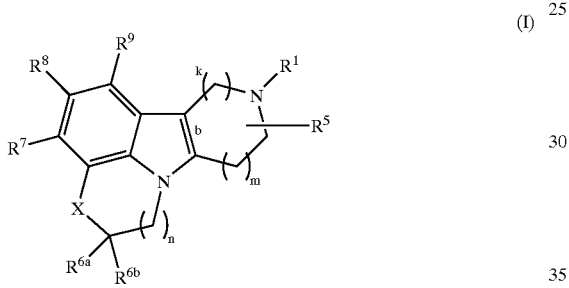

| Ex# | X | R7 | R8 | R9 | b | R1 |
|---|---|---|---|---|---|---|
| 426 | C=O | H | H | H | sgl | H |
| 427 | C=O | H | H | H | sgl | —CO$_2$-tButyl |
| 428 | C=O | H | 2,4-diCl-phenyl | H | sgl | —CO$_2$-tButyl |
| 429 | C=O | H | 2,4-diCl-phenyl | H | sgl | H |
| 430 | C=O | H | 2,4-diCl-phenyl | H | sgl | H |
| 431 | C=O | H | 2,4-diCl-phenyl | H | sgl | H |
| 432 | CH(OH) | H | 2,4-diCl-phenyl | H | sgl | H |
| 433 | CH(OH) | H | 2,4-diCl-phenyl | H | sgl | H |

What is claimed is:

1. A compound of the formula (I)

$$(I)$$

or stereoisomers or pharmaceutically acceptable salt forms thereof, wherein:

b is a single bond;
X is —NR$^{10A}$—;
R$^1$ is selected from
H,
C(=O)R$^2$,
C(=O)OR$^2$,
C$_{1-8}$ alkyl,
C$_{2-8}$ alkenyl,
C$_{2-8}$ alkynyl,
C$_{3-7}$ cycloalkyl,
C$_{1-6}$ alkyl substituted with Z,
C$_{2-6}$ alkenyl substituted with Z,
C$_{2-6}$ alkynyl substituted with Z,
C$_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
C$_{1-3}$ alkyl substituted with Y,
C$_{2-3}$ alkenyl substituted with Y,
C$_{2-3}$ alkynyl substituted with Y,
C$_{1-6}$ alkyl substituted with 0–2 R$^2$,
C$_{2-6}$ alkenyl substituted with 0–2 R$^2$,
C$_{2-6}$ alkynyl substituted with 0–2 R$^2$,
aryl substituted with 0–2 R$^2$, and
5–6 membered heterocyclic ring system containing at least one heteroatom selected from the group consisting of N, O, and S, said heterocyclic ring system substituted with 0–2 R$^2$;

Y is selected from
C$_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
C$_{3-6}$ cycloalkyl substituted with —(C$_{1-3}$ alkyl)-Z,
aryl substituted with —(C$_{1-3}$ alkyl)-Z, and
5–6 membered heterocyclic ring system containing at least one heteroatom selected from the group consisting of N, O, and S, said heterocyclic ring system substituted with —(C$_{1-3}$ alkyl)-Z;

Z is selected from H,
—CH(OH)R$^2$,
—C(ethylenedioxy)R$^2$,
—OR$^2$,
—SR$^2$,
—NR$^2$R$^3$,
—C(O)R$^2$,
—C(O)NR$^2$R$^3$,
—NR$^3$C(O)R$^2$,
—C(O)OR$^2$,
—OC(O) R$^2$,
—CH(=NR$^4$)NR$^2$R$^3$,
—NHC(=NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from halo,
C$_{1-3}$ haloalkyl,
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic group substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from H, C$_{1-4}$ alkyl, C$_{2-4}$ alkenyl, C$_{2-4}$ alkynyl, and C$_{1-4}$ alkoxy;

alternatively, R$^2$ and R$^3$ join to form a 5- or 6-membered ring optionally substituted with —O— or —N(R$^4$)—;

R$^4$, at each occurrence, is independently selected from H and C$_{1-4}$ alkyl;

R$^5$ is H or C$_{1-4}$ alkyl;

R$^{6a}$ and R$^{6b}$, at each occurrence, are independently selected from
H, —OH, —NR$^{46}$R$^{47}$, —CF$_3$, C$_{1-4}$ alkyl, C$_{2-4}$ alkenyl, C$_{2-4}$ alkynyl, C$_{1-4}$ alkoxy, C$_{1-4}$ haloalkyl, C$_{3-6}$ cycloalkyl, and
aryl substituted with 0–3 R$^{44}$;

R$^7$ and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{3-10}$ carbocyclic group substituted with 0–3 R$^{33}$,
aryl substituted with 0–5 R$^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^8$ is selected from
H, halo, $-CF_3$, $-OCF_3$, $-OH$, $-CN$, $-NO_2$,
$C_{1-8}$ alkyl, $C_{2-8}$ alkenyl, $C_{2-8}$ alkynyl, $C_{1-4}$ haloalkyl, $C_{1-8}$ alkoxy, $(C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{10A}$ is selected from H,
$C_{1-6}$ alkyl substituted with 0–1 $R^{10B}$,
$C_{2-6}$ alkenyl substituted with 0–1 $R^{10B}$,
$C_{2-6}$ alkynyl substituted with 0–1 $R^{10}$, and
$C_{1-6}$ alkoxy;

$R^{10B}$ is selected from
$C_{1-4}$ alkoxy,
$C_{3-6}$ cycloalkyl,
$C_{3-10}$ carbocyclic group substituted with 0–3 $R^{33}$,
phenyl substituted with 0–3 $R^{33}$, and
5–6 membered heterocyclic ring system containing 1, 2, or 3 heteroatoms selected from the group consisting of N, O, and S substituted with 0–2 $R^{44}$;

$R^{11}$ is selected from
H, halo, $-CF_3$, $-CN$, $-NO_2$,
$C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with $-O-$ or $-N(R^{14})-$;
alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H 12 and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
H, OH, halo, CN, $NO_2$, $CF_3$, $SO_2R^{45}$, $NR^{46}R^{47}$, $-C(=O)H$,
$C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{1-3}$ alkyloxy-;

$R^{31}$, at each occurrence, is independently selected from
H, OH, halo, $CF_3$, $SO_2R^{45}$, $NR^{46}R^{47}$, and $C_{1-4}$ alkyl;

$R^{33}$, at each occurrence, is independently selected from
H, OH, halo, CN, $NO_2$, $CF_3$, $SO_2R^{45}$, $NR^{46}R^{47}$, $-C(=O)H$,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)-, $C_{1-4}$ alkyl-C(=O)NH-,
$C_{1-4}$ alkyl-OC(=O)-,
$C_{1-4}$ alkyl-C(=O)O-, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and $C_{2-6}$ alkenyl substituted with OH, methoxy, ethoxy, propoxy, or butoxy;

$R^{41}$, at each occurrence, is independently selected from
H, $CF_3$, halo, OH, $-CO_2H$, $SO_2R^{45}$, $NR^{46}R^{47}$, $NO_2$, CN, $=O$;
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, $CH(=NH)NH_2$, $NHC(=NH)NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;
$R^{44}$, at each occurrence, is independently selected from
H,
halo, —OH, $NR^{46}R^{47}$, $CO_2H$, $SO_2R^{45}$, —$CF_3$,
—$OCF_3$, —CN, —$NO_2$,
$C_{1-4}$ alkyl, and $C_{1-4}$ alkoxy;
$R^{45}$ is $C_{1-4}$ alkyl;
$R^{46}$, at each occurrence, is independently selected from
H and $C_{1-4}$ alkyl;
$R^{47}$, at each occurrence, is independently selected from
H,
$C_{1-4}$ alkyl, —C(=O)NH($C_{1-4}$ alkyl), —$SO_2$ ($C_{1-4}$ alkyl),
—C(=O)O($C_{1-4}$ alkyl), —C(=O) ($C_{1-4}$ alkyl), and
—C(=O)H;
k is 1 or 2;
m is 0, 1, or 2; and
n is 1, 2, or 3;
provided when m is 0 or 1 then k is 1 or 2;
provided when m is 2 then k is 1.

2. A compound of claim 1 wherein:
X is —$NR^{10A}$—;
$R^1$ is selected from
H,
C(=O) $R^2$,
C(=O)$OR^2$,
$C_{1-8}$ alkyl,
$C_{2-8}$ alkenyl,
$C_{2-8}$ alkynyl,
$C_{3-7}$ cycloalkyl,
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$, aryl substituted with 0–2 $R^2$, and
5–6 membered heterocyclic ring system containing at least one heteroatom selected from the group consisting of N, O, and S, said heterocyclic ring system substituted with 0–2 $R^2$;
$R^2$, at each occurrence, is independently selected from
F, Cl, $CH_2F$, $CHF_2$, $CF_3$,
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic group substituted with 0–3 $R^{41}$, and
5–10 membered heterocyclic ring system containing from 1–4 heteroatoms selected from the group consisting of N, O, and S substituted with 0–3 $R^{41}$;
$R^5$ is H, methyl, ethyl, propyl, or butyl;
$R^{6a}$ is selected from
H, —OH, —$NR^{46}R^{47}$, —$CF_3$,
$C_{1-4}$ alkyl, $C_{1-4}$ alkoxy, $C_{1-4}$ haloalkyl, and
aryl substituted with 0–3 $R^{44}$;
$R^{6b}$ is H;
$R^7$ and $R^9$, at each occurrence, are independently selected from
H, halo, —$CF_3$, —$OCF_3$, —OH, —CN, —$NO_2$, —$NR^{46}R^{47}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, $S(O)_2R^{12}$, S(O) $NR^{12}R^{13}$ $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)$ $NHR^{15}$;
$R^8$ is selected from
H, halo, —$CF_3$, —$OCF_3$, —OH, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, $S(O)_2R^{12}$, S(O) $NR^{12}R^{13}$, $S(O)_2NR^{12}R^{13}$, $NR^{14}S(O) R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;
$R^{10A}$ is selected from H,
$C_{1-6}$ alkyl substituted with 0–1 $R^{10B}$,
$C_{2-6}$ alkenyl substituted with 0–1 $R^{10B}$,
$C_{2-6}$ alkynyl substituted with 0–1 $R^{10B}$, and
$C_{1-6}$ alkoxy;
$R^{10B}$ is selected from
$C_{1-4}$ alkoxy,
$C_{3-6}$ cycloalkyl,
$C_{3-10}$ carbocyclic group substituted with 0–3 $R^{33}$,
phenyl substituted with 0–3 $R^{33}$, and
5–6 membered heterocyclic ring system containing 1, 2, or 3 heteroatoms selected from the group consisting of N, O, and S substituted with 0–2 $R^{44}$;
$R^{11}$ is selected from
H, halo, —$CF_3$, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, $S(O)_2R^{12}$, S(O)$NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)$ $NHR^{15}$;
$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic group substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
H, OH, halo, CN, $NO_2$, $CF_3$, $SO_2R^{45}$, $NR^{46}R^{47}$, —C(=O)H,
$C_{1-4}$ alkyl, $C_{2-4}$ alkenyl, $C_{2-4}$ alkynyl, $C_{1-4}$ haloalkyl, $C_{1-3}$ haloalkyl-oxy-, and $C_{13}$ alkyloxy-;

$R^{31}$, at each occurrence, is independently selected from
H, OH, halo, $CF_3$, $SO_2R^{45}$, $NR^{46}R^{47}$, and $C_{1-4}$ alkyl;

$R^{33}$, at each occurrence, is independently selected from
H, OH, halo, CN, $NO_2$, $CF_3$, $SO_2R^{45}$, $NR^{46}R^{47}$, —C(=O)H,
$C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-,
$C_{1-4}$ alkylthio-, $C_{1-4}$ alkyl-C(=O)—, $C_{1-4}$ alkyl-C(=O)NH—,
$C_{1-4}$ alkyl-OC(=O)—,
$C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, or butoxy; and
$C_{2-6}$ alkenyl substituted with OH, methoxy, ethoxy, propoxy, or butoxy;

$R^{41}$, at each occurrence, is independently selected from
H, $CF_3$, halo, OH, $CO_2H$, $SO_2R^{45}$, $NR^{46}R^{47}$, $NO_2$, CN;
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

k is 1 or 2;

m is 0, 1, or 2; and n is 1, 2, or 3.

3. A compound of claim 2 wherein:

X is —$NR^{10A}$—;

$R^1$ is selected from
H,
C(=O)$R^2$,
C(=O)O$R^2$,
$C_{1-6}$ alkyl,
$C_{2-6}$ alkenyl,
$C_{2-6}$ alkynyl,
$C_{3-6}$ cycloalkyl,
$C_{1-4}$ alkyl substituted with 0–2 $R^2$,
$C_{2-4}$ alkenyl substituted with 0–2 $R^2$, and
$C_{2-4}$ alkynyl substituted with 0–2 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic group substituted with 0–3 $R^{41}$, and
5–10 membered heterocyclic ring system containing from 1–4 heteroatoms selected from the group consisting of N, O, and S substituted with 0–3 $R^{41}$;

$R^5$ is H, methyl, ethyl, propyl, or butyl;

$R^{6a}$ is selected independently from
H, —OH, —$NR^{46}R^{47}$, —$CF_3$, $C_{1-3}$ alkyl, and $C_{1-3}$ alkoxy;

$R^{6b}$ is H;

$R^7$ and $R^9$, at each occurrence, are independently selected from
H, halo, —$CF_3$, —$OCF_3$, —OH, —CN, —$NO_2$, —$NR^{46}R^{47}$,
$C_{1-6}$ alkyl, $C_{2-6}$ alkenyl, $C_{2-6}$ alkynyl, $C_{16}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
O$R^{12}$, S$R^{12}$, $NR^{12}R^{13}$, C(O)H, C(O)$R^{12}$ C(O)$NR^{12}R^{13}$, $NR^{14}$C(O)$R^{12}$, C(O)O$R^{12}$, OC(O)$R^{12}$, OC(O)O$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, and $NR^{14}$S(O)$_2R^{12}$;

$R^8$ is selected from
H, halo, —$CF_3$, —$OCF_3$, —OH, —CN, —$NO_2$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic group substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;

OR$^{12}$, SR$^{12}$, NR$^{12}$R$^{13}$, C(O)H, C(O)R$^{12}$, C(O)
NR$^{12}$R$^{13}$, NR$^{14}$C(O)R$^{12}$, C(O)OR$^{12}$, OC(O)R$^{12}$,
OC(O)OR$^{12}$, CH(=NR$^{14}$)NR$^{12}$R$^{13}$, NHC(=NR$^{14}$)
NR$^{12}$R$^{13}$, S(O)R$^{12}$, S(O)$_2$R$^{12}$, S(O) NR$^{12}$R$^{13}$,
S(O)$_2$NR$^{12}$R$^{13}$, NR$^{14}$S(O) R$^{12}$, NR$^{14}$S(O)$_2$R$^{12}$,
NR$^{12}$C(O)R$^{15}$, NR$^{12}$C(O)OR$^{15}$, NR$^{12}$S(O)$_2$R$^{15}$, and
NR$^{12}$C(O) NHR$^{15}$;

R$^{10A}$ is selected from H,
  C$_{1-4}$ alkyl substituted with 0–1 R$^{10B}$,
  C$_{2-4}$ alkenyl substituted with 0–1 R$^{10B}$,
  C$_{2-4}$ alkynyl substituted with 0–1 R$^{10B}$, and
  C$_{1-6}$ alkoxy;

R$^{10B}$ is selected from
  C$_{1-4}$ alkoxy,
  C$_{3-6}$ cycloalkyl,
  phenyl substituted with 0–3 R$^{33}$, and
  5–6 membered heterocyclic ring system containing 1, 2, or 3 heteroatoms selected from the group consisting of N, O, and S substituted with 0–2 R$^{44}$;

R$^{11}$ is selected from
  H, halo, —CF$_3$, —CN, —NO$_2$, C$_{1-6}$ alkyl,
  C$_{2-6}$ alkenyl, C$_{2-6}$ alkynyl, C$_{1-4}$ haloalkyl, C$_{1-6}$ alkoxy,
  C$_{3-10}$ cycloalkyl,
  C$_{3-10}$ carbocyclic group substituted with 0–3 R$^{33}$,
  aryl substituted with 0–5 R$^{33}$,
  5–10 membered heterocyclic ring system containing from 1–4 heteroatoms selected from the group consisting of N, O, and S substituted with 0–3 R$^{31}$;
  OR$^{12}$, SR$^{12}$, NR$^{12}$R$^{13}$, C(O)H, C(O)R$^{12}$, C(O)
  NR$^{12}$R$^{13}$, NR$^{14}$C(O)R$^{12}$, C(O)OR$^{12}$, OC(O)R$^{12}$,
  OC(O)OR$^{12}$, CH(=NR$^{14}$)NR$^{12}$R$^{13}$, NHC(=NR$^{14}$)
  NR$^{12}$R$^{13}$, S(O)R$^{12}$, S(O)$_2$R$^{12}$, S(O)NR$^{12}$R$^{13}$,
  S(O)$_2$NR$^{12}$R$^{13}$, NR$^{14}$S(O) R$^{12}$, and NR$^{14}$S(O)$_2$R$^{12}$;

R$^{12}$, at each occurrence, is independently selected from
  C$_{1-4}$ alkyl substituted with 0–1 R$^{12a}$,
  C$_{2-4}$ alkenyl substituted with 0–1 R$^{12a}$,
  C$_{2-4}$ alkynyl substituted with 0–1 R$^{12a}$,
  C$_{3-6}$ cycloalkyl substituted with 0–3 R$^{33}$,
  phenyl substituted with 0–5 R$^{33}$;
  C$_{3-10}$ carbocyclic group substituted with 0–3 R$^{33}$, and
  5–10 membered heterocyclic ring system containing from 1–4 heteroatoms selected from the group consisting of N, O, and S substituted with 0–3 R$^{31}$;

R$^{12a}$, at each occurrence, is independently selected from
  phenyl substituted with 0–5 R$^{33}$;
  C$_{3-10}$ carbocyclic group substituted with 0–3 R$^{33}$, and
  5–10 membered heterocyclic ring system containing from 1–4 heteroatoms selected from the group consisting of N, O, and S substituted with 0–3 R$^{31}$;

R$^{13}$, at each occurrence, is independently selected from
  H, C$_{1-4}$ alkyl, C$_{2-4}$ alkenyl, and C$_{2-4}$ alkynyl;
  alternatively, R$^{12}$ and R$^{13}$ join to form a 5- or 6-membered ring optionally substituted with —O— or —N(R$^{14}$)—;

alternatively, R$^{12}$ and R$^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 R$^{16}$;

R$^{14}$, at each occurrence, is independently selected from H, methyl, ethyl, propyl, and butyl;

R$^{15}$, at each occurrence, is independently selected from H, C$_{1-4}$ alkyl, C$_{2-4}$ alkenyl, and C$_{2-4}$ alkynyl;

R$^{16}$, at each occurrence, is independently selected from
  H, OH, F, Cl, CN, NO$_2$, CF$_3$, SO$_2$R$^{45}$, NR$^{46}$R$^{47}$,
  —C(=O)H,
  methyl, ethyl, methoxy, ethoxy, trifluoromethyl, and trifluoromethoxy;

R$^{31}$, at each occurrence, is independently selected from
  H, OH, halo, CF$_3$, SO$_2$R$^{45}$, NR$^{46}$R$^{47}$, and C$_{1-4}$ alkyl;

R$^{33}$, at each occurrence, is independently selected from
  H, OH, halo, CN, NO$_2$, CF$_3$, SO$_2$R$^{45}$, NR$^{46}$R$^{47}$,
  —C(=O)H,
  C$_{1-6}$ alkyl, C$_{2-6}$ alkenyl, C$_{2-6}$ alkynyl,
  C$_{3-6}$ cycloalkyl, C$_{1-4}$ haloalkyl, C$_{1-4}$ haloalkyl-oxy-,
  C$_{1-4}$ alkyloxy-,
  C$_{1-4}$ alkylthio-, C$_{1-4}$ alkyl-C(=O)—, C$_{1-4}$ alkyl-C(=O)NH—,
  C$_{1-4}$ alkyl-OC(=O)—,
  C$_{1-4}$ alkyl-C(=O)O—, C$_{3-6}$ cycloalkyl-oxy-, C$_{3-6}$ cycloalkylmethyl-oxy-;
  C$_{1-6}$ alkyl substituted with OH, methoxy, ethoxy, propoxy, or butoxy; and
  C$_{2-6}$ alkenyl substituted with OH, methoxy, ethoxy, propoxy, or butoxy;

R$^{41}$, at each occurrence, is independently selected from
  H, CF$_3$, halo, OH, CO$_2$H, SO$_2$R$^{45}$, NR$^{46}$R$^{47}$, NO$_2$, CN,
  C$_{2-8}$ alkenyl, C$_{2-8}$ alkynyl, C$_{1-4}$ alkoxy, C$_{1-4}$ haloalkyl
  C$_{1-4}$ alkyl substituted with 0–1 R$^{43}$,
  aryl substituted with 0–3 R$^{42}$, and
  5–10 membered heterocyclic ring system containing from 1–4 heteroatoms selected from the group consisting of N, O, and S substituted with 0–3 R$^{44}$;

R$^{42}$, at each occurrence, is independently selected from
  H, CF$_3$, halo, OH, CO$_2$H, SO$_2$R$^{45}$, NR$^{46}$R$^{47}$, NO$_2$, CN,
  CH(=NH)NH$_2$, NHC(=NH)NH$_2$,
  C$_{2-6}$ alkenyl, C$_{2-6}$ alkynyl, C$_{1-4}$ alkoxy, C$_{1-4}$ haloalkyl,
  C$_{3-6}$ cycloalkyl,
  C$_{1-4}$ alkyl substituted with 0–1 R$^{43}$,
  aryl substituted with 0–3 R$^{44}$, and
  5–10 membered heterocyclic ring system containing from 1–4 heteroatoms selected from the group consisting of N, O, and S substituted with 0–3 R$^{44}$;

R$^{43}$ is C$_{3-6}$ cycloalkyl or aryl substituted with 0–3 R$^{44}$;

R$^{44}$, at each occurrence, is independently selected from H,
  halo, —OH, NR$^{46}$R$^{47}$, CO$_2$H, SO$_2$R$^{45}$, —CF$_3$,—OCF$_3$, —CN, —NO$_2$,
  C$_{1-4}$ alkyl, and C$_{1-4}$ alkoxy;

R$^{45}$ is C$_{1-4}$ alkyl;

R$^{46}$, at each occurrence, is independently selected from H and C$_{1-4}$ alkyl;

R$^{47}$, at each occurrence, is independently selected from H and C$_{1-4}$ alkyl;

k is 1 or 2;

m is 0 or 1; and n is 1 or 2.

4. A compound of claim 2 wherein:

X is —NH—;

R$^1$ is selected from
  H,
  C$_{1-4}$ alkyl,
  C$_{2-4}$ alkenyl,
  C$_{2-4}$ alkynyl,
  C$_{3-4}$ cycloalkyl,
  C$_{1-3}$ alkyl substituted with 0–1 R$^2$,
  C$_{2-3}$ alkenyl substituted with 0–1 R$^2$, and
  C$_{2-3}$ alkynyl substituted with 0–1 R$^2$;

$R^2$, at each occurrence, is independently selected from
- $C_{1-4}$ alkyl,
- $C_{2-4}$ alkenyl,
- $C_{2-4}$ alkynyl,
- $C_{3-6}$ cycloalkyl,
- phenyl substituted with 0–5 $R^{42}$;
- $C_{3-6}$ carbocyclic group substituted with 0–3 $R^{41}$, and
- 5–6 membered heterocyclic ring system containing 1, 2, or 3 heteroatoms selected from the group consisting of N, O, and S substituted with 0–3 $R^{41}$;

$R^5$ is H, methyl, ethyl, propyl, or butyl;

$R^{6a}$ is H, methyl, ethyl, methoxy, —OH, or —$CF_3$;

$R^{6b}$ is H;

$R^7$ and $R^9$, at each occurrence, are independently selected from
- H, halo, —$CF_3$, —$OCF_3$, —OH, —CN, —$NO_2$, —$NR^{46}R^{47}$,
- $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
- $C_{3-10}$ cycloalkyl substituted with 0–2 $R^{33}$,
- $C_{1-4}$ alkyl substituted with 0–2 $R^{11}$,
- $C_{3-10}$ carbocyclic group substituted with 0–3 $R^{33}$, aryl substituted with 0–5 $R^{33}$, and 5–6 membered heterocyclic ring system containing 1, 2, or 3 heteroatoms selected from the group consisting of N, O, and S substituted with 0–3 $R^{31}$;

$R^8$ is selected from
- H, halo, —$CF_3$, —$OCF_3$, —OH, —CN, —$NO_2$,
- $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
- $C_{3-10}$ cycloalkyl substituted with 0–2 $R^{33}$,
- $C_{1-4}$ alkyl substituted with 0–2 $R^{11}$,
- $C_{2-4}$ alkenyl substituted with 0–2 $R^{11}$,
- $C_{2-4}$ alkynyl substituted with 0–1 $R^{11}$,
- $C_{3-10}$ carbocyclic group substituted with 0–3 $R^{33}$, aryl substituted with 0–5 $R^{33}$,
- 5–6 membered heterocyclic ring system containing 1, 2, or 3 heteroatoms selected from the group consisting of N, O, and S substituted with 0–3 $R^{31}$;
- $OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
- H, halo, —$CF_3$, —CN, —$NO_2$,
- $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
- $C_{3-10}$ cycloalkyl substituted with 0–2 $R^{33}$,
- $C_{3-10}$ carbocyclic group substituted with 0–3 $R^{33}$, aryl substituted with 0–5 $R^{33}$, and
- 5–6 membered heterocyclic ring system containing 1, 2, or 3 heteroatoms selected from the group consisting of N, O, and S substituted with 0–3 $R^{31}$;

$R^{12}$, at each occurrence, is independently selected from
- $C_{1-4}$ alkyl substituted with 0–1 $R^{12a}$,
- $C_{2-4}$ alkenyl substituted with 0–1 $R^{12a}$,
- $C_{2-4}$ alkynyl substituted with 0–1 $R^{12a}$,
- $C_{3-6}$ cycloalkyl substituted with 0–3 $R^{33}$,
- phenyl substituted with 0–5 $R^{33}$;
- $C_{3-10}$ carbocyclic group substituted with 0–3 $R^{33}$, and
- 5–10 membered heterocyclic ring system containing from 1–4 heteroatoms selected from the group consisting of N, O, and S substituted with 0–3 $R^{31}$;

$R^{12a}$, at each occurrence, is independently selected from
- phenyl substituted with 0–5 $R^{33}$;
- $C_{3-10}$ carbocyclic group substituted with 0–3 $R^{33}$, and
- 5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —$N(R^{14})$—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from
- H, OH, halo, CN, $NO_2$, $CF_3$, $SO_2R^{45}$, $NR^{46}R^{47}$, —C(=O)H,
- $C_{1-6}$ alkyl, $C_{2-6}$ alkenyl, $C_{2-6}$ alkynyl,
- $C_{3-6}$ cycloalkyl, $C_{1-4}$ haloalkyl, $C_{1-4}$ haloalkyl-oxy-,
- $C_{1-4}$ alkyloxy-,
- $C_{1-4}$ alkylthio-, $C_{1-4}$ alkyl-C(=O)—, $C_{1-4}$ alkyl-C(=O)NH—,
- $C_{1-4}$ alkyl-OC(=O)—,
- $C_{1-4}$ alkyl-C(=O)O—, $C_{3-6}$ cycloalkyl-oxy-, $C_{3-6}$ cycloalkylmethyl-oxy-;
- $C_{1-6}$ alkyl substituted with OH, methoxy, ethoxy, propoxy, or butoxy; and
- $C_{2-6}$ alkenyl substituted with OH, methoxy, ethoxy, propoxy, or butoxy;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

k is 1;

m is 1; and n is 1 or 2.

5. A compound of claim 2 wherein:

X is —NH—;

$R^1$ is selected from
  H,
  $C_{1-4}$ alkyl,
  $C_{2-4}$ alkenyl,
  $C_{2-4}$ alkynyl,
  $C_{3-4}$ cycloalkyl,
  $C_{1-3}$ alkyl substituted with 0–1 $R^2$,
  $C_{2-3}$ alkenyl substituted with 0–1 $R^2$, and
  $C_{2-3}$ alkynyl substituted with 0–1 $R^2$;
$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{42}$;
  $C_{3-6}$ carbocyclic group substituted with 0–3 $R^{41}$, and
  5–6 membered heterocyclic ring system containing 1, 2, or 3 heteroatoms selected from the group consisting of N, O, and S substituted with 0–3 $R^{41}$;
$R^5$ is H, methyl, ethyl, propyl, or butyl;
$R^{6a}$ is H, methyl, ethyl, methoxy, —OH, or —$CF_3$;
$R^{6b}$ is H;
$R^7$ and $R^9$, at each occurrence, are independently selected from
  H, F, $C_1$-$CH_3$, —$OCH_3$, —$CF_3$, —$OCF_3$, —CN, and —$NO_2$,
$R^8$ is selected from
  H, F, Cl, Br, —$CF_3$, —$OCF_3$, —OH, —CN, —$NO_2$,
  $C_{1-4}$ alkyl, $C_{2-4}$ alkenyl, $C_{2-4}$ alkynyl, $C_{1-4}$ haloalkyl,
  $C_{1-4}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{2-4}$ alkenyl substituted with 0–2 $R^{11}$,
  $C_{2-4}$ alkynyl substituted with 0–1 $R^{11}$,
  $C_{3-10}$ carbocyclic group substituted with 0–3 $R^{33}$,
  aryl substituted with 0–5 $R^{33}$,
  5–6 membered heterocyclic ring system containing 1, 2, or 3 heteroatoms selected from the group consisting of N, O, and S substituted with 0–3 $R^{31}$;
  $OR^{12}$, $SR^{12}$, $NR^{12}R^{13}$, $NR^{12}C(O)R^{15}$, $NR^{12}C(O)OR^{15}$, $NR^{12}S(O)_2R^{15}$, and $NR^{12}C(O)NHR^{15}$; $R^{11}$ is selected from
  H, halo, —$CF_3$, —CN, —$NO_2$,
  $C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
  $C_{3-10}$ cycloalkyl substituted with 0–2 $R^{33}$,
  $C_{3-10}$ carbocyclic group substituted with 0–3 $R^{33}$,
  aryl substituted with 0–5 $R^{33}$, and
  5–6 membered heterocyclic ring system containing 1, 2, or 3 heteroatoms selected from the group consisting of N, O, and S substituted with 0–3 $R^{31}$;
$R^{12}$, at each occurrence, is independently selected from
  $C_{1-4}$ alkyl substituted with 0–1 $R^{12a}$,
  $C_{2-4}$ alkenyl substituted with 0–1 $R^{12a}$,
  $C_{2-4}$ alkynyl substituted with 0–1 $R^{12a}$,
  $C_{3-6}$ cycloalkyl substituted with 0–3 $R^{33}$,
  phenyl substituted with 0–5 $R^{33}$;
  $C_{3-10}$ carbocyclic group substituted with 0–3 $R^{33}$, and
  5–10 membered heterocyclic ring system containing from 1–4 heteroatoms selected from the group consisting of N, O, and S substituted with 0–3 $R^{31}$;
$R^{12a}$, at each occurrence, is independently selected from
  phenyl substituted with 0–5 $R^{33}$;
  $C_{3-10}$ carbocyclic group substituted with 0–3 $R^{33}$, and
  5–10 membered heterocyclic ring system containing from 1–4 heteroatoms selected from the group consisting of N, O, and S substituted with 0–3 $R^{31}$;

$R^{13}$, at each occurrence, is independently selected from
  H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N($R^{14}$)—;
alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;
$R^{14}$, at each occurrence, is independently selected from H, methyl, ethyl, propyl, and butyl;
$R^{15}$, at each occurrence, is independently selected from H, methyl, ethyl, propyl, and butyl;
$R^{16}$, at each occurrence, is independently selected from H, OH, F, Cl, CN, $NO_2$, methyl, ethyl, methoxy, ethoxy, trifluoromethyl, and trifluoromethoxy;
$R^{31}$, at each occurrence, is independently selected from H, OH, halo, $CF_3$, methyl, ethyl, and propyl;
$R^{33}$, at each occurrence, is independently selected from
  H, OH, halo, CN, $NO_2$, $CF_3$, $SO_2R^{45}$, $NR^{46}R^{47}$,
  —C(=O)H,
  $C_{1-6}$ alkyl, $C_{2-6}$ alkenyl, $C_{2-6}$ alkynyl,
  $C_{3-6}$ cycloalkyl, $C_{1-4}$ haloalkyl, $C_{1-4}$ haloalkyl-oxy-,
  $C_{1-4}$ alkyloxy-,
  $C_{1-4}$ alkylthio-, $C_{1-4}$ alkyl-C(=O)—, $C_{1-4}$ alkyl-C(=O)NH—,
  $C_{1-4}$ alkyl-OC(=O)—,
  $C_{1-4}$ alkyl-C(=O)O—, $C_{3-6}$ cycloalkyl-oxy-, $C_{3-6}$ cycloalkylmethyl-oxy-;
  $C_{1-6}$ alkyl substituted with OH, methoxy, ethoxy, propoxy, or butoxy; and
  $C_{2-6}$ alkenyl substituted with OH, methoxy, ethoxy, propoxy, or butoxy;
$R^{41}$, at each occurrence, is independently selected from
  H, $CF_3$, halo, OH, $CO_2H$, $SO_2R^{45}$, $NR^{46}R^{47}$, $NO_2$, CN,
  $C_{2-4}$ alkenyl, $C_{2-4}$ alkynyl, $C_{13}$ alkoxy, $C_{1-3}$ haloalkyl, and $C_{1-3}$ alkyl;
$R^{42}$, at each occurrence, is independently selected from
  H, $CF_3$, halo, OH, $CO_2H$, $SO_2R^{45}$, $NR^{46}R^{47}$, $NO_2$, CN, CH(=NH)$NH_2$, NHC(=NH)$NH_2$,
  $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;
$R^{43}$ is cyclopropyl, cyclobutyl, cyclopentyl, cyclohexyl, phenyl, or pyridyl, each substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$,
  methyl, ethyl, propyl, butyl, methoxy, ethoxy, propoxy, and butoxy;
$R^{45}$ is methyl, ethyl, propyl, or butyl;
$R^{46}$, at each occurrence, is independently selected from H, methyl, ethyl, propyl, and butyl;
$R^{47}$, at each occurrence, is independently selected from from H, methyl, ethyl, propyl, and butyl;
k is 1;
m is 1; and
n is 1 or 2.

6. A compound of claim 2 wherein:

X is —NH—;

$R^1$ is selected from H,
 $C_{1-5}$ alkyl substituted with 0–1 $R^2$,
 $C_{2-5}$ alkenyl substituted with 0–1 $R^2$, and
 $C_{2-3}$ alkynyl substituted with 0–1 $R^2$;

$R^2$ is $C_{3-6}$ cycloalkyl;

$R^5$ is H, methyl, ethyl, or propyl;

$R^{6a}$ is H, methyl, or ethyl;

$R^{6b}$ is H;

$R^7$ and $R^9$, at each occurrence, are independently selected from
 H, F, Cl, —$CH_3$, —$OCH_3$, —$CF_3$, —$OCF_3$, —CN, and —$NO_2$, $R^8$ is selected from
 methyl substituted with $R^{11}$;
 ethenyl substituted with $R^{11}$;
 $OR^{12}$e $SR^{12}$, $NR^{12}R^-3$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
 phenyl-substituted with 0–5 fluoro;
 2-($H_3CCH_2C(=O)$)-phenyl-substituted with $R^{33}$;
 2-($H_3CC(=O)$)-phenyl-substituted with $R^{33}$;
 2-(HC(=O))-phenyl-substituted with $R^{33}$;
 2-($H_3CCH(OH)$)-phenyl-substituted with $R^{33}$;
 2-($H_3CCH_2CH(OH)$)-phenyl-substituted with $R^{33}$;
 2-($HOCH_2$)-phenyl-substituted with $R^{33}$;
 2-($HOCH_2CH_2$)-phenyl-substituted with $R^{33}$;
 2-($H_3COCH_2$)-phenyl-substituted with $R^{33}$;
 2-($H_3COCH_2CH_2$)-phenyl-substituted with $R^{33}$;
 2-($H_3CCH(OMe)$)-phenyl-substituted with $R^{33}$;
 2-($H_3COC(=O)$)-phenyl-substituted with $R^{33}$;
 2-($HOCH_2CH=CH$)-phenyl-substituted with $R^{33}$;
 2-((MeOC=O)CH=CH)-phenyl-substituted with $R^{33}$;
 2-(methyl)-phenyl-substituted with $R^{33}$;
 2-(ethyl)-phenyl-substituted with $R^{33}$;
 2-(i-propyl)-phenyl-substituted with $R^{33}$;
 2-($F_3C$)-phenyl-substituted with $R^{33}$;
 2-(NC)-phenyl-substituted with $R^{33}$;
 2-($H_3CO$)-phenyl-substituted with $R^{33}$;
 2-(fluoro)-phenyl-substituted with $R^{33}$;
 2-(chloro)-phenyl-substituted with $R^{33}$;
 3-(NC)-phenyl-substituted with $R^{33}$;
 3-($H_3CO$)-phenyl-substituted with $R^{33}$;
 3-(fluoro)-phenyl-substituted with $R^{33}$;
 3-(chloro)-phenyl-substituted with $R^{33}$;
 4-(NC)-phenyl-substituted with $R^{33}$;
 4-(fluoro)-phenyl-substituted with $R^{33}$;
 4-(chloro)-phenyl-substituted with $R^{33}$;
 4-($H_3CS$)-phenyl-substituted with $R^{33}$;
 4-($H_3CO$)-phenyl-substituted with $R^{33}$;
 4-(ethoxy)-phenyl-substituted with $R^{33}$;
 4-(i-propoxy)-phenyl-substituted with $R^{33}$;
 4-(i-butoxy)-phenyl-substituted with $R^{33}$;
 4-($H_3CCH_2CH_2C(=O)$)-phenyl-substituted with $R^{33}$;
 4-(($H_3C)_2CHC(=O)$)-phenyl-substituted with $R^{33}$;
 4-($H_3CCH_2C(=O)$)-phenyl-substituted with $R^{33}$;
 4-($H_3CC(=O)$)-phenyl-substituted with $R^{33}$;
 4-($H_3CCH_2CH_2CH(OH)$)-phenyl-substituted with $R^{33}$;
 4-(($H_3C)_2CHCH(OH)$)-phenyl-substituted with $R^{33}$;
 4-($H_3CCH_2CH(OH)$)-phenyl-substituted with $R^{33}$;
 4-($H_3CCH(OH)$)-phenyl-substituted with $R^{33}$;
 4-(cyclopropyloxy)-phenyl-substituted with $R^{33}$;
 4-(cyclobutyloxy)-phenyl-substituted with $R^{33}$; and
 4-(cyclopentyloxy)-phenyl-substituted with $R^{33}$;

$R^{12}$ is selected from
 phenyl-substituted with 0–5 fluoro;
 2-($H_3CCH_2C(=O)$)-phenyl-substituted with $R^{33}$;
 2-($H_3CC(=O)$)-phenyl-substituted with $R^{33}$;
 2-(HC(=O))-phenyl-substituted with $R^{33}$;
 2-($H_3CCH(OH)$)-phenyl-substituted with $R^{33}$;
 2-($H_3CCH_2CH(OH)$)-phenyl-substituted with $R^{33}$;
 2-($HOCH_2$)-phenyl-substituted with $R^{33}$;
 2-($HOCH_2CH_2$)-phenyl-substituted with $R^{33}$;
 2-($H_3COCH_2$)-phenyl-substituted with $R^{33}$;
 2-($H_3COCH_2CH_2$)-phenyl-substituted with $R^{33}$;
 2-($H_3CCH(OMe)$)-phenyl-substituted with $R^{33}$;
 2-($H_3COC(=O)$)-phenyl-substituted with $R^{33}$;
 2-($HOCH_2CH=CH$)-phenyl-substituted with $R^{33}$;
 2-((MeOC=O)CH=CH)-phenyl-substituted with $R^{33}$;
 2-(methyl)-phenyl-substituted with $R^{33}$;
 2-(ethyl)-phenyl-substituted with $R^{33}$;
 2-(i-propyl)-phenyl-substituted with $R^{33}$;
 2-($F_3C$)-phenyl-substituted with $R^{33}$;
 2-(NC)-phenyl-substituted with $R^{33}$;
 2-($H_3CO$)-phenyl-substituted with $R^{33}$;
 2-(fluoro)-phenyl-substituted with $R^{33}$;
 2-(chloro)-phenyl-substituted with $R^{33}$;
 3-(NC)-phenyl-substituted with $R^{33}$;
 3-($H_3CO$)-phenyl-substituted with $R^{33}$;
 3-(fluoro)-phenyl-substituted with $R^{33}$;
 3-(chloro)-phenyl-substituted with $R^{33}$;
 4-(NC)-phenyl-substituted with $R^{33}$;
 4-(fluoro)-phenyl-substituted with $R^{33}$;
 4-(chloro)-phenyl-substituted with $R^{33}$;
 4-($H_3CS$)-phenyl-substituted with $R^{33}$;
 4-($H_3CO$)-phenyl-substituted with $R^{33}$;
 4-(ethoxy)-phenyl-substituted with $R^{33}$;
 4-(i-propoxy)-phenyl-substituted with $R^{33}$;
 4-(i-butoxy)-phenyl-substituted with $R^{33}$;
 4-($H_3CCH_2CH_2C(=O)$)-phenyl-substituted with $R^{33}$;
 4-(($H_3C)_2CHC(=O)$)-phenyl-substituted with $R^{33}$;
 4-($H_3CCH_2C(=O)$)-phenyl-substituted with $R^{33}$;
 4-($H_3CC(=O)$)-phenyl-substituted with $R^{33}$;
 4-($H_3CCH_2CH_2CH(OH)$)-phenyl-substituted with $R^{33}$;
 4-(($H_3C)_2CHCH(OH)$)-phenyl-substituted with $R^{33}$;
 4-($H_3CCH_2CH(OH)$)-phenyl-substituted with $R^{33}$;
 4-($H_3CCH(OH)$)-phenyl-substituted with $R^{33}$;
 4-(cyclopropyloxy)-phenyl-substituted with $R^{33}$;
 4-(cyclobutyloxy)-phenyl-substituted with $R^{33}$; and
 4-(cyclopentyloxy)-phenyl-substituted with $R^{33}$;

$R^{13}$ is H, methyl, or ethyl;

alternatively, $R^{12}$ and $R^{13}$ join to form a 5- or 6-membered ring selected from pyrrolyl, pyrrolidinyl, imidazolyl, piperidinyl, piperizinyl, methylpiperizinyl, and morpholinyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, benzoxazolyl, benzoxazolinyl, benzthiazolyl, and dioxobenzthiazolyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{33}$, at each occurrence, is independently selected from H, F, Cl, —CH$_3$, —OCH$_3$, —CF$_3$, —OCF$_3$, —CN, and —NO$_2$;

k is 1;

m is 1; and n is 1 or 2.

7. A compound of claim 2 of Formula (I-a)

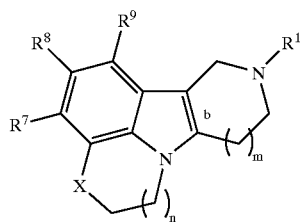

(I-a)

wherein:

b is a single bond;

X is —NR$^{10A}$—;

$R^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, benzyl, 2-methylbenzyl, 3-methylbenzyl, 4-methylbenzyl, 2,5-dimethylbenzyl, 2,4-dimethylbenzyl, 3,5-dimethylbenzyl, 2,4,6-trimethyl-benzyl, 3-methoxy-benzyl, 3,5-dimethoxy-benzyl, pentafluorobenzyl, 2-phenylethyl, 1-phenyl-2-propyl, 4-phenylbutyl, 4-phenylbenzyl, 2-phenylbenzyl, (2,3-dimethoxy-phenyl)C(=O)—, (2,5-dimethoxy-phenyl)C(=O)—, (3,4-dimethoxy-phenyl)C(=O)—, (3,5-dimethoxy-phenyl)C(=O)—, cyclopropyl-C(=O)—, isopropyl-C(=O)—, ethyl-CO$_2$-, propyl-CO$_2$-, t-butyl-CO$_2$-, 2,6-dimethoxy-benzyl, 2,4-dimethoxy-benzyl, 2,4,6-trimethoxy-benzyl, 2,3-dimethoxy-benzyl, 2,4,5-trimethoxy-benzyl, 2,3,4-trimethoxy-benzyl, 3,4-dimethoxy-benzyl, 3,4,5-trimethoxy-benzyl, (4-fluoro-phenyl)ethyl, —CH=CH$_2$, —CH$_2$—CH=CH$_2$, —CH=CH—CH$_3$, —C≡CH, —C≡C—CH$_3$, and —CH$_2$—C≡—CH;

$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, methylC(=O)—, ethylC(=O)—, propylC(=O)—, isopropylC(=O)—, butylC(=O)—, phenylC(=O)—, methylCO$_2$-, ethylCO$_2$-, propylCO$_2$-, isopropylCO$_2$-, butylCO$_2$-, phenylCO$_2$-, dimethylamino-S(=O)—, diethylamino-S(=O)—, dipropylamino-S(=O)—, di-isopropylamino-S(=O)—, dibutylamino-S(=O)—, diphenylamino-S(=O)—, dimethylamino-SO$_2$-, diethylamino-SO$_2$-, dipropylamino-SO$_2$-, di-isopropylamino-SO$_2$-, dibutylamino-SO$_2$-, diphenylamino-SO$_2$-, dimethylamino-C(=O)—, diethylamino-C(=O)—, dipropylamino-C(=O)—, di-isopropylamino-C(=O)—, dibutylamino-C(=O)—, diphenylamino-C(=O)—, 2-chlorophenyl, 2-fluorophenyl, 2-bromophenyl, 2-cyanophenyl, 2-methylphenyl, 2-trifluoromethylphenyl, 2-methoxyphenyl, 2-trifluoromethoxyphenyl, 3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl, 4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl, 2,3-dichlorophenyl, 2,3-difluorophenyl, 2,3-dimethylphenyl, 2, 3-ditrifluoromethylphenyl, 2,3-dimethoxyphenyl, 2,3-ditrifluoromethoxyphenyl, 2,4-dichlorophenyl, 2,4-difluorophenyl, 2,4-dimethylphenyl, 2,4-ditrifluoromethylphenyl, 2,4-dimethoxyphenyl, 2,4-ditrifluoromethoxyphenyl, 2,5-dichlorophenyl, 2,5-difluorophenyl, 2,5-dimethylphenyl, 2,5-ditrifluoromethylphenyl, 2,5-dimethoxyphenyl, 2,5-ditrifluoromethoxyphenyl, 2,6-dichlorophenyl, 2,6-difluorophenyl, 2,6-dimethylphenyl, 2,6-ditrifluoromethylphenyl, 2,6-dimethoxyphenyl, 2,6-ditrifluoromethoxyphenyl, 3,4-dichlorophenyl, 3,4-difluorophenyl, 3,4-dimethylphenyl, 3,4-ditrifluoromethylphenyl, 3,4-dimethoxyphenyl, 3,4-ditrifluoromethoxyphenyl, 2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl, 2-chloro-4-CF$_3$-phenyl, 2-fluoro-3-chloro-phenyl, 2-chloro-4-CF$_3$-phenyl, 2-chloro-4-methoxy-phenyl, 2-methoxy-4-isopropyl-phenyl, 2-CF$_3$-4-methoxy-phenyl, 2-methyl-4-methoxy-5-fluoro-phenyl, 2-methyl-4-methoxy-phenyl, 2-chloro-4-CF₃O-phenyl,
2,4,5-trimethyl-phenyl, 2-methyl-4-chloro-phenyl,
methyl-C(=O)NH—, ethyl-C(=O)NH—, propyl-C(=O)NH—,
isopropyl-C(=O)NH—, butyl-C(=O)NH—, phenyl-C(=O)NH—,
4-acetylphenyl, 3-acetamidophenyl, 4-pyridyl, 2-furanyl,
2-thiophenyl, 2-naphthyl;
2-Me-5-F-phenyl, 2-F-5-Me-phenyl, 2-MeO-5-F-phenyl,
2-Me-3-Cl-phenyl, 3-NO₂-phenyl, 2-NO₂-phenyl,
2-Cl-3-Me-phenyl, 2-Me-4-EtO-phenyl, 2-Me-4-F-phenyl,
2-Cl-6-F-phenyl, 2-Cl-4-(CHF₂)O-phenyl,
2,4-diMeO-6-F-phenyl, 2-CF₃-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-CF₃-4-EtO-phenyl, 2-CF₃-4-iPrO-phenyl,
2-CF₃-4-Cl-phenyl, 2-CF₃-4-F-phenyl, 2-Cl-4-EtO-phenyl,
2-C-4-iPrO-phenyl, 2-Et-4-MeO-phenyl,
2-CHO-4-MeO-phenyl, 2-CH(OH)Me-4-MeO-phenyl,
2-CH(OMe)Me-4-MeO-phenyl, 2-C(=O)Me-4-MeO-phenyl,
2-CH₂(OH)-4-MeO-phenyl, 2-CH₂(OMe)-4-MeO-phenyl,
2-CH(OH)Et-4-MeO-phenyl, 2-C(=O)Et-4-MeO-phenyl,
(Z)-2-CH=CHCO₂Me-4-MeO-phenyl,
2-CH₂CH₂CO₂Me-4-MeO-phenyl,
(Z)-2-CH=CHCH₂(OH)-4-MeO-phenyl,
(E)-2-CH=CHCO₂Me-4-MeO-phenyl,
(E)-2-CH=CHCH₂(OH)-4-MeO-phenyl,
2-CH₂CH₂OMe-4-MeO-phenyl,
2-F-4-MeO-phenyl, 2-Cl-4-F-phenyl,
(2-Cl-phenyl)-CH=CH—, (3-Cl-phenyl)-CH=CH—,
(2,6-diF-phenyl)-CH=CH—, —CH₂CH=CH₂,
phenyl-CH=CH—, (2-Me-4-MeO-phenyl)-CH=CH—,
cyclohexyl, cyclopentyl, cyclohexylmethyl,
—CH₂CH₂CO₂Et, —(CH₂)₃CO₂Et, —(CH₂)₄CO₂Et,
benzyl, 2-F-benzyl, 3-F-benzyl, 4-F-benzyl,
3-MeO-benzyl, 3-OH-benzyl, 2-MeO-benzyl,
2-OH-benzyl, 2-CO₂Me-3-MeO-phenyl,
2-Me-4-CN-phenyl, 2-Me-3-CN-phenyl, 2-CF₃-4-CN-phenyl,
3-CHO-phenyl, 3-CH₂(OH)-phenyl, 3-CH₂(OMe)-phenyl,
3-CH₂(NMe₂)-phenyl, 3-CN-4-F-phenyl,
3-CONH₂-4-F-phenyl, 2-CH₂(NH₂)-4-MeO-phenyl-,
phenyl-NH—, (4-F-phenyl)-NH—, (2,4-diCl-phenyl)-NH—,
phenyl-C(=O)NH—, benzyl-NH—, (2-Me-4-MeO-phenyl)-NH—,
(2-F-4-MeO-phenyl)-NH—, (2-Me-4-F-phenyl)-NH—,
phenyl-S—, —NMe₂, 1-pyrrolidinyl, and —N(tosylate)₂,
provided that two of R⁷, R⁸, and R⁹, are independently selected from hydrogen, fluoro, chloro, bromo, cyano,
methyl, ethyl, propyl, isopropyl, butyl, t-butyl, nitro, trifluoromethyl, methoxy, ethoxy, isopropoxy, and trifluoromethoxy;
R¹⁰ᴬ is selected from hydrogen, methyl, ethyl, benzyl and 4-fluorobenzyl;
m is 1; and
n is 1 or 2.

8. A compound of claim 7 of Formula (IV)

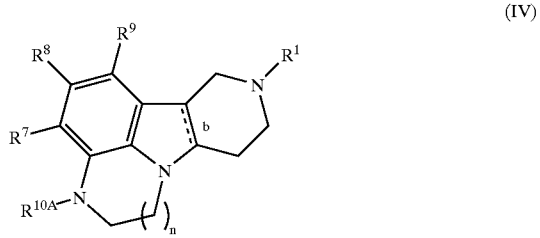

(IV)

wherein:
b is a single bond, wherein the bridge hydrogens are in a cis position;
R¹ is selected from
hydrogen, methyl, ethyl, n-propyl, n-butyl, s-butyl,
t-butyl, n-pentyl, n-hexyl, 2-propyl, 2-butyl, 2-pentyl,
2-hexyl, 2-methylpropyl, 2-methylbutyl, 2-methylpentyl,
2-ethylbutyl, 3-methylpentyl, 3-methylbutyl,
4-methylpentyl, 2-fluoroethyl, 2,2-difluoroethyl,
2,2,2-trifluoroethyl, 2-propenyl, 2-methyl-2-propenyl,
trans-2-butenyl, 3-methyl-butenyl, 3-butenyl,
trans-2-pentenyl, cis-2-pentenyl, 4-pentenyl,
4-methyl-3-pentenyl, 3,3-dichloro-2-propenyl,
trans-3-phenyl-2-propenyl, cyclopropyl, cyclobutyl,
cyclopentyl, cyclohexyl, cyclopropylmethyl,
cyclobutylmethyl, cyclopentylmethyl, cyclohexylmethyl,
—CH=CH₂, —CH₂—CH=CH₂, —CH=CH—CH₃,
—C≡CH, —C≡C—CH₃,
and —CH₂—C≡CH;
R⁷ and R⁹, at each occurrence, are independently selected from hydrogen, fluoro, methyl, trifluoromethyl, and methoxy;
R⁸ is selected from
hydrogen, fluoro, chloro, bromo, cyano, methyl, ethyl, propyl, isopropyl, butyl, t-butyl, nitro,
trifluoromethyl, methoxy, ethoxy, isopropoxy, trifluoromethoxy, phenyl,
methylC(=O)—, ethylC(=O)—, propylC(=O)—, isopropylC(=O)—,
butylC(=O)—, phenylC(=O)—,
methylCO₂—, ethylCO₂—, propylCO₂—, isopropylCO₂—,
butylCO₂—, phenylCO₂—,
dimethylamino-S(=O)—, diethylamino-S(=O)—,
dipropylamino-S(=O)—, di-isopropylamino-S(=O)—,
dibutylamino-S(=O)—, diphenylamino-S(=O)—,
dimethylamino-SO₂—, diethylamino-SO₂—,
dipropylamino-SO₂—, di-isopropylamino-SO₂—,
dibutylamino-SO₂—,
diphenylamino-SO₂—,
dimethylamino-C(=O)—, diethylamino-C(=O)—,
dipropylamino-C(=O)—, di-isopropylamino-C(=O)—,
dibutylamino-C(=O)—, diphenylamino-C(=O)—, 2-chlorophenyl, 2-fluorophenyl, 2-bromophenyl, 2-cyanophenyl, 2-methylphenyl, 2-trifluoromethylphenyl,
2-methoxyphenyl, 2-trifluoromethoxyphenyl,
3-chlorophenyl, 3-fluorophenyl, 3-bromophenyl, 3-cyanophenyl, 3-methylphenyl, 3-ethylphenyl, 3-propylphenyl, 3-isopropylphenyl, 3-butylphenyl, 3-trifluoromethylphenyl, 3-methoxyphenyl, 3-isopropoxyphenyl, 3-trifluoromethoxyphenyl, 3-thiomethoxyphenyl,
4-chlorophenyl, 4-fluorophenyl, 4-bromophenyl, 4-cyanophenyl, 4-methylphenyl, 4-ethylphenyl, 4-propylphenyl, 4-isopropylphenyl, 4-butylphenyl, 4-trifluoromethylphenyl, 4-methoxyphenyl, 4-isopropoxyphenyl, 4-trifluoromethoxyphenyl, 4-thiomethoxyphenyl,
2,3-dichlorophenyl, 2,3-difluorophenyl, 2,3-dimethylphenyl,
2,3-ditrifluoromethylphenyl, 2,3-dimethoxyphenyl, 2,3-ditrifluoromethoxyphenyl,
2,4-dichlorophenyl, 2,4-difluorophenyl, 2,4-dimethylphenyl,
2,4-ditrifluoromethylphenyl, 2,4-dimethoxyphenyl, 2,4-ditrifluoromethoxyphenyl,
2,5-dichlorophenyl, 2,5-difluorophenyl, 2,5-dimethylphenyl,
2,5-ditrifluoromethylphenyl, 2,5-dimethoxyphenyl, 2,5-ditrifluoromethoxyphenyl,
2,6-dichlorophenyl, 2,6-difluorophenyl, 2,6-dimethylphenyl,
2,6-ditrifluoromethylphenyl, 2,6-dimethoxyphenyl, 2,6-ditrifluoromethoxyphenyl,
3,4-dichlorophenyl, 3,4-difluorophenyl, 3,4-dimethylphenyl,
3,4-ditrifluoromethylphenyl, 3,4-dimethoxyphenyl, 3,4-ditrifluoromethoxyphenyl,
2,4,6-trichlorophenyl, 2,4,6-trifluorophenyl, 2,4,6-trimethylphenyl, 2,4,6-tritrifluoromethylphenyl, 2,4,6-trimethoxyphenyl, 2,4,6-tritrifluoromethoxyphenyl,
2-chloro-4-$CF_3$-phenyl, 2-fluoro-3-chloro-phenyl, 2-chloro-4-$CF_3$-phenyl, 2-chloro-4-methoxy-phenyl, 2-methoxy-4-isopropyl-phenyl, 2-$CF_3$-4-methoxy-phenyl,
2-methyl-4-methoxy-5-fluoro-phenyl,
2-methyl-4-methoxy-phenyl, 2-chloro-4-$CF_3$O-phenyl, 2,4,5-trimethyl-phenyl, 2-methyl-4-chloro-phenyl,
methyl-C(=O)NH—, ethyl-C(=O)NH—, propyl-C(=O)NH—,
isopropyl-C(=O)NH—, butyl-C(=O)NH—, phenyl-C(=O)NH—,
4-acetylphenyl, 3-acetamidophenyl, 4-pyridyl, 2-furanyl,
2-thiophenyl, 2-naphthyl;
2-Me-5-F-phenyl, 2-F-5-Me-phenyl, 2-MeO-5-F-phenyl,
2-Me-3-Cl-phenyl, 3-$NO_2$-phenyl, 2-$NO_2$-phenyl,
2-Cl-3-Me-phenyl, 2-Me-4-EtO-phenyl, 2-Me-4-F-phenyl,
2-Cl-6-F-phenyl, 2-Cl-4-($CHF_2$)O-phenyl,
2,4-diMeO-6-F-phenyl, 2-$CF_3$-6-F-phenyl,
2-MeS-phenyl, 2,6-diCl-4-MeO-phenyl,
2,3,4-triF-phenyl, 2,6-diF-4-Cl-phenyl,
2,3,4,6-tetraF-phenyl, 2,3,4,5,6-pentaF-phenyl,
2-$CF_3$-4-EtO-phenyl, 2-$CF_3$-4-iPrO-phenyl,
2-$CF_3$-4-Cl-phenyl, 2-$CF_3$-4-F-phenyl, 2-Cl-4-EtO-phenyl,
2-Cl-4-iPrO-phenyl, 2-Et-4-MeO-phenyl,
2-CHO-4-MeO-phenyl, 2-CH(OH)Me-4-MeO-phenyl,
2-CH(OMe)Me-4-MeO-phenyl, 2-C(=O)Me-4-MeO-phenyl,
2-$CH_2$(OH)-4-MeO-phenyl, 2-$CH_2$(OMe)-4-MeO-phenyl,
2-CH(OH)Et-4-MeO-phenyl, 2-C(=O)Et-4-MeO-phenyl,
(Z)-2-CH=CHCO$_2$Me-4-MeO-phenyl,
2-$CH_2CH_2CO_2$Me-4-MeO-phenyl,
(Z)-2-CH=CH$CH_2$(OH)-4-MeO-phenyl,
(E)-2-CH=CHC$_2$Me-4-MeO-phenyl,
(E)-2-CH=CH$CH_2$(OH)-4-MeO-phenyl,
2-$CH_2CH_2$OMe-4-MeO-phenyl,
2-F-4-MeO-phenyl, 2-Cl-4-F-phenyl,
(2-Cl-phenyl)-CH=CH—, (3-Cl-phenyl)-CH=CH—, (2,6-diF-phenyl)-CH=CH—, —$CH_2$CH=$CH_2$,
phenyl-CH=CH—, (2-Me-4-MeO-phenyl)-CH=CH—,
cyclohexyl, cyclopentyl, cyclohexylmethyl,
—$CH_2CH_2CO_2$Et, —$(CH_2)_3CO_2$Et, —$(CH_2)_4CO_2$Et,
benzyl, 2-F-benzyl, 3-F-benzyl, 4-F-benzyl,
3-MeO-benzyl, 3-OH-benzyl, 2-MeO-benzyl,
2-OH-benzyl, 2-$CO_2$Me-3-MeO-phenyl,
2-Me-4-CN-phenyl, 2-Me-3-CN-phenyl, 2-$CF_3$-4-CN-phenyl,
3-CHO-phenyl, 3-$CH_2$(OH)-phenyl, 3-$CH_2$(OMe)-phenyl,
3-$CH_2$(NMe$_2$)-phenyl, 3-CN-4-F-phenyl,
3-CONH$_2$-4-F-phenyl, 2-$CH_2$(NH$_2$)-4-MeO-phenyl-,
phenyl-NH—, (4-F-phenyl)-NH—, (2,4-diCl-phenyl)-NH—,
phenyl-C(=O)NH—, benzyl-NH—, (2-Me-4-MeO-phenyl)-NH—,
(2-F-4-MeO-phenyl)-NH—, (2-Me-4-F-phenyl)-NH—,
phenyl-S—, —NMe$_2$, 1-pyrrolidinyl, and —N(tosylate)$_2$;

$R^{10A}$ is selected from hydrogen, methyl, ethyl, 4-fluorobenzyl and benzyl; and n is 1 or 2.

9. A compound of claim 1 wherein:

X is —NR$^{10A}$—;

$R^1$ is selected from
$C_{1-6}$ alkyl substituted with Z,
$C_{2-6}$ alkenyl substituted with Z,
$C_{2-6}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$,
aryl substituted with 0–2 $R^2$, and
5–6 membered heterocyclic ring system containing at least one heteroatom selected from the group consisting of N, O, and S, said heterocyclic ring system substituted with 0–2 $R^2$;

Z is selected from H,
—CH(OH)R$^2$,
—C(ethylenedioxy)R$^2$,
—OR$^2$,
—SR$^2$,

—NR$^2$R$^3$,
—C(O) R$^2$,
—C(O)NR$^2$R$^3$,
—NR$^3$C(O)R$^2$,
—C(O)OR$^2$,
—OC(O)R$^2$,
—CH(=NR$^4$)NR$^2$R$^3$,
—NHC(=NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic group substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from H, C$_{1-4}$ alkyl, C$_{2-4}$ alkenyl, C$_{2-4}$ alkynyl, and C$_{1-4}$ alkoxy;
alternatively, R$^2$ and R$^3$ join to form a 5- or 6-membered ring optionally substituted with —O— or —N(R$^4$)—;

R$^4$, at each occurrence, is independently selected from H, methyl, ethyl, propyl, and butyl;

R$^5$ is H, methyl, ethyl, propyl, or butyl;

R$^{6a}$ is selected from
H, —OH, —NR$^{46}$R$^{47}$, —CF$_3$,
C$_{1-4}$ alkyl, C$_{2-4}$ alkenyl, C$_{2-4}$ alkynyl, C$_{1-4}$ alkoxy, C$_{1-4}$ haloalkyl, C$_{3-6}$ cycloalkyl, and
aryl substituted with 0–3 R$^{44}$;

R$^{6b}$ is H;

R$^7$, R$^8$, and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{1-4}$ alkyl substituted with 0–2 R$^{11}$,
C$_{3-10}$ carbocyclic group substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O) R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{10A}$ is selected from H,
C$_{1-6}$ alkyl substituted with 0–1 R$^{10B}$,
C$_{2-6}$ alkenyl substituted with 0–1 R$^{10B}$,
C$_{2-6}$ alkynyl substituted with 0–1 R$^{10B}$, and
C$_{1-6}$ alkoxy;

R$^{10B}$ is selected from
C$_{1-4}$ alkoxy,
C$_{3-6}$ cycloalkyl,
C$_{3-10}$ carbocyclic group substituted with 0–3 R$^{33}$,
phenyl substituted with 0–3 R$^{33}$, and
5–6 membered heterocyclic ring system containing 1, 2, or 3 heteroatoms selected from the group consisting of N, O, and S substituted with 0–2 R$^{44}$;

R$^{11}$ is selected from
H, halo, —CF$_3$, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
C$_{3-10}$ carbocyclic group substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R12, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;

R$^{12}$, at each occurrence, is independently selected from
C$_{1-4}$ alkyl,
C$_{2-4}$ alkenyl,
C$_{2-4}$ alkynyl,
C$_{3-6}$ cycloalkyl,
phenyl substituted with 0–5 R$^{33}$;
C$_{3-10}$ carbocyclic group substituted with 0–3 R$^{33}$, and
5–10 membered heterocyclic ring system containing from 1–4 heteroatoms selected from the group consisting of N, O, and S substituted with 0–3 R$^{31}$;

R$^{13}$, at each occurrence, is independently selected from H, C$_{1-4}$ alkyl, C$_{2-4}$ alkenyl, and C$_{2-4}$ alkynyl;
alternatively, R$^{12}$ and R$^{13}$ join to form a 5- or 6-membered ring optionally substituted with —O— or —N(R$^{14}$)—;

R$^{14}$, at each occurrence, is independently selected from H and C$_{1-4}$ alkyl;

R$^{31}$, at each occurrence, is independently selected from H, OH, halo, CF$_3$, SO$_2$R$^{45}$, NR$^{46}$R$^{47}$, methyl, ethyl, and propyl;

R$^{33}$, at each occurrence, is independently selected from
H, OH, halo, CN, NO$_2$, CF$_3$, SO$_2$R$^{45}$, NR$^{46}$R$^{47}$,
C$_{1-3}$ alkyl, C$_{2-3}$ alkenyl, C$_{2-3}$ alkynyl, C$_{3-5}$ cycloalkyl, C$_{1-3}$ haloalkyl, C$_{1-3}$ haloalkyl-oxy-, C$_{1-3}$ alkyloxy-, C$_{1-3}$ alkylthio-, C$_{1-3}$ alkyl-C(=O)—, and C$_{1-3}$ alkyl-C(=O)NH—;

R$^{41}$, at each occurrence, is independently selected from
H, CF$_3$, halo, OH, CO$_2$H, SO$_2$R$^{45}$, NR$^{46}$R$^{47}$, NO$_2$, CN, =O,
C$_{2-8}$ alkenyl, C$_{2-8}$ alkynyl, C$_{1-4}$ alkoxy, C$_{1-4}$ haloalkyl
C$_{1-4}$ alkyl substituted with 0–1 R$^{43}$,
aryl substituted with 0–3 R$^{42}$, and
5–10 membered heterocyclic ring system containing from 1–4 heteroatoms selected from the group consisting of N, O, and S substituted with 0–3 R$^{44}$;

R$^{42}$, at each occurrence, is independently selected from
H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
C$_{2-6}$ alkenyl, C$_{2-6}$ alkynyl, C$_{1-4}$ alkoxy, C$_{1-4}$ haloalkyl, C$_{3-6}$ cycloalkyl,
C$_{1-4}$ alkyl substituted with 0–1 R$^{43}$,
aryl substituted with 0–3 R$^{44}$, and
5–10 membered heterocyclic ring system containing from 1–4 heteroatoms selected from the group consisting of N, O, and S substituted with 0–3 R$^{44}$;

R$^{43}$ is C$_{3-6}$ cycloalkyl or aryl substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$,
C$_{1-4}$ alkyl, and C$_{1-4}$ alkoxy;

R$^{45}$ is C$_{1-4}$ alkyl;

R$^{46}$, at each occurrence, is independently selected from H and C$_{1-4}$ alkyl;

$R^{47}$, at each occurrence, is independently selected from H,
$C_{1-4}$ alkyl, —C(=O)NH($C_{1-4}$ alkyl), —SO$_2$($C_{1-4}$ alkyl),
—SO$_2$(phenyl), —C(=O)O($C_{1-4}$ alkyl), —C(=O)($C_{1-4}$ alkyl),
and —C(=O)H;

$R^{48}$, at each occurrence, is independently selected from H,
$C_{1-4}$ alkyl, —C(=O)NH($C_{1-4}$ alkyl), —C(=O)O($C_{1-4}$ alkyl),
—C(=O)($C_{1-4}$ alkyl), and —C(=O)H;

k is 1 or 2;
m is 0, 1, or 2; and
n is 1 or 2.

10. A compound of claim 9 wherein:
X is —NR$^{10A}$—;
$R^1$ is selected from
  $C_{2-5}$ alkyl substituted with Z,
  $C_{2-5}$ alkenyl substituted with Z,
  $C_{2-5}$ alkynyl substituted with Z,
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{1-5}$ alkyl substituted with 0–2 $R^2$,
  $C_{2-5}$ alkenyl substituted with 0–2 $R^2$, and
  $C_{2-5}$ alkynyl substituted with 0–2 $R^2$;

Z is selected from H,
  —CH(OH)R$^2$,
  —C(ethylenedioxy)R$^2$,
  —OR$^2$,
  —SR$^2$,
  —NR$^2$R$^3$,
  —C(O) R$^2$,
  —C(O) NR$^2$R$^3$,
  —NR$^3$C(O)R$^2$,
  —C(O) OR$^2$,
  —OC(O)R$^2$,
  —CH(=NR$^4$)NR$^2$R$^3$,
  —NHC(=NR$^4$)NR$^2$R$^3$,
  —S(O)R$^2$,
  —S(O)$_2$R$^2$,
  —S(O)$_2$NR$^2$R$^3$, and —NR$^3$S(O)$_2$R$^2$;

$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  aryl substituted with 0–5 $R^{42}$;
  $C_{3-10}$ carbocyclic group substituted with 0–3 $R^{41}$, and
  5–10 membered heterocyclic ring system containing from, 1–4 heteroatoms selected from the group consisting of N, O, and S substituted with 0–3 $R^{41}$;

$R^3$, at each occurrence, is independently selected from
  H, $C_{1-4}$ alkyl, $C_{2-4}$ alkenyl, $C_{2-4}$ alkynyl, and $C_{1-4}$ alkoxy;
alternatively, $R^2$ and $R^3$ join to form a 5- or 6-membered ring optionally substituted with —O— or —N(R$^4$)—;

$R^4$, at each occurrence, is independently selected from H, methyl, ethyl, propyl, and butyl;
$R^5$ is H, methyl, or ethyl;
$R^{6a}$ is selected from
  H, —OH, —NR$^{46}$R$^{47}$, —CF$_3$,
  $C_{1-4}$ alkyl, $C_{2-4}$ alkenyl, $C_{2-4}$ alkynyl, $C_{1-4}$ alkoxy, $C_{1-4}$ haloalkyl, and $C_{3-6}$ cycloalkyl;

$R^{6b}$ is H;
$R^7$, $R^8$, and $R^9$, at each occurrence, are independently selected from
  H, halo, —CF$_3$, —OCF$_3$, —OH, —OCH$_3$, —CN, —NO$_2$, —NR$^{46}$R$^{47}$,
  $C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
  $C_{1-4}$ alkyl substituted with 0–2 $R^{11}$,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)$_2$NR$^{12}$R$^{13}$, NR$^{14}$S(O)$_2$R$^{12}$, NR$^{14}$S(O)R$^{12}$, NR$^{14}$S(O)$_2$R$^{12}$, NR$^{12}$C(O) R$^{15}$, NR$^{12}$C(O)OR$^{15}$, NR$^{12}$S(O)$_2$R$^{15}$, and NR$^{12}$C(O)NHR$^{15}$;

$R^{10A}$ is selected from H,
  $C_{1-6}$ alkyl substituted with 0–1 $R^{10B}$,
  $C_{2-6}$ alkenyl substituted with 0–1 $R^{10B}$,
  $C_{2-6}$ alkynyl substituted with 0–1 $R^{10B}$, and
  $C_{1-6}$ alkoxy;

$R^{10B}$ is selected from
  $C_{1-4}$ alkoxy,
  $C_{3-6}$ cycloalkyl,
  $C_{3-6}$ carbocyclic group substituted with 0–3 $R^{33}$,
  phenyl substituted with 0–3 $R^{33}$, and
  5–6 membered heterocyclic ring system containing 1, 2, or 3 heteroatoms selected from the group consisting of N, O, and S substituted with 0–2 $R^{44}$;

$R^{11}$ is selected from
  H, halo, —CF$_3$, —OCF$_3$, —OH, —OCH$_3$, —CN, —NO$_2$, —NR$^{46}$R$^{47}$,
  $C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
  $C_{3-10}$ carbocyclic group substituted with 0–3 $R^{33}$,
  aryl substituted with 0–5 $R^{33}$,
  5–10 membered heterocyclic ring system containing from 1–4 heteroatoms selected from the group consisting of N, O, and S substituted with 0–3 $R^{31}$;
  OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, CH(=NR$^{14}$)NR$^{12}$R$^{13}$, NHC(=NR$^{14}$)NR$^{12}$R$^{13, S(O)R12}$, S(O)$_2$R$^{12}$, S(O)$_2$NR$^{12}$R$^{13}$, and NR$^{14}$S(O)$_2$R$^{12}$;

$R^{12}$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{33}$;
  $C_{3-10}$ carbocyclic group substituted with 0–3 $R^{33}$, and
  5–10 membered heterocyclic ring system containing from 1–4 heteroatoms selected from the group consisting of N, O, and S substituted with 0–3 $R^{31}$;

$R^{13}$, at each occurrence, is independently selected from
  H, $C_{1-4}$ alkyl, $C_{2-4}$ alkenyl, and $C_{2-4}$ alkynyl;
alternatively, $R^{12}$ and $R^{13}$ join to form a 5- or 6-membered ring optionally substituted with —O— or —N(R$^{14}$)—;

$R^{14}$, at each occurrence, is independently selected from H and $C_{1-4}$ alkyl;

$R^{31}$, at each occurrence, is independently selected from H, OH, halo, CF$_3$, methyl, and ethyl;

$R^{33}$, at each occurrence, is independently selected from H, OH, halo, CN, $NO_2$, $CF_3$, methyl, and ethyl;

$R^{41}$, at each occurrence, is independently selected from H, $CF_3$, halo, OH, $CO_2H$, $SO_2R^{45}$, $NR^{46}R^{47}$, $NO_2$, CN, =O,
  $C_{2-8}$ alkenyl, $C_{2-8}$ alkynyl, $C_{1-4}$ alkoxy, $C_{1-4}$ haloalkyl,
  $C_{1-4}$ alkyl substituted with 0–1 $R^{43}$,
  aryl substituted with 0–3 $R^{42}$, and
  5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$,
  $C_{2-6}$ alkenyl, $C_{2-6}$ alkynyl, $C_{1-4}$ alkoxy, $C_{1-4}$ haloalkyl, $C_{3-6}$ cycloalkyl,
  $C_{1-4}$ alkyl substituted with 0–1 $R^{43}$,
  aryl substituted with 0–3 $R^{44}$, and
  5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, $—CF_3$, $—OCF_3$, —CN, $—NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-3}$ alkyl;

$R^{47}$, at each occurrence, is independently selected from H, $C_{1-4}$ alkyl, —C(=O)NH($C_{1-4}$ alkyl), $—SO_2(C_{1-4}$ alkyl),
  $—SO_2$(phenyl), —C(=O)O($C_{1-4}$ alkyl), —C(=O)($C_{1-4}$ alkyl),
  and —C(=O)H;

$R^{48}$, at each occurrence, is independently selected from H, $C_{1-4}$ alkyl, —C(=O)NH($C_{1-4}$ alkyl), —C(=O)O($C_{1-4}$ alkyl),
  —C(=O) ($C_{1-4}$ alkyl), and —C(=O)H;

k is 1 or 2;

m is 0, 1, 2; and n is 1 or 2.

11. A compound of claim 9 wherein:

X is $—NR^{10A}—$;

$R^1$ is selected from
  $C_{2-4}$ alkyl substituted with Z,
  $C_{2-4}$ alkenyl substituted with Z,
  $C_{2-4}$ alkynyl substituted with Z,
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{2-4}$ alkyl substituted with 0–2 $R^2$, and
  $C_{2-4}$ alkenyl substituted with 0–2 $R^2$;

Z is selected from H,
  —CH(OH)$R^2$,
  —C(ethylenedioxy)$R^2$,
  $—OR^2$,
  $—SR^2$,
  $—NR^2R^3$,
  —C(O)$R^2$,
  —C(O)$NR^2R^3$,
  $—NR^3C(O)R^2$,
  —C(O)$OR^2$,
  —S(O)$R^2$,
  $—S(O)_2R^2$,
  $—S(O)_2NR^2R^3$, and $—NR^3S(O)_2R^2$;

$R^2$, at each occurrence, is independently selected from phenyl substituted with 0–5 $R^{42}$;
  $C_{3-10}$ carbocyclic group substituted with 0–3 $R^{41}$, and
  5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or $—N(R^4)—$;

$R^4$, at each occurrence, is independently selected from H, methyl, ethyl, propyl, and butyl;

$R^5$ is H;

$R^{6a}$ is selected from H, —OH, $—CF_3$, methyl, ethyl, propyl, butyl, methoxy, and, ethoxy;

$R^{6b}$ is H;

$R^7$, $R^8$, and $R^9$, at each occurrence, are independently selected from
  H, halo, $—CF_3$, $—OCF_3$, —OH, $—OCH_3$, —CN, $—NO_2$,
  $C_{1-4}$ alkyl, $C_{1-4}$ haloalkyl, $C_{1-4}$ alkoxy, ($C_{1-3}$ haloalkyl)oxy, and
  $C_{1-4}$ alkyl substituted with 0–2 $R^{11}$;

$R^{10A}$ is selected from H, $C_{1-6}$ alkyl, $C_{1-4}$ alkoxy, and $C_{1-2}$ alkyl substituted with 0–1 $R^{10B}$;

$R^{10B}$ is $C_{3-6}$ cycloalkyl or phenyl substituted with 0–3 $R^{33}$;

$R^{11}$ is selected from
  H, halo, $—CF_3$, $—OCF_3$, —OH, $—OCH_3$, —CN, $—NO_2$,
  $C_{1-4}$ alkyl, , $C_{1-4}$ haloalkyl, $C_{1-4}$ alkoxy, and ($C_{1-3}$ haloalkyl)oxy;

$R^{33}$, at each occurrence, is independently selected from H, OH, halo, $CF_3$, and methyl;

$R^{41}$, at each occurrence, is independently selected from H, $CF_3$, halo, OH, $CF_2H$, $SO_2R^{45}$, $NR^{46}R^{47}$, $NO_2$, CN, =O,
  $C_{2-8}$ alkenyl, $C_{2-8}$ alkynyl, $C_{1-4}$ alkoxy, $C_{1-4}$ haloalkyl,
  $C_{1-4}$ alkyl substituted with 0–1 $R^{43}$,
  aryl substituted with 0–3 $R^{42}$, and
  5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$,
  $C_{2-6}$ alkenyl, $C_{2-6}$ alkynyl, $C_{1-4}$ alkoxy, $C_{1-4}$ haloalkyl, $C_{3-6}$ cycloalkyl,
  $C_{1-4}$ alkyl substituted with 0–1 $R^{43}$,
  aryl substituted with 0–3 $R^{44}$, and
  5–10 membered heterocyclic ring system containing from 1–4 heteroatoms selected from the group consisting of N, O, and S substituted with 0–3 $R^{44}$;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, $—SF_3$, $—OCF_3$, —CN, $—NO_2$,
  methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(=O)NH(methyl), —C(=O)NH(ethyl), —SO$_2$(methyl), —SO$_2$(ethyl), —SO$_2$(phenyl), —C(=O)O(methyl), —C(=O)O(ethyl), —C(=O)(methyl), —C(=O)(ethyl), and —C(=O)H;

$R^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1;

m is 0, 1, or 2; and n is 1 or 2.

12. A compound of claim 9 wherein:

X is —NH—;

$R^1$ is selected from
  ethyl substituted with Z,
  propyl substituted with Z,
  butyl substituted with Z,
  propenyl substituted with Z,
  butenyl substituted with Z,
  ethyl substituted with $R^2$,
  propyl substituted with $R^2$,
  butyl substituted with $R^2$,
  propenyl substituted with $R^2$ and
  butenyl substituted with $R^2$;

Z is selected from H,
  —HC(OH) $R^2$,
  —S$R^2$,
  —N$R^2R^3$,
  —C(O)$R^2$,
  —C(O)N$R^2R^3$,
  —N$R^3$C(O) $R^2$,
  —C(O)O$R^2$,
  —S(O)$R^2$,
  —S(O)$_2R^2$,
  —S(O)$_2$N$R^2R^3$, and —N$R^3$S(O)$_2R^2$;

$R^2$, at each occurrence, is independently selected from
  phenyl substituted with 0–3 $R^{42}$;
  naphthyl substituted with 0–3 $R^{42}$;
  cyclopropyl substituted with 0–3 $R^{41}$;
  cyclobutyl substituted with 0–3 $R^{41}$;
  cyclopentyl substituted with 0–3 $R^{41}$;
  cyclohexyl substituted with 0–3 $R^{41}$;
  pyridyl substituted with 0–3 $R^{41}$;
  indolyl substituted with 0–3 $R^{41}$;
  indolinyl substituted with 0–3 $R^{41}$;
  benzimidazolyl substituted with 0–3 $R^{41}$;
  benzotriazolyl substituted with 0–3 $R^{41}$;
  benzothienyl substituted with 0–3 $R^{41}$;
  benzofuranyl substituted with 0–3 $R^{41}$;
  phthalimid-1-yl substituted with 0–3 $R^{41}$;
  inden-2-yl substituted with 0–3 $R^{41}$;
  2,3-dihydro-1H-inden-2-yl substituted with 0–3 $R^{41}$;
  indazolyl substituted with 0–3 $R^{41}$;
  tetrahydroquinolinyl substituted with 0–3 $R^{41}$; and
  tetrahydro-isoquinolinyl substituted with 0–3 $R^{41}$;

$R^3$, at each occurrence, is independently selected from H, methyl, and ethyl;

$R^5$ is H;

$R^{6a}$ is selected from H, —OH, methyl, and methoxy;

$R^{6b}$ is H;

$R^7$, $R^8$, and $R^9$, at each occurrence, are independently selected from H, F, Cl, methyl, ethyl, methoxy, —CF$_3$, and —OCF$_3$;

$R^{41}$, at each occurrence, is independently selected from H, F, Cl, Br, OH, CF$_3$, NO$_2$, CN, =O, methyl, ethyl, propyl, butyl, methoxy, and ethoxy;

$R^{42}$, at each occurrence, is independently selected from H, F, Cl, Br, OH, CF$_3$, SO$_2R^{45}$, S$R^{45}$, N$R^{46}R^{47}$, O$R^{48}$, NO$_2$, CN, =O, methyl, ethyl, propyl, butyl, methoxy, and ethoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from H, methyl, ethyl, n-propyl, i-propyl, n-butyl, i-butyl, —C(=O)NH(methyl), —C(=O)NH(ethyl), —SO$_2$(methyl), —SO2(ethyl), —SO2(phenyl), —C(=O)O(methyl), —C(=O)O(ethyl), —C(=O)(methyl), —C(=O)(ethyl), and —C(=O)H;

$R^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

k is 1;

m is 0, 1, or 2; and n is 1 or 2.

13. A compound of claim 9 of Formula (I-a)

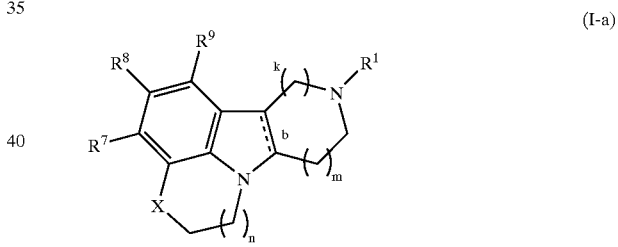

(I-a)

wherein:
  b is a single bond;
  X is —N$R^{10A}$—;
  $R^1$ is selected from
    —(CH$_2$)$_3$C(=O)(4-fluoro-phenyl),
    —(CH$_2$)$_3$C(=O)(4-bromo-phenyl),
    —(CH$_2$)$_3$C(=O)(4-methyl-phenyl),
    —(CH$_2$)$_3$C(=O)(4-methoxy-phenyl),
    —(CH$_2$)$_3$C(=O)(4-(3,4-dichloro-phenyl)phenyl),
    —(CH$_2$)$_3$C(=O)(3-methyl-4-fluoro-phenyl),
    —(CH$_2$)$_3$C(=O)(2,3-dimethoxy-phenyl),
    —(CH$_2$)$_3$C(=O)(phenyl),
    —(CH$_2$)3C(=O)(4-chloro-phenyl),
    —(CH$_2$)$_3$C(=O)(3-methyl-phenyl),
    —(CH$_2$)$_3$C(=O)(4-t-butyl-phenyl),
    —(CH$_2$)$_3$C(=O)(3,4-difluoro-phenyl),
    —(CH$_2$)$_3$C(=O)(2-methoxy-5-fluoro-phenyl),
    —(CH$_2$)$_3$C(=O)(4-fluoro-1-naphthyl),
    —(CH$_2$)$_3$C(=O)(benzyl),
    —(CH$_2$)$_3$C(=O)(4-pyridyl),
    —(CH$_2$)$_3$C(=O)(3-pyridyl),
    —(CH$_2$)$_3$CH(OH)(4-fluoro-phenyl), —(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O)(4-fluoro-phenyl),
—(CH$_2$)$_3$SO$_2$(3-fluoro-phenyl),
—(CH$_2$)$_3$SO$_2$(4-fluoro-phenyl),
—(CH$_2$)$_3$O(4-fluoro-phenyl),
—(CH$_2$)$_3$O(phenyl),
—(CH$_2$)$_3$O(3-pyridyl),
—(CH$_2$)$_3$O(4-pyridyl),
—(CH$_2$)$_3$O(2-NH$_2$-phenyl),
—(CH$_2$)$_3$O(2-NH$_2$-5-F-phenyl),
—(CH$_2$)$_3$O(2-NH$_2$-4-F-phenyl),
—(CH$_2$)$_3$O(2-NH$_2$-3-F-phenyl),
—(CH$_2$)$_3$O(2-NH$_2$-4-Cl-phenyl),
—(CH$_2$)$_3$O(2-NH$_2$-4-OH-phenyl),
—(CH$_2$)$_3$O(2-NH$_2$-4-Br-phenyl),
—(CH$_2$)$_3$O(2-NHC(=O)Me-4-F-phenyl),
—(CH$_2$)$_3$O(2-NHC(=O)Me-phenyl),
—(CH$_2$)$_3$NH(4-fluoro-phenyl),
—(CH$_2$)$_3$N (methyl)(4-fluoro-phenyl),
—(CH$_2$)$_3$CO$_2$(ethyl),
—(CH$_2$)$_3$C(=O)N(methyl)(methoxy),
—(CH$_2$)$_3$C(=O)NH(4-fluoro-phenyl),
—(CH$_2$)$_2$NHC(=O)(phenyl),
—(CH$_2$)$_2$NMeC(=O)(phenyl),
—(CH$_2$)$_2$NHC(=O)(2-fluoro-phenyl),
—(CH$_2$)$_2$NMeC(=O)(2-fluoro-phenyl),
—(CH$_2$)$_2$NHC(=O)(4-fluoro-phenyl),
—(CH$_2$)$_2$NMeC(=O)(4-fluoro-phenyl),
—(CH$_2$)$_2$NHC(=O)(2,4-difluoro-phenyl),
—(CH$_2$)$_2$NMeC(=O)(2,4-difluoro-phenyl),
—(CH$_2$)$_3$(3-indolyl),
—(CH$_2$)$_3$(1-methyl-3-indolyl),
—(CH$_2$)$_3$(1-indolyl),
—(CH$_2$)$_3$(1-indolinyl),
—(CH$_2$)$_3$(1-benzimidazolyl),
—(CH$_2$)$_3$(1H-1,2,3-benzotriazol-1-yl),
—(CH$_2$)$_3$(1H-1,2,3-benzotriazol-2-yl),
—(CH$_2$)$_2$(1H-1,2,3-benzotriazol-1-yl),
—(CH$_2$)$_2$(1H-1,2,3-benzotriazol-2-yl),
—(CH$_2$)$_3$(3,4 dihydro-1(2H)-quinolinyl),
—(CH$_2$)$_2$C(=O)(4-fluoro-phenyl),
—(CH$_2$)$_2$C(=O)NH(4-fluoro-phenyl),
—CH$_2$CH$_2$(3-indolyl),
—CH$_2$CH$_2$(1-phthalimidyl),
—(CH$_2$)$_4$C(=O)N(methyl)(methoxy),
—(CH$_2$)$_4$CO$_2$(ethyl),
—(CH$_2$)$_4$C(=O)(phenyl),
—(CH$_2$)$_4$(cyclohexyl),
—(CH$_2$)$_3$CH(phenyl)$_2$,
—CH$_2$CH$_2$CH=C(phenyl)$_2$,
—CH$_2$CH$_2$CH=CMe(4-F-phenyl),
—(CH$_2$)$_3$CH(4-fluoro-phenyl)$_2$,
—CH$_2$CH$_2$CH=C(4-fluoro-phenyl)$_2$,
—(CH$_2$)$_2$(2,3-dihydro-1H-inden-2-yl),
—(CH$_2$)$_3$C(=O)(2-NH$_2$-phenyl),
—(CH$_2$)$_3$C(=O)(2-NH$_2$-5-F-phenyl),
—(CH$_2$)$_3$C(=O)(2-NH$_2$-4-F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$C(=O)(2-NH$_2$-4-OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-Cl-1H-indazol-3-yl),
—(CH$_2$)$_3$(6-Br-1H-indazol-3-yl),
—(CH$_2$)$_3$C(=O)(2-NHMe-phenyl),
—(CH$_2$)$_3$(1-benzothien-3-yl),
—(CH$_2$)$_3$(6-F-1H-indol-1-yl),
—(CH$_2$)$_3$(5-F-1H-indol-1-yl),
—(CH$_2$)$_3$(6-F-2,3-dihydro-1H-indol-1-yl),
—(CH$_2$)$_3$(5-F-2,3-dihydro-1H-indol-1-yl),
—(CH$_2$)$_3$(6-F-1H-indol-3-yl),
—(CH$_2$)$_3$(5-F-1H-indol-3-yl),
—(CH$_2$)$_3$(5-F-1H-indol-3-yl),
—(CH$_2$)$_3$(9H-purin-9-yl),
—(CH$_2$)$_3$(7H-purin-7-yl),
—(CH$_2$)$_3$(6-F-1H-indazol-3-yl),
—(CH$_2$)$_3$C(=O)(2-NHSO$_2$Me-4-F-phenyl),
—(CH$_2$)$_3$C(=O)(2-NHC(=O)Me-4-F-phenyl),
—(CH$_2$)$_3$C(=O)(2-NHC(=O)Me-phenyl),
—(CH$_2$)$_3$C(=O)(2-NHCO$_2$Et-4-F-phenyl),
—(CH$_2$)$_3$C(=O)(2-NHC(=O)NHEt-4-F-phenyl),
—(CH$_2$)$_3$C(=O)(2-NHCHO-4-F-phenyl),
—(CH$_2$)$_3$C(=O)(2-OH-4-F-phenyl),
—(CH$_2$)$_3$C(=O)(2-MeS-4-F-phenyl),
—(CH$_2$)$_3$C(=O)(2-NHSO$_2$Me-4-F-phenyl),
—(CH$_2$)$_2$C(Me)CO$_2$Me,
—(CH$_2$)$_2$C(Me)CH(OH)(4-F-phenyl)$_2$,
—(CH$_2$)$_2$C(Me)CH(OH)(4-Cl-phenyl)$_2$,
—(CH$_2$)$_2$C(Me)C(=O)(4-F-phenyl),
—(CH$_2$)$_2$C(Me)C(=O)(2-MeO-4-F-phenyl),
—(CH$_2$)$_2$C(Me)C(=O)(3-Me-4-F-phenyl),
—(CH$_2$)$_2$C(Me)C(=O)(2-Me-phenyl),
—(CH$_2$)$_2$C(Me) C(=O)phenyl,

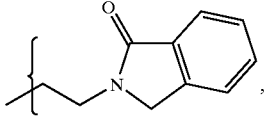,

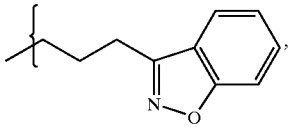,

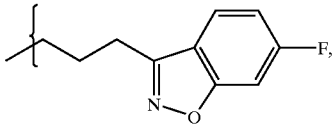,

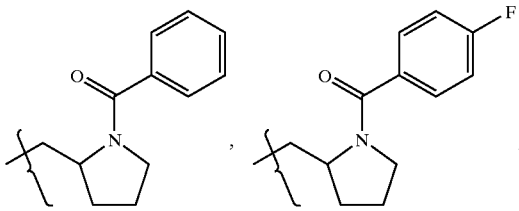

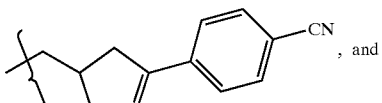, and

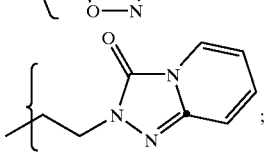;

R$^7$, R$^8$, and R$^9$, at each occurrence, are independently selected from
hydrogen, fluoro, chloro, bromo, cyano, methyl, ethyl,
propyl, isopropyl, butyl, t-butyl, nitro,
trifluoromethyl, methoxy, ethoxy, isopropoxy,
trifluoromethoxy, phenyl, benzyl,
HC(=O)—, methylC(=O)—, ethylC(=O)—, propylC(=O)—,
isopropylC(=O)—, n-butylC(=O)—, isobutylC(=O)—,
secbutylC(=O)—, tertbutylC(=O)—, phenylC(=O)—,
methylC(=O)NH—, ethylC(=O)NH—, propylC(=O)NH—,
isopropylC(=O)NH—, n-butylC(=O)NH—, isobutylC(=O)NH—,
secbutylC(=O)NH—, tertbutylC(=O)NH—, phenylC(=O)NH—,
methylamino-, ethylamino-, propylamino-, isopropylamino-,
n-butylamino-, isobutylamino-, secbutylamino-, tertbutylamino-, phenylamino-,
provided that two of substituents R$^7$, R$^8$, and R$^9$, are independently selected from hydrogen, fluoro, chloro,
bromo, cyano, methyl, ethyl, propyl, isopropyl, butyl, t-butyl,
nitro, trifluoromethyl, methoxy, ethoxy, isopropoxy, and trifluoromethoxy;
R$^{10A}$ is selected from hydrogen, methyl, ethyl, propyl, isopropyl, butyl, benzyl, 2-chlorobenzyl, 2-fluorobenzyl, 2-bromobenzyl, 2-methylbenzyl, 2-trifluoromethylbenzyl, 2-methoxybenzyl, 2-trifluoromethoxybenzyl, 3-chlorobenzyl, 3-fluorobenzyl, 3-bromobenzyl, 3-methylbenzyl, 3-trifluoromethylbenzyl, 3-methoxybenzyl, 3-trifluoromethoxybenzyl, 4-chlorobenzyl, 4-fluorobenzyl, 4-bromobenzyl, 4-methylbenzyl, 4-trifluoromethylbenzyl, 4-methoxybenzyl, and 4-trifluoromethoxybenzyl;
k is 1 or 2;
m is 1 or 2; and
n is 1 or 2.

14. A compound of claim 13 of Formula (IV-a)

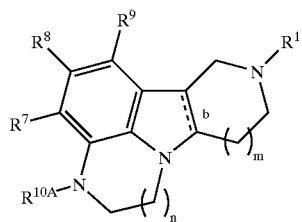

(IV-a)

wherein:
b is a single bond, wherein the bridge hydrogens are in a cis position;
R$^1$ is selected from
—(CH$_2$)$_3$C(=O) (4-fluoro-phenyl),
—(CH$_2$)$_3$C(=O) (4-bromo-phenyl),
—(CH$_2$)3C(=O) (4-methyl-phenyl),
—(CH$_2$)$_3$C(=O) (4-methoxy-phenyl),
—(CH$_2$)$_3$C(=O)(4-(3,4-dichloro-phenyl)phenyl),
—(CH$_2$)$_3$C(=O) (3-methyl-4-fluoro-phenyl),
—(CH$_2$)$_3$C(=O) (2,3-dimethoxy-phenyl),
—(CH$_2$)$_3$C(=O) (phenyl),
—(CH$_2$)$_3$C(=O) (4-chloro-phenyl),
—(CH$_2$)$_3$C(=O) (3-methyl-phenyl),
—(CH$_2$)$_3$C(=O) (4-t-butyl-phenyl),
—(CH$_2$)$_3$C(=O) (3,4-difluoro-phenyl),
—(CH$_2$)$_3$C(=O) (2-methoxy-5-fluoro-phenyl),
—(CH$_2$)$_3$C(=O) (4-fluoro-1-naphthyl),
—(CH$_2$)$_3$C(=O) (benzyl),
—(CH$_2$)$_3$C(=O) (4-pyridyl),
—(CH$_2$)$_3$C(=O) (3-pyridyl),
—(CH$_2$)$_3$CH(OH) (4-fluoro-phenyl),
—(CH$_2$)$_3$CH(OH) (4-pyridyl),
—(CH$_2$)$_3$CH(OH) (2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O) (4-fluoro-phenyl),
—(CH$_2$)$_3$SO$_2$(3-fluoro-phenyl),
—(CH$_2$)$_3$SO$_2$) (4-fluoro-phenyl),
—(CH$_2$)$_3$O(4-fluoro-phenyl),
—(CH$_2$)$_3$O(phenyl),
—(CH$_2$)$_3$NH(4-fluoro-phenyl),
—(CH$_2$)$_3$N(methyl) (4-fluoro-phenyl),
—(CH$_2$)$_3$CO$_2$(ethyl),
—(CH$_2$)$_3$C(=O)N(methyl) (methoxy),
—(CH$_2$)$_3$C(=O)NH(4-fluoro-phenyl),
—(CH$_2$)$_2$NHC(=O) (phenyl),
—(CH$_2$)$_2$NMeC(=O) (phenyl),
—(CH$_2$)$_2$NHC(=O) (2-fluoro-phenyl),
—(CH$_2$)$_2$NMeC(=O) (2-fluoro-phenyl),
—(CH$_2$)$_2$NHC(=O) (4-fluoro-phenyl),
—(CH$_2$)$_2$NMeC(=O) (4-fluoro-phenyl),
—(CH$_2$)$_2$NHC(=O) (2,4-difluoro-phenyl),
—(CH$_2$)$_2$NMeC(=O) (2,4-difluoro-phenyl),
—(CH$_2$)$_3$(3-indolyl)
—(CH$_2$)3(1-methyl-3-indolyl),
—(CH$_2$)$_3$(1-indolyl),
—(CH$_2$)$_3$(1-indolinyl),
—(CH$_2$)$_3$(1-benzimidazolyl),
—(CH$_2$)$_3$(1H-1,2,3-benzotriazol-1-yl),
—(CH$_2$)$_3$(1H-1,2,3-benzotriazol-2-yl),
—(CH$_2$)$_2$ (1H-1,2,3-benzotriazol-1-yl)
—(CH$_2$)$_2$(1H-1,2,3-benzotriazol-2-yl),
—(CH$_2$)$_3$(3,4 dihydro-1(2H)-quinolinyl),
—(CH$_2$)$_2$C(=O) (4-fluoro-phenyl),
—(CH$_2$)$_2$C(=O)NH(4-fluoro-phenyl),
—CH$_2$CH$_2$(3-indolyl),
—CH$_2$CH$_2$(1-phthalimidyl),
—(CH$_2$)$_4$C(=O)N(methyl) (methoxy),
—(CH$_2$)$_4$CO$_2$(ethyl),
—(CH$_2$)$_4$C(=O) (phenyl),
—(CH$_2$)$_4$(cyclohexyl),
—(CH$_2$)$_3$CH(phenyl)$_2$,
—CH$_2$CH$_2$CH=C(phenyl)$_2$,
—CH$_2$CH$_2$CH=CMe(4-F-phenyl),
—(CH$_2$)$_3$CH(4-fluoro-phenyl)$_2$,
—CH$_2$CH$_2$CH=C(4-fluoro-phenyl)$_2$,
—(CH$_2$)$_2$ (2,3-dihydro-1H-inden-2-yl),
—(CH$_2$)$_3$C(=O) (2-NH$_2$-phenyl),
—(CH$_2$)$_3$C(=O) (2-NH$_2$-5-F-phenyl),
—(CH$_2$)$_3$C(=O) (2-NH$_2$-4-F-phenyl),
—(CH$_2$)$_3$C(=O) (2-NH$_2$-3-F-phenyl),
—(CH$_2$)$_3$C(=O) (2-NH$_2$-4-Cl-phenyl),
—(CH$_2$)$_3$C(=O) (2-NH$_2$-4-OH-phenyl),
—(CH$_2$)$_3$C(=O) (2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl), —(CH₂)₃(6-Cl-1H-indazol-3-yl),
—(CH₂)₃(6-Br-1H-indazol-3-yl),
—(CH₂)₃C(=O) (2-NHMe-phenyl),
—(CH₂)₃(1-benzothien-3-yl),
—(CH₂)₃(6-F-1H-indol-1-yl),
—(CH₂)₃(5-F-1H-indol-1-yl),
—(CH₂)₃(6-F-2,3-dihydro-1H-indol-1-yl),
—(CH₂)₃(5-F-2,3-dihydro-1H-indol-1-yl),
—(CH₂)₃(6-F-1H-indol-3-yl),
—(CH₂)₃(5-F-1H-indol-3-yl)
—(CH₂)₃(5-F-1H-indol-3-yl),
—(CH₂)₃(9H-purin-9-yl),
—(CH₂)₃(7H-purin-7-yl),
—(CH₂)₃(6-F-1H-indazol-3-yl),
—(CH₂)₃C(=O) (2-NHSO₂Me-4-F-phenyl),
—(CH₂)₃C(=O) (2-NHC(=O)Me-4-F-phenyl),
—(CH₂)₃C(=O) (2-NHC(=O)Me-4-F-phenyl),
—(CH₂)₃C(=O) (2-NHCO₂Et-4-F-phenyl),
—(CH₂)₃C(=O) (2-NHC(=O)NHEt-4-F-phenyl),
—(CH₂)₃C(=O) (2-NHCHO-4-F-phenyl),
—(CH₂)₃C(=O) (2-OH-4-F-phenyl),
—(CH₂)₃C(=O) (2-MeS-4-F-phenyl),
—(CH₂)₃C(=O) (2-NHSO₂Me-4-F-phenyl),
—(CH₂)₂C(Me)CO₂Me,
—(CH₂)₂C(Me)CH(OH) (4-F-phenyl)₂
—(CH₂)₂C(Me)CH(OH) (4-Cl-phenyl)₂,
—(CH₂)₂C(Me)C(=O) (4-F-phenyl),
—(CH₂)₂C(Me)C(=O) (2-MeO-4-F-phenyl)
—(CH₂)₂C(Me)C(=O) (3-Me-4-F-phenyl),
—(CH₂)₂C(Me)C(=O) (2-Me-phenyl),
—(CH₂)₂C(Me)C(=O) phenyl,

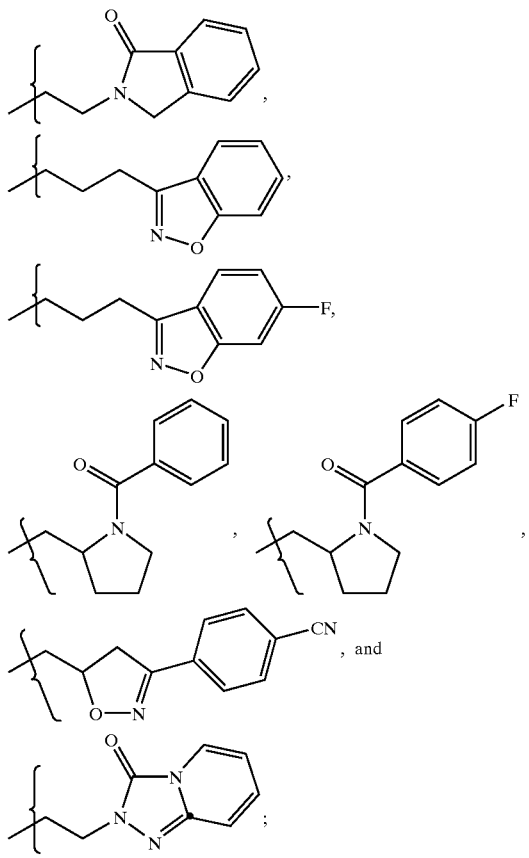

$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, methylC(=O)—, ethylC(=O)—, propylC(=O)—, isopropylC(=O)—, methylC(=O)NH—, ethylC(=O)NH—, propylC(=O)NH—, isopropylC(=O)NH, methylamino-, ethylamino-, propylamino-, and isopropylamino-, provided that two of substituents $R^7$, $R^8$, and $R^9$, are independently selected from hydrogen, fluoro, chloro, methyl, trifluoromethyl, methoxy, and trifluoromethoxy;

$R^{10A}$ is selected from hydrogen, methyl, ethyl, propyl, isopropyl, butyl, benzyl, 2-chlorobenzyl, 2-fluorobenzyl, 2-bromobenzyl, 2-methylbenzyl, 2-trifluoromethylbenzyl, 2-methoxybenzyl, 2-trifluoromethoxybenzyl, 3-chlorobenzyl, 3-fluorobenzyl, 3-bromobenzyl, 3-methylbenzyl, 3-trifluoromethylbenzyl, 3-methoxybenzyl, 3-trifluoromethoxybenzyl, 4-chlorobenzyl, 4-fluorobenzyl, 4-bromobenzyl, 4-methylbenzyl, 4-trifluoromethylbenzyl, 4-methoxybenzyl, and 4-trifluoromethoxybenzyl;

m is 1 or 2; and n is 1 or 2.

15. A compound of selected from the group consisting of 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-pyridinyl)-1-butanone hydrochloride;

(6bR,10aS)-2,3,6b,7,8,9,10,10a-octahydro-1H-pyrido[3',4':4,5]pyrrolo[1,2,3-de]quinoxaline;

(6bR,10aS)-2,3,6b,9,10,10a-hexahydro-1H-pyrido[3',4':4,5]pyrrolo[1,2,3-de]quinoxalin-8(7H)-yl)-1-(4-fluorophenyl)-1-butanone;

(6bR,10aS)-8-[3-(6-fluoro-1,2-benzisoxazol-3-yl)propyl]-3-methyl-2,3,6b,7,8,9,10,10a-octahydro-1H-pyrido[3',4':4,5]pyrrolo[1,2,3-de]quinoxaline hydrochloride;

(6bR,10aS)-8-[3-(1,2-benzisoxazol-3-yl)propyl]-3-methyl-2,3,6b,7,8,9,10,10a-octahydro-1H-pyrido[3',4':4,5]pyrrolo[1,2,3-de]quinoxaline hydrochloride;

(6bR, 10aS)-3-methyl-2,3,6b,7,8,9,10,10a-octahydro-1H-pyrido[3',4':4,5]pyrrolo[1,2,3-de]quinoxaline;

(6bR,10aS)-3-ethyl-2,3,6b,7,8,9,10,10a-octahydro-1H-pyrido[3',4':4,5]pyrrolo[1,2,3-de]quinoxaline;

(6bR,10aS)-3-propyl-2,3,6b,7,8,9,10,10a-octahydro-1H-pyrido[3',4':4,5]pyrrolo[1,2,3-de]quinoxaline;

(6bR,10aS)-3-is propyl-2,3,6b,7,8,9,10,10a-octahydro-1H-pyrido[3',4':4,5]pyrrolo[1,2,3-de]quinoxaline;

(6bR,10aS)-3-butyl-2,3,6b,7,8,9,10,10a-octahydro-1H-pyrido[3',4':4,5]pyrrolo[1,2,3-de]quinoxaline;

(6bR,10aS)-3-benzyl-2,3,6b,7,8,9,10,10a-octahydro-1H-pyrido[3',4':4,5]pyrrolo[1,2,3-de]quinoxaline;

4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone;

4-((6bR,10aS)-3-ethyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone;

4-((6bR,10aS)-3-isopropyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone;

4-((6bR,10aS)-3-benzyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone;

(6bR,10aS)-8-[3-(4-fluorophenoxy)propyl]-3-methyl-2,3,6b,7,8,9,10,10a-octahydro-1H-pyrido[3',4':4,5]pyrrolo[1,2,3-de]quinoxaline;

(6bR,10aS)-5-(2,4-dichlorophenyl)-3-methyl-2,3,6b,7,8,9,10,10a-octahydro-1H-pyrido[3',4':4,5]pyrrolo[1,2,3-de]quinoxaline;

(6bR,10aS)-5-(2,4-dichlorophenyl)-2,3,6b,7,8,9,10,10a-octahydro-1H-pyrido[3',4':4,5]pyrrolo[1,2,3-de]quinoxaline hydrochloride;

4-((6bR,10aS)-5-bromo-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone;

4-((6bR,10aR)-5-methoxy-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone;

(8aS,12aR)-2-(2,4-dichlorophenyl)-4,5,6,7,8a,9,10,11,12,12a-decahydro[1,4]diazepino[3,2,1-hi]pyrido[4,3-b]indole hydrochloride;

(8aS,12aR)-2-(4-methoxy-2-methylphenyl)-4,5,6,7,8a,9,10,11,12,12a-decahydro[1,4]diazepino[3,2,1-hi]pyrido[4,3-b]indole hydrochloride;

(6bS,11aS)-3-methyl-2,3,7,8,9,10,11,11a-octahydro-1H,6bH-azepino[4',5':4,5]pyrrolo[1,2,3-de]quinoxaline;

4-(3-methyl-2,3,6b,7,8,10,11,11a-octahydro-1H,9H-azepino[4',5':4,5]pyrrolo[1,2,3-de]quinoxalin-9-yl)-1-(4-fluorophenyl)-1-butanone; and (+/−)-1,1,3-Trimethyl-2,3,6b,7,8,9,10,10a-octahydro-1H-pyrido[3',4':4,5]pyrrolo[1,2,3-de]quinoxaline.

16. A pharmaceutical composition comprising a pharmaceutically acceptable carrier and a therapeutically effective amount of a compound of claim 1, 2, 3, 4, 5, 6, 7, 8, 9, 10, 11, 12, 13, 14, or 15, or a pharmaceutically acceptable salt thereof.

17. A method for treating a human suffering from a disorder associated with 5HT2C receptor modulation selected from obesity, anorexia, bulemia, depression, a anxiety, psychosis, schizophrenia, migraine, obsessive-compulsive disorder, and sexual disorders; comprising administering to a patient in need thereof a therapeutically effective amount of a compound of claim 1, 2, 3, 4, 5, 6, 7, or 8 or a pharmaceutically acceptable salt thereof.

18. A method for treating a human suffering from a disorder associated with 5HT2A receptor modulation selected from depression, psychosis, schizophrenia, migraine, attention deficit disorder, attention deficit hyperactivity disorder, and obsessive-compulsive disorder; comprising administering to a patient in need thereof a therapeutically effective amount of a compound of claim 1, 9, 10, 11, 12, 13, or 14; or a pharmaceutically acceptable salt thereof.

19. A method for treating obesity comprising administering to a patient in need thereof a therapeutically effective amount of a compound of claim 1, 2, 3, 4, 5, 6, 7, or 8, or a pharmaceutically acceptable salt thereof.

20. A method for treating schizophrenia comprising administering to a patient in need thereof a therapeutically effective amount of a compound of claim 1, 2, 3, 4, 5, 6, 7, 8, 9, 10, 11, 12, 13, or 14, or a pharmaceutically acceptable salt thereof.

21. A method for treating depression comprising administering to a patient in need thereof a therapeutically effective amount of a compound of claim 1, 2, 3, 4, 5, 6, 7, 8, 9, 10, 11, 12, 13, or 14, or a pharmaceutically acceptable salt thereof.

* * * * *